US011963966B2

(12) United States Patent
Garraway et al.

(10) Patent No.: US 11,963,966 B2
(45) Date of Patent: Apr. 23, 2024

(54) COMPOSITIONS AND METHODS FOR TREATING OVARIAN TUMORS

(71) Applicants: Dana-Farber Cancer Institute, Inc., Boston, MA (US); The Broad Institute, Inc., Cambridge, MA (US); Massachusetts Institute of Technology, Cambridge, MA (US)

(72) Inventors: Levi Garraway, Boston, MA (US); Benjamin Izar, Boston, MA (US); Aviv Regev, Cambridge, MA (US); Orit Rozenblatt-Rosen, Cambridge, MA (US); Asaf Rotem, Boston, MA (US); Elizabeth Stover, Boston, MA (US); Itay Tirosh, Cambridge, MA (US)

(73) Assignees: Dana-Farber Cancer Institute, Inc., Boston, MA (US); The Broad Institute, Inc., Cambridge, MA (US); Massachusetts Institute of Technology, Cambridge, MA (US)

(*) Notice: Subject to any disclaimer, the term of this patent is extended or adjusted under 35 U.S.C. 154(b) by 616 days.

(21) Appl. No.: 16/499,393

(22) PCT Filed: Mar. 30, 2018

(86) PCT No.: PCT/US2018/025491
§ 371 (c)(1),
(2) Date: Sep. 30, 2019

(87) PCT Pub. No.: WO2018/183908
PCT Pub. Date: Oct. 4, 2018

(65) Prior Publication Data
US 2020/0390786 A1 Dec. 17, 2020

Related U.S. Application Data

(60) Provisional application No. 62/565,470, filed on Sep. 29, 2017, provisional application No. 62/479,885, filed on Mar. 31, 2017.

(51) Int. Cl.
*A61K 31/575* (2006.01)
*A61K 9/00* (2006.01)
*A61K 33/243* (2019.01)
*A61K 35/17* (2015.01)
*A61K 39/395* (2006.01)

(52) U.S. Cl.
CPC .......... *A61K 31/575* (2013.01); *A61K 9/0019* (2013.01); *A61K 33/243* (2019.01); *A61K 35/17* (2013.01); *A61K 39/39533* (2013.01)

(58) Field of Classification Search
CPC .. A61K 31/575; A61K 33/243; A61K 9/0019; A61K 35/17
See application file for complete search history.

(56) References Cited

U.S. PATENT DOCUMENTS

| 5,686,281 | A | 11/1997 | Roberts |
| 5,843,728 | A | 12/1998 | Seed et al. |
| 5,851,828 | A | 12/1998 | Seed et al. |
| 5,858,358 | A | 1/1999 | June et al. |
| 5,869,326 | A | 2/1999 | Hofmann |
| 5,883,223 | A | 3/1999 | Gray |
| 5,906,936 | A | 5/1999 | Eshhar et al. |
| 5,912,170 | A | 6/1999 | Seed et al. |
| 5,912,172 | A | 6/1999 | Eshhar et al. |
| 6,004,811 | A | 12/1999 | Seed et al. |
| 6,040,177 | A | 3/2000 | Riddell et al. |
| 6,284,240 | B1 | 9/2001 | Seed et al. |
| 6,297,238 | B1 | 10/2001 | Doyle et al. |
| 6,352,694 | B1 | 3/2002 | June et al. |
| 6,392,013 | B1 | 5/2002 | Seed et al. |
| 6,410,014 | B1 | 6/2002 | Seed et al. |
| 6,479,626 | B1 | 11/2002 | Kim et al. |
| 6,489,458 | B2 | 12/2002 | Hackett et al. |
| 6,534,055 | B1 | 3/2003 | June et al. |
| 6,534,261 | B1 | 3/2003 | Cox et al. |
| 6,607,882 | B1 | 8/2003 | Cox et al. |
| 6,746,838 | B1 | 6/2004 | Choo et al. |
| 6,753,162 | B1 | 6/2004 | Seed et al. |
| 6,794,136 | B1 | 9/2004 | Eisenberg et al. |
| 6,797,514 | B2 | 9/2004 | Berenson et al. |
| 6,824,978 | B1 | 11/2004 | Cox et al. |

(Continued)

FOREIGN PATENT DOCUMENTS

EP 2 764 103 A2 8/2014
EP 2 771 468 A1 9/2014
(Continued)

OTHER PUBLICATIONS

O'Shea et al., The JAK-STAT Pathway: Impact on Human Disease and Therapeutic Intervention, Annu. Rev. Med. 66:311-328, Publication year: 2015 (Year: 2015).*
Tang et al., Inhibitor of signal transducer and activator of transcription 3 (STAT3) suppresses ovarian cancer growth, migration and invasion and enhances the effect of cisplatin in vitro, Genetics and Molecular Research, 14(1): 2450-2460, Publication Date:Mar. 30, 2015 (Year: 2015).*
Murray, The JAK-STAT Signaling Pathway: Input and Output Integration1, The Journal of Immunology, 178:2623-2629, Publication Year: 2007 (Year: 2007).*
Bukowska et al., Two drugs are better than one. A short history of combined therapy of ovarian cancer, Contemp Oncol (Pozn) 19 (5): 350-353, Publication Year: 2015 (Year: 2015).*

(Continued)

*Primary Examiner* — Peter J Reddig
*Assistant Examiner* — Cheng Lu
(74) *Attorney, Agent, or Firm* — F. Brent Nix, Esq.; Johnson, Marcou, Isaacs & Nix, LLC

(57) ABSTRACT

Described herein are compositions and methods of using single-cell RNA-sequencing to identify treatment resistance in patients with ovarian cancer. Also, described herein are compositions and methods for treatment targeting resistance in patients with ovarian cancer.

21 Claims, 86 Drawing Sheets
Specification includes a Sequence Listing.

(56) References Cited

U.S. PATENT DOCUMENTS

| | | |
|---|---|---|
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Kim et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0138189 A1 | 7/2004 | Sebti et al. |
| 2004/0171156 A1 | 9/2004 | Hartley et al. |
| 2004/0224402 A1 | 11/2004 | Bonyhadi et al. |
| 2007/0060521 A1 | 3/2007 | Jove et al. |
| 2009/0123932 A1 | 5/2009 | Mes-Masson et al. |
| 2009/0247495 A1* | 10/2009 | Xie .................... A61K 31/58 |
| | | 514/178 |
| 2010/0104509 A1 | 4/2010 | King et al. |
| 2011/0178154 A1 | 7/2011 | Birrer et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0018410 A1 | 1/2015 | Jiang et al. |
| 2015/0184139 A1 | 7/2015 | Zhang et al. |
| 2015/0322530 A1 | 11/2015 | Orsulic et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0208243 A1 | 7/2016 | Zhang et al. |
| 2017/0211142 A1 | 7/2017 | Smargon et al. |

FOREIGN PATENT DOCUMENTS

| | | |
|---|---|---|
| EP | 2 784 162 A1 | 10/2014 |
| EP | 3 009 511 A2 | 4/2016 |
| WO | 92/15322 A1 | 9/1992 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |

(56) References Cited

FOREIGN PATENT DOCUMENTS

| | | |
|---|---|---|
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/187528 A1 | 12/2015 |
| WO | 2016/000304 A1 | 1/2016 |
| WO | 2016/011210 A2 | 1/2016 |
| WO | 2016/028682 A1 | 2/2016 |
| WO | 2016/040476 A1 | 3/2016 |
| WO | 2016/049024 A2 | 3/2016 |
| WO | 2016/049163 A2 | 3/2016 |
| WO | 2016/049258 A2 | 3/2016 |
| WO | 2016/070061 A1 | 5/2016 |
| WO | 2016/094867 A1 | 6/2016 |
| WO | 2016/094874 A1 | 6/2016 |
| WO | 2016/094880 A1 | 6/2016 |
| WO | 2016/106236 A1 | 6/2016 |
| WO | 2016/106244 A1 | 6/2016 |
| WO | 2016/094872 A1 | 8/2016 |
| WO | 2016/125169 A1 | 8/2016 |
| WO | 2016/161516 A1 | 10/2016 |
| WO | 2016/168584 A1 | 10/2016 |
| WO | 2016/191756 A1 | 12/2016 |
| WO | 2016/196388 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/070605 A1 | 4/2017 |
| WO | 2017/075294 A1 | 5/2017 |
| WO | 2017/075549 A1 | 5/2017 |
| WO | 2017/164936 A1 | 9/2017 |
| WO | 2017/219027 A1 | 12/2017 |
| WO | 2018/035250 A1 | 2/2018 |
| WO | 2018/170333 A1 | 9/2018 |
| WO | 2018/183908 A1 | 10/2018 |
| WO | 2019/005866 A1 | 1/2019 |

OTHER PUBLICATIONS

Saini et al., Elevated STAT3 expression in ovarian cancer ascites promotes invasion and metastasis: a potential therapeutic target, Oncogene, 36, 168-181 and Supp., Publication Date: Jun. 13, 2016 (Year: 2016).*
Ahmed et al., Getting to know ovarian cancer ascites: opportunities for targeted therapy-based translational research, Frontiers in Oncology, vol. 3, article 256, Publication Date: Sep. 25, 2013 (Year: 2013).*
Kipps et al., Meeting the challenge of ascites in ovarian cancer: new avenues for therapy and research, Nature Reviews/Cancer, vol. 13, p. 273-282, Publication Date: Apr. 2013 (Year: 2013).*
Selvendiran et al., Anticancer Efficacy of a Difluorodiarylidenyl Piperidone (HO-3867) in Human Ovarian Cancer Cells and Tumor Xenografts, Mol Cancer Ther; 9(5), p. 1169-1179, Publication Date: May 2010 (Year: 2010).*
Kim et al., Ascites modulates cancer cell behavior, contributing to tumor heterogeneity in ovarian cancer, Cancer Science, vol. 107, No. 9, 1173-1178, Publication Date: Sep. 2016 (Year: 2016).*
Alvarez, et al., "Identification of a Genetic Signature of Activated Signal Transducer and Activator of Transcription 3 in Human Tumors", Cancer Research, vol. 65, No. 12, Jun. 15, 2005, 5054-5062.
Amatschek, et al., "Tissue-Wide Expression Profiling Using cDNA Subtraction and Microarrays to Identify Tumor-Specific Genes", Cancer Research, vol. 64, Feb. 1, 2004, 844-856.
Armstrong, et al., "Intraperitoneal Cisplatin and Paclitaxel in Ovarian Cancer", The New England Journal of Medicine, vol. 354, Jan. 5, 2006, 34-43.
Birner, et al., "STAT3 Tyrosine Phosphorylation Influences Survival in Glioblastoma", Journal of Neuro-Oncology, vol. 100, No. 3, Dec. 2010, 339-343.
Bowman, et al., "STATs in Oncogenesis", Oncogene, vol. 19, No. 21, May 15, 2000, 2474-2488.
Bublik, et al., "Regulatory Module Involving FGF13, Mir-504, and P53 Regulates Ribosomal Biogenesis and Supports Cancer Cell Survival", Proceedings of the National Academy of Sciences, vol. 114, No. 4, Jan. 24, 2017, E496-E505.
Cancer Genome Atlas Research Net, "Integrated Genomic Analyses of Ovarian Carcinoma", Nature, vol. 474, No. 7353, Jun. 29, 2011, 609-615.
Coward, et al., "Interleukin-6 as a Therapeutic Target in Human Ovarian Cancer", Clinical Cancer Research, vol. 17, No. 18, Sep. 15, 2011, 6083-6096.
Dijkgraaf, et al., "A Phase I Trial Combining Carboplatin/Doxorubicin with Tocilizumab, an Anti-IL-6R Monoclonal Antibody, and Interferon-Alpha 2B in Patients with Recurrent Epithelial Ovarian Cancer", Annals of Oncology, vol. 26, No. 10, Oct. 2015, 2141-2149.
Duan, et al., "Signal Transducers and Activators of Transcription 3 Pathway Activation in Drug-Resistant Ovarian Cancer", Clinical Cancer Research, vol. 12, No. 17, Sep. 1, 2006, 5055-5063.
Frank, "STAT Inhibition in the Treatment of Cancer: Transcription Factors as Targets for Molecular Therapy", Current Cancer Therapy Reviews, vol. 2, Issue 1, 2006, 57-65.
Frank, "StAT Signaling in Cancer: Insights into Pathogenesis and Treatment Strategies", Cancer Treatment and Research, vol. 115, 2003, 267-291.
Gaillard, et al., "The Role of Immune Checkpoint Inhibition in the Treatment of Ovarian Cancer", Gynecologic Oncology Research and Practice, vol. 3, Article No. 11, 2016, 14 pages.
Horiguchi, et al., "Activation of Signal Transducer and Activator of Transcription 3 in Renal Cell Carcinoma: A Study of Incidence and its Association with Pathological Features and Clinical Outcome", The Journal of Urology, vol. 168, No. 2, Aug. 1, 2002, 762-765.
Iliopoulos, et al., "An Epigenetic Switch Involving NF-Kb, Lin28, Let-7 Microrna, and IL6 Links Inflammation to Cell Transformation", Cell, vol. 139, No. 4, Nov. 13, 2009, 693-706.
Kolomeyevskaya, et al., "Cytokine Profiling of Ascites at Primary Surgery Identifies an Interaction of Tumor Necrosis Factor-α and Interleukin-6 in Predicting Reduced Progression-Free Survival in Epithelial Ovarian Cancer", Gynecologic Oncology, vol. 138, No. 2, May 20, 2015, 1-16.
Kulbe, et al., "A Dynamic Inflammatory Cytokine Network in the Human Ovarian Cancer Microenvironment", Cancer Research, vol. 72, No. 1, Jan. 1, 2012, 66-75.
Lane, et al., "Prognostic Significance of IL-6 and IL-8 Ascites Levels in Ovarian Cancer Patients", BMC Cancer, vol. 11, No. 210, May 30, 2011, 1-6.
Liu, et al., "Activation of STAT3 is Involved in Malignancy Mediated by CXCL12-CXCR4 Signaling in Human Breast Cancer", Oncology Reports, vol. 32, 2014, 2760-2768.
Lloyd, et al., "Prediction of Resistance to Chemotherapy in Ovarian Cancer: A Systematic Review", BMC Cancer, vol. 15, Mar. 11, 2015, 1-32.
Matte, et al., "Profiling of Cytokines in Human Epithelial Ovarian Cancer Ascites", American Journal of Cancer Research, vol. 2, No. 5, 2012, 566-580.

(56) References Cited

OTHER PUBLICATIONS

Mcfarland, et al., "Activation of the NF-κB Pathway by the STAT3 Inhibitor JSI-124 in Human Glioblastoma Cells", Molecular Cancer Research, vol. 11, No. 5, May 2013, 494-505.
Messina, et al., "Activated STAT-3 in Melanoma", Cancer Control, vol. 15, No. 3, Jul. 2008, 196-201.
Mirtti, et al., "Nuclear Stat5a/b Predicts Early Recurrence and Prostate Cancer-Specific Death in Patients Treated by Radical Prostatectomy", Human Pathlogy, vol. 44, No. 3, Mar. 2013, 310-319.
Okada, et al., "Upregulated Expression of FGF13/FHF2 Mediates Resistance to Platinum Drugs in Cervical Cancer Cells", Scientific Reports, vol. 3, No. 2899, 2013, 8 pages.
Patch, et al., "Whole-Genome Characterization of Chemoresistant Ovarian Cancer", Nature, vol. 521, No. 7553, May 28, 2015, 489-494.
Pectasides, et al., "Nuclear Localization of Signal Transducer and Activator of Transcription 3 (STAT3) in Head and Neck Squamous Cell Carcinoma Is Associated with a Better Prognosis", Clinical Cancer Research, vol. 16, No. 8, Apr. 15, 2010, 2427-2434.
Pfeiffer, et al., "Alternative Implication of CXCR4 in JAK2/STAT3 Activation in Small Cell Lung Cancer", British Journal of Cancer, vol. 100, 2009, 1949-1956.
Popple, et al., "The Chemokine, CXCL12, is an Independent Predictor of Poor Survival in Ovarian Cancer", British Journal of Cancer, vol. 106, No. 7, Mar. 13, 2012, 1306-1313.
Saini, et al., "Elevated STAT3 Expression in Ovarian Cancer Ascites Promotes Invasion and Metastasis: A Potential Therapeutic Target", Oncogene, vol. 36, No. 2, Jan. 12, 2017, 168-181.
Shield, et al., "Multicellular Spheroids in Ovarian Cancer Metastases: Biology and Pathology", Gynecologic Oncology, vol. 113, No. 1, Apr. 2009, 143-148.
Silva, et al., "Aldehyde Dehydrogenase in Combination with CD133 Defines Angiogenic Ovarian Cancer Stem Cells That Portend Poor Patient Survival", Cancer Research, vol. 71, Issue 11, Jun. 2011, 3991-4001.
Sonnenblick, et al., "Tumor STAT3 Tyrosine Phosphorylation Status, as a Predictor of Benefit from Adjuvant Chemotherapy for Breast Cancer", Breast Cancer Research and Treatment, vol. 138, No. 2, Apr. 2013, 407-413.
Stone, et al., "Paraneoplastic Thrombocytosis in Ovarian Cancer", The New England Journal of Medicine, vol. 366, Feb. 16, 2012, 610-618.
Tirosh, et al., "Dissecting the Multicellular Ecosystem of Metastatic Melanoma by Single-Cell RNA-Seq", Science, vol. 352, No. 6282, Apr. 8, 2016, 189-196.
Wen, et al., "Targeting JAK1/STAT3 Signaling Suppresses Tumor Progression and Metastasis in a Peritoneal Model of Human Ovarian Cancer", Molecular Cancer Therapeutics, vol. 13, No. 12, Oct. 2014, 3037-3048.
Wu, et al., "AXL Kinase as a Novel Target for Cancer Therapy", Oncotarget, vol. 5, No. 20, Oct. 2014, 9546-9563.
Xu, et al., "A Meta-Analysis of STAT3 and Phospho-STAT3 Expression and Survival of Patients with Non-Small-Cell Lung Cancer", European Journal of Surgical Oncology, vol. 40, No. 3, Mar. 2014, 311-317.
Vainchenker, et al., "JAK/STAT Signaling in Hematological Malignancies," Oncogene, vol. 32, 2013, 2601-2613.
Blaskovich, et al., ""Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice,"", Cancer Research, Mar. 15, 2003, pp. 1270-1279.
Dana-Farber Cancer Institute,, "Notification of Transmittal of the International Search Report and the Written Opinion of the International Searching Authority, or the Declaration", Jun. 25, 2018, 5 pages.
Ferriss, et al., ""Multi-Gene Expression Predictors of Single Drug Responses to Adjuvant Chemotherapy in Ovarian Carcinoma: Predicting Platinum Resistance,"", PLoS One, Feb. 10, 2012, pp. 1-9.

* cited by examiner

Rationale

Single-cell sequencing

Bulk sequencing

- Directly measure heterogeneity
- Detection of sub-populations
- Infer genetic information
- Cell Cycle
- Genotype-phenotype correlation
- Pharmakodynamic measure

SEQUENCE LISTING

```
<160> NUMBER OF SEQ ID NOS: 8

<210> SEQ ID NO 1
<211> LENGTH: 770
<212> TYPE: PRT
<213> ORGANISM: Homo sapiens

<400> SEQUENCE: 1

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45
```

```
Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Gln Gln Gly Gly Gln
        115                 120                 125

Ala Asn His Pro Thr Ala Ala Val Val Thr Glu Lys Gln Gln Met Leu
130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
```

```
                465                 470                 475                 480
Asn Met Leu Thr Asn Asn Pro Lys Asn Val Asn Phe Phe Thr Lys Pro
                    485                 490                 495
Pro Ile Gly Thr Trp Asp Gln Val Ala Glu Val Leu Ser Trp Gln Phe
                500                 505                 510
Ser Ser Thr Thr Lys Arg Gly Leu Ser Ile Glu Gln Leu Thr Thr Leu
            515                 520                 525
Ala Glu Lys Leu Leu Gly Pro Gly Val Asn Tyr Ser Gly Cys Gln Ile
        530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
                580                 585                 590
Arg Glu Arg Ala Ile Leu Ser Thr Lys Pro Pro Gly Thr Phe Leu Leu
                595                 600                 605
Arg Phe Ser Glu Ser Ser Lys Glu Gly Gly Val Thr Phe Thr Trp Val
            610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                    645                 650                 655
Tyr Lys Ile Met Asp Ala Thr Asn Ile Leu Val Ser Pro Leu Val Tyr
                660                 665                 670
Leu Tyr Pro Asp Ile Pro Lys Glu Glu Ala Phe Gly Lys Tyr Cys Arg
            675                 680                 685
Pro Glu Ser Gln Glu His Pro Glu Ala Asp Pro Gly Ser Ala Ala Pro
        690                 695                 700
Tyr Leu Lys Thr Lys Phe Ile Cys Val Thr Pro Thr Thr Cys Ser Asn
705                 710                 715                 720
Thr Ile Asp Leu Pro Met Ser Pro Arg Thr Leu Asp Ser Leu Met Gln
                    725                 730                 735
Phe Gly Asn Asn Gly Glu Gly Ala Glu Pro Ser Ala Gly Gly Gln Phe
                740                 745                 750
Glu Ser Leu Thr Phe Asp Met Glu Leu Thr Ser Glu Cys Ala Thr Ser
            755                 760                 765
Pro Met
    770

<210> SEQ ID NO 2
<211> LENGTH: 4978
<212> TYPE: DNA
<213> ORGANISM: Homo sapiens

<400> SEQUENCE: 2
ggtttccgga gctgcggcgg cgcagactgg gaggggagc cggggttcc gacgtcgcag      60 ccgagggaac aagccccaac cggatcctgg acaggcaccc cggcttggcg ctgtctctcc    120
ccctcggctc ggagaggccc ttcggcctga gggagcctcg ccgcccgtcc ccggcacacg    180
cgcagccccg gcctctcggc tctgccggaa gaaacagttg ggaccctga ttttagcagg    240 atggcccaat ggaatcagct acagcagctt gacacacggt acctggagca gctccatcag    300
ctctacagtg acagcttccc aatggagctg cggcagtttc tggccccttg gattgagagt    360
```

| | |
|---|---|
| caagattggg catatgcggc cagcaaagaa tcacatgcca ctttggtgtt tcataatctc | 420 |
| ctgggagaga ttgaccagca gtatagccgc ttcctgcaag agtcgaatgt tctctatcag | 480 |
| cacaatctac gaagaatcaa gcagtttctt cagagcaggt atcttgagaa gccaatggag | 540 |
| attgcccgga ttgtggcccg gtgcctgtgg gaagaatcac gccttctaca gactgcagcc | 600 |
| actgcggccc agcaaggggg ccaggccaac caccccacag cagccgtggt gacggagaag | 660 |
| cagcagatgc tggagcagca ccttcaggat gtccggaaga gagtgcagga tctagaacag | 720 |
| aaaatgaaag tggtagagaa tctccaggat gactttgatt tcaactataa aaccctcaag | 780 |
| agtcaaggag acatgcaaga tctgaatgga acaaccagt cagtgaccag gcagaagatg | 840 |
| cagcagctgg aacagatgct cactgcgctg gaccagatgc ggagaagcat cgtgagtgag | 900 |
| ctggcggggc ttttgtcagc gatggagtac gtgcagaaaa ctctcacgga cgaggagctg | 960 |
| gctgactgga agaggcggca acagattgcc tgcattggag gcccgcccaa catctgccta | 1020 |
| gatcggctag aaaactggat aacgtcatta gcagaatctc aacttcagac ccgtcaacaa | 1080 |
| attaagaaac tggaggagtt gcagcaaaaa gtttcctaca aaggggaccc cattgtacag | 1140 |
| caccggccga tgctggagga gagaatcgtg gagctgttta gaaacttaat gaaaagtgcc | 1200 |
| tttgtggtgg agcggcagcc ctgcatgccc atgcatcctg accggcccct cgtcatcaag | 1260 |
| accggcgtcc agttcactac taaagtcagg ttgctggtca aattccctga gttgaattat | 1320 |
| cagcttaaaa ttaaagtgtg cattgacaaa gactctgggg acgttgcagc tctcagagga | 1380 |
| tcccggaaat ttaacattct gggcacaaac acaaaagtga tgaacatgga agaatccaac | 1440 |
| aacggcagcc tctctgcaga attcaaacac ttgaccctga gggagcagag atgtgggaat | 1500 |
| gggggccgag ccaattgtga tgcttccctg attgtgactg aggagctgca cctgatcacc | 1560 |
| tttgagaccg aggtgtatca ccaaggcctc aagattgacc tagagaccca ctccttgcca | 1620 |
| gttgtggtga tctccaacat ctgtcagatg ccaaatgcct gggcgtccat cctgtggtac | 1680 |
| aacatgctga ccaacaatcc caagaatgta aactttttta ccaagccccc aattggaacc | 1740 |
| tgggatcaag tggccgaggt cctgagctgg cagttctcct ccaccaccaa gcgaggactg | 1800 |
| agcatcgagc agctgactac actggcagag aaactcttgg gacctggtgt gaattattca | 1860 |
| gggtgtcaga tcacatgggc taaattttgc aaagaaaaca tggctggcaa gggcttctcc | 1920 |
| ttctgggtct ggctggacaa tatcattgac cttgtgaaaa agtacatcct ggcccttttgg | 1980 |
| aacgaagggt acatcatggg ctttatcagt aaggagcggg agcgggccat cttgagcact | 2040 |
| aagcctccag gcaccttcct gctaagattc agtgaaagca gcaaagaagg aggcgtcact | 2100 |
| ttcacttggg tggagaagga catcagcggt aagacccaga tccagtccgt ggaaccatac | 2160 |
| acaaagcagc agctgaacaa catgtcattt gctgaaatca tcatgggcta taagatcatg | 2220 |
| gatgctacca atatcctggt gtctccactg gtctatctct atcctgacat tcccaaggag | 2280 |
| gaggcattcg gaaagtattg tcggccgaga gccaggagc atcctgaagc tgacccaggt | 2340 |
| agcgctgccc catacctgaa gaccaagttt atctgtgtga caccaacgac ctgcagcaat | 2400 |
| accattgacc tgccgatgtc cccccgcact ttagattcat tgatgcagtt tggaaataat | 2460 |
| ggtgaaggtg ctgaaccctc agcaggaggg cagtttgagt ccctcacctt tgacatggag | 2520 |
| ttgacctcgg agtgcgctac ctcccccatg tgaggagctg agaacggaag ctgcagaaag | 2580 |
| atacgactga ggcgcctacc tgcattctgc caccccctcac acagccaaac cccagatcat | 2640 |
| ctgaaactac taactttgtg gttccagatt tttttttaatc tcctacttct gctatctttg | 2700 |
| agcaatctgg gcacttttaa aaatagagaa atgagtgaat gtgggtgatc tgcttttatc | 2760 |

```
taaatgcaaa taaggatgtg ttctctgaga cccatgatca ggggatgtgg cgggggggtgg    2820
ctagagggag aaaaaggaaa tgtcttgtgt tgttttgttc ccctgccctc ctttctcagc    2880
agctttttgt tattgttgtt gttgttctta gacaagtgcc tcctggtgcc tgcggcatcc    2940
ttctgcctgt ttctgtaagc aaatgccaca ggccacctat agctacatac tcctggcatt    3000
gcactttta  accttgctga catccaaata gaagatagga ctatctaagc cctaggtttc    3060
tttttaaatt aagaaataat aacaattaaa gggcaaaaaa cactgtatca gcatagcctt    3120
tctgtattta agaaacttaa gcagccgggc atggtggctc acgcctgtaa tcccagcact    3180
ttgggaggcc gaggcggatc ataaggtcag gagatcaaga ccatcctggc taacacggtg    3240
aaacccgtc  tctactaaaa gtacaaaaaa ttagctgggt gtggtggtgg gcgcctgtag    3300
tcccagctac tcgggaggct gaggcaggag aatcgcttga acctgagagg cggaggttgc    3360
agtgagccaa aattgcacca ctgcacactg cactccatcc tgggcgacag tctgagactc    3420
tgtctcaaaa aaaaaaaaaa aaaaagaaa  cttcagttaa cagcctcctt ggtgctttaa    3480
gcattcagct tccttcaggc tggtaattta tataatccct gaaacgggct tcaggtcaaa    3540
cccttaagac atctgaagct gcaacctggc ctttggtgtt gaaataggaa ggtttaagga    3600
gaatctaagc attttagact ttttttttata aatagactta ttttcctttg taatgtattg    3660
gccttttagt gagtaaggct gggcagaggg tgcttacaac cttgactccc tttctccctg    3720
gacttgatct gctgtttcag aggctaggtt gtttctgtgg gtgccttatc agggctggga    3780
tacttctgat tctggcttcc ttcctgcccc accctcccga ccccagtccc cctgatcctg    3840
ctagaggcat gtctccttgc gtgtctaaag gtccctcatc ctgtttgttt taggaatcct    3900
ggtctcagga cctcatggaa gaagaggggg agagagttac aggttggaca tgatgcacac    3960
tatgggccc  cagcgacgtg tctggttgag ctcagggaat atggttctta gccagtttct    4020
tggtgatatc cagtggcact tgtaatgcg  tcttcattca gttcatgcag ggcaaaggct    4080
tactgataaa cttgagtctg ccctcgtatg agggtgtata cctggcctcc ctctgaggct    4140
ggtgactcct ccctgctggg gccccacagg tgaggcagaa cagctagagg gcctccccgc    4200
ctgcccgcct tggctggcta gctcgcctct cctgtgcgta tgggaacacc tagcacgtgc    4260
tggatgggct gcctctgact cagaggcatg gccggatttg gcaactcaaa accaccttgc    4320
ctcagctgat cagagtttct gtggaattct gtttgttaaa tcaaattagc tggtctctga    4380
attaagggggg agacgacctt ctctaagatg aacagggttc gccccagtcc tcctgcctgg    4440
agacagttga tgtgtcatgc agagctctta cttctccagc aacactcttc agtacataat    4500
aagcttaact gataaacaga atatttagaa aggtgagact tgggcttacc attgggttta    4560
aatcataggg acctagggcg agggttcagg gcttctctgg agcagatatt gtcaagttca    4620
tggccttagg tagcatgtat ctggtcttaa ctctgattgt agcaaaagtt ctgagaggag    4680
ctgagccctg ttgtgggccca ttaaagaaca gggtcctcag gccctgcccg cttcctgtcc    4740
actgcccct  cccatcccc  agcccagccg agggaatccc gtgggttgct tacctaccta    4800
taaggtggtt tataagctgc tgtcctggcc actgcattca aattccaatg tgtacttcat    4860
agtgtaaaaa tttatattat tgtgaggttt tttgtctttt tttttttttt tttttttgg    4920
tatattgctg tatctacttt aacttccaga aataaacgtt atataggaac cgtaaaaa     4978
```

<210> SEQ ID NO 3
<211> LENGTH: 356
<212> TYPE: PRT

<213> ORGANISM: Homo sapiens

<400> SEQUENCE: 3

```
Met Gly Ser Gly Gly Gly Ser Glu Gly Ala Pro Lys Lys Lys Arg
1               5                   10                  15

Lys Val Gly Ser Ser Leu Gly Thr Gly Asn Arg Cys Val Lys Gly Asp
            20                  25                  30

Ser Leu Ser Leu Lys Gly Glu Thr Val Asn Asp Cys His Ala Glu Ile
            35                  40                  45

Ile Ser Arg Arg Gly Phe Ile Arg Phe Leu Tyr Ser Glu Leu Met Lys
50                      55                  60

Tyr Asn Ser Gln Thr Ala Lys Asp Ser Ile Phe Glu Pro Ala Lys Gly
65                  70                  75                  80

Gly Glu Lys Leu Gln Ile Lys Lys Thr Val Ser Phe His Leu Tyr Ile
                85                  90                  95

Ser Thr Ala Pro Cys Gly Asp Gly Ala Leu Phe Asp Lys Ser Cys Ser
                100                 105                 110

Asp Arg Ala Met Glu Ser Thr Glu Ser Arg His Tyr Pro Val Phe Glu
            115                 120                 125

Asn Pro Lys Gln Gly Lys Leu Arg Thr Lys Val Glu Asn Gly Gln Gly
            130                 135                 140

Thr Ile Pro Val Glu Ser Ser Asp Ile Val Pro Thr Trp Asp Gly Ile
145                 150                 155                 160

Arg Leu Gly Glu Arg Leu Arg Thr Met Ser Cys Ser Asp Lys Ile Leu
                165                 170                 175

Arg Trp Asn Val Leu Gly Leu Gln Gly Ala Leu Leu Thr His Phe Leu
            180                 185                 190

Gln Pro Ile Tyr Leu Lys Ser Val Thr Leu Gly Tyr Leu Phe Ser Gln
            195                 200                 205

Gly His Leu Thr Arg Ala Ile Cys Cys Arg Val Thr Arg Asp Gly Ser
        210                 215                 220

Ala Phe Glu Asp Gly Leu Arg His Pro Phe Ile Val Asn His Pro Lys
225                 230                 235                 240

Val Gly Arg Val Ser Ile Tyr Asp Ser Lys Arg Gln Ser Gly Lys Thr
                245                 250                 255

Lys Glu Thr Ser Val Asn Trp Cys Leu Ala Asp Gly Tyr Asp Leu Glu
            260                 265                 270

Ile Leu Asp Gly Thr Arg Gly Thr Val Asp Gly Pro Arg Asn Glu Leu
            275                 280                 285

Ser Arg Val Ser Lys Lys Asn Ile Phe Leu Leu Phe Lys Lys Leu Cys
290                 295                 300

Ser Phe Arg Tyr Arg Arg Asp Leu Leu Arg Leu Ser Tyr Gly Glu Ala
305                 310                 315                 320

Lys Lys Ala Ala Arg Asp Tyr Glu Thr Ala Lys Asn Tyr Phe Lys Lys
                325                 330                 335

Gly Leu Lys Asp Met Gly Tyr Gly Asn Trp Ile Ser Lys Pro Gln Glu
            340                 345                 350

Glu Lys Asn Phe
        355
```

<210> SEQ ID NO 4
<211> LENGTH: 288
<212> TYPE: PRT
<213> ORGANISM: Artificial Sequence
<220> FEATURE:

<223> OTHER INFORMATION: Synthetic

<400> SEQUENCE: 4

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
50                  55                  60

Ser Ala Asp Ser Phe Ser Asp Leu Leu Arg Gln Phe Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285
```

<210> SEQ ID NO 5
<211> LENGTH: 183
<212> TYPE: PRT
<213> ORGANISM: Artificial Sequence
<220> FEATURE:
<223> OTHER INFORMATION: Synthetic

<400> SEQUENCE: 5

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
50                  55                  60
```

```
His Arg Val Ala Asp His Ala Gln Val Val Arg Val Leu Gly Phe Phe
 65                  70                  75                  80

Gln Cys His Ser His Pro Ala Gln Ala Phe Asp Asp Ala Met Thr Gln
             85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 6
<211> LENGTH: 107
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
  1               5                  10                  15

Gly Thr Ile Ile His Val Lys Gly Lys His Leu Cys Pro Ser Pro Leu
             20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
 50                  55                  60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 7
<211> LENGTH: 9
<212> TYPE: PRT
<213> ORGANISM: Homo sapiens

<400> SEQUENCE: 7

Ile Glu Val Met Tyr Pro Pro Pro Tyr
  1               5

<210> SEQ ID NO 8
<211> LENGTH: 107
<212> TYPE: PRT
<213> ORGANISM: Homo sapiens

<400> SEQUENCE: 8

Ile Glu Val Met Tyr Pro Pro Pro Tyr Leu Asp Asn Glu Lys Ser Asn
  1               5                  10                  15

Gly Thr Ile Ile His Val Lys Gly Lys His Leu Cys Pro Ser Pro Leu
             20                  25                  30
```

```
Phe Pro Gly Pro Ser Lys Pro Phe Trp Val Leu Val Val Gly Gly
        35              40              45

Val Leu Ala Cys Tyr Ser Leu Leu Val Thr Val Ala Phe Ile Ile Phe
    50              55              60

Trp Val Arg Ser Lys Arg Ser Arg Leu Leu His Ser Asp Tyr Met Asn
65              70              75              80

Met Thr Pro Arg Arg Pro Gly Pro Thr Arg Lys His Tyr Gln Pro Tyr
            85              90              95

Ala Pro Pro Arg Asp Phe Ala Ala Tyr Arg Ser
            100             105
```

- ...

COMPOSITIONS AND METHODS FOR TREATING OVARIAN TUMORS

CROSS-REFERENCE TO RELATED APPLICATIONS

This application is a U.S. National Stage of International Application No. PCT/US2018/025491, filed Mar. 30, 2018, and claims the benefit of U.S. Provisional Application Nos. 62/479,885, filed Mar. 31, 2017 and 62/565,470, filed Sep. 29, 2017. The entire contents of the above-identified applications are hereby fully incorporated herein by reference.

REFERENCE TO AN ELECTRONIC SEQUENCE LISTING

The contents of the electronic sequence listing (BROD-2321WP_ST25.txt"; Size is 22,347 bytes and it was created on Mar. 31, 2018) is herein incorporated by reference in its entirety.

TECHNICAL FIELD

The subject matter disclosed herein is generally directed to compositions and methods for treating ovarian tumors by targeting JAK/STAT signaling.

BACKGROUND

There are over 22,000 new cases of ovarian cancer diagnosed in the United States every year. Up to 75% of women with advanced ovarian cancer relapse within two years after successfully responding to initial chemotherapy treatment. Accordingly, one of the main obstacles to overcome in improving outcomes among ovarian cancer patients is resistance to chemotherapy. As such, prior to the invention described herein, there was a pressing need to develop methods to identify genetic profiles of treatment-resistant ovarian cancer to identify therapeutic targets for recurrent disease.

SUMMARY

Described herein is the use of signal transducer and activator of transcription 3 (STAT3) inhibitors, as a single drug or as an adjuvant, to treat ovarian tumors. Specifically, provided are methods for treating or preventing a gynecological tumor in a subject, e.g., a human subject, comprising identifying a subject with a gynecological tumor, administering to the subject a therapeutically effective amount of a STAT3 activity inhibitor, thereby treating or preventing the gynecological tumor in the subject. An exemplary gynecological tumor comprises an ovarian tumor.

In one aspect, the subject is identified as having elevated STAT3 activity, or the subject is identified as in need of inhibiting STAT3 activity. For example, the STAT3 activity is selected from the group consisting of STAT3 phosphorylation, STAT3 dimerization, STAT3 binding to a polynucleotide comprising a STAT3 binding site, STAT3 binding to genomic DNA, activation of a STAT3 responsive gene and STAT3 nuclear translocation.

In one case, the STAT3 activity inhibitor is administered intraperitoneally. Suitable STAT3 inhibitors include pyrimethamine, atovaquone, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-b enzodioxo1-5-yl)-1,6-dimethyl-pyrimido[5,4-e]-1,2,4-triazine-5,7(-1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof.

In one aspect, the STAT3 activity inhibitor comprises JSI-124 (cucurbitacin I). For example, the JSI-124 (cucurbitacin I) is administered at a dose of about 0.01 μM to about 10.0 μM, e.g., 0.01 μM, 0.02 μM, 0.03 μM, 0.04 μM, 0.06 μM, 0.07 μM, 0.08 μM, 0.09 μM, 0.1 μM, 0.2 μM, 0.3 μM, 0.4 μM, 0.5 μM, 0.6 μM, 0.7 μM, 0.8 μM, 0.9 μM, 1.0 μM, 2.0 μM, 3.0 μM, 4.0 μM, 5.0 μM, 6.0 μM, 7.0 μM, 8.0 μM, 9.0 μM, or 10.0 μM. Alternatively, the JSI-124 is administered at a dose of 1 mg/kg/day.

For example, the STAT3 inhibitor is administered three times per day, once per day, three times per week, once per week, three times per month, once per month, once every three months, or once every six months. In some cases, the STAT3 inhibitor is administered for one month, three months, six months, one year, or more.

The subject's gynecological cancer is inhibited, e.g., by at least 5%, at least 10%, at least 20%, at least 30%, at least 40%, at least 50%, at least 60%, at least 70%, at least 80%, at least 90%, or 100%. In one example, tumor cell growth in the subject's abdomen is inhibited. For example, the methods described herein prevent ovarian tumor cell spheroid formation, disrupt and disintegrate spheroids, prevent attachment of spheroids to other organs, and prevent the development of metastases. In another example, subcutaneous tumor cell growth in the subject is inhibited. In yet another aspect, ovarian tumor cell metastases in the subject are inhibited. In some cases, malignant abdominal fluid (ascites) is inhibited, e.g., tumor spheroids in malignant abdominal fluid are inhibited.

The methods described herein prevent tumor recurrence. For example, tumor recurrence is inhibited for one week, one month, three months, six months, one year, three years, five years, or more.

In some cases, the methods further comprise administering a therapeutically effective amount of a chemotherapeutic agent. For example, the chemotherapeutic agent comprises a platinum-based chemotherapeutic agent or a taxane-based chemotherapeutic agent. Suitable platinum-based chemotherapeutic agents include cisplatin and carboplatin. For example, the chemotherapeutic agent is administered prior to, simultaneously with, or subsequent to administration of the STAT3 activity inhibitor.

In one aspect, the subject has received prior treatment for the gynecological tumor. In some cases, the gynecological tumor is resistant to platinum-based chemotherapy. For example, the subject has minimal residual disease (MRD) following platinum-based chemotherapy.

Methods for treating a gynecological tumor in a subject are carried out by identifying a subject with a gynecological tumor, administering to the subject a therapeutically effective amount of a chemotherapeutic agent to inhibit the gynecological tumor, and administering to the subject a therapeutically effective amount of a STAT3 activity inhibitor to prevent recurrence of the gynecological tumor and development of metastases, thereby treating or preventing the gynecological tumor in the subject. For example, the STAT3 activity inhibitor is administered at least one month after administration of the chemotherapeutic agent, e.g., at least 2 months, at least 3 months, at least 4 months, at least 5 months, at least 6 months, at least 9 months, or at least 1 year after administration of the chemotherapeutic agent.

Also provided are methods for treating a platinum-resistant gynecological tumor in a subject comprising identifying a subject with a platinum-resistant gynecological tumor, administering to the subject a therapeutically effective amount of a STAT3 activity inhibitor, and administering to the subject a therapeutically effective amount of a chemotherapeutic agent, thereby treating the platinum-resistant gynecological tumor in the subject. In some cases, the STAT3 activity inhibitor is administered prior to administration of the chemotherapeutic agent, e.g., 1 month, 2 months, 3 months, 4 months, 5 months, 6 months, 9 months, 1 year, or more prior to administration of the chemotherapeutic agent.

Also, described herein are methods of determining and/or monitoring a gene expression profile in a subject with ovarian cancer. Specifically, these methods are carried out by identifying a subject with ovarian cancer; providing a tumor sample from the subject; disaggregating the tumor sample into a population of single cells; performing single-cell RNA sequencing (scRNA-seq) on the sample, thereby determining a gene expression profile in a subject with ovarian cancer. In some cases, the disaggregation further comprises removing red blood cells from the tissue sample. In one aspect, the ovarian cancer is resistant to therapy. Optionally, the gene expression profile is determined prior to administration of therapy to the subject. Alternatively, the gene expression profile is determined at the time of minimal residual disease (MRD) or relapse. For example, the tissue sample is dissected into pieces<10 mm$^3$, e.g., less than 9 mm$^3$, less than 8 mm$^3$, less than 7 mm$^3$, less than 6 mm$^3$, less than 5 mm$^3$, less than 4 mm$^3$, less than 3 mm$^3$, less than 2 mm$^3$, or less than 1 mm$^3$. Preferably, the tissue sample is dissected into pieces<1 mm$^3$, e.g., less than 0.1 mm 3 or less than 0.01 mm$^3$. Optionally, the tissue sample is dissected with a scalpel.

Also provided are methods of treating or preventing ovarian cancer comprising administering 1 mg/kg/day of JSI-124 (cucurbitacin I) to the subject. For example, JSI-124 is administered at a dose of 10 uM. In some cases, monitoring of the ovarian cancer is performed prior to and after administration of a therapeutic agent to determine a resistance profile of the therapeutic agent.

In another aspect, the present invention provides for a method of treating platinum-based chemotherapy resistant ovarian cancer comprising treating a subject in need thereof with an inhibitor of the JAK/STAT pathway. The subject may have minimal residue disease (MRD) or the ovarian cancer is a relapse. The inhibitor may be JSI-124. The inhibitor may comprise a therapeutic antibody, bi-specific antibody, antibody fragment, antibody-like protein scaffold, aptamer, genetic modifying agent or small molecule.

In another aspect, the present invention provides for a method of treating ovarian cancer comprising treating a subject in need thereof with an agent capable of inhibiting or modulating expression or activity of one or more genes or polypeptides selected from the group consisting of JAK1, STAT3, STAT2, STAT1, OSMR, STAT6, RELA, ERBB2, GF1R, ERBB3, IL10RB, FGFR1, CXCR4, CXCL2, CXCL10, CXCL11, HLA-DRA, HLA-DRB1, HLA-DQB1, IDO1, MYBL2 and FGF13 or a gene selected from FIG. 4D,E. In certain embodiments, the agent comprises a therapeutic antibody, bi-specific antibody, antibody fragment, antibody-like protein scaffold, aptamer, genetic modifying agent or small molecule. The gene or polypeptide may be a surface or secreted gene. The agent may target a secreted protein or a receptor for the secreted protein. The agent may target a ligand for a surface receptor. The method may further comprise administering platinum-based chemotherapy.

In certain embodiments, the ovarian cancer is chemotherapy resistant. In certain embodiments, the ovarian cancer is platinum-based chemotherapy resistant.

In another aspect, the present invention provides for a method of predicting a response to platinum-based chemotherapy in a subject suffering from ovarian cancer comprising detecting in a tumor sample obtained from the subject expression of one or more genes selected from the group consisting of JAK1, STAT3, STAT2, STAT1, OSMR, STAT6, RELA, ERBB2, GF1R, ERBB3, IL10RB, FGFR1, CXCR4, CXCL2, CXCL10, CXCL11, HLA-DRA, HLA-DRB1, HLA-DQB1, IDO1, MYBL2 and FGF13 or a gene selected from FIG. 4D,E. In certain embodiments, high expression in the tumor sample indicates a weak response to platinum-based chemotherapy and low expression indicates a strong response to platinum-based chemotherapy.

In another aspect, the present invention provides for a method of detecting ovarian cancer stem cells in a tumor sample obtained from a subject suffering from ovarian cancer comprising detecting expression of a gene signature comprising one or more genes selected from the group consisting of ALDH1A3, CD24, CD133, FN1, ACTA2, MYL9, GAS6, IGFBP5, FGFR1, CALD1, CFI, CRB2, PRDX4, IGFBP6 and RPS20.

In another aspect, the present invention provides for a method of treating ovarian cancer comprising treating a subject in need thereof with an agent capable of targeting ovarian cancer stem cells characterized by a gene signature comprising one or more genes selected from the group consisting of ALDH1A3, CD24, CD133, FN1, ACTA2, MYL9, GAS6, IGFBP5, FGFR1, CALD1, CFI, CRB2, PRDX4, IGFBP6 and RPS20.

The agent may target a surface protein on the ovarian cancer stem cells. The agent may comprise a therapeutic antibody, bispecific antibody, antibody fragment, antibody-like protein scaffold, aptamer or CAR T cell. The method may further comprise administering platinum-based chemotherapy.

The method of treatment according to any embodiment herein may be administered as an adjuvant or neoadjuvant therapy.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A is a t-distributed stochastic neighbor embedding (tSNE) analysis dot plot of number of single cells from number of samples profiled by the droplet-based scRNA-seq. Cells are colored by their assignment to 20 clusters whose indices are indicated in the center of each cluster. FIG. 1B is a bar plot showing the number of cells from each sample which are assigned to each cluster. FIG. 1C is a heatmap of average expression in each of the clusters. Included are the top 30 cluster-specific genes of each of the clusters, which are presented in the order defined by hierarchical clustering. Subsets of genes which include cell type-specific markers are highlighted (lines to the right of the heatmap). FIG. 1D is a heatmap of average expression in each of the clusters that correspond to ovarian cancer cells (left), macrophages (middle) and fibroblasts (right). In each panel, included are the top 30 cluster-specific genes of each cluster (compared to other clusters in that panel), which are presented in the order defined by hierarchical clustering.

FIG. 2A is a tSNE dot plot of the number of single cells from the number of samples profiled by the plate-based single cell RNA-seq. Cells are colored by their assignment to the clusters whose indices are indicated in the center of each cluster. FIG. 2B is a bar plot showing the number of cells from each sample which are assigned to each cluster. FIG. 2C is a heatmap of average expression in each of the clusters. Included are the top 30 cluster-specific genes of each of the clusters, which are presented in the order defined by hierarchical clustering. Subsets of genes which include cell type-specific markers are highlighted (lines to the right of the heatmap). FIG. 2C also shows a heatmap with columns representing the average expression of cells from clusters in the tSNE after specific interrogation using defined signatures from TCGA (differentiated, proliferative, etc. FIG. 2D is a graph of inference of chromosomal copy-number variations (CNVs) from gene expression. For each cluster, the relative copy number in each chromosomal position was estimated by the average expression of the 100 genes surrounding that position. Left: this approach predicted widespread amplifications and deletions in each of the cancer cell clusters (clusters 1-6 corresponding to the cancer cells from each of the patient samples, respectively) compared to the non-cancer cells which were used as a reference. Right: when randomly ordering the genes across the genome and repeating the analysis, the signal for CNV is eliminated, supporting the predicted CNVs. FIG. 2E is a graph of subtype scores for cancer cell clusters and a gene expression profile (heatmap). Each of the clusters was scored for the four Cancer Genome Atlas (TCGA) subtypes, based on the average expression of subtype-specific genes.

FIG. 3A is a heatmap showing relative expression of module-specific genes across GL-13 cells from patients. FIG. 3B is a heatmap showing relative expression of module-specific genes across GL-15 cells from patients (modules in individual tumors). FIG. 3C is a heatmap showing relative expression of module-specific genes across GL-17 cells from patients. In each case, expression modules were defined by non-negative matrix factorization (NMF) and are shown from top to bottom by the top 30 module-specific genes for each module, and with annotation of selected genes; cells were ordered by hierarchical clustering. FIG. 3D is a heatmap showing the overlap in the top genes between each pair of modules (across all patients) as a measure of module similarity. Modules were ordered by hierarchical clustering, and their patient-of-origin is indicated at the top. FIG. 3E is a graph of shared programs of selected cell cycle (top) and immune-related (bottom) genes among the top genes of modules (across all patients), with modules ordered as in FIG. 3D. Genes among the 30 of a given module are indicated by black squares while those only among the top 50 genes are indicated by gray squares. FIG. 3F is a graph of expression of highly-abundant transcripts in single-cells indicate disproportionally high expression of key nodes of the JAK/STAT pathway, including JAK1, STAT1, STAT3, and others.

FIG. 4A is a plot of tumor burden of PDX model DF20. PDX model DF20 response to carboplatin was assessed. Triangles indicate vehicle mice, squares indicate relapsed mice, and asterisks indicates MRD animals. MRD and relapsed tumors were treated with three cycles of carboplatin and harvested for single-cell RNA-sequencing at the last indicated time point in this graph. FIG. 4B is a heatmap showing the similarities and clustering of average expression profiles for each of the samples corresponding to three PDX models, with samples collected before treatments (vehicle), MRD and full relapse for each of the models. FIG. 4C is a plot of expression of highly-abundant transcripts in single-cells indicate disproportionally high expression of key nodes of the JAK/STAT pathway, including STAT2 and STAT3, and others. FIG. 4D is a heatmap showing differential expression between each MRD sample and the vehicle samples of the respective PDX model, for genes which are upregulated in at least two MRD samples; genes were ordered by hierarchical clustering. FIG. 4E is a heatmap showing differential expression between each relapse sample and the vehicle samples of the respective PDX model, for genes which are upregulated in at least two relapse samples; genes were ordered by hierarchical clustering.

FIG. 5A is a heatmap showing relative expression of module-specific genes across DF20 cancer cells from PDX models. FIG. 5B is a heatmap showing relative expression of module-specific genes across DF68 cancer cells from PDX models. FIG. 5C is a heatmap showing relative expression of module-specific genes across DF101 cancer cells from PDX models. In each case, expression modules were defined by NMF and are shown from top to bottom by the top 30 module-specific genes for each module, and with annotation of selected genes; cells were ordered by hierarchical clustering. FIG. 5D is a heatmap showing the overlap in the top genes between each pair of modules from PDX samples (columns) and patient ascites samples (rows) as a measure of module similarity. Patient ascites modules were ordered as in FIG. 3D, and PDX modules were ordered by hierarchical clustering, with their model-of-origin indicated at the top. FIG. 5E selected cell cycle (top), immune-related (middle) and other genes (bottom) among the top genes of each PDX module, with modules ordered as in FIG. 5D. All genes included were shared between the corresponding PDX module and the highest-overlapping patient ascites modules. Genes which are among the top 30 of a given module are indicated by black squares while those only among the top 50 genes are indicated by gray squares.

FIG. 6A a histogram (FIG. 11B), showing drug screening with 14 compounds (at 1 µM) inhibiting the JAK/STAT pathway in OVACR4. Relative viability compared to DMSO control measured by CTG. JSI-124 shows significant activity compared to other JAK/STAT inhibitors. The same library was screened in 2D-cultures of OVACR4 (FIG. 11A), and 2D-cultures of OVACR8 (FIG. 11C) and 3D-cultures of OVACR8 (FIG. 11D). FIG. 6B is a series of plots showing drug sensitivity testing using the GILA assay in platinum-resistant ex vivo spheroid cultures of patients DF3291 and DF3266, The X-axis indicates the log µM concentration of drugs indicated in the legend, Y-axis indicates the percentage of luminescence signal as indicator for viability relatively to DMSO treated cells. In both patients, half maximal effective concentration ($EC_{50}$) were ~100 nM and ~10 nM, respectively, while other drugs routinely used for the treatment of (platinum-resistant) ovarian cancer had $EC_{50}$>10 µM. FIG. 6C is a series of images of microscopic analysis of spheroids with different drug treatments to highlight the morphologic changes during therapy with drugs listed. Inhibition of JAK/STAT pathway disrupts ex vivo spheroid cultures. FIG. 6D is a histogram depicting impact of JSI-124 compared to carboplatin and control on the formation of spheroids in five established ovarian cancer cell lines. The X-axis indicates established ovarian cancer cell line ID. Y-axis indicates the relative number of formed spheroids when treated with either JSI-124 or carboplatin compared to untreated parental controls. Error bars indicate the standard deviation from the mean number of spheroids. At 100 nM, JSI-124 completely abolished the ability of cell lines to establish spheroids. JAK/STAT inhibition prevents spheroid formation. FIG. 6E is a histogram depicting quantitative assessment of mesothelial clearance by patient-derived spheroids (NCAT8) with prior treatment with JSI-124 (for either 30 minutes or 120 minutes) vs. DMSO. The Y-axis indicates the clearance ability (using arbitrary units). 20 spheroids clusters were analyzed for each iteration. Data is shown as mean (horizontal bar), interquartile range (box), and minimum and maximum (whiskers). Statistical analysis was performed using 1-way analysis of variance (ANOVA) and post hoc Tukey-Kramer **$P<0.05$. FIG. 6F is a histogram depicting results following treatment with JSI-124 for 30 minutes of the two ovarian cancer cell lines OVCAR8 and TYKNU. FIG. 6G is a histogram showing the inhibition of the JAK/STAT pathway.

FIG. 7A is a diagram of a study design to investigate the effect of JSI-124 on PDX model DF20. Each of these were performed following intraperitoneal (IP) or subcutaneous (SC) injection of cancer cells followed by IP therapy with JSI-124 vs. vehicle. Each group includes 5 mice. The inverted triangle indicates the time=0 of cancer cell injection. FIG. 7B is a plot of a comparison of mice injected with DF20 intraperitoneally (IP) and treated with JSI-124 (IP) or vehicle. Mice were injected IP with tumor cells and one week later started treatment for a total 14 days. Each group includes 5 mice. Y-axis indicates log of bioluminescence imaging (BLI) signal (log total flux in p/s). Values are given as mean of log BLI signal, error bars indicate standard deviation from the mean. *$p<0.0001$ (two-sided t test comparing mean±STDEV at Day 15 of treatment). FIG. 7C is a plot of a comparison of mice injected with DF20 IP and treated with JSI-124 or vehicle. Mice were injected IP with tumor cells and malignant ascites was allowed to form for 21 days followed by treatment with JSI-124 (IP) or vehicle for a total 14 days. Each group includes 5 mice. Y-axis indicates log BLI signal (log total flux in p/s). Values are given as mean of log BLI signal, error bars indicate standard deviation from the mean. *$p<0.0001$ (two-sided t test comparing mean±STDEV at Day 15 of treatment). FIG. 7D is a plot of a comparison of mice injected with DF20 subcutaneously (SC) and treated with JSI-124 (IP) or vehicle. Mice were injected SC with tumor cells and one week later started treatment for a total 14 days. Each group includes 5 mice. Y-axis indicates log BLI signal (log total flux in p/s). Values are given as mean of log BLI signal, error bars indicate standard deviation from the mean. *$p<0.0001$ (two-sided t test comparing mean±STDEV at Day 15 of treatment). FIG. 7E is a plot of a comparison of mice injected with DF20 SC and treated with JSI-124 or vehicle. Mice were injected SC with tumor cells and tumors were allowed to form for 21 days followed by treatment treatment with JSI-124 (IP) or vehicle for a total 14 days. Each group includes 5 mice. Y-axis indicates log BLI signal (log total flux in p/s). Values are given as mean of log BLI signal, error bars indicate standard deviation from the mean. *$p<0.0001$ (two-sided t test comparing mean±STDEV at Day 15 of treatment).

FIG. 8A is a heatmap showing relative expression of module-specific genes across GL10_cancer cells from patients. FIG. 8B is a heatmap showing relative expression of module-specific genes across GL17 cancer cells from patients. In each case, expression modules were defined by NMF and are shown from top to bottom by the top 30 module-specific genes for each module, and with annotation of selected genes; cells were ordered by hierarchical clustering. FIG. 8C is a heatmap showing the relative expression of three putative stemness markers in cells from GL10, sorted by their average expression of the three markers. FIG. 8D is a heatmap showing the relative expression of the top genes positively (top) or negatively (bottom) correlated with the stemness scores shown in FIG. 8C in cells from GL10, as in FIG. 8C. FIG. 8E is the same heatmap as FIG. 8D for GL13 cells, demonstrating that the expression program associated with stemness markers in GL10 is not conserved in other patient ascites samples, with GL13 as an example. Shown are the genes positively (top) or negatively (bottom) correlated with the stemness scores of GL10 cells, for GL13 cells sorted by their average expression of the putative stemness markers.

FIG. 11A is a histogram of OVCAR4 cells in high attachment dishes (2D culture). FIG. 11B is a histogram of OVCAR4 cells in ultra low attachment dishes (3D culture). FIG. 11C is a histogram of OVCAR8 cells in high attachment dishes. FIG. 11D is a histogram of OVCAR8 cells in ultra low attachment dishes. FIG. 11E is a histogram of STAT3-dependent luciferase activity in Heya8 cells that were pre-treated with JSI-124 vs. DMSO for 1 hour and followed by stimulation of oncostatin M (OSM). This histogram shows JSI-124 leads to a significant reduction in STAT-dependent expression, indicating its on-target activity.

FIG. 12A is a series of plots of ovarian cancer cell lines were grown for 4 days in ultra-low attachment conditions eliciting formation of spheroids, followed by treatment with JSI-124, carboplatin, paclitaxel, cisplatin or olaparib at indicated doses (log µM concentrations as indicated on X-axis). Viability was measured as relative luminescence signal compared to DMSO control. FIG. 12B is a series of plots depicting ovarian cancer cell liens were grown for 4 days in regular plastic culture surfaces and treated with drugs as indicated in FIG. 12A.

FIG. 16A is a graph depicting RDG Q value (TCGA, Nature 2012). FIG. 16B is a heatmap depicting tumor and gene expression groups. FIG. 16C is histograms of the number of mutations and number of non-silent coding mutations in tumors and ascites (Patch, Nature 2015).

FIG. 19A is a heatmap assaying unique cell states of GL10 cells. In this effort, isolated single-cells from malignant effusions from patient with highly resistant ovarian cancer. One hundred and six single-cell transcriptomes from a patient were analyzed and CNVs were inferred. For ovarian cancer, a large burden of CNVs was found. While most of the CNVs were shared among cells, subpopulations were identified that carried unique aberrations, such as chromosome 12 deletion. FIG. 19B is an additional heatmap depicting isolated single-cells from malignant effusions.

FIG. 20A is a line graph depicting probing platinum-resistance in ovarian PDX-models (Liu Jet al, CcR 2016). FIG. 20B is a series of photographs of mice showing results of probing cancer treatment resistance in PDX-models.

Figure 1A:
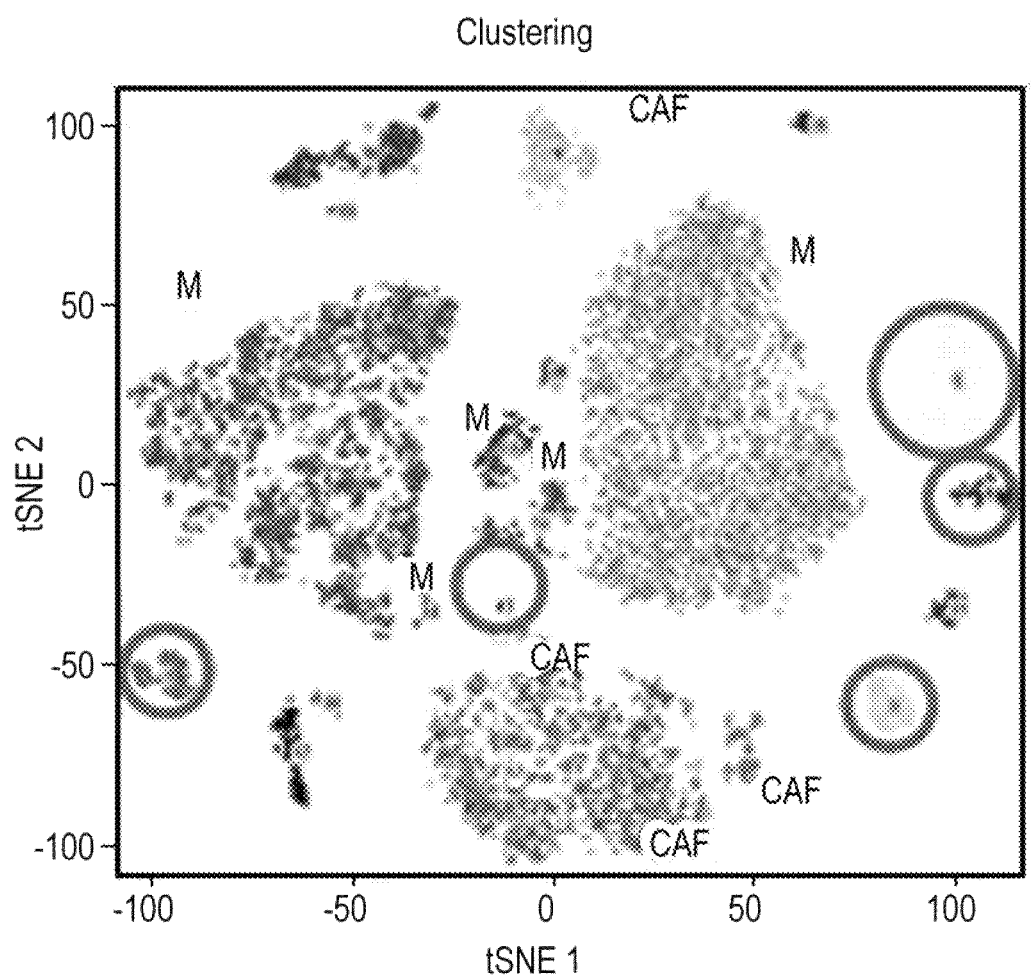
FIG. 1A-FIG. 1D are a series of dot plots, bar charts, and gene expression profiles (heatmaps) depicting inter-tumor heterogeneity and charting the ovarian cancer ascites by droplet-based single cell RNA-seq. Heterogeneity of malignant and non-malignant cells was assessed.
Figure 1B:
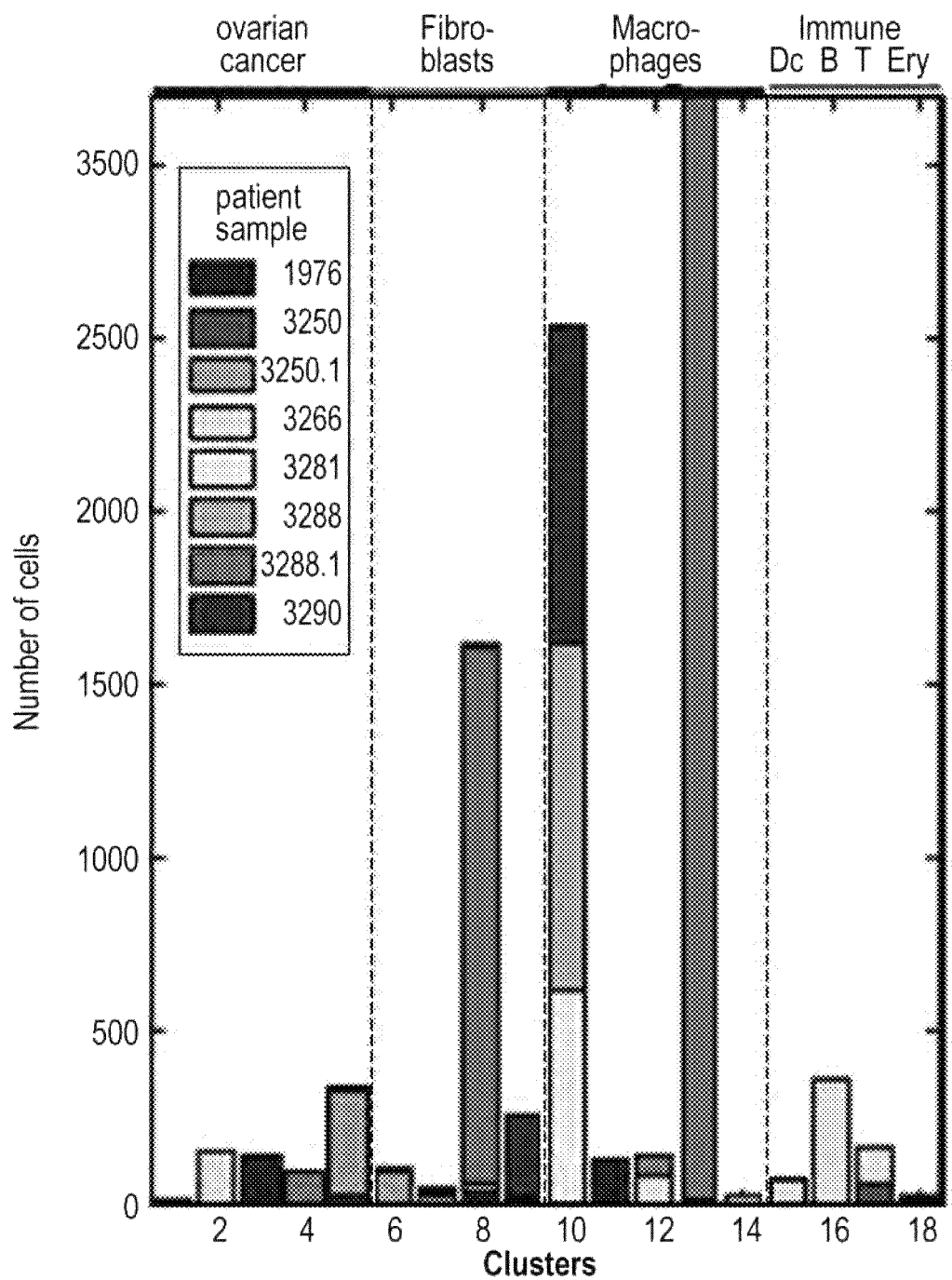

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); "Oligonucleotide Synthesis" (Gait, 1984); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed. Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "antineoplastic agent" is used herein to refer to agents that have the functional property of inhibiting a development or progression of a neoplasm in a human. Inhibition of metastasis is frequently a property of antineoplastic agents.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

By "binding to" a molecule is meant having a physicochemical affinity for that molecule. By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, P-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence, or amount of the agent (e.g., a nucleic acid molecule, for example deoxyribonucleic acid (DNA) or ribonucleic acid (RNA)) to be detected.

By "detectable label" is meant a composition that when linked (e.g., joined —directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties amplifies a detectable signal. For example, useful labels include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthalaldehyde and fluorescamine. The molecule can also be detectably labeled using fluorescence emitting metals such as 152 Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid. The types of detection methods in which probes can be used include Western blots, Southern blots, dot or slot blots, and Northern blots.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the term "disaggregate" is meant to separate something into its component parts. Thus, "disaggregating" a tissue sample into a population of single cells means to separate a tissue sample into the single cells which together form the tissue sample.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., cancer, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "expression profile" is used broadly to include a genomic expression profile. Profiles may be generated by any convenient means for determining a level of a nucleic acid sequence, e.g., quantitative hybridization of microRNA, labeled microRNA, amplified microRNA, complementary/synthetic DNA (cDNA), etc., quantitative polymerase chain reaction (PCR), and ELISA for quantitation, and allow the analysis of differential gene expression between two samples. A subject or patient tumor sample is assayed. Samples are collected by any convenient method, as known in the art. According to some embodiments, the term "expression profile" means measuring the relative abundance of the nucleic acid sequences in the measured samples.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by high-performance liquid chromatography (HPLC) analysis.

The term "immobilized" or "attached" refers to a probe (e.g., nucleic acid or protein) and a solid support in which the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule to the support and the non-covalent binding of a biotinylated probe to the molecule. Immobilization may also involve a combination of covalent and non-covalent interactions.

By "marker" is meant any protein or polynucleotide having an alteration in expression level or activity that is associated with a disease or disorder, e.g., cancer.

By "modulate" is meant alter (increase or decrease). Such alterations are detected by standard art-known methods such as those described herein.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

As used herein, "obtaining" as in "obtaining an agent" includes synthesizing, purchasing, or otherwise acquiring the agent.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

The terms "preventing" and "prevention" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

The term "prognosis," "staging," and "determination of aggressiveness" are defined herein as the prediction of the degree of severity of the neoplasia, e.g., cancer, and of its evolution as well as the prospect of recovery as anticipated from usual course of the disease.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

The term "sample" as used herein refers to a biological sample obtained for the purpose of evaluation in vitro. Exemplary tissue samples for the methods described herein include tissue samples from tumors or the surrounding microenvironment (i.e., the stroma). With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Other samples include whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer (e.g., cancer) is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, $200$%, or more.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Any compositions or methods provided herein can be combined with one or more of any of the other compositions and methods provided herein.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, published patent documents, and patent applications cited herein are hereby incorporated by reference to the same extent as though each individual publication, published patent document, or patent application was specifically and individually indicated as being incorporated by reference. Genbank and NCBI submissions indicated by accession number cited herein are incorporated herein by reference.

Overview

Embodiments disclosed herein describe the examination of drug sensitivity of patient-derived cells isolated from ovarian cancer patients' ascites. The initial observation was that cells obtained from platinum-resistant patient demonstrate resistance to platinum-based chemotherapy also at the ex-vivo experimental system. Next, a single-cell RNA-sequences from patient and animal models hinted that an immune gene signature/STAT3 pathway are involved in the recurrent of the disease. A STAT3 inhibitor (JSI-124, Sigma-Aldrich®) was added to the study and experimental results indicated that the cells are very sensitive to the drug, as compared to the clinically-available chemotherapy. Additionally, a functional assay supported experimental results by showing that the use of JSI-124 inhibits invasiveness of spheres that originated from patient-derived cells. Inhibition of invasiveness was surprisingly fast and suggested a potential rationale for the fast effect of JSI-124. Described herein is the treatment of animals by intra-peritoneum injection of JSI-124 and to test the effect on recurrent of tumor growth. The results presented herein indicate that JSI-124 reduces malignancy, and in particular invasiveness, of tumor cells.

As described herein, targeting STAT3 helps to inhibit invasiveness of tumor cells (short term) and, together with chemotherapy, to prevent the spread of the disease (long term).

Prior to the invention described herein, injection of a STAT3 inhibitor into the peritoneum was not examined for reduction of malignancy of gynecological tumors. Additionally, prior to the invention described herein, many treatments failed to prevent tumor recurrent, as usually happens in ovarian cancer. Presented herein is an approach that directly regulates the spread of the disease using a drug that demonstrates significant efficiency as compared to the clinical drugs.

Tumors, including ovarian tumors, are complex ecosystems defined by spatiotemporal interactions between heterogeneous cell types, including malignant, immune, and stromal cells (D. Hanahan and R. A. Weinberg, 2011 Cell, 144: 646-674). Each tumor's cellular composition, as well as the interplay between these components, exerts critical roles in cancer development (C. E. Meacham and S. J. Morrison, 2013 Nature, 501: 328-337). However, prior to the invention described herein, the specific components, their salient biological functions, and the means by which they collectively define tumor behavior were incompletely characterized in ovarian cancer.

Tumor cellular diversity poses both challenges and opportunities for cancer therapy. This is most clearly demonstrated by the remarkable, but varied, clinical efficacy achieved in malignant melanoma with targeted therapies and immunotherapies. First, immune checkpoint inhibitors produce substantial clinical responses in some patients with metastatic melanomas (Hodi et al., 2010 N. Engl. J. Med., 363: 711-723; Brahmer et al., 2010 J. Clin. Oncol. Off. J. Am. Soc. Clin. Oncol., 28: 3167-3175; Brahmer et al., 2012 N. Engl. J. Med., 366: 2455-2465; Topalian et al., 2012 N. Engl. J. Med., 366: 2443-2454; and Hamid et al., 2013 N. Engl. J. Med., 369: 134-144); however, prior to the invention described herein, the genomic and molecular determinants of response to these agents was poorly understood. Collectively, these factors highlight the need for a deeper understanding of melanoma composition and its impact on clinical course.

The next wave of therapeutic advances in cancer are accelerated by emerging technologies that systematically assess the malignant, microenvironmental, and immunologic states most likely to inform treatment response and resistance. An ideal approach would assess salient cellular heterogeneity by quantifying variation in oncogenic signaling pathways, drug-resistant tumor cell subsets, and the spectrum of immune, stromal and other cell states that inform immunotherapy response. Toward this end, emerging single-cell genomic approaches enable detailed evaluation of genetic and transcriptional features present in 100s-1000s of individual cells per tumor (Shalek et al., 2013 Nature, 498: 236-240; Patel et al., 2014 Science, 344: 1396-1401; Macosko et al., 2015 Cell, 161: 1202-1214). In principle, this approach provides a comprehensive means to identify all major cellular components simultaneously and to determine their individual genomic and molecular states (Patel et al., 2014 Science, 344: 1396-1401), and ascertain which of these features predict or explain clinical responses to anti-cancer agents.

Resistance to therapy is a major impediment to improving outcomes in ovarian cancer. Due to the lack of effective screening approaches, most patients are diagnosed at an advanced stage (Matulonis et al., 2016 Nat. Rev. Dis. Primer, 2:16061). Advanced-stage ovarian cancer is treated with surgery and chemotherapy with platinum and taxane agents. While 10-15% of patients exhibit intrinsic resistance to initial chemotherapy, most patients typically have a good response and achieve disease remission following chemotherapy; however, residual disease is frequently present and leads to relapse in 80% of patients within months to several years (Matulonis et al., 2016 Nat. Rev. Dis. Primer, 2:16061; Siegel et al., 2016 Cancer J. Clin., 66:7-30). Despite recent advances in treatment, recurrent ovarian cancer is incurable and portends a poor prognosis with median survival of approximately one year (Siegel et al., 2016 Cancer J. Clin., 66:7-30). Development of resistance to platinum-based chemotherapy and associated development malignant abdominal fluid (ascites) are the major impediment to improving outcomes for patients with advanced ovarian cancer. To date, the mechanisms of drug resistance remain poorly understood. Lack of discovery of recurrent genomic features of drug resistance is likely, in part, due to the significant heterogeneity of ovarian cancer, which biases analyses using bulk tissue specimens or ascites fluid. Inter-tumor and particularly intra-tumor heterogeneity of ovarian cancer cells and associated non-cancer cells is an important factor driving treatment resistance, but remains poorly understood. New insights into molecular mechanisms of intrinsic and acquired treatment resistance are required to identify critical resistance pathways that reveal new therapeutic targets for recurrent disease. Understanding inter-tumor and intra-tumor heterogeneity of ovarian cancer cells is a component of identifying critical resistance pathways and new therapeutic targets for recurrent disease.

Inter-tumor and particularly intra-tumor heterogeneity of ovarian cancer cells and associated non-cancer cells is an important factor driving treatment resistance, but remains poorly understood. High-grade serous ovarian cancer (HGSC), the most common and aggressive histological subtype, has been studied extensively by large-scale genomic studies such as TCGA, which revealed TP53 mutations, defects in homologous recombination and extensive copy-number aberrations in most tumors (T.C.G.A.R. Network, 2011 Nature, 474:609-615). In addition to these consistent features, HGSC tumors were also classified into transcriptional subtypes by TCGA and other studies of DNA repair and chemotherapy resistance (Patch et al., 2015 Nature, 521:489-494). However, these signatures have poor reproducibility (Lloyd et al., 2015 BMC Cancer, 15:117) and are based on bulk profiles, which represent the average of cancer and non-cancer cells mixed within any tumor sample, and do not recapitulate the inherent tumor heterogeneity.

As described herein, single-cell RNA-sequencing offers a powerful approach for characterizing tumors by resolving the expression profiles of diverse cancer cells, infiltrating immune cells, and stromal cells, each of which contribute to treatment resistance through distinct mechanisms (Tirosh et al., 2016 Science, 352:189-196). In particular, bidirectional signaling between tumor cells and immune cells has been suggested as a mode of ovarian cancer cell survival via immune evasion, and a deeper understanding of these pathways is critical to successful application of immunotherapies (Gaillard et al., 2016 Gynecology Oncol. Res. Pract., 3:11). In addition to profiling of tumors with abundant cancer cells, the high sensitivity of scRNA-seq enables analysis of samples with low purity, such as ascites, or with very low cell numbers, such as minimal residual disease (MRD), which are not detectable using current methods. As described in detail below, scRNA-seq was applied to both of these clinically important scenarios.

Ascites cancer cells, free-floating single cells and spheroids within a patient's peritoneal fluid, represent a critical feature of ovarian cancer biology and clinical evolution. Ascites is present in one-third of patients at the time of diagnosis, and develops in the majority of patients with chemotherapy resistant disease (Ahmed et al., 2013 Front. Oncol., 3). Rather than a homogenous suspension of single cells, ascites fluid is comprised of a multicellular collection of cancer cells, immune cells, and fibroblasts which contribute to disease progression (Kipps et al., 2013 Nat. Rev. Cancer, 13:273-282). Ovarian cancer spheroids within ascites are multicellular aggregates that can promote intraperitoneal metastasis and that are associated with chemotherapy resistance (Shield et al., 2009 Gynecology Oncol., 113:143-148).

Presented herein is the first comprehensive analysis of patient ovarian cancer ascites using scRNA-seq. Extensive heterogeneity of cancer cells and cancer-associated macrophages and fibroblasts is demonstrated. As described in detail below, to examine the changes in tumor cells occurring during therapy and following relapse, scRNA-seq was performed on cells isolated from patient-derived xenograft (PDX) ovarian cancer models pre-treatment, at minimal residual disease (MRD) and during progressive disease. As described herein, a common theme of cancer-intrinsic inflammatory signaling, including the activation of the JAK/STAT pathway, was identified. As described in the examples blow, inhibition of the JAK2/STAT3 pathway is toxic to platinum-resistant, patient-derived ex vivo models, inhibits the formation, coherence and invasive behavior of spheroids in vitro, and shows anti-tumor activity in PDX models, suggesting that JAK/STAT inhibition represents a clinically feasible therapeutic avenue for platinum-resistant ovarian cancer.

Ovarian Cancer

Ovarian cancer is a cancer that forms in or on an ovary. Symptoms may include bloating, pelvic pain, abdominal swelling, and loss of appetite, among others. Common areas to which the cancer may spread include the lining of the abdomen, lymph nodes, lungs, and liver. The most common type of ovarian cancer is ovarian carcinoma (>95% of all cases). There are five main subtypes of ovarian carcinoma, of which high-grade serous carcinoma is the most common. These tumors are believed to start in the cells covering the ovaries, though some may form at the Fallopian tubes. Less common types of ovarian cancer include germ cell tumors and sex cord stromal tumors. A diagnosis of ovarian cancer is confirmed through a biopsy of tissue, usually removed during surgery.

If caught and treated in an early stage, ovarian cancer is often curable. Treatment usually includes some combination of surgery, radiation therapy, and chemotherapy. Outcomes depend on the extent of the disease, the subtype of cancer present, and other medical conditions. The overall five-year survival rate in the United States is 45%.

If ovarian cancer recurs, it is considered partially platinum-sensitive or platinum-resistant, based on the time since the last recurrence treated with platins: partially platinum-sensitive cancers recurred 6-12 months after last treatment, and platinum-resistant cancers have an interval of less than 6 months.

For platinum-sensitive tumors, platins are utilized for second-line chemotherapy, often in combination with other cytotoxic agents. Regimens include carboplatin combined with pegylated liposomal doxorubicin, gemcitabine, or paclitaxel. If the tumor is determined to be platinum-resistant, vincristine, dactinomycin, and cyclophosphamide (VAC) or some combination of paclitaxel, gemcitabine, and oxaliplatin can be used as a second-line therapy.

Prior to the invention described herein, there were no high-efficacy chemotherapy options for platinum-resistant tumors.

STAT Molecules

Members of the signal transducer and activator of transcription (STAT) protein family are intracellular transcription factors that mediate many aspects of cellular immunity, proliferation, apoptosis and differentiation. There are seven mammalian STAT family members that have been identified: STAT1, STAT2, STAT3, STAT4, STAT5 (STAT5A and STAT5B), and STAT6. STAT proteins are primarily activated by membrane receptor-associated Janus kinases (JAK). Dysregulation of the JAK/STAT pathway is frequently observed in primary tumors and leads to increased angiogenesis, enhanced survival of tumors, and immunosuppression. STAT proteins are involved in the development and function of the immune system and play a role in maintaining immune tolerance and tumor surveillance.

STAT proteins are present in the cytoplasm of cells under basal conditions. When activated by tyrosine phosphorylation, STAT proteins form dimers and translocate to the nucleus where they can bind specific nine base pair sequences in the regulatory regions of target genes, thereby activating transcription. A variety of tyrosine kinases, including polypeptide growth factor receptors, Src family members, and other kinases can catalyze this phosphorylation. While tyrosine phosphorylation is essential for their activation, STAT proteins can also be phosphorylated on unique serine residues. Although this is not sufficient to induce dimerization and DNA binding, STAT serine phosphorylation modulates the transcriptional response mediated by a tyrosine-phosphorylated STAT dimer, and may mediate distinct biological effects (Zhang X, et al. Science 1995; 267:1990-1994; Wen Z, et al. Cell 1995; 82:241-250; Kumar A, et al. Science 1997; 278:1630-1632). STAT proteins have been found to function inappropriately in many human malignancies (Alvarez J V, et al., Cancer Res 2005; 65(12): 5054-62; Frank D A, et al. Cancer Treat. Res. 2003; 115: 267-291; Bowman T, et al. Oncogene 2000; 19(21):2474-88).

STAT3 and STAT Modulators

STAT3 is activated in several human tumors, including common epithelial cancers such as cancer of the breast, prostate, lung, pancreas, and ovary; hematologic cancers such as multiple myeloma, and acute leukemias; and diverse tumors such as melanoma and gliomas (Frank D A, et al. Cancer Treat. Res. 2003; 115:267-291). Many of the target genes of STAT3 code for proteins involved in cell survival, cell cycle progression, differentiation inhibition, invasion, and angiogenesis, all of the essential processes necessary for tumor formation and maintenance (Alvarez J V, et al., Cancer Res 2005; 65(12):5054-62). Inhibition of STAT3 function in cancer cells associated with enhanced STAT3 activity leads to a loss of proliferation and survival of the cancer cells (Frank D A. Curr. Cancer Therapy Reviews 2006; 2:57-65). Despite the central role that STAT3 plays in these diverse processes in tumor cell biology, loss of STAT3 function in normal adult cells has few if any serious consequences, and may in fact decrease the ability of a cell to become transformed.

An exemplary human STAT3 amino acid sequence is set forth below (SEQ ID NO: 1; GenBank Accession No: AAH14482, Version 1, incorporated herein by reference):

```
  1 maqwnqlqql dtryleqlhq lysdsfpmel rqflapwies qdwayaaske shativfhnl
 61 lgeidqqysr flqesnvlyq hnlrrikqfl qsrylekpme iarivarclw eesrllqtaa
121 taaqqgggan hptaavvtek qqmleghlqd vrkrvqdleq kmkvvenlqd dfdfnyktlk
181 sqgdmqdlng nnqsvtrqkm qqlegmltal dqmrrsivse lagllsamey vqktltdeel
241 adwkrrqqia ciggppnicl drlenwitsl aesqlqtrqq ikkleelqqk vsykgdpivq
301 hrpmleeriv elfrnlmksa fvverqpcmp mhpdrplvik tgvqfttkvr llvkfpelny
361 qlkikvcidk dsgdvaalrg srkfnilgtn tkvmnmeesn ngslsaefkh ltlreqrcgn
421 ggrancdasl ivteelhlit fetevyhqgl kidlethslp vvvisnicqm pnawasilwy
481 nmltnnpknv nfftkppigt wdqvaevlsw qfssttkrgl sieqlttlae kllgpgvnys
541 gcgitwakfc kenmagkgfs fwvwldniid lvkkyilalw negyimgfis kererailst
601 kppgtfllrf sesskeggvt ftwvekdisg ktgigsvepy tkqqlnnmsf aeiimgykim
661 datnilvspl vylypdipke eafgkycrpe sqehpeadpg saapylktkf icvtpttcsn
721 tidlpmsprt ldslmqfgnn gegaepsagg qfesltfdme ltsecatspm
```

An exemplary human STAT3 nucleic acid sequence is set forth below (SEQ ID NO: 2; GenBank Accession No: NM_139276, Version 2, incorporated herein by reference):

```
  1 ggtttccgga gctgcggcgg cgcagactgg gaggggagc cggggttcc gacgtcgcag
 61 ccgagggaac aagccccaac cggatcctga acaggcaccc cggcttggcg ctgtctctcc
121 ccctcggctc ggagaggccc ttcggcctga gggagcctcg ccgcccgtcc ccggcacacg
181 cgcagccccg gcctctcggc ctctgccgga gaaacagttg ggacccctga ttttagcagg
241 atggcccaat ggaatcagct acagcagctt gacacacggt acctggagca gctccatcag
301 ctctacagtg acagcttccc aatggagctg cggcagtttc tggcccttg gattgagagt
361 caagattggg catatgcggc cagcaaagaa tcacatgcca ctttggtgtt tcataatctc
421 ctgggagaga ttgaccagca gtatagccgc ttcctgcaag agtcgaatgt tctctatcag
481 cacaatctac gaagaatcaa gcagtttctt cagagcaggt atcttgagaa gccaatggag
541 attgcccgga ttgtggcccg gtgcctgtgg gaagaatcac gccttctaca gactgcagcc
601 actgcggccc agcaagggg ccaggccaac cacccacag cagccgtggt gacggagaag
661 cagcagatgc tggagcagca ccttcaggat gtccggaaga gagtgcagga tctagaacag
```

-continued

```
 721 aaaatgaaag tggtagagaa tctccaggat gactttgatt tcaactataa aaccctcaag
 781 agtcaaggag acatgcaaga tctgaatgga acaaccagt cagtgaccag gcagaagatg
 841 cagcagctgg aacagatgct cactgcgctg gaccagatgc ggagaagcat cgtgagtgag
 901 ctggcgggc ttttgtcagc gatggagtac gtgcagaaaa ctctcacgga cgaggagctg
 961 gctgactgga gaggcggca acagattgcc tgcattggag gcccgcccaa catctgccta
1021 gatcggctag aaaactggat aacgtcatta gcagaatctc aacttcagac ccgtcaacaa
1081 attaagaaac tggaggagtt gcagcaaaaa gtttcctaca aaggggaccc cattgtacag
1141 caccggccga tgctgaggga gagaatcgtg gagctgttta gaaacttaat gaaaagtgcc
1201 tttgtggtgg agcggcagcc ctgcatgccc atgcatcctg accggcccct cgtcatcaag
1261 accggcgtcc agttcactac taaagtcagg ttgctggtca aattccctga gttgaattat
1321 cagcttaaaa ttaaagtgtg cattgacaaa gactctgggg acgttgcagc tctcaggga
1381 tcccggaaat ttaacattct gggcacaaac acaaaagtga tgaacatgga agaatccaac
1441 aacggcagcc tctctgcaga attcaaacac ttgaccctga gggagcagag atgtgggaat
1501 gggggccgag ccaattgtga tgcttccctg attgtgactg aggagctgca cctgatcacc
1561 tttgagaccg aggtgtatca ccaaggcctc aagattgacc tagagaccca ctccttgcca
1621 gttgtggtga tctccaacat ctgtcagatg ccaaatgcct gggcgtccat cctgtggtac
1681 aacatgctga ccaacaatcc caagaatgta actttttta ccaagccccc aattggaacc
1741 tgggatcaag tggccgaggt cctgagctgg cagttctcct ccaccaccaa gcgaggactg
1801 agcatcgagc agctgactac actggcagag aaactcttgg gacctggtgt gaattattca
1861 gggtgtcaga tcacatgggc taaattttgc aaagaaaaca tggctggcaa gggcttctcc
1921 ttctgggtct ggctggacaa tatcattgac cttgtgaaaa agtacatcct ggccctttgg
1981 aacgaagggt acatcatggg ctttatcagt aaggagcggg agcgggccat cttgagcact
2041 aagcctccag gcaccttcct gctaagattc agtgaaagca gcaaagaagg aggcgtcact
2101 ttcacttggg tggagaagga catcagcggt aagacccaga tccagtccgt ggaaccatac
2161 acaaagcagc agctgaacaa catgtcattt gctgaaatca tcatgggcta taagatcatg
2221 gatgctacca atatcctggt gtctccactg gtctatctct atcctgacat tcccaaggag
2281 gaggcattcg gaaagtattg tcggccagag agccaggagc atcctgaagc tgacccaggt
2341 agcgctgccc catacctgaa gaccaagttt atctgtgtga caccaacgac ctgcagcaat
2401 accattgacc tgccgatgtc ccccgcact ttagattcat tgatgcagtt tggaaataat
2461 ggtgaaggtg ctgaaccctc agcaggaggg cagtttgagt ccctcacctt tgacatggag
2521 ttgacctcgg agtgcgctac ctcccccatg tgaggagctg agaacggaag ctgcagaaag
2581 atacgactga ggcgcctacc tgcattctgc caccctcac acagccaaac cccagatcat
2641 ctgaaactac taactttgtg gttccagatt ttttttaatc tcctacttct gctatctttg
2701 agcaatctgg gcacttttaa aaatagagaa atgagtgaat gtgggtgatc tgcttttatc
2761 taaatgcaaa taaggatgtg ttctctgaga cccatgatca ggggatgtgg cgggggtgg
2821 ctagagggag aaaaaggaaa tgtcttgtgt tgttttgttc ccctgccctc ctttctcagc
2881 agcttttgt tattgttgtt gttgttctta gacaagtgcc tcctggtgcc tgcggcatcc
2941 ttctgcctgt ttctgtaagc aaatgccaca ggccacctat agctacatac tcctggcatt
3001 gcacttttta accttgctga catccaaata gaagatagga ctatctaagc cctaggtttc
3061 ttttaaatt aagaaataat aacaattaaa gggcaaaaaa cactgtatca gcatagcctt
3121 tctgtattta agaaacttaa gcagccgggc atggtggctc acgcctgtaa tcccagcact
```

```
-continued 3181 ttgggaggcc gaggcggatc ataaggtcag gagatcaaga ccatcctggc taacacggtg 3241 aaacccgtc tctactaaaa gtacaaaaaa ttagctgggt gtggtggtgg gcgcctgtag 3301 tcccagctac tcgggaggct gaggcaggag aatcgcttga acctgagagg cggaggttgc 3361 agtgagccaa aattgcacca ctgcacactg cactccatcc tgggcgacag tctgagactc 3421 tgtctcaaaa aaaaaaaaaa aaaaagaaa cttcagttaa cagcctcctt ggtgctttaa 3481 gcattcagct tccttcaggc tggtaattta tataatccct gaaacgggct tcaggtcaaa 3541 cccttaagac atctgaagct gcaacctggc ctttggtgtt gaaataggaa ggtttaagga 3601 gaatctaagc attttagact tttttttata aatagactta ttttcctttg taatgtattg 3661 gccttttagt gagtaaggct gggcagaggg tgcttacaac cttgactccc tttctccctg 3721 gacttgatct gctgtttcag aggctaggtt gtttctgtgg gtgccttatc agggctggga 3781 tacttctgat tctggcttcc ttcctgcccc accctcccga ccccagtccc cctgatcctg 3841 ctagaggcat gtctccttgc gtgtctaaag gtccctcatc ctgtttgttt taggaatcct 3901 ggtctcagga cctcatggaa gaagagggg agagagttac aggttggaca tgatgcacac 3961 tatggggccc cagcgacgtg tctggttgag ctcagggaat atggttctta gccagtttct 4021 tggtgatatc cagtggcact tgtaatggcg tcttcattca gttcatgcag ggcaaaggct 4081 tactgataaa cttgagtctg ccctcgtatg agggtgtata cctggcctcc ctctgaggct 4141 ggtgactcct ccctgctggg gccccacagg tgaggcagaa cagctagagg gcctcccgc 4201 ctgcccgcct tggctggcta gctcgcctct cctgtgcgta tgggaacacc tagcacgtgc 4261 tggatgggct gcctctgact cagaggcatg gccggatttg gcaactcaaa accaccttgc 4321 ctcagctgat cagagtttct gtggaattct gtttgttaaa tcaaattagc tggtctctga 4381 attaagggg agacgacctt ctctaagatg aacagggttc gccccagtcc tcctgcctgg 4441 agacagttga tgtgtcatgc agagctctta cttctccagc aacactcttc agtacataat 4501 aagcttaact gataaacaga atatttagaa aggtgagact tgggcttacc attgggttta 4561 aatcataggg acctagggcg agggttcagg gcttctctgg agcagatatt gtcaagttca 4621 tggccttagg tagcatgtat ctggtcttaa ctctgattgt agcaaaagtt ctgagaggag 4681 ctgagccctg ttgtggccca ttaaagaaca gggtcctcag gccctgcccg cttcctgtcc 4741 actgccccct ccccatcccc agcccagccg agggaatccc gtgggttgct tacctaccta 4801 taaggtggtt tataagctgc tgtcctggcc actgcattca aattccaatg tgtacttcat 4861 agtgtaaaaa tttatattat tgtgaggttt tttgtctttt tttttttttt tttttttgg 4921 tatattgctg tatctacttt aacttccaga aataaacgtt atataggaac cgtaaaaa
```

The following compounds are STAT3 inhibitors: pyrimethamine, atovaquone, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(-1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof. These compounds are commercially available through various sources.

Another exemplary STAT3 inhibitor includes JSI-124. Cucurbitacin I (JSI-124) is a selective inhibitor of the janus kinase 2/signal transducer and activator of transcription 3 (JAK2/STAT3) signaling pathway with anti-proliferative and anti-tumor properties. The structure of JSI-124 (cucurbitacin I) is set forth below (Blaskovich et al., 2003 Cancer Res., 63(6): 1270-1279; incorporated herein by reference).

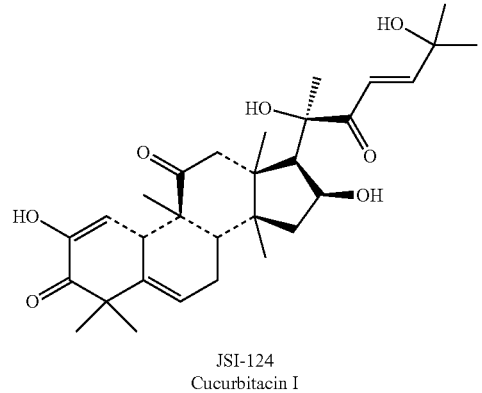 [SMILES: CC(C)(O)/C=C/C(=O)[C@](C)(O)[C@H]1[C@@H](O)C[C@@]2(C)[C@@H]3CC=C4[C@H](C=C(O)C(=O)C4(C)C)[C@]3(C)C(=O)C[C@]12C]

JSI-124
Cucurbitacin I

Single-cell RNA-sequencing of ovarian cancer in patients and PDX models guides strategies to overcome platinum-resistance.

Ovarian cancer is one of the leading causes of cancer-related deaths in women. Many women with OvCa experience relapse characterized by minimal residual disease following platinum-based chemotherapy, development of malignant abdominal fluid (ascites) with tumor spheroids, and extensive tumor heterogeneity: features not easily captured by current genomic profiling approaches. Resistance to platinum-based therapies and development of ascites constitutes the major life-limiting factor in women with ovarian cancer, and the underlying mechanisms remain unknown. To capture inherent heterogeneity and complexity of this ecosystem, single-cell RNA-sequencing was applied to ~17,500 cells, isolated from 11 OvCa patients, to map the cellular ascites ecosystem. Significant inter-individual variability in the cellular composition of ascites and the immunomodulatory functions of non-malignant cells, such as interleukin-6 producing cancer-associated fibroblasts (CAFs), was observed. Previously described "immunoreactive" and "mesenchymal" expression subtypes of OvCa are rather reflective of infiltration with immune cells and CAFs, respectively. A common feature of resistance, and also a driver of heterogeneity among malignant cells, is the cancer cell-autonomous expression of inflammatory pathways, including the JAK/STAT-pathway. To systematically interrogate this observation regarding platinum-resistance, PDX models were treated with carboplatin, and scRNA-seq was performed on pre-treatment, at the time of minimal residual disease (MRD) and on relapse. Expression of JAK/STAT pathway components were found to be expressed in MRD/relapse. Specifically, a common feature of MRD/relapsed cells was expression of interferon signaling and robust expression of JAK/STAT pathway components, indicating an important role of this pathway in platinum-resistance. JAK/STAT-inhibition (using JSI-124 at nano-molar concentrations) of platinum-resistant patient-derived ex vivo cultures led to inhibition of formation and invasion of spheroids through a mesothelial monolayer, and resulted in disintegration of spheroids. JAK/STAT-inhibition efficiently overcame platinum-resistance in patient-derived ex vivo cultures, inhibits metastatic potential and invasion, prevents formation of malignant ascites and leads to tumor regression in PDX models. The results presented herein indicate that IP-injected JSI-124 prevented formation and disrupted malignant ascites and sub-cutaneous tumors PDX models, indicating a potentially unique therapeutic niche for patients with advanced OvCa, in which IP chemo is frequently administered. In summary, the ecosystem of platinum-resistant ovarian cancer using scRNA-seq in patients and PDX models was mapped herein, and this ecosystem provides a therapeutic strategy for platinum-resistant disease.

Tumors are multicellular assemblies that encompass cells with distinct genotypic and phenotypic states. Thus, single-cell RNA-seq was applied to ovarian cancer samples. Overall, the analysis described in detail below unravels the cellular ecosystem of ovarian tumors and shows that single cell genomics offers new insights with implications for both targeted and immune therapies.

Described herein is the first comprehensive single-cell transcriptome analysis of malignant ascites in platinum-resistant ovarian cancer patients. Analysis reveals significant variability of the cellular composition and diversity among malignant and non-malignant cells in ascites. In line with prior single-cell studies in melanoma and glioma solid tumors, the patient of origin primarily determined heterogeneity among cancer cells. However, in contrast to these other cancers, a significant inter-individual heterogeneity of non-malignant cells was observed, both in their abundance and transcriptional cell states. This variability was particularly distinct within some non-malignant cell populations, such as macrophages and cancer-associated fibroblasts (CAFs). While CAFs expressed common genes, such as complement factors, populations were identified with discrete expression patterns of immunomodulatory genes, including inflammatory and immunosuppressive cytokines, such as IL-6 and IL-10, respectively. Elevated levels of IL-6 in the ascites have previously been associated with poor clinical outcomes; however, the source of IL-6 has been unknown. While several cell types express IL-6, including cancer cells, CAFs showed the strongest expression. Thus, non-malignant cells significantly contribute to shaping the ascites milieu.

Resistance to platinum-based chemotherapy invariably develops in patients with advanced ovarian cancer and is frequently associated with the development of malignant abdominal fluid (ascites). The mechanisms of drug resistance are poorly understood. A recent whole-genome sequencing study of 92 chemoresistant patients revealed frequent TP53 mutations, but no recurrent or potentially actionable oncogenic drivers (Patch et al., 2015 Nature, 521:489-494). This study emphasized the previously described vast genomic heterogeneity (T. C. G. A. R. Network, 2011 Nature, 474:609-615) and adaptability of ovarian cancer, underscoring the need for additional, high-resolution phenotypic analysis of platinum-resistance. In this study, the first comprehensive single-cell transcriptome analysis of malignant ascites in ovarian cancer patients was performed. The analysis reveals significant variability of the cellular composition and diversity among malignant and non-malignant cells in ascites. In line with prior single-cell studies in melanoma and glioma solid tumors, the patient of origin primarily determined heterogeneity among cancer cells (Tirosh et al., 2016 Science, 352:189-196). However, a significant inter-individual heterogeneity of non-malignant cells, both in their abundance and transcriptional cell states, was observed. This variability was particularly distinct within some non-malignant cell populations, such as macrophages and cancer-associated fibroblasts (CAFs). While CAFs expressed common genes, such as complement factors, populations with discrete expression patterns of immunomodulatory genes were identified, including inflammatory and immunosuppressive cytokines, such as IL-6 and IL-10, respectively. Elevated levels of IL-6 in the ascites have previously been associated with poor clinical outcomes (Lane et al., 2011 BMC Cancer, 11:210; Kolomeyevskaya et al., 2015 Gynecol. Oncol., 138:352-357); however, the proposed source of IL-6 has been variable across studies. While several cell types express TL-6, including cancer cells, CAFs showed the strongest expression. Together, these initial insights suggest that non-malignant cells significantly contribute to shaping the ascites milieu. Furthermore, the strength of the single cell profiling techniques detailed above was crucial in later identifying a sub-population of CAFs as a major source of IL6 within the ascites ecosystem.

Using previously described methods (Tirosh et al., 2016 Science, 352:189-196), large-scale CNVs were inferred. In line with prior studies (Patch et al., 2015 Nature, 521:489-494), CNVs were not identified in cancer cell sub-populations that account for resistant cells, but rather minimal changes in the CNV patterns in those patients where sequential samples were available. The study also investigated whether ovarian cancer subtypes described by TCGA (T.C.G.A.R. Network, 2011 Nature, 474:609-615) contribute to variability among patients and samples. Surprisingly, cancer cells from all patients strongly expressed the "differentiated" subtype program and cells from one patient also expressed the "proliferative" subtype. In contrast, the previously described "mesenchymal" and "immunoreactive" subtypes were not expressed within cancer cells, but were rather reflecting programs expressed by CAFs and macrophages, respectively. This result indicates that the mesenchymal and immunoreactive subtypes are infiltrated with CAFs or immune cells, respectively, and highlight how single-cell profiling resolves the multicellular composition of cancers and identifies the cell-type specific origin of transcriptional programs. A similar observation of "transcriptional mimicry" was made in colorectal cancer, where two studies identified transcriptomes of CAFs as source for a tumor sub-type (Isella et al., 2015 Nat. Genet., 47:312-319; Calon et al., 2015 Nat. Genet. 47: 320-329).

Previously identified were recurrent transcriptional cell states characterized by high expression of AXL and low expression of lineage-markers, such as MITF, conferring resistance to drug therapies in melanoma (Tirosh et al., 2016 Science, 352:189-196). In contrast, results did not find a consistent platinum-resistance program across patients with ovarian cancer. While several factors contribute to this observation, two key differences between ovarian cancer and other cancers are critical: (i) there are no highly recurrent targetable oncogenic drivers and (ii) effects of platinum-based therapies are pleiotropic and provoke variable cellular responses, and therefore variable mechanisms of resistance. However, a consistent observation across platinum-resistant patients was the cancer cell-autonomous expression of major inflammatory pathways, including the JAK/STAT pathway, interferon signaling and expression of several inflammatory cytokines, such as tumor necrosis factor (TNF) alpha. In particular, positive regulatory circuits involving the JAK/STAT pathway have been shown to promote malignant transformation and maintenance in breast cancer. Moreover, prior studies suggested that regulatory circuits involving the JAK/STAT pathway promotes malignant growth in ovarian cancer (Kulbe et al., 2012 Cancer Res., 72:66-75; Wen et al., 2014 Mol. Cancer Ther. 13:3037-3048; Saini et al., 2017 Oncogene, 36:168-181). To obtain a more controlled perspective on changes that occur over time following platinum chemotherapy, scRNA-seq was performed on cells from PDX models obtained a) before treatment, b) at the time of maximal response (or minimal residual disease, MRD) to carboplatin and c) at the time of relapse. Similar to the findings in ascites, residual or relapsed disease following platinum treatment was associated with distinct profiles across models derived from different patients, and a recurrent program within MRD/relapse across models was not found. However, consistent with findings in clinically platinum-resistant patients, MRD/relapse samples exhibited specific expression of several immune related genes, including key components of the JAK/STAT pathway, interferon signaling, the CXCL-12 receptor C-X-C chemokine receptor type 4 (CXCR4) and other inflammatory genes. Together with the extensive variability in immune-related programs and the widespread expression of interleukin (IL)-6, these results suggested that ovarian cancer cells depend on upstream regulators of inflammatory pathways and suggested a role of these pathways in platinum-resistance. The consistent expression in PDX models independent of prior platinum therapy indicates that these programs are relevant for both platinum-naïve and platinum-resistant disease.

Among other ligands, IL6 and C-X-C motif chemokine ligand 12 (CXCL-12) are strong upstream activators of JAK/STAT signaling, and were strongly expressed by non-malignant cells in platinum-resistant cells. The CXLC-12 receptor CXCR-4 was furthermore strongly upregulated in a portion of cancer cells from ascites and PDX-derived cells at MRD and relapse, indicating its role in platinum-resistance, and has been correlated with poor prognosis (Popple et al., 2012 Br. J. Cancer., 106:1306-1313). JAK/STAT pathway activation has been described in various solid tumors. Clinical assessment by immunohistochemistry (IHC) of STAT3 or phosphorylated STAT3 (pSTAT3) yielded variable prognostic or predictive roles across cancers, including breast (Sonnenblick et al., 2013 Breast Cancer Res. Treat., 138:407-413), prostate (Mirtti et al., 2013 Hum. Pathol., 44:310-319), lung (Y. H. Xu and S. Lu, 2014 Eur. J. Surg. Oncol. J. Eur. Soc. Surg. Oncol. Br. Assoc. Surg. Oncol., 40:311-317), head and neck (Pectasides et al., 2010 Clin. Cancer Res. Off. J. Am. Assoc. Cancer Res., 16:2427-2434), renal cell cancer (Horiguchi et al., 2002 J. Urol., 168:762-765), melanoma (Messina et al., 2008 Cancer control J. Moffitt Cancer Cent., 15:196-201) and glioblastoma (Birner et al., 2010 J. Neurooncol, 100:339-343). In myeloproliferative disorders, such as essential thrombocythemia (ET) and polycythemia vera (PV), treatment with JAK/STAT inhibitors (such as ruxolitinib) results in improved disease control (W. Vainchenker and S. N. Constantinescu, 2013 Oncogene, 32:26012613); interestingly, these agents are effective irrespective of the JAK2 mutation status, indicating that JAK/STAT inhibition is a feasible therapeutic avenue in other contexts with known JAK/STAT pathway activation. Previous work indicates increased IL-6-dependent activation of JAK/STAT signaling in cells isolated from patient-derived ascites (Saini et al., 2017 Oncogene, 36:168-18). Both autocrine and paracrine IL-6 signaling has been described in ovarian cancer, and the IL-6 receptor and soluble IL-6 receptor appear to modulate ovarian cancer growth. IL-6 is also implicated in a feedback circuit with paraneoplastic thrombocytosis that enhances ovarian cancer growth (Stone et al., 2012 N. Engl. J. Med., 366: 610-618). Targeting IL-6 with an anti-IL-6 antibody siltuximab (Coward et al., 2011 Clin. Cancer Res. Off. J. Am. Assoc. Cancer Res., 17:6083-6096) or an anti-IL6-R antibody tocilizumab (Dijkgraaf et al., 2015 Ann. Oncol. Off. J. Eur. Soc. Med. Oncol., 26: 2141-2149) has been explored in phase I trials in ovarian cancer.

Despite these intriguing results, the role of JAK/STAT signaling in platinum-resistance and its potential as a therapeutic target in ovarian cancer are incompletely understood. JSI-124 (also known as Cucurbitacin I) has previously been identified as a selective JAK/STAT inhibitor among a library of STAT3 inhibitors, and was safely administered to lung cancer and melanoma mouse models (Blaskovich et al., 2003 Cancer Res., 63: 1270-1279). Therefore, the effects of JSI-124 on several critical steps of ovarian cancer pathogenesis and drug resistance were examined. The results presented herein show that treatment of ovarian cancer cell lines and primary ovarian cancer ascites cells with JSI-124 can, i) prevent or reduce the formation of spheroids in a dose-dependent manner in vitro, ii) inhibit invasion of spheroids through a mesothelial monolayer ex vivo and in vitro, and iii) effectively and selectively kill cancer cells in formed spheroids derived from patients with platinum-resistance, that are resistant to other federal drug administration (FDA)-approved chemotherapies for ovarian cancer. In a BRCA-wild type (WT) PDX model, IP administered JSI-124 effectively i) prevents formation of malignant ascites, ii) kills established malignant ascites iii) prevents growth of SC injected tumors, and iv) leads to regression of established SC tumors. Together, these results indicate that IP-injected JSI-124 has local and systemic activity against ovarian cancer. IP therapy with cisplatin (in combination with IV paclitaxel) is a frequently used therapeutic modality in patients with stage III/IV ovarian cancer and improves progression-free and overall survival in some settings (Armstrong et al., 2006 N. Engl. J. Med., 354: 34-43). Therefore, IP drug administration is a unique therapeutic niche in the treatment of ovarian cancer. While toxicities require further investigation, the use of JSI-124 as adjuvant or neoadjuvant therapy and/or in the context of platinum resistance represents a feasible therapeutic strategy. Indeed, a recently launched phase I/II trial (NCT02713386) examines the safety and efficacy of JAK/STAT inhibition (using ruxolitinib) in combination with carboplatin and paclitaxel in the neo-adjuvant and adjuvant setting in patients with advanced gynecologic cancers, including ovarian cancer.

In summary, provided herein are a comprehensive map of single-cell transcriptomes of platinum-resistant ascites from patients with ovarian cancer and a sequential profiling of PDX models following platinum treatment. These data comprise a significant data resource to investigate cellular heterogeneity and platinum resistance in ovarian cancer. The results highlight the importance of cancer cell-autonomous expression of various inflammatory pathways. Results from these analyses guided subsequent identification of activation of the JAK/STAT pathway as a recurrent feature of ovarian cancer cells and associated non-malignant cells, particularly in the context of platinum resistance. In other words, results for these analyses guided identification of a putative mechanism of resistance, i.e., the activation of the JAK/STAT pathway. Further, results herein show that JAK/STAT inhibition using JSI-124, when compared to other routinely used agents in ovarian cancer, shows superior activity abrogating several key steps in ovarian cancer metastatic pathogenesis and inhibiting established malignant ascites and tumors ex vivo and in vivo. This analysis highlights the potential of single-cell genomic studies to provide rationale for the development of therapeutic strategies that are feasible for translation into clinical patient care.

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, intraperitoneal, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

Human dosage amounts can initially be determined by extrapolating from the amount of compound used in mice, as a skilled artisan recognizes it is routine in the art to modify the dosage for humans compared to animal models. In certain embodiments, it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

In some cases, the compound or composition of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005, incorporated herein by reference.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some aspects, the prophylactic and/or therapeutic regimens comprise titrating the dosages administered to the patient so as to achieve a specified measure of therapeutic efficacy. Such measures include a reduction in the cancer cell population in the patient.

In certain cases, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one aspect, the reference sample is a specimen extracted from the same patient, prior to receiving the prophylactic and/or therapeutic regimen. For example, the number or amount of cancer cells in the test specimen is at least 2%, 5%, 10%, 15%, 20%, 30%, 40%, 50%, 60%, 70%, 80%, 90%, 95% or 99% lower than in the reference sample.

In some cases, the dosage of the compound of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. For example, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these cases, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one aspect, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. For example, the frequency of administration ranges from once a day up to about once every eight weeks. In another example, the frequency of administration ranges from about once a week up to about once every six weeks. In another example, the frequency of administration ranges from about once every three weeks up to about once every four weeks.

Generally, the dosage of a compound of the invention administered to a subject to prevent, treat, and/or manage cancer is in the range of 0.01 to 500 mg/kg, e.g., in the range of 0.1 mg/kg to 100 mg/kg, of the subject's body weight. For example, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight. In another example, the dosage of a compound of the invention administered to a subject to prevent, treat, and/or manage cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another example, the dosage of a compound of the invention administered to a subject to prevent, treat, and/or manage cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In another example, the dosage of a compound of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body weight. For example, the dosage administered to a subject is in the range of 0.5 g/m$^2$ to 5 g/m$^2$, or 1 g/m$^2$ to 5 g/m$^2$ of the subject's body's surface area.

In another example, the prophylactic and/or therapeutic regimen comprises administering to a patient one or more doses of an effective amount of a compound of the invention, wherein the dose of an effective amount achieves a plasma level of at least 0.1 μg/mL, at least 0.5 μg/mL, at least 1 μg/mL, at least 2 μg/mL, at least 5 μg/mL, at least 6 μg/mL, at least 10 μg/mL, at least 15 μg/mL, at least 20 μg/mL, at least 25 μg/mL, at least 50 μg/mL, at least 100 μg/mL, at least 125 μg/mL, at least 150 μg/mL, at least 175 μg/mL, at least 200 μg/mL, at least 225 μg/mL, at least 250 μg/mL, at least 275 μg/mL, at least 300 μg/mL, at least 325 μg/mL, at least 350 μg/mL, at least 375 μg/mL, or at least 400 μg/mL of the compound of the invention.

In another example, the prophylactic and/or therapeutic regimen comprises administering to a patient a plurality of doses of an effective amount of a compound of the invention, wherein the plurality of doses maintains a plasma level of at least 0.1 μg/mL, at least 0.5 μg/mL, at least 1 μg/mL, at least 2 μg/mL, at least 5 μg/mL, at least 6 μg/mL, at least 10 μg/mL, at least 15 μg/mL, at least 20 μg/mL, at least 25

µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

In other embodiments, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

Combination Therapy

In one example, the active compounds are administered in combination therapy, i.e., combined with other agents, e.g., therapeutic agents, that are useful for treating pathological conditions or disorders, such as various forms of cancer. The term "in combination" in this context means that the agents are given substantially contemporaneously, either simultaneously or sequentially. If given sequentially, at the onset of administration of the second compound, the first of the two compounds is in some cases still detectable at effective concentrations at the site of treatment.

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Accordingly, in some examples, the prophylactic and/or therapeutic regimen comprises administration of a compound of the invention in combination with one or more additional anticancer therapeutics. In one example, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., Goodman & Gilman's The Pharmacological Basis Of Basis Of Therapeutics, 10th ed., McGraw-Hill, New York, 2001; Physician's Desk Reference (60$^{th}$ ed., 2006), which is incorporated herein by reference in its entirety.

The compound of the invention and the one or more additional anticancer therapeutics can be administered separately, simultaneously, or sequentially. In various aspects, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In another example, two or more anticancer therapeutics are administered within the same patient visit.

In certain aspects, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In another example, the anticancer therapeutics are administered concurrently to a subject in separate compositions. The combination anticancer therapeutics of the invention may be administered to a subject by the same or different routes of administration.

When a compound of the invention and the additional anticancer therapeutic are administered to a subject concurrently, the term "concurrently" is not limited to the administration of the anticancer therapeutics at exactly the same time, but rather, it is meant that they are administered to a subject in a sequence and within a time interval such that they can act together (e.g., synergistically to provide an increased benefit than if they were administered otherwise). For example, the anticancer therapeutics may be administered at the same time or sequentially in any order at different points in time; however, if not administered at the same time, they should be administered sufficiently close in time so as to provide the desired therapeutic effect, preferably in a synergistic fashion. The combination anticancer therapeutics of the invention can be administered separately, in any appropriate form and by any suitable route. When the components of the combination anticancer therapeutics are not administered in the same pharmaceutical composition, it is understood that they can be administered in any order to a subject in need thereof. For example, a compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the anticancer therapeutics are administered within the same office visit. In another example, the combination anticancer therapeutics of the invention are administered at 1 minute to 24 hours apart.

Release of Pharmaceutical Compositions

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules,

Screen for Identifying Agents

In certain embodiments, the methods described herein can be used to identify agents that can complement treatment with STAT3 inhibitors or can identify more specific or targeted agents. For example, although JSI-124 may show potential antitumor effects through inhibition of STAT3, other off-target proinflammatory pathways are activated, emphasizing that more careful and thorough preclinical investigations must be implemented to prevent potential harmful effects (see, e.g., McFarland et al., Activation of the NF-κB pathway by the STAT3 inhibitor JSI-124 in human glioblastoma cells, Mol Cancer Res. 2013 May; 11(5):494-505). Thus, agents that provide a comparable or enhanced therapeutic effect can be identified. Agents providing less side effects may also be identified. In certain embodiments, the agents are identified from a small molecule library as known in the art.

In certain embodiments, screening methods employ microfluidic devices, such as described in WO 2017/075549, "High-Throughput Dynamic Reagent Delivery System." For example, the microfluidic device can be used to establish a gradient of one compound (e.g., JSI-124) and another compound can be tested for synergistic effects. Such an assay may be used to identify combination treatments that require lower doses and thus less potential side effects.

In certain embodiments, one or more agents targeting one or more genes as described herein are used in a combination treatment (e.g., STAT3 inhibitor and another agent targeting a gene as described herein).

In certain embodiments, screening methods employ PDX mouse models as described herein. In certain embodiments, PDX models can be treated with a chemotherapeutic agent (e.g., platinum based therapy). Agents can be screened for the ability to sensitize or over-come platinum resistance. In certain embodiments, tumor cells grown in culture can be screened as described herein for JSI-124. In certain embodiments 2D or 3D cultures are screened. In certain embodiments, OVACR4, OVACR8, OVASHO or TYKNU cells are screened. In certain embodiments, combination therapies are screened. In certain embodiments, ex vivo cultures of platinum resistant patients are screened. In certain embodiments, reporter cell lines expressing a reporter (e.g., luciferase) are used to screen for compounds capable of modulating a gene signature as described herein. The reporter can be specific for a gene as described herein. One or more reporters for one or more genes may also be used. In certain embodiments, spheroid cultures are screened.

In certain embodiments, methods of screening utilize next generation sequencing. In certain embodiments, single cell sequencing is performed. In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, the agents according to the present invention are screened in a perturbation assay. For example, a perturbation library is introduced to a population of cells followed by treatment with one or more test agents (e.g., JSI-124). Genes can be identified that when perturbed cause an increase or decrease in efficacy of the one or more agents. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). In certain embodiments, the network of genes affected by an agent may be identified. In one embodiment, the method comprises (1) introducing single-order or combinatorial perturbations to a population of cells, (2) treating the cells with an agent, (3) measuring genomic, genetic, proteomic, epigenetic and/or phenotypic differences in single cells and (4) assigning a perturbation(s) to the single cells.

In certain embodiments, a CRISPR system is used to create an INDEL at a target gene. In other embodiments, epigenetic screening is performed by applying CRISPRa/i/x technology (see, e g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimizing deaminase fusions for genome editing, Nat Commun. 7:13330; Hess et al., 2016, Directed evolution using dCas9-targeted somatic hypermutation in mammalian cells. Nature Methods 13, 1036-1042: and Ma et al., 2016, Targeted AID-mediated mutagenesis (TAM) enables efficient genomic diversification in mammalian ceils. Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, an agent screened is a genetic modifying agent. In certain embodiments, the inhibitor as described herein for treating or preventing a gynecological tumor in a subject comprises a genetic modifying agent.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals. org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoide cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, *Nat Biotechnol.* 33(9):985-9, doi: 10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS,* E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU (SEQ. I.D. Nos. 1-4).

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas proten (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the compelementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver BP et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline<15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc. (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extented length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023. which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: Leptotrichia, *Listeria, Corynebacter, Sutterella, Legionella, Treponema, Filifactor, Eubacterium, Streptococcus, Lactobacillus, Mycoplasma, Bacteroides, Flavivirus, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*, or the C2c2 effector protein is an organism selected from the group consisting of: Leptotrichia shahii, Leptotrichia *wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif In certain embodiments, the WYL domain containing accessory protein is WYL1. WYL1 is a single WYL-domain protein associated primarily with Ruminococcus.

In other example embodiments, the Type VI RNA-targeting Cas enzyme is Cas13d. In certain embodiments, Cas13d is *Eubacterium siraeum* DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).
Cas13 RNA Editing In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient. In one embodiment, the modified cell for cell therapy is a CAR-T cell capable of recognizing and/or attacking a tumor cell.

Cytosine Deaminase

Programmable deamination of cytosine has been reported and may be used for correction of A→G and T→C point mutations. For example, Komor et al., Nature (2016) 533: 420-424 reports targeted deamination of cytosine by APOBEC1 cytidine deaminase in a non-targeted DNA stranded displaced by the binding of a Cas9-guide RNA complex to a targeted DNA strand, which results in conversion of cytosine to uracil. See also Kim et al., Nature Biotechnology (2017) 35:371-376; Shimatani et al., Nature Biotechnology (2017) doi:10.1038/nbt.3833; Zong et al., Nature Biotechnology (2017) doi:10.1038/nbt.3811; Yang Nature Communication (2016) doi:10.1038/ncomms13330.

Adenosine Deaminase

The term "adenosine deaminase" or "adenosine deaminase protein" as used herein refers to a protein, a polypeptide, or one or more functional domain(s) of a protein or a polypeptide that is capable of catalyzing a hydrolytic deamination reaction that converts an adenine (or an adenine moiety of a molecule) to a hypoxanthine (or a hypoxanthine moiety of a molecule), as shown below. In some embodiments, the adenine-containing molecule is an adenosine (A), and the hypoxanthine-containing molecule is an inosine (I). The adenine-containing molecule can be deoxyribonucleic acid (DNA) or ribonucleic acid (RNA).

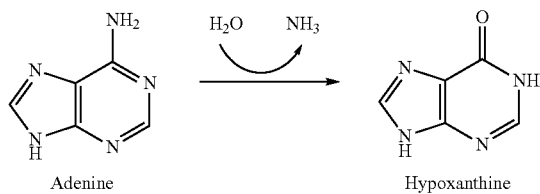

According to the present disclosure, adenosine deaminases that can be used in connection with the present disclosure include, but are not limited to, members of the enzyme family known as adenosine deaminases that act on RNA (ADARs), members of the enzyme family known as adenosine deaminases that act on tRNA (ADATs), and other adenosine deaminase domain-containing (ADAD) family members. According to the present disclosure, the adenosine deaminase is capable of targeting adenine in a RNA/DNA heteroduplex. Indeed, Zheng et al. (Nucleic Acids Res. 2017, 45(6): 3369-3377) has demonstrated that ADARs can carry out adenosine to inosine editing reactions on RNA/DNA heteroduplexes. In particular embodiments, the adenosine deaminase has been modified to increase its ability to edit DNA in a RNA/DNA heteroduplex as detailed herein.

In some embodiments, the adenosine deaminase is derived from one or more metazoa species, including but not limited to, mammals, birds, frogs, squids, fish, flies and worms. In some embodiments, the adenosine deaminase is a human, squid or Drosophila adenosine deaminase.

In some embodiments, the adenosine deaminase is a human ADAR, including hADAR1, hADAR2, hADAR3. In some embodiments, the adenosine deaminase is a Caenorhabditis elegans ADAR protein, including ADR-1 and ADR-2. In some embodiments, the adenosine deaminase is a Drosophila ADAR protein, including dAdar. In some embodiments, the adenosine deaminase is a squid Loligo pealeii ADAR protein, including sqADAR2a and sqADAR2b. In some embodiments, the adenosine deaminase is a human ADAT protein. In some embodiments, the adenosine deaminase is a Drosophila ADAT protein. In some embodiments, the adenosine deaminase is a human ADAD protein, including TENR (hADAD1) and TENRL (hADAD2).

In some embodiments, the adenosine deaminase protein recognizes and converts one or more target adenosine residue(s) in a double-stranded nucleic acid substrate into inosine residues (s). In some embodiments, the double-stranded nucleic acid substrate is a RNA-DNA hybrid duplex. In some embodiments, the adenosine deaminase protein recognizes a binding window on the double-stranded substrate. In some embodiments, the binding window contains at least one target adenosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the adenosine deaminase protein comprises one or more deaminase domains. Not intended to be bound by theory, it is contemplated that the deaminase domain functions to recognize and convert one or more target adenosine (A) residue(s) contained in a double-stranded nucleic acid substrate into inosine (I) residues (s). In some embodiments, the deaminase domain comprises an active center. In some embodiments, the active center comprises a zinc ion. In some embodiments, during the A-to-I editing process, base pairing at the target adenosine residue is disrupted, and the target adenosine residue is "flipped" out of the double helix to become accessible by the adenosine deaminase. In some embodiments, amino acid residues in or near the active center interact with one or more nucleotide(s) 5' to a target adenosine residue. In some embodiments, amino acid residues in or near the active center interact with one or more nucleotide(s) 3' to a target adenosine residue. In some embodiments, amino acid residues in or near the active center further interact with the nucleotide complementary to the target adenosine residue on the opposite strand. In some embodiments, the amino acid residues form hydrogen bonds with the 2' hydroxyl group of the nucleotides.

In some embodiments, the adenosine deaminase comprises human ADAR2 full protein (hADAR2) or the deaminase domain thereof (hADAR2-D). In some embodiments, the adenosine deaminase is an ADAR family member that is homologous to hADAR2 or hADAR2-D.

Particularly, in some embodiments, the homologous ADAR protein is human ADAR1 (hADAR1) or the deaminase domain thereof (hADAR1-D). In some embodiments, glycine 1007 of hADAR1-D corresponds to glycine $^{487}$ hADAR2-D, and glutamic Acid $^{1008}$ of hADAR1-D corresponds to glutamic acid $^{488}$ of hADAR2-D.

In some embodiments, the adenosine deaminase comprises the wild-type amino acid sequence of hADAR2-D. In some embodiments, the adenosine deaminase comprises one or more mutations in the hADAR2-D sequence, such that the editing efficiency, and/or substrate editing preference of hADAR2-D is changed according to specific needs.

Certain mutations of hADAR1 and hADAR2 proteins have been described in Kuttan et al., Proc Natl Acad Sci USA. (2012) 109(48):E3295-304; Want et al. ACS Chem Biol. (2015) 10(11):2512-9; and Zheng et al. Nucleic Acids Res. (2017) 45(6):3369-337, each of which is incorporated herein by reference in its entirety.

In some embodiments, the adenosine deaminase comprises a mutation at glycine$^{336}$ of the hADAR2-D amino acid sequence, or a corresponding position in a homologous ADAR protein. In some embodiments, the glycine residue at position 336 is replaced by an aspartic acid residue (G336D).

In some embodiments, the adenosine deaminase comprises a mutation at Glycine$^{487}$ of the hADAR2-D amino acid sequence, or a corresponding position in a homologous ADAR protein. In some embodiments, the glycine residue at position 487 is replaced by a non-polar amino acid residue with relatively small side chains. For example, in some embodiments, the glycine residue at position 487 is replaced by an alanine residue (G487A). In some embodiments, the glycine residue at position 487 is replaced by a valine residue (G487V). In some embodiments, the glycine residue at position 487 is replaced by an amino acid residue with relatively large side chains. In some embodiments, the glycine residue at position 487 is replaced by a arginine residue (G487R). In some embodiments, the glycine residue at position 487 is replaced by a lysine residue (G487K). In some embodiments, the glycine residue at position 487 is replaced by a tryptophan residue (G487W). In some embodiments, the glycine residue at position 487 is replaced by a tyrosine residue (G487Y).

In some embodiments, the adenosine deaminase comprises a mutation at glutamic acid$^{488}$ of the hADAR2-D amino acid sequence, or a corresponding position in a homologous ADAR protein. In some embodiments, the glutamic acid residue at position 488 is replaced by a glutamine residue (E488Q). In some embodiments, the glutamic acid residue at position 488 is replaced by a histidine residue (E488H). In some embodiments, the glutamic acid residue at position 488 is replace by an arginine residue (E488R). In some embodiments, the glutamic acid residue at position 488 is replace by a lysine residue (E488K). In some embodiments, the glutamic acid residue at position 488 is replace by an asparagine residue (E488N). In some embodiments, the glutamic acid residue at position 488 is replace by an alanine residue (E488A). In some embodiments, the glutamic acid residue at position 488 is replace by a Methionine residue (E488M). In some embodiments, the glutamic acid residue at position 488 is replace by a serine residue (E488S). In some embodiments, the glutamic acid residue at position 488 is replace by a phenylalanine residue (E488F). In some embodiments, the glutamic acid residue at position 488 is replace by a lysine residue (E488L). In some embodiments, the glutamic acid residue at position 488 is replace by a tryptophan residue (E488W).

In some embodiments, the adenosine deaminase comprises a mutation at threonine$^{490}$ of the hADAR2-D amino acid sequence, or a corresponding position in a homologous ADAR protein. In some embodiments, the threonine residue at position 490 is replaced by a cysteine residue (T490C). In some embodiments, the threonine residue at position 490 is replaced by a serine residue (T490S). In some embodiments, the threonine residue at position 490 is replaced by an alanine residue (T490A). In some embodiments, the threonine residue at position 490 is replaced by a phenylalanine residue (T490F). In some embodiments, the threonine residue at position 490 is replaced by a tyrosine residue (T490Y). In some embodiments, the threonine residue at position 490 is replaced by a serine residue (T490R). In some embodiments, the threonine residue at position 490 is replaced by an alanine residue (T490K). In some embodiments, the threonine residue at position 490 is replaced by a phenylalanine residue (T490P). In some embodiments, the threonine residue at position 490 is replaced by a tyrosine residue (T490E).

In some embodiments, the adenosine deaminase comprises a mutation at valine$^{493}$ of the hADAR2-D amino acid sequence, or a corresponding position in a homologous ADAR protein. In some embodiments, the valine residue at position 493 is replaced by an alanine residue (V493A). In some embodiments, the valine residue at position 493 is replaced by a serine residue (V493S). In some embodiments, the valine residue at position 493 is replaced by a threonine residue (V493T). In some embodiments, the valine residue at position 493 is replaced by an arginine residue (V493R). In some embodiments, the valine residue at position 493 is replaced by an aspartic acid residue (V493D). In some embodiments, the valine residue at position 493 is replaced by a proline residue (V493P). In some embodiments, the valine residue at position 493 is replaced by a glycine residue (V493G).

In some embodiments, the adenosine deaminase comprises a mutation at alanine$^{589}$ of the hADAR2-D amino acid sequence, or a corresponding position in a homologous ADAR protein. In some embodiments, the alanine residue at position 589 is replaced by a valine residue (A589V).

In some embodiments, the adenosine deaminase comprises a mutation at asparagine$^{597}$ of the hADAR2-D amino acid sequence, or a corresponding position in a homologous ADAR protein. In some embodiments, the asparagine residue at position 597 is replaced by a lysine residue (N597K). In some embodiments, the adenosine deaminase comprises a mutation at position 597 of the amino acid sequence, which has an asparagine residue in the wild type sequence. In some embodiments, the asparagine residue at position 597 is replaced by an arginine residue (N597R). In some embodiments, the adenosine deaminase comprises a mutation at position 597 of the amino acid sequence, which has an asparagine residue in the wild type sequence. In some embodiments, the asparagine residue at position 597 is replaced by an alanine residue (N597A). In some embodiments, the adenosine deaminase comprises a mutation at position 597 of the amino acid sequence, which has an asparagine residue in the wild type sequence. In some embodiments, the asparagine residue at position 597 is replaced by a glutamic acid residue (N597E). In some embodiments, the adenosine deaminase comprises a mutation at position 597 of the amino acid sequence, which has an asparagine residue in the wild type sequence. In some embodiments, the asparagine residue at position 597 is replaced by a histidine residue (N597H). In some embodiments, the adenosine deaminase comprises a mutation at position 597 of the amino acid sequence, which has an asparagine residue in the wild type sequence. In some embodiments, the asparagine residue at position 597 is replaced by a glycine residue (N597G). In some embodiments, the adenosine deaminase comprises a mutation at position 597 of the amino acid sequence, which has an asparagine residue in the wild type sequence. In some embodiments, the asparagine residue at position 597 is replaced by a tyrosine residue (N597Y). In some embodiments, the asparagine residue at position 597 is replaced by a phenylalanine residue (N597F).

In some embodiments, the adenosine deaminase comprises a mutation at serine$^{599}$ of the hADAR2-D amino acid sequence, or a corresponding position in a homologous ADAR protein. In some embodiments, the serine residue at position 599 is replaced by a threonine residue (S599T).

In some embodiments, the adenosine deaminase comprises a mutation at asparagine$^{613}$ of the hADAR2-D amino acid sequence, or a corresponding position in a homologous ADAR protein. In some embodiments, the asparagine residue at position 613 is replaced by a lysine residue (N613K). In some embodiments, the adenosine deaminase comprises a mutation at position 613 of the amino acid sequence, which has an asparagine residue in the wild type sequence. In some embodiments, the asparagine residue at position 613 is replaced by an arginine residue (N613R). In some embodiments, the adenosine deaminase comprises a mutation at position 613 of the amino acid sequence, which has an asparagine residue in the wild type sequence. In some embodiments, the asparagine residue at position 613 is replaced by an alanine residue (N613A) In some embodiments, the adenosine deaminase comprises a mutation at position 613 of the amino acid sequence, which has an asparagine residue in the wild type sequence. In some embodiments, the asparagine residue at position 613 is replaced by a glutamic acid residue (N613E).

In some embodiments, to improve editing efficiency, the adenosine deaminase may comprise one or more of the mutations: G336D, G487A, G487V, E488Q, E488H, E488R, E488N, E488A, E488S, E488M, T490C, T490S, V493T, V493S, V493A, V493R, V493D, V493P, V493G, N597K, N597R, N597A, N597E, N597H, N597G, N597Y, A589V, S599T, N613K, N613R, N613A, N613E, based on amino acid sequence positions of hADAR2-D, and mutations in a homologous ADAR protein corresponding to the above.

In some embodiments, to reduce editing efficiency, the adenosine deaminase may comprise one or more of the mutations: E488F, E488L, E488W, T490A, T490F, T490Y, T490R, T490K, T490P, T490E, N597F, based on amino acid sequence positions of hADAR2-D, and mutations in a homologous ADAR protein corresponding to the above. In particular embodiments, it can be of interest to use an adenosine deaminase enzyme with reduced efficacy to reduce off-target effects.

The terms "editing specificity" and "editing preference" are used interchangeably herein to refer to the extent of A-to-I editing at a particular adenosine site in a double-stranded substrate. In some embodiment, the substrate editing preference is determined by the 5' nearest neighbor and/or the 3' nearest neighbor of the target adenosine residue. In some embodiments, the adenosine deaminase has preference for the 5' nearest neighbor of the substrate ranked as U>A>C>G (">" indicates greater preference). In some embodiments, the adenosine deaminase has preference for the 3' nearest neighbor of the substrate ranked as G>C~A>U (">" indicates greater preference; "~" indicates similar preference). In some embodiments, the adenosine deaminase has preference for the 3' nearest neighbor of the substrate ranked as G>C>U-A (">" indicates greater preference; "~" indicates similar preference). In some embodiments, the adenosine deaminase has preference for the 3' nearest neighbor of the substrate ranked as G>C>A>U (">" indicates greater preference). In some embodiments, the adenosine deaminase has preference for the 3' nearest neighbor of the substrate ranked as C~G~A>U (">" indicates greater preference; "~" indicates similar preference). In some embodiments, the adenosine deaminase has preference for a triplet sequence containing the target adenosine residue ranked as TAG>AAG>CAC>AAT>GAA>GAC (">" indicates greater preference), the center A being the target adenosine residue.

In some embodiments, the substrate editing preference of an adenosine deaminase is affected by the presence or absence of a nucleic acid binding domain in the adenosine deaminase protein. In some embodiments, to modify substrate editing preference, the deaminase domain is connected with a double-strand RNA binding domain (dsRBD) or a double-strand RNA binding motif (dsRBM). In some embodiments, the dsRBD or dsRBM may be derived from an ADAR protein, such as hADAR1 or hADAR2. In some embodiments, a full length ADAR protein that comprises at least one dsRBD and a deaminase domain is used. In some embodiments, the one or more dsRBM or dsRBD is at the N-terminus of the deaminase domain. In other embodiments, the one or more dsRBM or dsRBD is at the C-terminus of the deaminase domain.

In some embodiments, the substrate editing preference of an adenosine deaminase is affected by amino acid residues near or in the active center of the enzyme. In some embodiments, to modify substrate editing preference, the adenosine deaminase may comprise one or more of the mutations: G336D, G487R, G487K, G487W, G487Y, E488Q, E488N, T490A, V493A, V493T, V493S, N597K, N597R, A589V, S599T, N613K, N613R, based on amino acid sequence positions of hADAR2-D, and mutations in a homologous ADAR protein corresponding to the above.

Particularly, in some embodiments, to reduce editing specificity, the adenosine deaminase can comprise one or more of mutations E488Q, V493A, N597K, N613K, based on amino acid sequence positions of hADAR2-D, and mutations in a homologous ADAR protein corresponding to the above. In some embodiments, to increase editing specificity, the adenosine deaminase can comprise mutation T490A.

In some embodiments, to increase editing preference for target adenosine (A) with an immediate 5' G, such as substrates comprising the triplet sequence GAC, the center A being the target adenosine residue, the adenosine deaminase can comprise one or more of mutations G336D, E488Q, E488N, V493T, V493S, V493A, A589V, N597K, N597R, S599T, N613K, N613R, based on amino acid sequence positions of hADAR2-D, and mutations in a homologous ADAR protein corresponding to the above.

Particularly, in some embodiments, the adenosine deaminase comprises mutation E488Q or a corresponding mutation in a homologous ADAR protein for editing substrates comprising the following triplet sequences: GAC, GAA, GAU, GAG, CAU, AAU, UAC, the center A being the target adenosine residue.

In some embodiments, to reduce off-target effects, the adenosine deaminase comprises one or more of mutations at R348, V351, T375, K376, E396, C451, R455, N473, R474, K475, R477, R481, S486, E488, T490, S495, R510, based on amino acid sequence positions of hADAR2-D, and mutations in a homologous ADAR protein corresponding to the above. In some embodiments, the adenosine deaminase comprises mutation at E488 and one or more additional positions selected from R348, V351, T375, K376, E396, C451, R455, N473, R474, K475, R477, R481, S486, T490, S495, R510. In some embodiments, the adenosine deaminase comprises mutation at T375, and optionally at one or more additional positions. In some embodiments, the adenosine deaminase comprises mutation at N473, and optionally at one or more additional positions. In some embodiments, the adenosine deaminase comprises mutation at V351, and optionally at one or more additional positions. In some embodiments, the adenosine deaminase comprises mutation at E488 and T375, and optionally at one or more additional positions. In some embodiments, the adenosine deaminase comprises mutation at E488 and N473, and optionally at one or more additional positions. In some embodiments, the adenosine deaminase comprises mutation E488 and V351, and optionally at one or more additional positions. In some embodiments, the adenosine deaminase comprises mutation at E488 and one or more of T375, N473, and V351.

In some embodiments, to reduce off-target effects, the adenosine deaminase comprises one or more of mutations selected from R348E, V351L, T375G, T375S, R455G, R455S, R455E, N473D, R474E, K475Q, R477E, R481E, S486T, E488Q, T490A, T490S, S495T, and R510E, based on amino acid sequence positions of hADAR2-D, and mutations in a homologous ADAR protein corresponding to the above. In some embodiments, the adenosine deaminase comprises mutation E488Q and one or more additional mutations selected from R348E, V351L, T375G, T375S, R455G, R455S, R455E, N473D, R474E, K475Q, R477E, R481E, S486T, T490A, T490S, S495T, and R510E. In some embodiments, the adenosine deaminase comprises mutation T375G or T375S, and optionally one or more additional mutations. In some embodiments, the adenosine deaminase comprises mutation N473D, and optionally one or more additional mutations. In some embodiments, the adenosine deaminase comprises mutation V351L, and optionally one or more additional mutations. In some embodiments, the adenosine deaminase comprises mutation E488Q, and T375G or T375G, and optionally one or more additional mutations. In some embodiments, the adenosine deaminase comprises mutation E488Q and N473D, and optionally one or more additional mutations. In some embodiments, the adenosine deaminase comprises mutation E488Q and V351L, and optionally one or more additional mutations. In some embodiments, the adenosine deaminase comprises mutation E488Q and one or more of T375G/S, N473D and V351L.

Crystal structures of the human ADAR2 deaminase domain bound to duplex RNA reveal a protein loop that binds the RNA on the 5' side of the modification site. This 5' binding loop is one contributor to substrate specificity differences between ADAR family members. See Wang et al., Nucleic Acids Res., 44(20):9872-9880 (2016), the content of which is incorporated herein by reference in its entirety. In addition, an ADAR2-specific RNA-binding loop was identified near the enzyme active site. See Mathews et al., Nat. Struct. Mol. Biol., 23(5):426-33 (2016), the content of which is incorporated herein by reference in its entirety. In some embodiments, the adenosine deaminase comprises one or more mutations in the RNA binding loop to improve editing specificity and/or efficiency.

In some embodiments, the adenosine deaminase comprises a mutation at alanine$^{454}$ of the hADAR2-D amino acid sequence, or a corresponding position in a homologous ADAR protein. In some embodiments, the alanine residue at position 454 is replaced by a serine residue (A454S). In some embodiments, the alanine residue at position 454 is replaced by a cysteine residue (A454C). In some embodiments, the alanine residue at position 454 is replaced by an aspartic acid residue (A454D).

In some embodiments, the adenosine deaminase comprises a mutation at arginine$^{455}$ of the hADAR2-D amino acid sequence, or a corresponding position in a homologous ADAR protein. In some embodiments, the arginine residue at position 455 is replaced by an alanine residue (R455A). In some embodiments, the arginine residue at position 455 is replaced by a valine residue (R455V). In some embodiments, the arginine residue at position 455 is replaced by a histidine residue (R455H). In some embodiments, the arginine residue at position 455 is replaced by a glycine residue (R455G). In some embodiments, the arginine residue at position 455 is replaced by a serine residue (R455S). In some embodiments, the arginine residue at position 455 is replaced by a glutamic acid residue (R455E).

In some embodiments, the adenosine deaminase comprises a mutation at isoleucine$^{456}$ of the hADAR2-D amino acid sequence, or a corresponding position in a homologous ADAR protein. In some embodiments, the isoleucine residue at position 456 is replaced by a valine residue (I456V). In some embodiments, the isoleucine residue at position 456 is replaced by a leucine residue (I456L). In some embodiments, the isoleucine residue at position 456 is replaced by an aspartic acid residue (I456D).

In some embodiments, the adenosine deaminase comprises a mutation at phenylalanine$^{457}$ of the hADAR2-D amino acid sequence, or a corresponding position in a homologous ADAR protein. In some embodiments, the phenylalanine residue at position 457 is replaced by a tyrosine residue (F457Y). In some embodiments, the phenylalanine residue at position 457 is replaced by an arginine residue (F457R). In some embodiments, the phenylalanine residue at position 457 is replaced by a glutamic acid residue (F457E).

In some embodiments, the adenosine deaminase comprises a mutation at serine$^{458}$ of the hADAR2-D amino acid sequence, or a corresponding position in a homologous ADAR protein. In some embodiments, the serine residue at position 458 is replaced by a valine residue (S458V). In some embodiments, the serine residue at position 458 is replaced by a phenylalanine residue (S458F). In some embodiments, the serine residue at position 458 is replaced by a proline residue (S458P).

In some embodiments, the adenosine deaminase comprises a mutation at proline$^{459}$ of the hADAR2-D amino acid sequence, or a corresponding position in a homologous ADAR protein. In some embodiments, the proline residue at position 459 is replaced by a cysteine residue (P459C). In some embodiments, the proline residue at position 459 is replaced by a histidine residue (P459H). In some embodiments, the proline residue at position 459 is replaced by a tryptophan residue (P459W).

In some embodiments, the adenosine deaminase comprises a mutation at histidine$^{460}$ of the hADAR2-D amino acid sequence, or a corresponding position in a homologous ADAR protein. In some embodiments, the histidine residue at position 460 is replaced by an arginine residue (H460R). In some embodiments, the histidine residue at position 460 is replaced by an isoleucine residue (H460I). In some embodiments, the histidine residue at position 460 is replaced by a proline residue (H460P).

In some embodiments, the adenosine deaminase comprises a mutation at proline$^{462}$ of the hADAR2-D amino acid sequence, or a corresponding position in a homologous ADAR protein. In some embodiments, the proline residue at position 462 is replaced by a serine residue (P462S). In some embodiments, the proline residue at position 462 is replaced by a tryptophan residue (P462W). In some embodiments, the proline residue at position 462 is replaced by a glutamic acid residue (P462E).

In some embodiments, the adenosine deaminase comprises a mutation at aspartic acid$^{469}$ of the hADAR2-D amino acid sequence, or a corresponding position in a homologous ADAR protein. In some embodiments, the aspartic acid residue at position 469 is replaced by a glutamine residue (D469Q). In some embodiments, the aspartic acid residue at position 469 is replaced by a serine residue (D469S). In some embodiments, the aspartic acid residue at position 469 is replaced by a tyrosine residue (D469Y).

In some embodiments, the adenosine deaminase comprises a mutation at arginine$^{470}$ of the hADAR2-D amino acid sequence, or a corresponding position in a homologous ADAR protein. In some embodiments, the arginine residue at position 470 is replaced by an alanine residue (R470A). In some embodiments, the arginine residue at position 470 is replaced by an isoleucine residue (R470I). In some embodiments, the arginine residue at position 470 is replaced by an aspartic acid residue (R470D).

In some embodiments, the adenosine deaminase comprises a mutation at histidine$^{471}$ of the hADAR2-D amino acid sequence, or a corresponding position in a homologous ADAR protein. In some embodiments, the histidine residue at position 471 is replaced by a lysine residue (H471K). In some embodiments, the histidine residue at position 471 is replaced by a threonine residue (H471T). In some embodiments, the histidine residue at position 471 is replaced by a valine residue (H471V).

In some embodiments, the adenosine deaminase comprises a mutation at proline$^{472}$ of the hADAR2-D amino acid sequence, or a corresponding position in a homologous ADAR protein. In some embodiments, the proline residue at position 472 is replaced by a lysine residue (P472K). In some embodiments, the proline residue at position 472 is replaced by a threonine residue (P472T). In some embodiments, the proline residue at position 472 is replaced by an aspartic acid residue (P472D).

In some embodiments, the adenosine deaminase comprises a mutation at asparagine$^{473}$ of the hADAR2-D amino acid sequence, or a corresponding position in a homologous ADAR protein. In some embodiments, the asparagine residue at position 473 is replaced by an arginine residue (N473R). In some embodiments, the asparagine residue at position 473 is replaced by a tryptophan residue (N473W). In some embodiments, the asparagine residue at position 473 is replaced by a proline residue (N473P). In some embodiments, the asparagine residue at position 473 is replaced by an aspartic acid residue (N473D).

In some embodiments, the adenosine deaminase comprises a mutation at arginine$^{474}$ of the hADAR2-D amino acid sequence, or a corresponding position in a homologous ADAR protein. In some embodiments, the arginine residue at position 474 is replaced by a lysine residue (R474K). In some embodiments, the arginine residue at position 474 is replaced by a glycine residue (R474G). In some embodiments, the arginine residue at position 474 is replaced by an aspartic acid residue (R474D). In some embodiments, the arginine residue at position 474 is replaced by a glutamic acid residue (R474E).

In some embodiments, the adenosine deaminase comprises a mutation at lysine$^{475}$ of the hADAR2-D amino acid sequence, or a corresponding position in a homologous ADAR protein. In some embodiments, the lysine residue at position 475 is replaced by a glutamine residue (K475Q). In some embodiments, the lysine residue at position 475 is replaced by an asparagine residue (K475N). In some embodiments, the lysine residue at position 475 is replaced by an aspartic acid residue (K475D).

In some embodiments, the adenosine deaminase comprises a mutation at alanine$^{476}$ of the hADAR2-D amino acid sequence, or a corresponding position in a homologous ADAR protein. In some embodiments, the alanine residue at position 476 is replaced by a serine residue (A476S). In some embodiments, the alanine residue at position 476 is replaced by an arginine residue (A476R). In some embodiments, the alanine residue at position 476 is replaced by a glutamic acid residue (A476E).

In some embodiments, the adenosine deaminase comprises a mutation at arginine$^{477}$ of the hADAR2-D amino acid sequence, or a corresponding position in a homologous ADAR protein. In some embodiments, the arginine residue at position 477 is replaced by a lysine residue (R477K). In some embodiments, the arginine residue at position 477 is replaced by a threonine residue (R477T). In some embodiments, the arginine residue at position 477 is replaced by a phenylalanine residue (R477F). In some embodiments, the arginine residue at position 474 is replaced by a glutamic acid residue (R477E).

In some embodiments, the adenosine deaminase comprises a mutation at glycine$^{478}$ of the hADAR2-D amino acid sequence, or a corresponding position in a homologous ADAR protein. In some embodiments, the glycine residue at position 478 is replaced by an alanine residue (G478A). In some embodiments, the glycine residue at position 478 is replaced by an arginine residue (G478R). In some embodiments, the glycine residue at position 478 is replaced by a tyrosine residue (G478Y).

In some embodiments, the adenosine deaminase comprises a mutation at glutamine$^{479}$ of the hADAR2-D amino acid sequence, or a corresponding position in a homologous ADAR protein. In some embodiments, the glutamine residue at position 479 is replaced by an asparagine residue (Q479N). In some embodiments, the glutamine residue at position 479 is replaced by a serine residue (Q479S). In some embodiments, the glutamine residue at position 479 is replaced by a proline residue (Q479P).

In some embodiments, the adenosine deaminase comprises a mutation at arginine$^{348}$ of the hADAR2-D amino acid sequence, or a corresponding position in a homologous ADAR protein. In some embodiments, the arginine residue at position 348 is replaced by an alanine residue (R348A). In some embodiments, the arginine residue at position 348 is replaced by a glutamic acid residue (R348E).

In some embodiments, the adenosine deaminase comprises a mutation at valine$^{351}$ of the hADAR2-D amino acid sequence, or a corresponding position in a homologous ADAR protein. In some embodiments, the valine residue at position 351 is replaced by a leucine residue (V351L).

In some embodiments, the adenosine deaminase comprises a mutation at threonine$^{375}$ of the hADAR2-D amino acid sequence, or a corresponding position in a homologous ADAR protein. In some embodiments, the threonine residue at position 375 is replaced by a glycine residue (T375G). In some embodiments, the threonine residue at position 375 is replaced by a serine residue (T375S).

In some embodiments, the adenosine deaminase comprises a mutation at arginine$^{481}$ of the hADAR2-D amino acid sequence, or a corresponding position in a homologous ADAR protein. In some embodiments, the arginine residue at position 481 is replaced by a glutamic acid residue (R481E).

In some embodiments, the adenosine deaminase comprises a mutation at serine$^{486}$ of the hADAR2-D amino acid sequence, or a corresponding position in a homologous ADAR protein. In some embodiments, the serine residue at position 486 is replaced by a threonine residue (S486T).

In some embodiments, the adenosine deaminase comprises a mutation at threonine$^{490}$ of the hADAR2-D amino acid sequence, or a corresponding position in a homologous ADAR protein. In some embodiments, the threonine residue at position 490 is replaced by an alanine residue (T490A). In some embodiments, the threonine residue at position 490 is replaced by a serine residue (T490S).

In some embodiments, the adenosine deaminase comprises a mutation at serine$^{495}$ of the hADAR2-D amino acid sequence, or a corresponding position in a homologous ADAR protein. In some embodiments, the serine residue at position 495 is replaced by a threonine residue (S495T).

In some embodiments, the adenosine deaminase comprises a mutation at arginine$^{510}$ of the hADAR2-D amino acid sequence, or a corresponding position in a homologous ADAR protein. In some embodiments, the arginine residue at position 510 is replaced by a glutamine residue (R510Q). In some embodiments, the arginine residue at position 510 is replaced by an alanine residue (R510A). In some embodiments, the arginine residue at position 510 is replaced by a glutamic acid residue (R510E).

In some embodiments, the adenosine deaminase comprises a mutation at glycine$^{593}$ of the hADAR2-D amino acid sequence, or a corresponding position in a homologous ADAR protein. In some embodiments, the glycine residue at position 593 is replaced by an alanine residue (G593A). In some embodiments, the glycine residue at position 593 is replaced by a glutamic acid residue (G593E).

In some embodiments, the adenosine deaminase comprises a mutation at lysine$^{594}$ of the hADAR2-D amino acid sequence, or a corresponding position in a homologous ADAR protein. In some embodiments, the lysine residue at position 594 is replaced by an alanine residue (K594A).

In some embodiments, the adenosine deaminase comprises the wild-type amino acid sequence of hADAR1-D (e.g., MGSGGGGSEGAPKKKRKVGSSLGTGNRCV KGDSLSLKGE TVNDCHAEIISRRGFIRFLYSELMKYN SQTAKDSIFEPAKGGEKLQIKKTVSFHLYIST APCGD-GALFDKSCSDRAMESTESRHYPVFENPKQGKLRTKV ENGQGTIPVESSDIVP TWDGIRLGERLRTMSCSDKI LRWNVLGLQGALLTHFLQPIYLKSVTLGYLFSQGHLT RAICCRVTRDGSAFEDGLRHPFIVNHPKVGRVSIYD-SKRQSGKTKETSVNWCLADGY DLEILDGTRGTVD G PRNELSRVSKKNIFLLFKKLCSFRYRRDLLRLSYGE AKKAARD YETAKNYFKKGLKDMGYGNWISKP QE EKNF* (SEQ ID NO:3)). In some embodiments, the adenosine deaminase comprises one or more mutations in the hADAR1-D sequence, such that the editing efficiency, and/or substrate editing preference of hADAR1-D is changed according to specific needs.

In some embodiments, the adenosine deaminase comprises a mutation at Glycine$^{1007}$ of the hADAR1-D amino acid sequence, or a corresponding position in a homologous ADAR protein. In some embodiments, the glycine residue at position 1007 is replaced by a non-polar amino acid residue with relatively small side chains. For example, in some embodiments, the glycine residue at position 1007 is replaced by an alanine residue (G1007A). In some embodiments, the glycine residue at position 1007 is replaced by a valine residue (G1007V). In some embodiments, the glycine residue at position 1007 is replaced by an amino acid residue with relatively large side chains. In some embodiments, the glycine residue at position 1007 is replaced by an arginine residue (G1007R). In some embodiments, the glycine residue at position 1007 is replaced by a lysine residue (G1007K). In some embodiments, the glycine residue at position 1007 is replaced by a tryptophan residue (G1007W). In some embodiments, the glycine residue at position 1007 is replaced by a tyrosine residue (G1007Y). Additionally, in other embodiments, the glycine residue at position 1007 is replaced by a leucine residue (G1007L). In other embodiments, the glycine residue at position 1007 is replaced by a threonine residue (G1007T). In other embodiments, the glycine residue at position 1007 is replaced by a serine residue (G1007S).

In some embodiments, the adenosine deaminase comprises a mutation at glutamic acid$^{1008}$ of the hADAR1-D amino acid sequence, or a corresponding position in a homologous ADAR protein. In some embodiments, the glutamic acid residue at position 1008 is replaced by a polar amino acid residue having a relatively large side chain. In some embodiments, the glutamic acid residue at position 1008 is replaced by a glutamine residue (E1008Q). In some embodiments, the glutamic acid residue at position 1008 is replaced by a histidine residue (E1008H). In some embodiments, the glutamic acid residue at position 1008 is replaced by an arginine residue (E1008R). In some embodiments, the glutamic acid residue at position 1008 is replaced by a lysine residue (E1008K). In some embodiments, the glutamic acid residue at position 1008 is replaced by a nonpolar or small polar amino acid residue. In some embodiments, the glutamic acid residue at position 1008 is replaced by a phenylalanine residue (E1008F). In some embodiments, the glutamic acid residue at position 1008 is replaced by a tryptophan residue (E1008W). In some embodiments, the glutamic acid residue at position 1008 is replaced by a glycine residue (E1008G). In some embodiments, the glutamic acid residue at position 1008 is replaced by an isoleucine residue (E1008I). In some embodiments, the glutamic acid residue at position 1008 is replaced by a valine residue (E1008V). In some embodiments, the glutamic acid residue at position 1008 is replaced by a proline residue (E1008P). In some embodiments, the glutamic acid residue at position 1008 is replaced by a serine residue (E1008S). In other embodiments, the glutamic acid residue at position 1008 is replaced by an asparagine residue (E1008N). In other embodiments, the glutamic acid residue at position 1008 is replaced by an alanine residue (E1008A). In other embodiments, the glutamic acid residue at position 1008 is replaced by a Methionine residue (E1008M). In some embodiments, the glutamic acid residue at position 1008 is replaced by a leucine residue (E1008L).

In some embodiments, to improve editing efficiency, the adenosine deaminase may comprise one or more of the mutations: E1007S, E1007A, E1007V, E1008Q, E1008R, E1008H, E1008M, E1008N, E1008K, based on amino acid sequence positions of hADAR1-D, and mutations in a homologous ADAR protein corresponding to the above.

In some embodiments, to reduce editing efficiency, the adenosine deaminase may comprise one or more of the mutations: E1007R, E1007K, E1007Y, E1007L, E1007T, E1008G, E1008I, E1008P, E1008V, E1008F, E1008W, E1008S, E1008N, E1008K, based on amino acid sequence positions of hADAR1-D, and mutations in a homologous ADAR protein corresponding to the above.

In some embodiments, the substrate editing preference, efficiency and/or selectivity of an adenosine deaminase is affected by amino acid residues near or in the active center of the enzyme. In some embodiments, the adenosine deaminase comprises a mutation at the glutamic acid 1008 position in hADAR1-D sequence, or a corresponding position in a homologous ADAR protein. In some embodiments, the mutation is E1008R, or a corresponding mutation in a homologous ADAR protein. In some embodiments, the E1008R mutant has an increased editing efficiency for target adenosine residue that has a mismatched G residue on the opposite strand.

In some embodiments, the adenosine deaminase protein further comprises or is connected to one or more double-stranded RNA (dsRNA) binding motifs (dsRBMs) or domains (dsRBDs) for recognizing and binding to double-stranded nucleic acid substrates. In some embodiments, the interaction between the adenosine deaminase and the double-stranded substrate is mediated by one or more additional protein factor(s), including a CRISPR/CAS protein factor. In some embodiments, the interaction between the adenosine deaminase and the double-stranded substrate is further mediated by one or more nucleic acid component(s), including a guide RNA.

According to the present invention, the substrate of the adenosine deaminase is an RNA/DNA heteroduplex formed upon binding of the guide molecule to its DNA target which then forms the CRISPR-Cas complex with the CRISPR-Cas enzyme. The RNA/DNA or DNA/RNA heteroduplex is also referred to herein as the "RNA/DNA hybrid", "DNA/RNA hybrid" or "double-stranded substrate". The particular features of the guide molecule and CRISPR-Cas enzyme are detailed below.

The term "editing selectivity" as used herein refers to the fraction of all sites on a double-stranded substrate that is edited by an adenosine deaminase. Without being bound by theory, it is contemplated that editing selectivity of an adenosine deaminase is affected by the double-stranded substrate's length and secondary structures, such as the presence of mismatched bases, bulges and/or internal loops.

In some embodiments, when the substrate is a perfectly base-paired duplex longer than 50 bp, the adenosine deaminase may be able to deaminate multiple adenosine residues within the duplex (e.g., 50% of all adenosine residues). In some embodiments, when the substrate is shorter than 50 bp, the editing selectivity of an adenosine deaminase is affected by the presence of a mismatch at the target adenosine site. Particularly, in some embodiments, adenosine (A) residue having a mismatched cytidine (C) residue on the opposite strand is deaminated with high efficiency. In some embodiments, adenosine (A) residue having a mismatched guanosine (G) residue on the opposite strand is skipped without editing.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. Doi: 10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated>700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12-F.

EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle EL. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                              (SEQ. I.D. No: 4)
MDPIRSRTPSPARELLSGPQPDGVQPTADRGVSP

PAGGPLDGLPARRTMSRTRLPSPPAPSPAFSADS

FSDLLRQFDPSLFNTSLFDSLPPFGAHHTEAATG

EWDEVQSGLRAADAPPPTMRVAVTAARPPRAKPA

PRRRAAQPSDASPAAQVDLRTLGYSQQQQEKIKP

KVRSTVAQHHEALVGHGFTHAHIVALSQHPAALG

TVAVKYQDMIAALPEATHEAIVGVGKQWSGARAL

EALLTVAGELRGPPLQLDTGQLLKIAKRGGVTAV

EAVHAWRNALTGAPLN
```

An exemplary amino acid sequence of a C-terminal capping region is:

```
                                              (SEQ. I.D. No: 5)
RPALESIVAQLSRPDPALAALTNDHLVALACLG

GRPALDAVKKGLPHAPALIKRTNRRIPERTSHR

VADHAQVVRVLGFFQCHSHPAQAFDDAMTQFGM

SRHGLLQLFRRVGVTELEARSGTLPPASQRWDR

ILQASGMKRAKPSPTSTQTPDQASLHAFADSLE

RDLDAPSPMHEGDQTRAS
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Adoptive Cell Transfer

In certain embodiments, tumor cells are targeted by transferred immune cells. In certain embodiments, cancer stem cells are targeted. In certain embodiments, adoptive cell transfer is performed in combination with a JAK/STAT inhibitor described herein. In certain embodiments, transferred cells are specific for a tumor antigen.

As used herein, "ACT", "adoptive cell therapy" and "adoptive cell transfer" may be used interchangeably. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens or tumor specific neoantigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac(2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis (Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1)Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190 KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia. For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer.

Various strategies may for example be employed to genetically modify T cells by altering the specificity of the T cell receptor (TCR) for example by introducing new TCR α and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3):

```
IEVMYPPPYLDNEKSNGTIIHVKGKHLCPSPLFPGPSKPFWVLVVVGGV
LACYSLLVTVAFIIFWVRSKRSRLLHSDYMNMTPRRPGPTRKHYQPYAP
PRDFAAYRS)).
```

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ ID No: 7) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY and continuing all the way to the carboxy-terminus of the protein. The sequence is reproduced herein: IEVMYPPPYLDNE KSNGTIIHVKGKHLCPSPLFPGPSKPFWVLVVVGGV-LACYSLLVT VAFIIFWVRSKRSRLLHSDYMNMT-PRRPGPTRKHYQPYAPPRDFAAYRS (SEQ ID No: 8). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FεFRI gamma chain; or CD28-FεFRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administered into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administered in one or more doses. In another embodiment, the effective amount of cells are administered as a single dose. In another embodiment, the effective amount of cells are administered as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2016, Multiplex genome editing to generate universal CAR T cells resistant to PD1 inhibition, Clin Cancer Res. 2016 Nov. 4; and Qasim et al., 2017, Molecular remission of infant B-ALL after infusion of universal TALEN gene-edited CAR T cells, Sci Transl Med. 2017 Jan. 25; 9(374)). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell; to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MIHC constituent proteins in a cell; to activate a T cell; to modulate cells such that the cells are resistant to exhaustion or dysfunction; and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci.

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SUP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×106/ml. In other embodiments, the concentration used can be from about 1×105/ml to 1×106/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of 125I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™ BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

The invention is further described in the following examples, which do not limit the scope of the invention described in the claims.

EXAMPLES

Example 1—Charting the Ascites Ecosystem by scRNA-Seq

Figure 15:
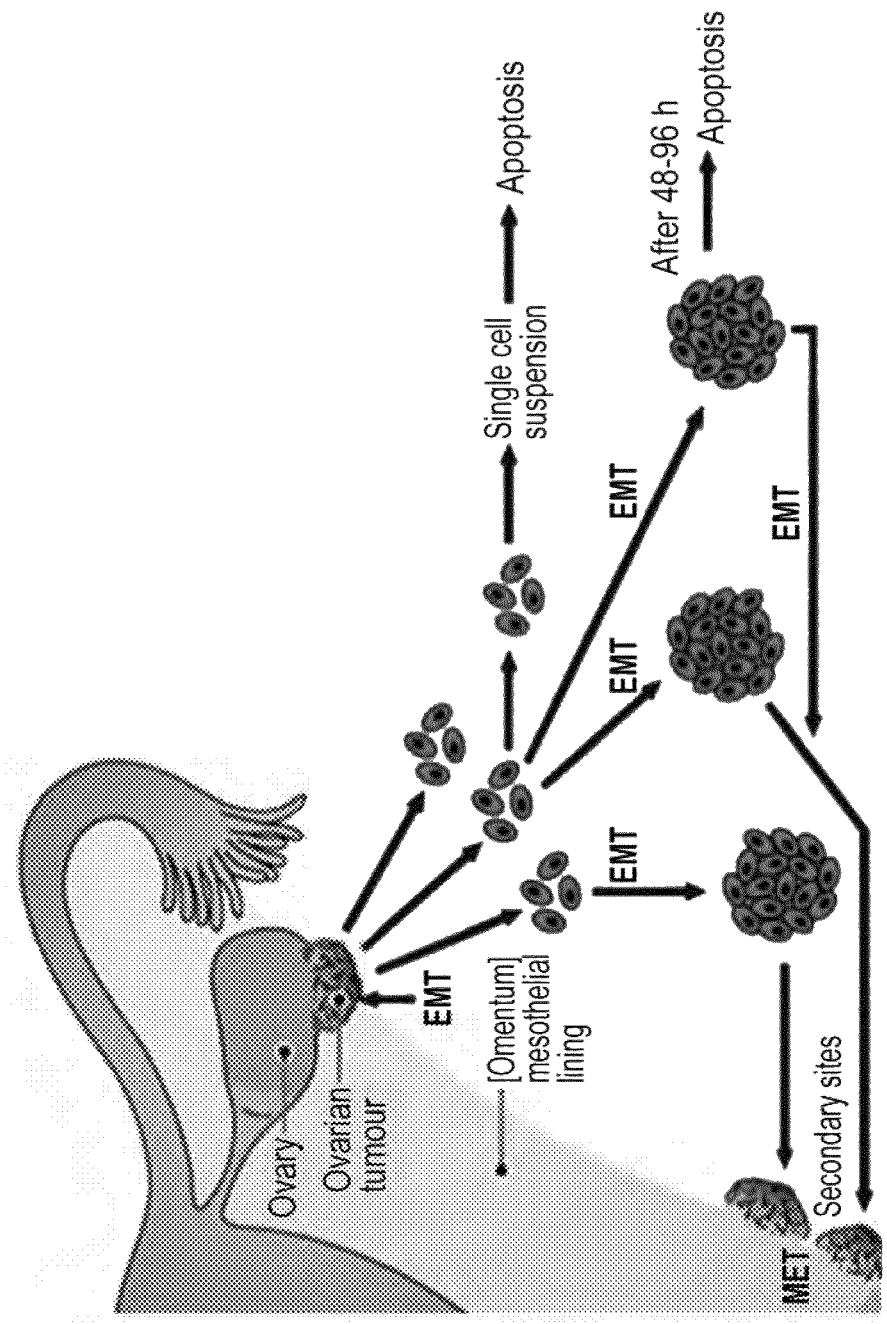
FIG. 15 is a schematic illustrating ascites in the female reproductive system. Ascites—the chicken and the egg. Ascites is a multicellular ecosystem including malignant cells, macrophages, and cancer-associated fibroblasts. One third (⅓) of all patients present with ascites—almost all patients at recurrence (Shield K, Gynecology Oncol, 2009).
Figure 17:
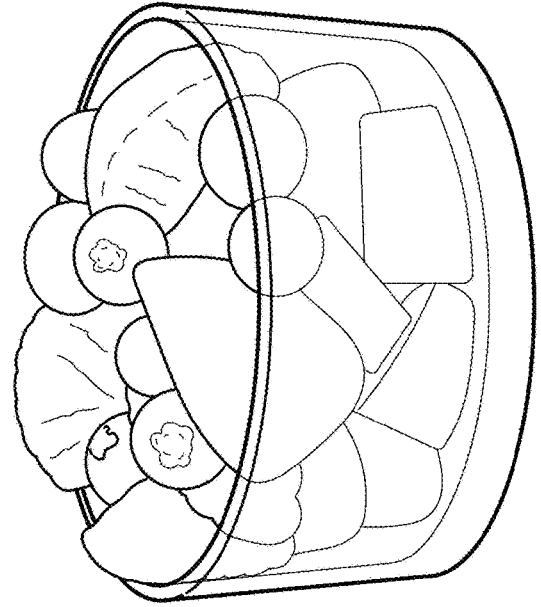
FIG. 17 is an illustration demonstrating the rationale of single-cell sequencing compared to bulk sequencing.
Figure 17:
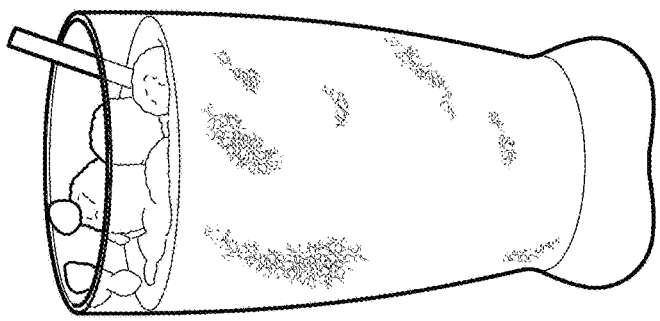
Figure 18:
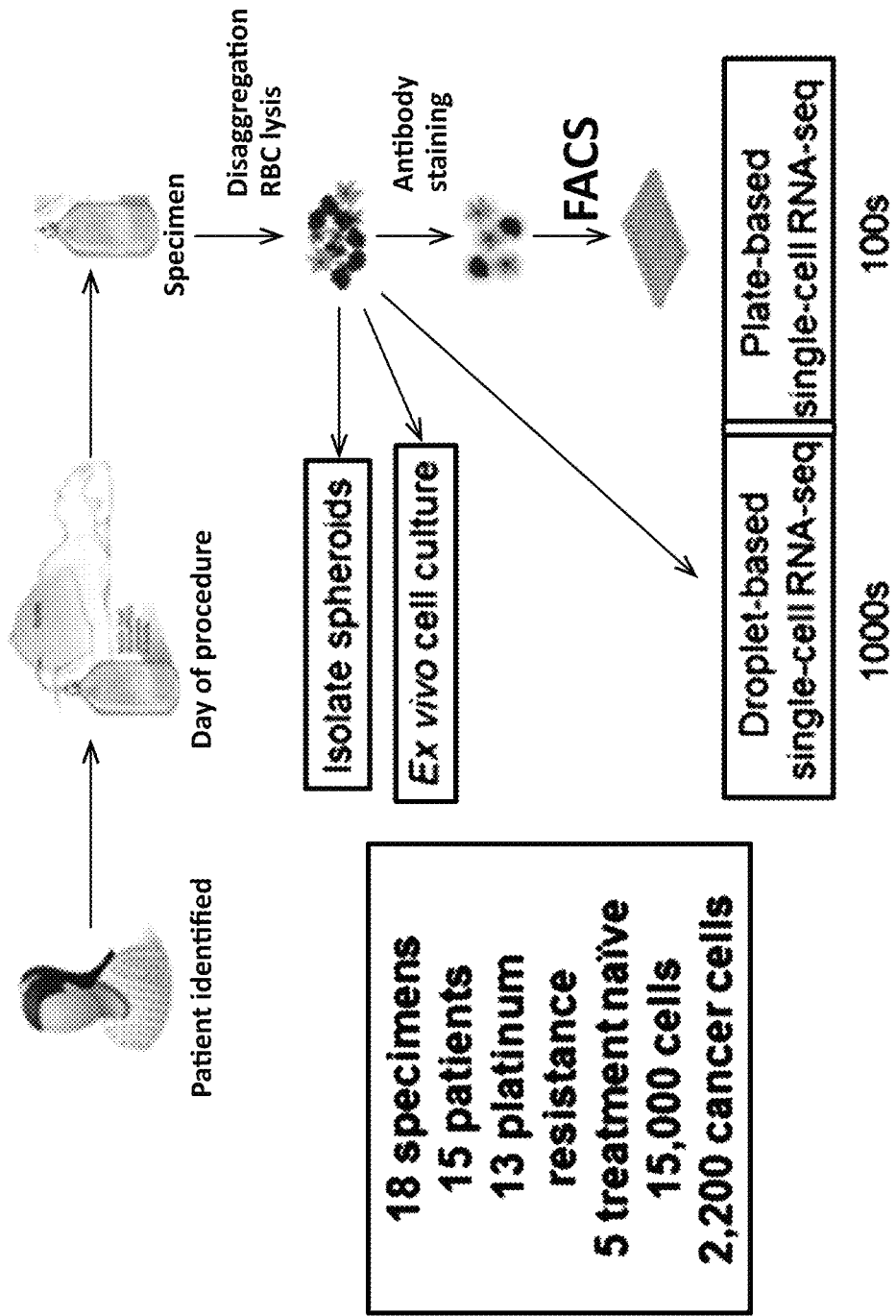
FIG. 18 is a schematic showing the design of a study using cancer patient samples to complete single-cell profiling and drug testing of ascites. Both droplet based sing-cell RNA-seq and plate based single-cell RNA-seq are used for ascites assessment.

A translational workflow was adopted from previous work (Tirosh et al., 2016 Science, 352:189-196; B. Izar and A. Rotem, 2016 Curr. Protoc. Mol. Biol., 116:28.8.1-28.8.12, FIG. 18) for scRNA-seq (FIG. 17 illustrates rationale for single-cell sequencing compared to bulk sequencing) of ascites (FIG. 15 illustrates ascites in the female reproductive system) from patients with HGSC. Upon drainage of ascites, fresh specimens were immediately processed by removal of red blood cells (RBCs), isolation of a cell pellet, depletion of CD45+ immune cells (a major component of ascites) and scRNA-seq profiling using the 10× Genomics droplet platform. Eight specimens were profiled, and following quality controls studies included single-cell profiles for further analysis. The number of cells profiled per patient, their prior treatments, baseline demographics and BRCA1/2 mutation status were determined. Notably, for two patients (3250 and 3288), specimens were collected at two different time points, and in one of those cases (3288) the first specimen was collected prior to any therapy, and the second (named 3288.1) was collected after the first cycle of treatment with carboplatin plus paclitaxel.

A t-distributed stochastic neighbor embedding (tSNE) analysis was performed, which revealed 20 distinct cell clusters (FIG. 1A and FIG. 1). Clusters were annotated based on the top differentially expressed genes as either epithelial (e.g. by epithelial cell adhesion molecule (EPCAM) and cytokeratins and kallikreins), macrophages (e.g. by cluster of differentiation (CD)14, allograft inflammatory factor (AIF)1, colony stimulating factor 1 receptor (CSF1R) and CD163) fibroblasts (e.g. by podoplanin (PDPN), decorin (DCN) and THY1 (CD90)), dendritic cells (e.g. by CD1C, CD1E, C-C motif chemokine receptor (CCR)7 and CD83), B cells (e.g. by CD19 and CD79A/B), T cells (e.g. by CD2 and CD3D/E/G) and erythrocytes (e.g. by GATA binding protein (GATA)1 and hemoglobin) (FIG. 1C). Even though studies depleted immune cells, the cellular composition was still dominated by immune cells and in particular by macrophages. Nevertheless, there was extensive variability in the proportions of cell types and clusters among patients (FIG. 1). For example, in three patients (3281, 3288 and 3290), the most abundant cell type was macrophages, in two patients it was epithelial cells and in one patient (3266) it was B cells. Some of these differences relate to differential efficiency in immune depletion or in cellular viability, yet other differences are more likely biological, such as the relative proportion of distinct immune cells (e.g. macrophage vs. lymphocytes) or non-immune cells (e.g. epithelial vs. fibroblasts).

After gleaning initial insights into the main cell types that constitute malignant ascites, studies were completed to resolve the diversity of cellular states that correspond to each cell type, including the four clusters of epithelial cells, four clusters of fibroblasts, four clusters of macrophages and two clusters of dendritic cells. For each cell type, differentially expressed genes between distinct clusters were identified (FIG. 1D). For example, the malignant cell clusters differed by the expression of GATA2, SRY (sex determining region Y)-box 2 (SOX2), claudin (CLDN)6/9, homeobox protein (HOX)B5 and other genes (FIG. 1D).

Within the immune cell types, analysis of differentially expressed genes suggested that the two dendritic clusters differ by their maturation, with immature CD83-high dendritic cells (DCs) and more mature CCR7-high cells. The four macrophage clusters differed in the expression of various genes including those involved in activation (e.g. FBJ murine osteosarcoma viral oncogene homolog B (FOSB)), proliferation (e.g. cyclin-dependent kinase (CDK) 1) and immune suppression (indoleamine 2,3-dioxygenase 1 (IDO1)).

Figure 1C:
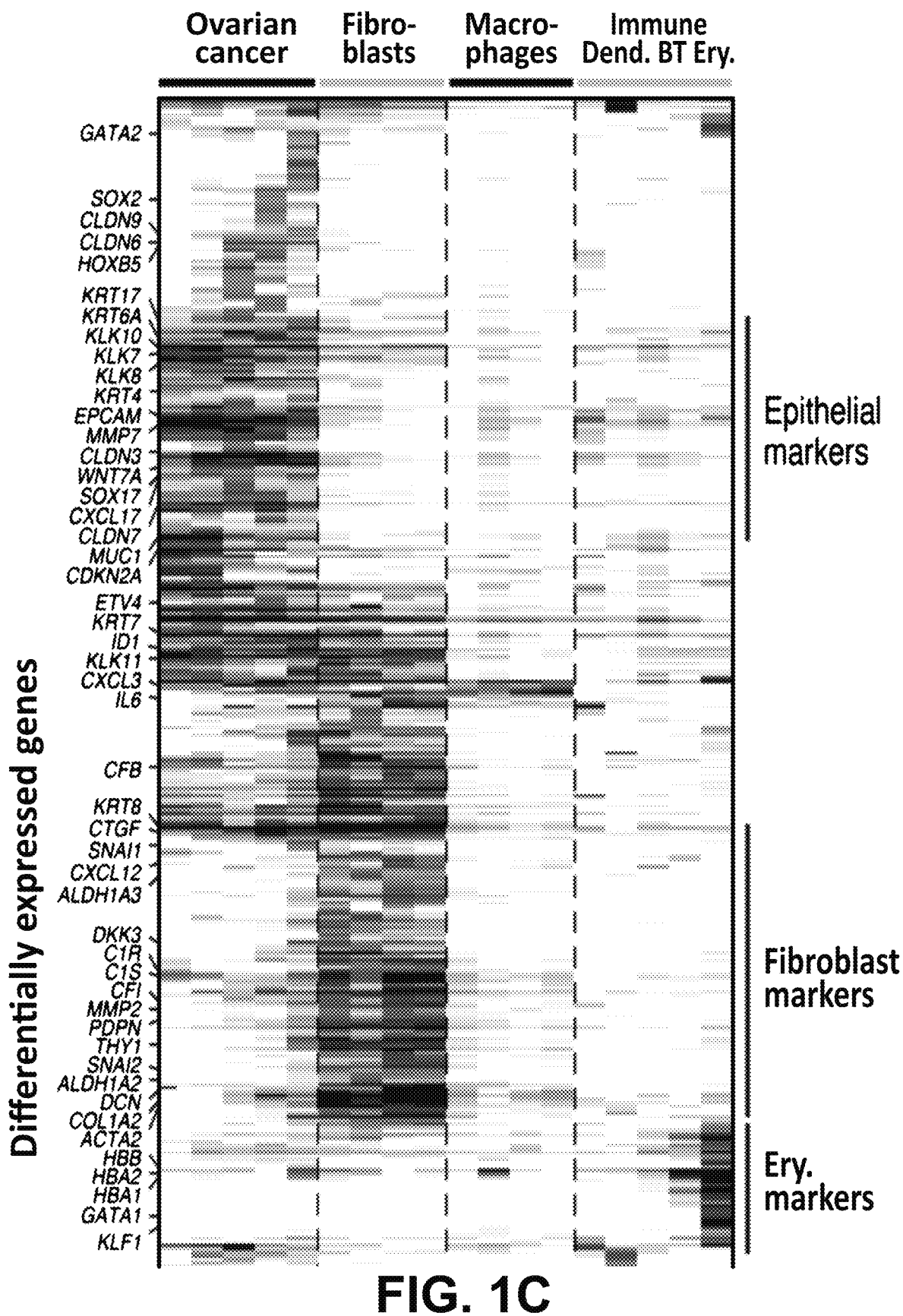
Figure 1C:
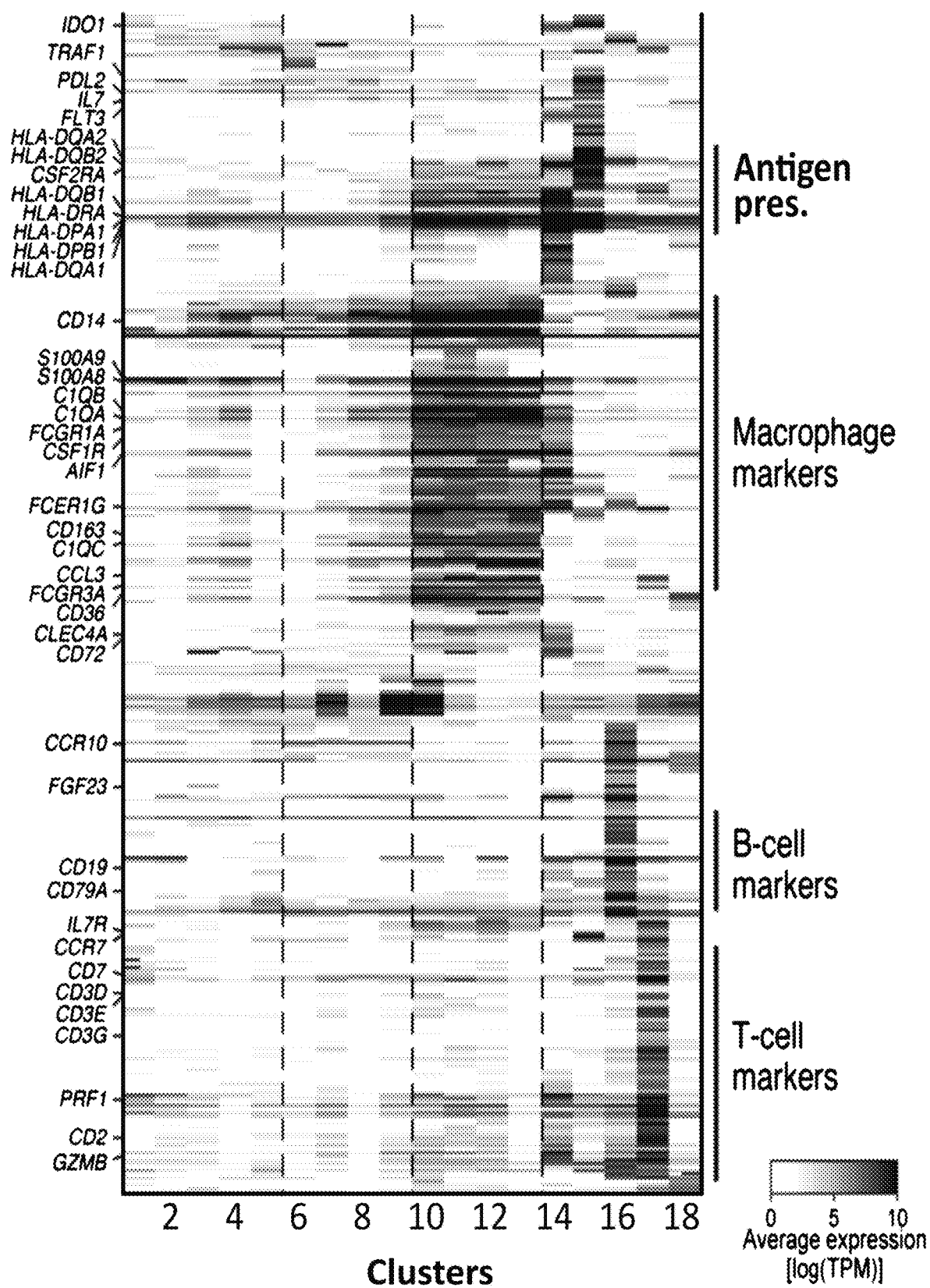
Figure 1C:
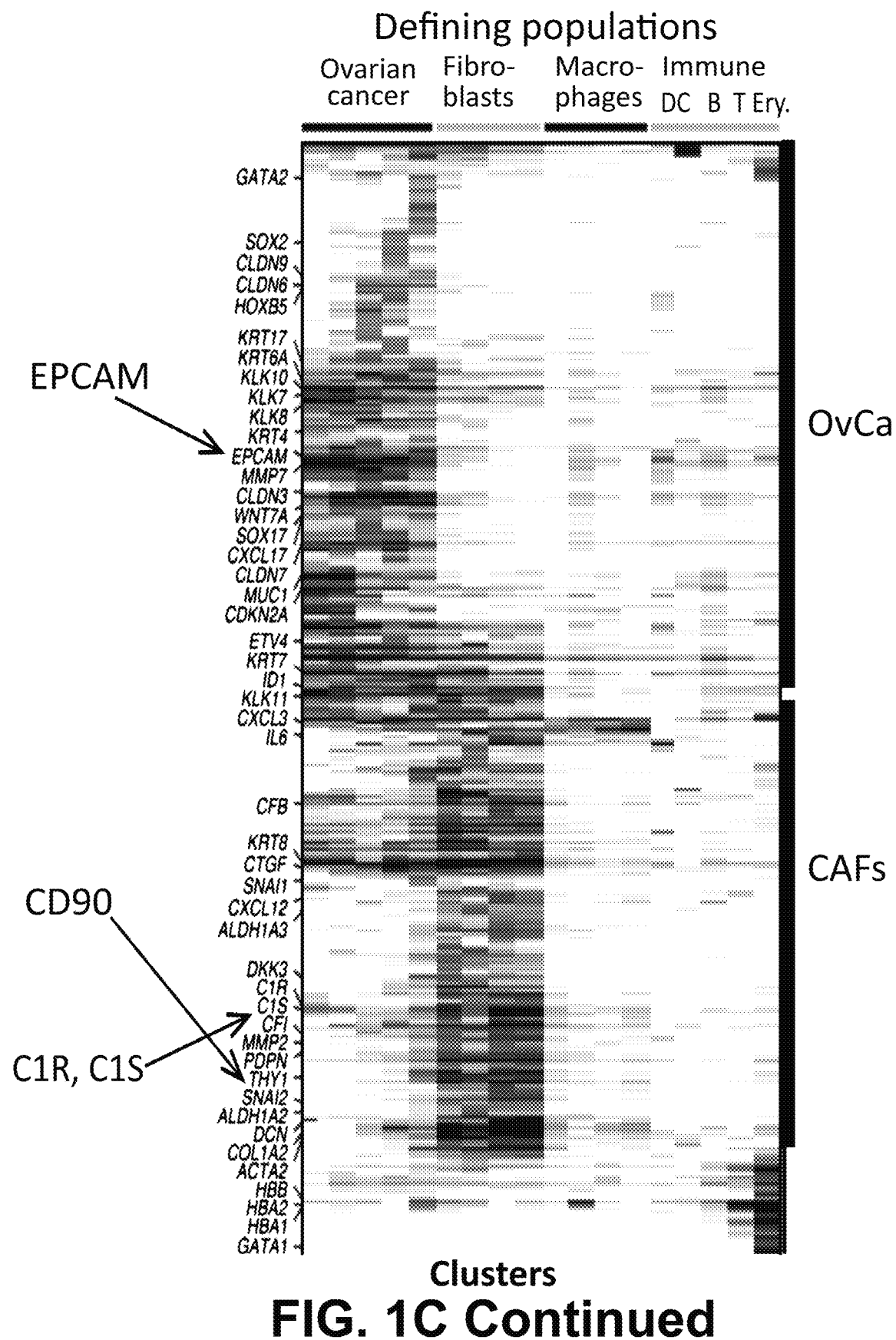
Figure 1C:
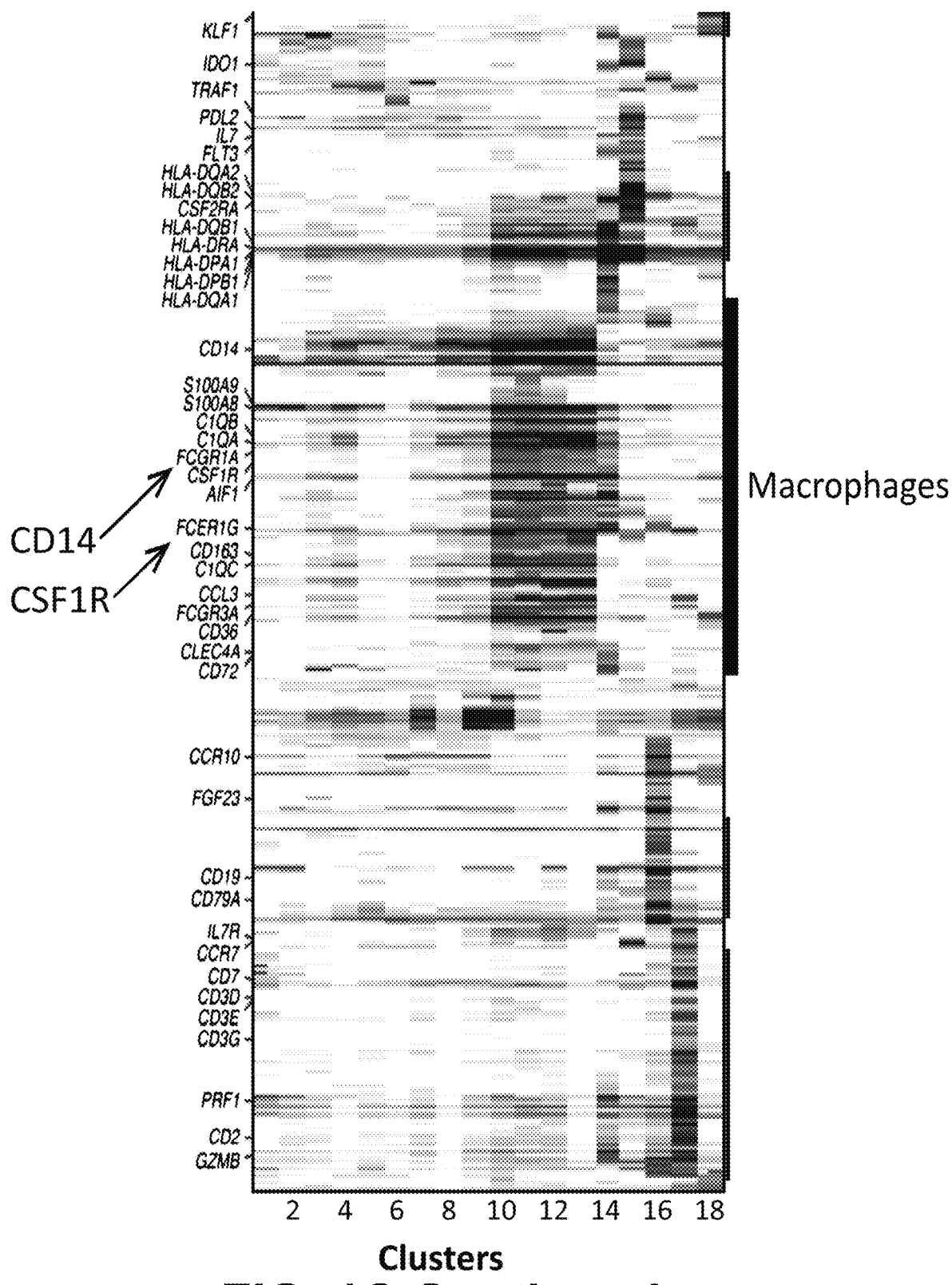
Figure 1D:
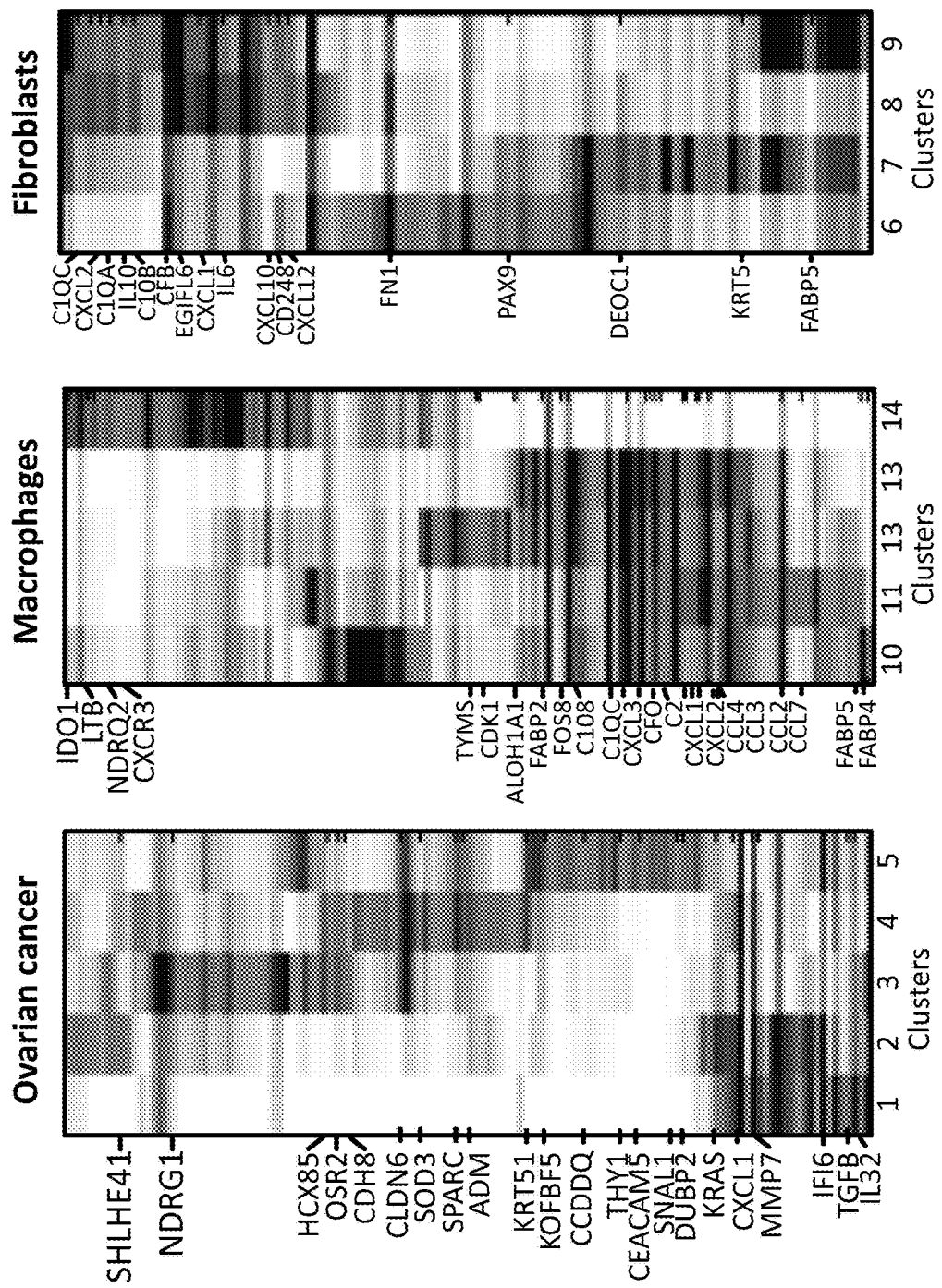
Figure 1D:
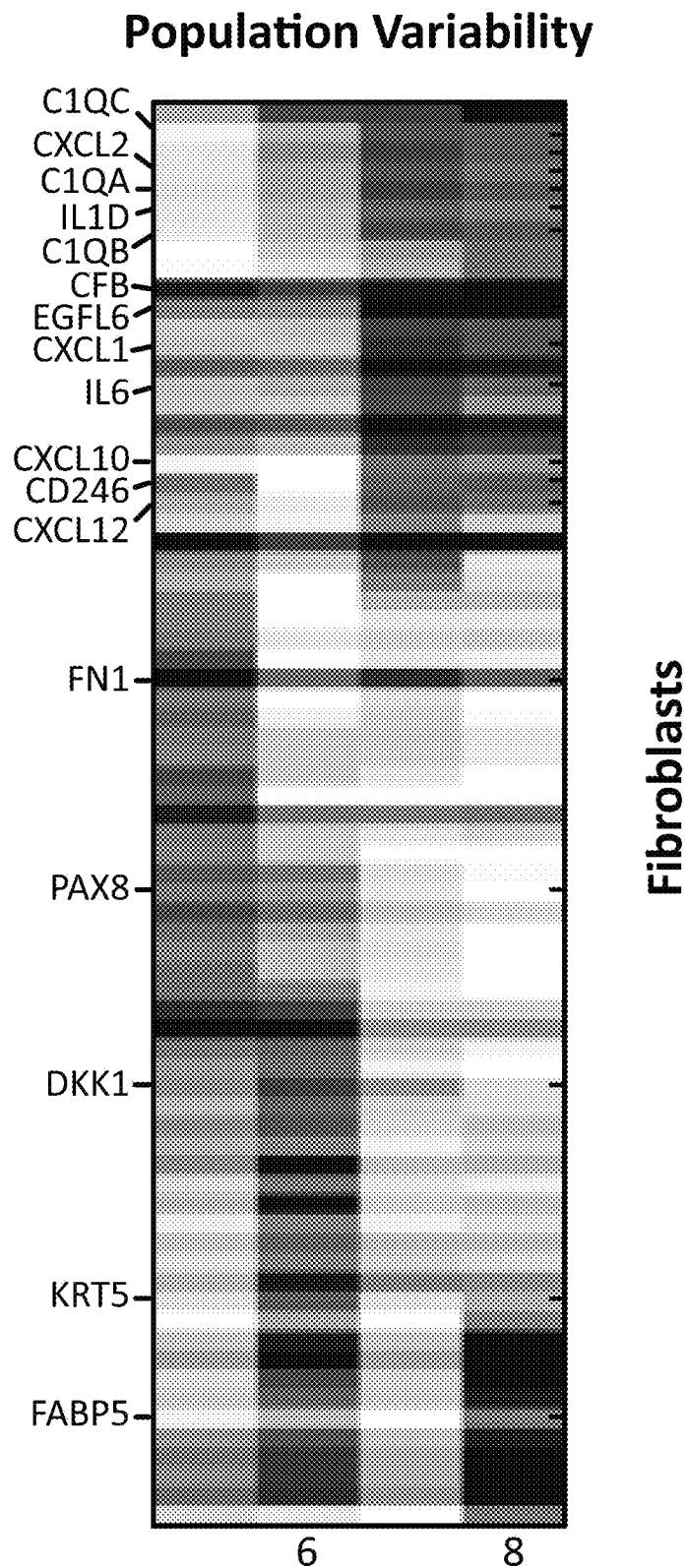

Interestingly, the fibroblasts demonstrated variability among sub-groups; the four clusters showed high expression of defining markers, including CD90 (THY1), DCN, connective tissue growth factor (CTGF), as well as several complement factors (complement component (C)1R, CIS, complement factor (CF)I), in line with prior observations in melanoma (Tirosh et al., 2016 Science, 352:189-196, FIG. 1C). However, the fibroblast clusters differed by the expression of additional complement factors (C1QA/B/C, CFB), chemokines (CXCL1/2/10/12), and cytokines (IL6 and IL10) (FIG. 1D). These immune-related genes were consistently higher in two of the fibroblasts clusters, suggesting that these reflect immunomodulatory fibroblasts (P. Cirri and P. Chiarugi, 2011 Am. J. Cancer Res., 1:482-497). Notably, CXCL12, the ligand for CXCR4 on ovarian cancer cells, was highly expressed by all fibroblast populations. The CXCL12-CXCR4 axis was shown to activate STAT3 signaling and driver metastasis in breast and lung cancer (X. Liu et al., 2014 Oncol. Rep., 32:2760-2768; M. Pfeiffer et al., 2009 Br. J. Cancer, 100:1949-1956), and this interaction has been therapeutically exploited (Kajiyama et al., 2008 Int. J. Cancer, 122:91-99).

IL-6, a cytokine with pleiotropic effects and the primary ligand that activates the JAK/STAT pathway (Darnell et al., 1994 Science, 264:1415-1421), constitutes a key cytokine in ovarian cancer ascites (Matte et al., 2012 Am. J. Cancer Res., 2:566-580), links inflammation to cancer (Iliopoulos et al., 2009 Cell, 139:693-706; Kulbe et al., 2012 Cancer Res., 72:66-75) and is associated with a poor prognosis (Coward et al., 2011 Clin. Cancer Res. Off. J. Am. Assoc. Cancer Res., 17:6083-6096). Most cells in the ascites ecosystem express IL6, but expression was particularly high by two fibroblast clusters 8 and 9. Thus, subsets of fibroblasts express distinct immunomodulatory programs that shape the immune environment in ascites.

Example 2—scRNA-Seq of Cancer Cells Reveals Inter- and Intra-Tumor Heterogeneity in HGSC The droplet-based profiling provided insights into transcriptomes of a large number of cells, but had a relatively low number of cancer cells and with limited coverage of each single cell transcriptome. To more deeply interrogate malignant cells isolated from ascites, studies were completed with enriching specifically for cancer cells. For this purpose, viable cancer cells were isolated by fluorophore-activated cell sorting (FACS) in 96-well plates staining for EPCAM and CD24. The combination of these surface markers was previously shown to be highly sensitive and specific for ovarian cancer cells (Peterson et al., 2013 Proc. Natl. Acad. Sci. U.S.A., 110:E4978-4986). Individually sorted cells were profiled using the modified Smart-Seq2 protocol (Picelli et al., 2013 Nat. Methods, 10:1096-1098; Tombetta et al., 2014 Curr. Protoc. Mol. Biol., 107:4.22.1-4.22.17). With this approach, significantly greater cancer cell proportions were obtained (see below along with higher transcriptome coverage). Fourteen specimens were collected and profiles passing quality control assessment were obtained.

In FIG. 2A-FIG. 2E using the same experimental design as FIG. 1A-FIG. 1D, tSNE was used to find that tumor cells cluster mostly based on their tumor of origin. Again, data find an overrepresentation of inflammatory pathways, including TNF-alpha signaling and STAT-3 signaling in these resistant patient single-cells.

Figure 2A:
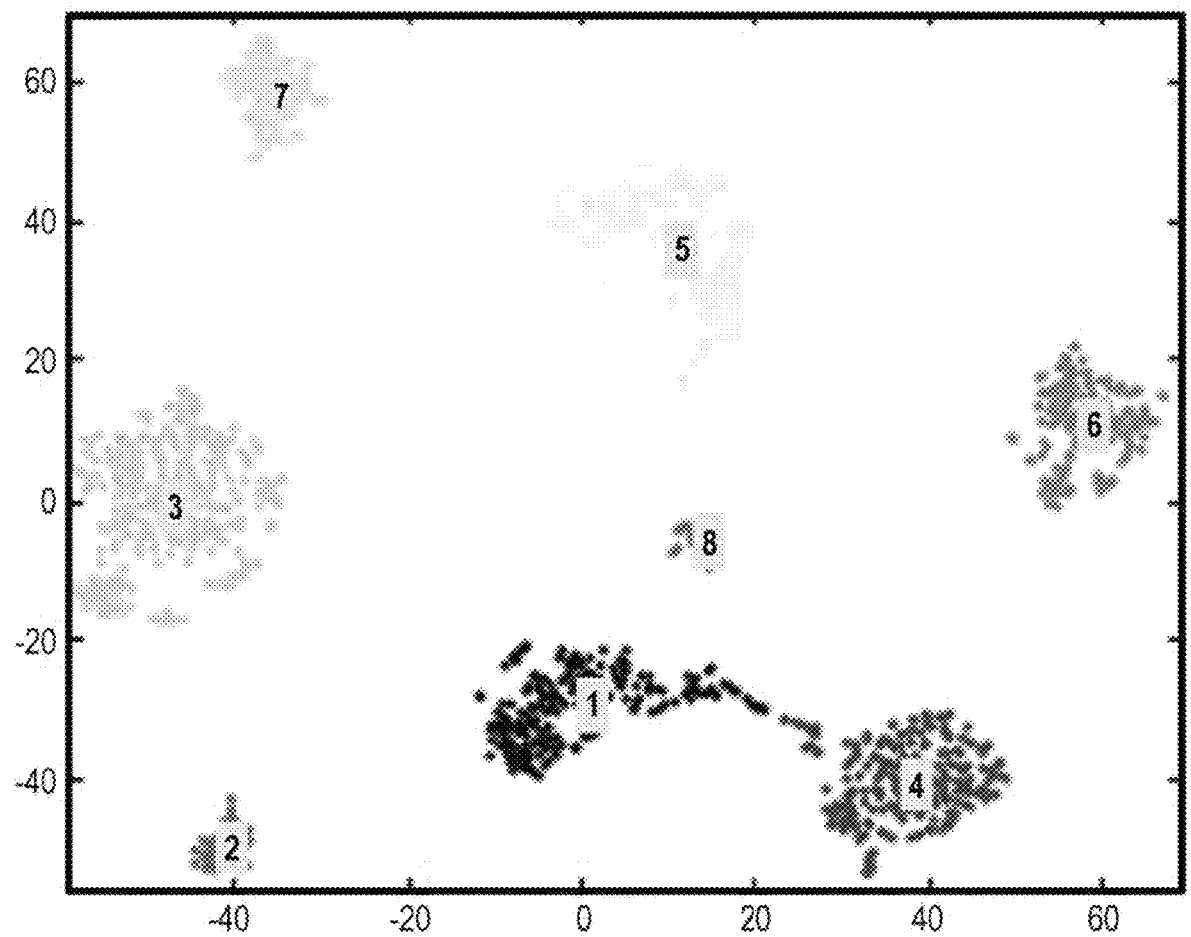
FIG. 2A-FIG. 2E are a series of dot plots, bar charts, and gene expression profiles (heatmaps) depicting tumor cell subtypes and highlighting diversity of cancer cell expression profiles as defined by plate-based single cell RNA-seq.
Figure 2B:
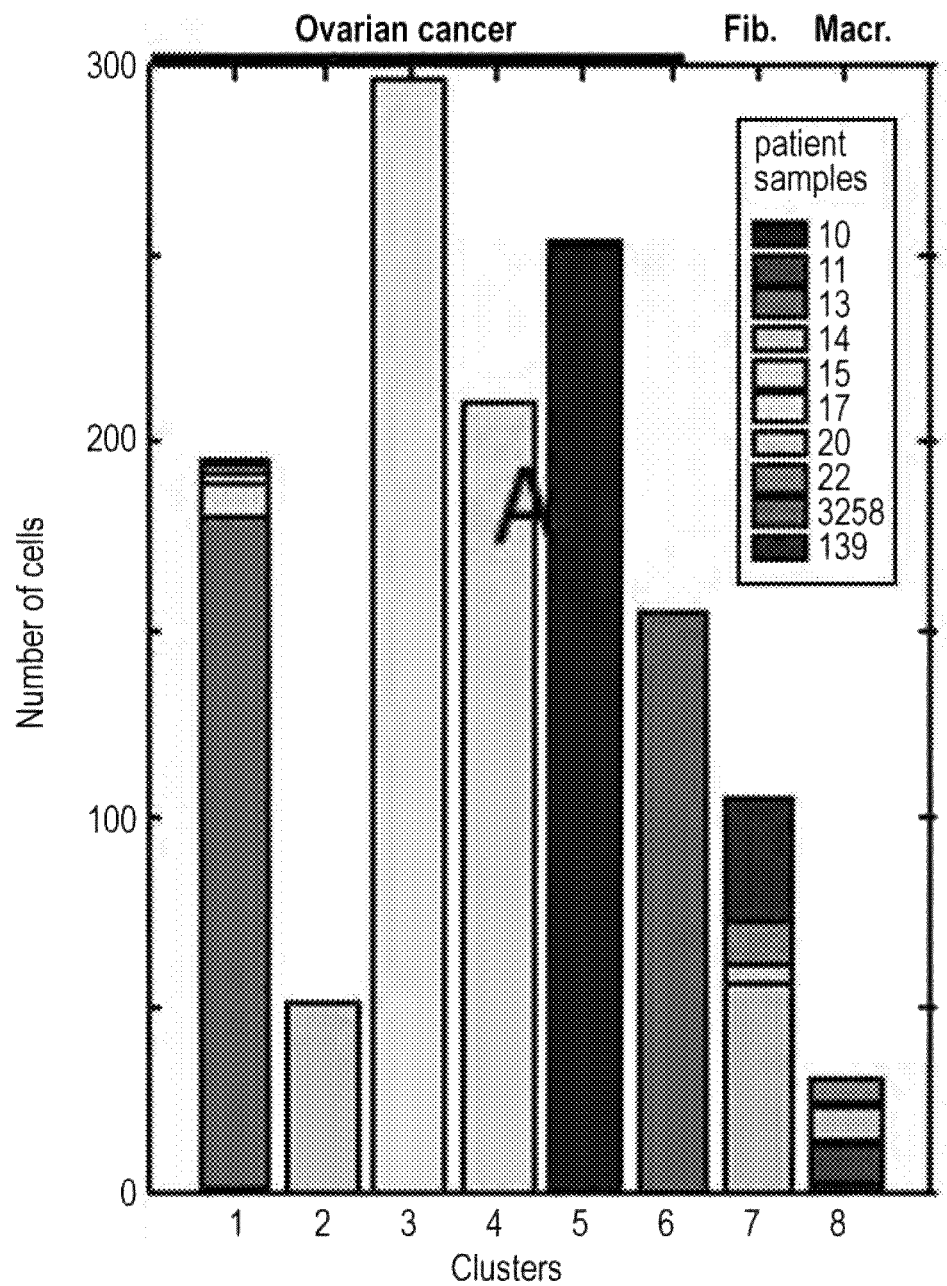
Figure 2C:
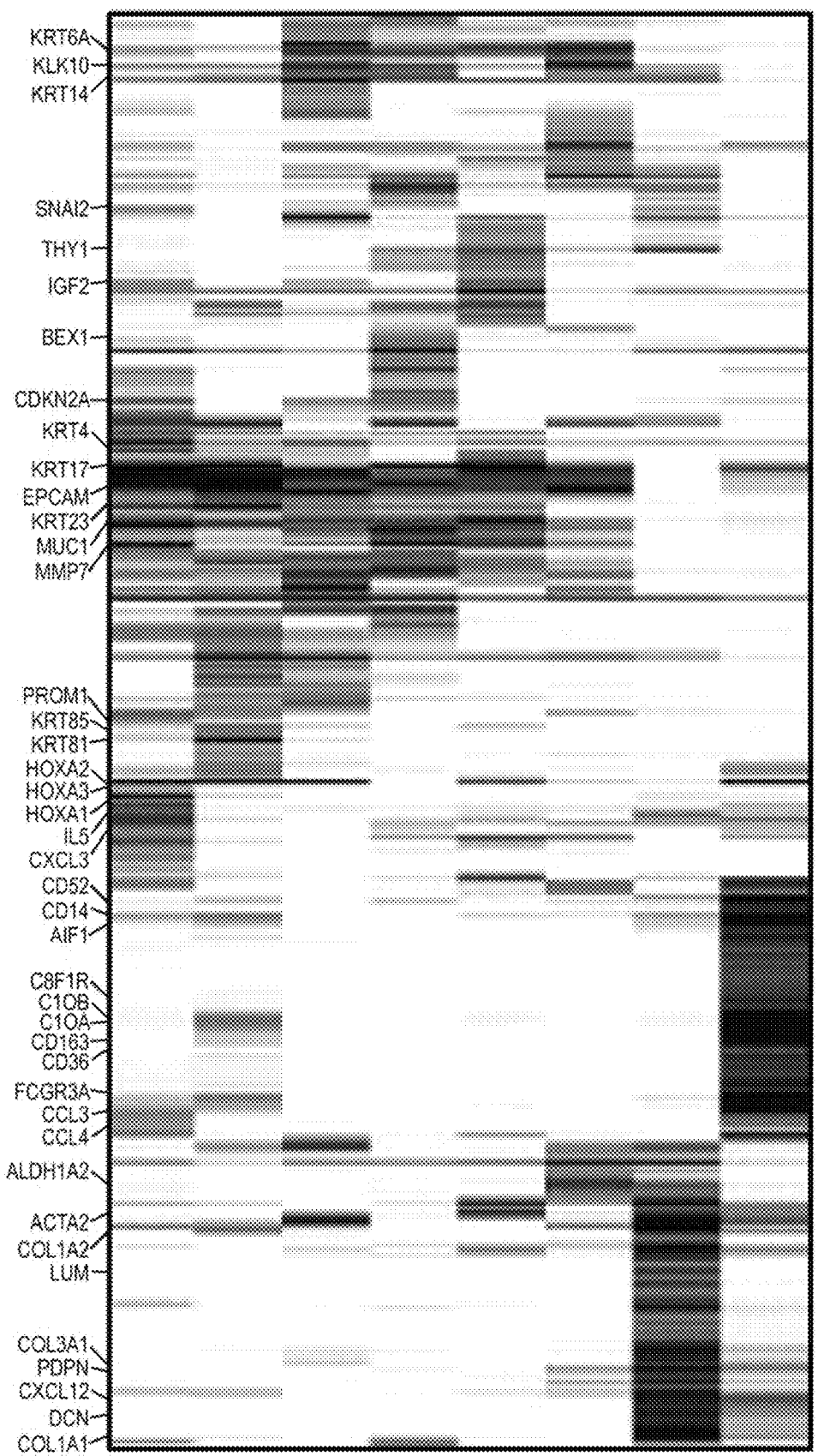
Figure 2C:
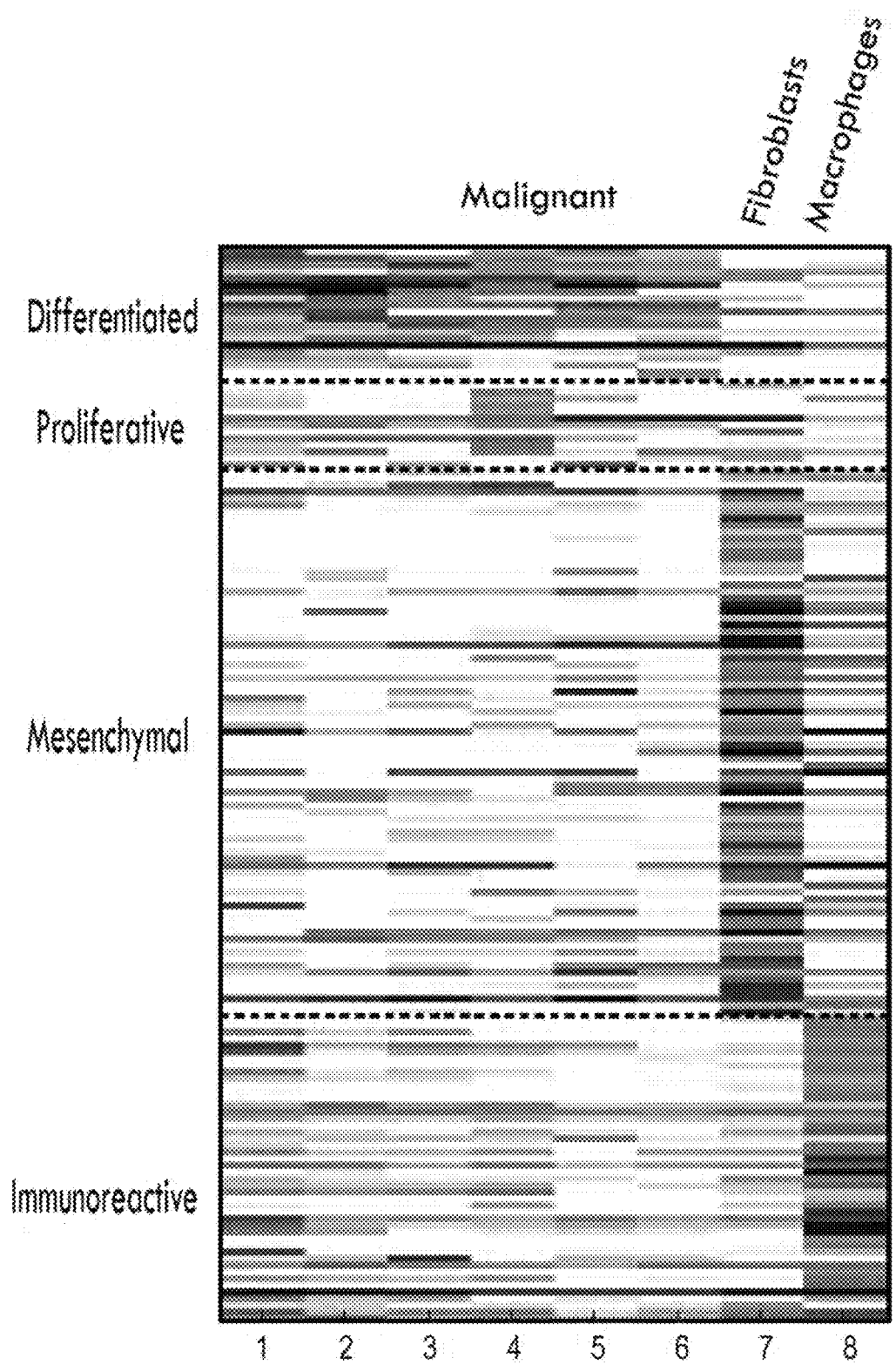

Eight clusters were identified by tSNE and density clustering (FIG. 2A and FIG. 2B). Differential expression across these clusters (FIG. 2C) indicated that the vast majority of cells were epithelial (clusters 1-6), while a small proportion of cells were fibroblasts (cluster 7) and macrophages (cluster 8). The cancer cells clustered primarily by their patient of origin (FIG. 2B), with inter-individual heterogeneity in the expression of many genes (FIG. 2B). For example, cluster 1 (mapping primarily to patient GL10) showed significantly higher expression of CD133, a cell surface marker frequently used to identify putative ovarian cancer stem cells. Other variable genes among the epithelial clusters included IL6 and CXCL3, indicating cancer cell-intrinsic inflammatory signaling.

Figure 2D:
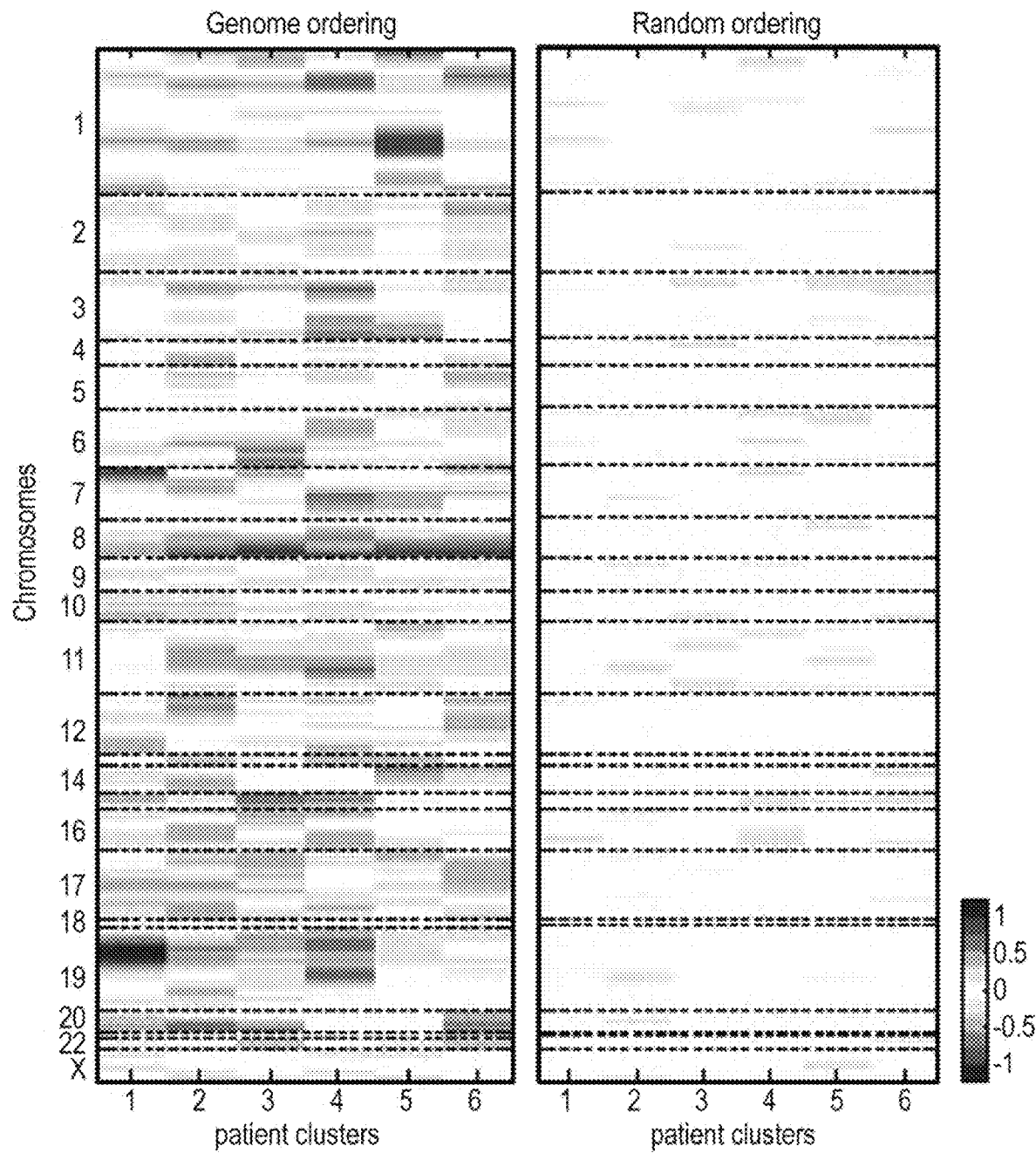

To further examine this inter-tumor heterogeneity, cells were restricted from each cluster to those from the dominant patient while excluding the few cells that map to cluster of a different patient. To validate that these epithelial clusters correspond to malignant cells, chromosomal copy number variations (CNVs) were inferred from the average expression of genes in each chromosomal region (FIG. 2D). As expected, a substantial burden of CNVs across the genomic landscape was found, which was not detected in a control analysis where the genes were randomly assigned to genomic locations (FIG. 2D), Using this approach, the majority of CNVs identified by whole-exome sequencing of 489 high-grade serous ovarian cancers were identified (T. C. G. A. R. Network, 2011 Nature, 474:609-615). While the resolution of this approach is restricted to inference of large-scale CNVs, CNVs were not detected that were exclusive to one cluster, indicating that variability in gene expression among clusters was not primarily due to genomic differences among patients.

Figure 2E:
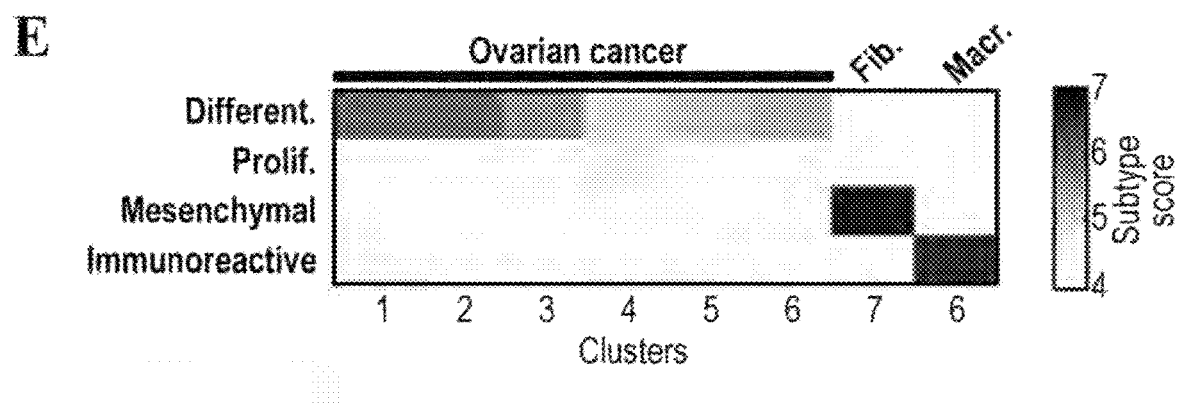

To investigate whether TCGA-identified subtypes (differentiated, proliferative, mesenchymal and immunoreactive) explain differences between patients, each cluster was scored for the expression of TCGA-derived subtype signatures. All six cancer cell clusters highly expressed the "differentiated" signature and only one cluster (cluster 4) strongly expressed the "proliferative" signature (FIG. 2E). Surprisingly, the "mesenchymal" and "immunoreactive" signatures showed weak or no expression in cancer cell clusters and were only reflective of fibroblast infiltration and immune cell infiltration, and not intrinsic to the tumor cells. The mesenchymal signature was primarily reflective of fibroblast gene expression, while the immunoreactive signature was primarily expressed by macrophages. These results suggest that (i) the mesenchymal and immunoreactive subtypes previously identified by bulk RNA-profiling probably represent the intratumoral abundance of fibroblasts and macrophages, respectively, in the tumor microenvironment; (ii) the differentiated subtype reflects a consistent program of cancer cells across HGSOC, and thus mapped to tumors of high purity; (T. C. G. A. R. Network, 2011 Nature, 474:609-615) the proliferative subtype is the subtype that truly reflects a unique program that is specific to a subset of HGSC tumors.

Figure 14:
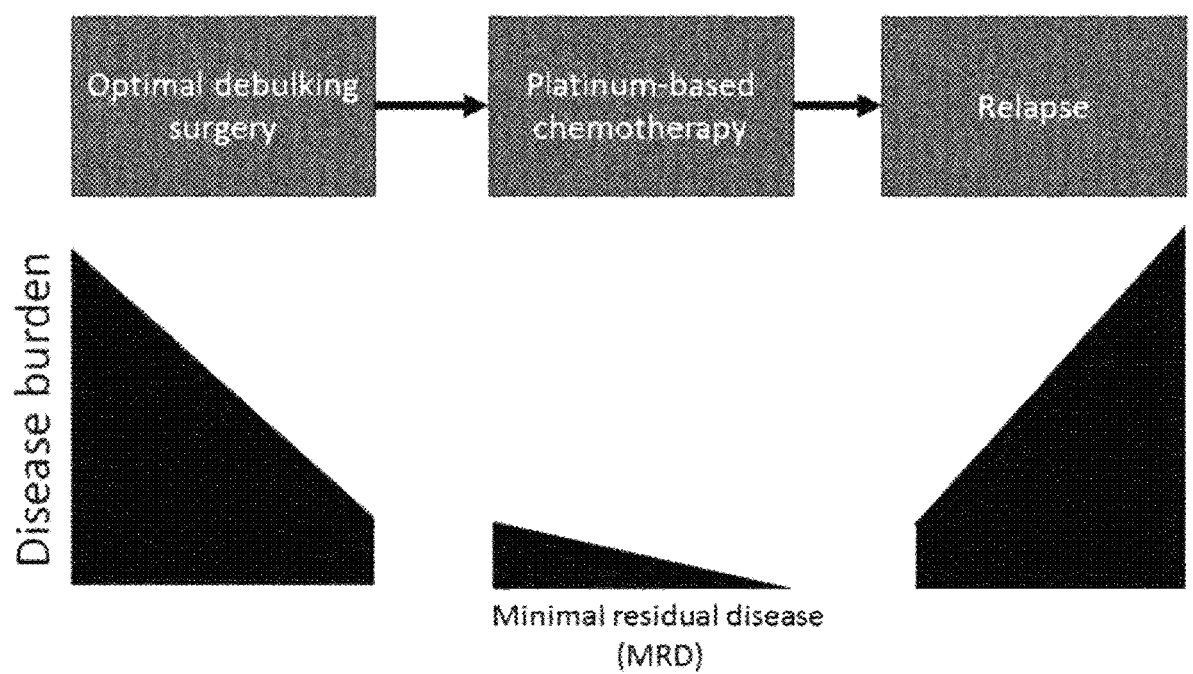
FIG. 14 is a schematic illustrating the typical results of ideal therapy for ovarian cancer.
Figure 16A:
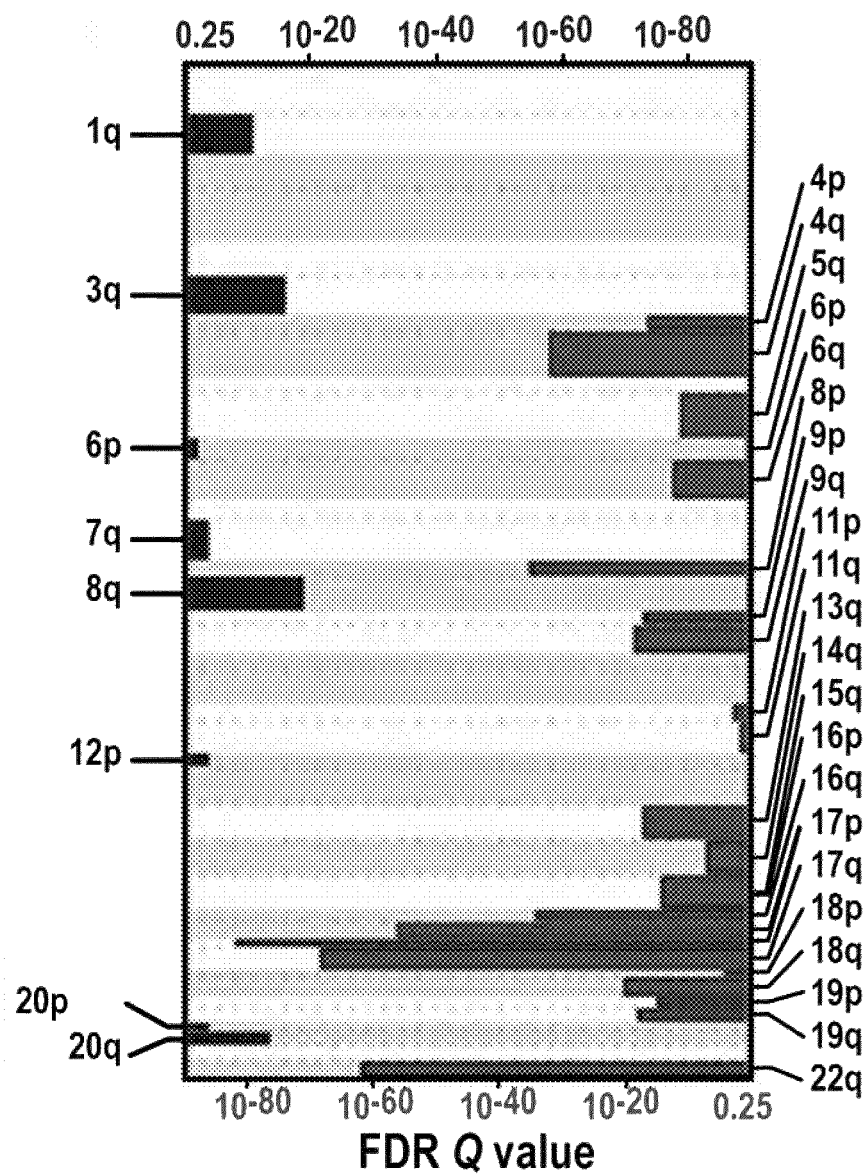
FIG. 16A-FIG. 16C are a series of bar charts and a gene expression profile illustrating genomic characterization of ovarian cancer (OvCa) and platinum-resistance.
Figure 16B:
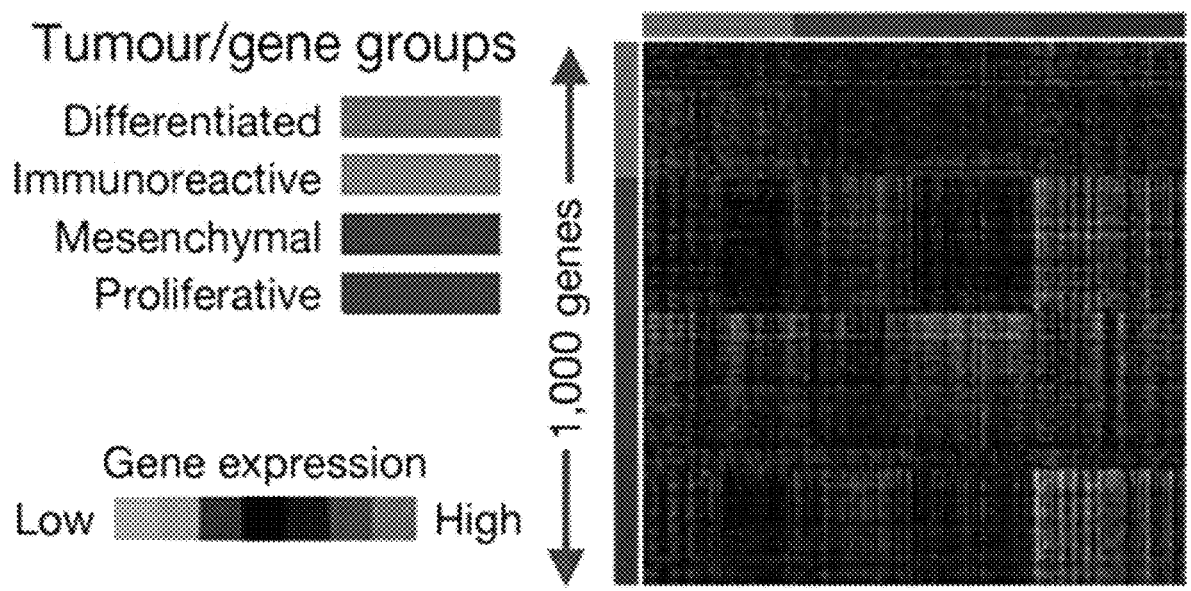
Figure 16C:
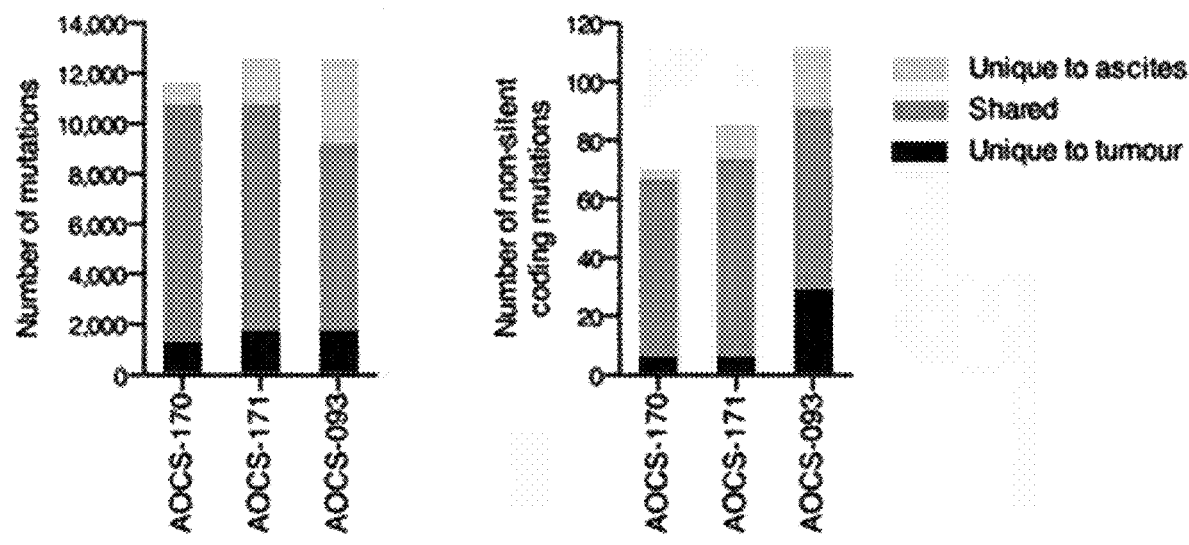

Example 3—Unbiased Analysis of Intra-Tumor Heterogeneity Reveals Expression of Distinct Inflammatory Programs and a Shared Activation of the JAK/STAT Pathway in Platinum-Resistant Ovarian Cancer FIG. 16A-FIG. 16C depict a series of bar charts and gene expression profiles illustrating previous genomic characterization of ovarian cancer and platinum-resistance (Tirosh et al., 2016 Science., 352:189-196; Gaillard et al., 2016 Gynecology Oncol. Res. Pract., 3:11). FIG. 14 illustrates ideal ovarian cancer therapy.

The next study completed assessed patterns of intra-tumor heterogeneity in five patients for which single-cell RNA-seq profiles of >100 cancer cells were obtained. For each patient, non-negative matrix factorization (NMF) was used to identify expression modules that consist of genes with coherent variability across cancer cells and highlight a subset of cells. Identified were 6-9 such modules in each tumor for a total of 35 modules (FIG. 3A-FIG. 3C, FIG. 10). Examining the top genes that correspond to each of these modules suggested diverse functions, including cell cycle (e.g. cyclin-A (CCNA)2, CCNB2, aurora kinase B (AURKB)), inflammation (e.g. IL6, IL32, TNF, interferon alpha inducible protein (IFI)6, and stress or activation (e.g. heat shock protein family A (HSPA)5-7, activating transcription factor (ATF)4, c-Jun Kinase (JNK), DNA damage-inducible transcript 3 (DDIT3)).

Figure 8A:
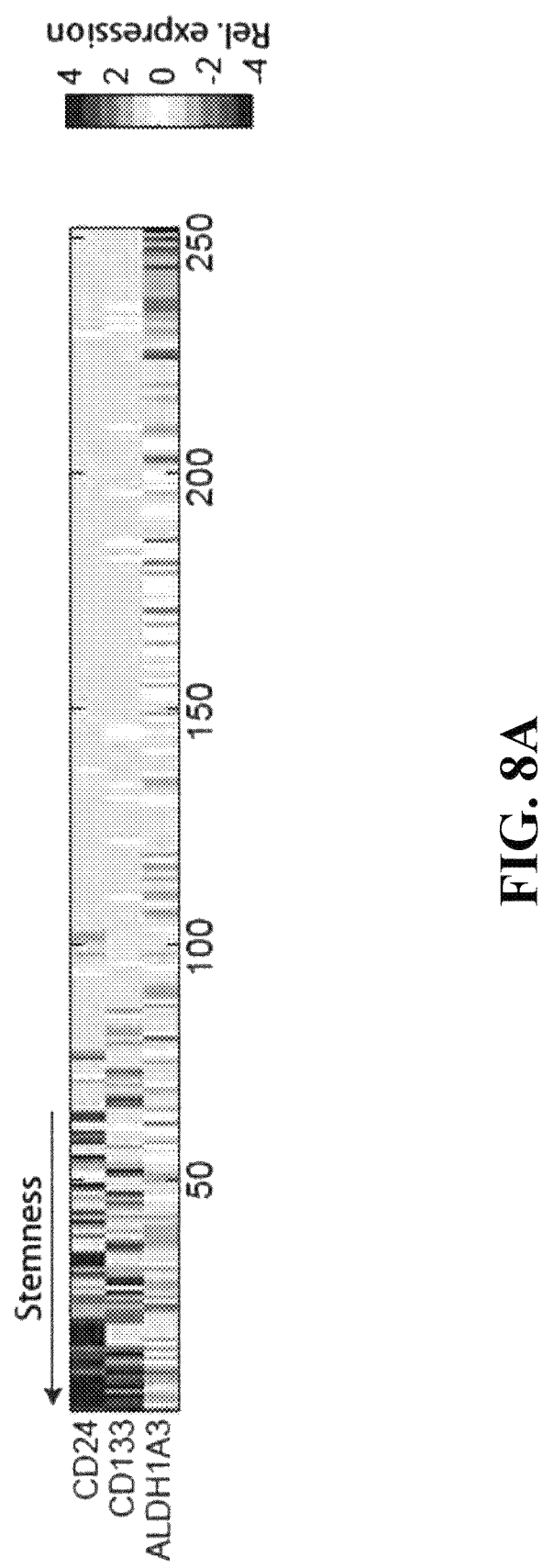
FIG. 8A-FIG. 8E are a series of graphs depicting expression modules from patient ascites samples and a putative stemness program.
Figure 8B:
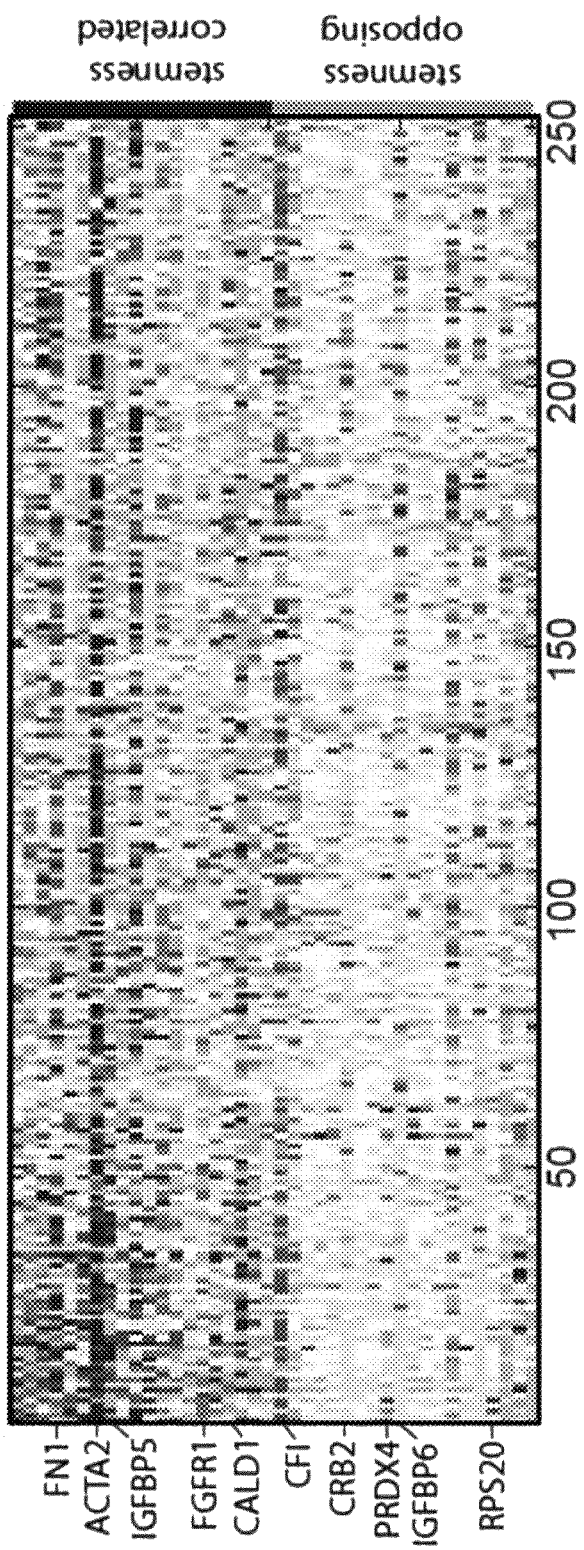
Figure 8C:
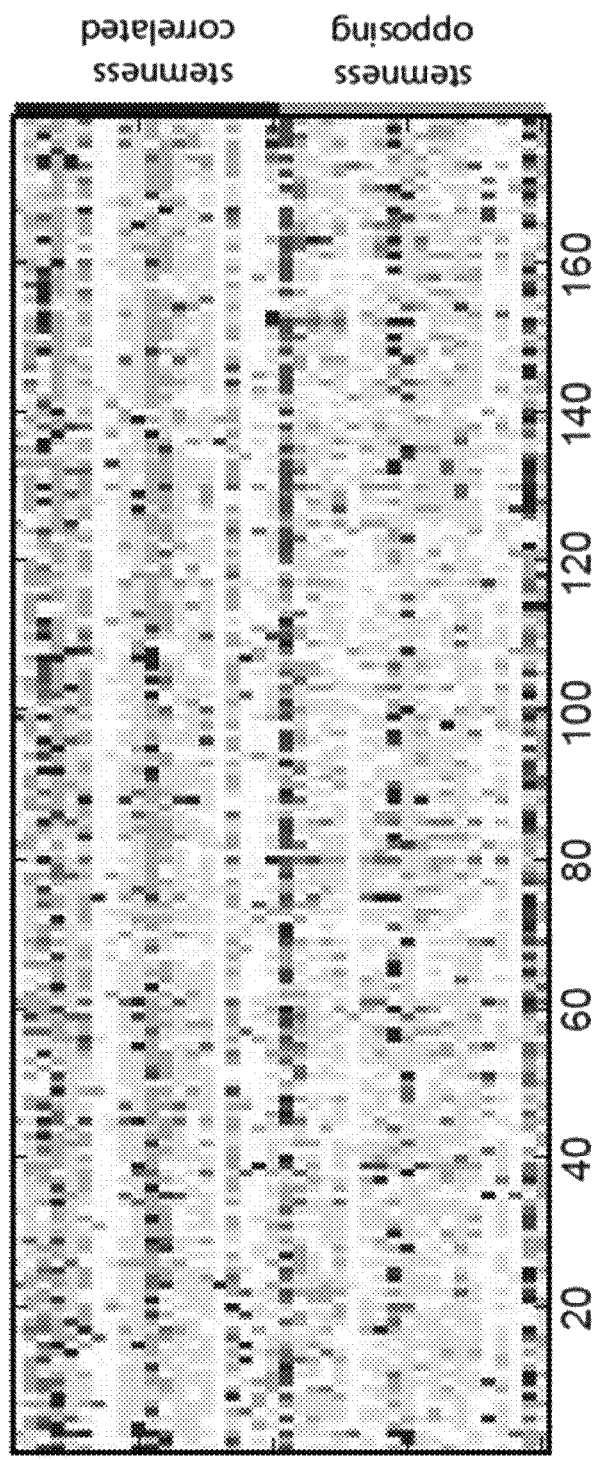
Figure 8D:
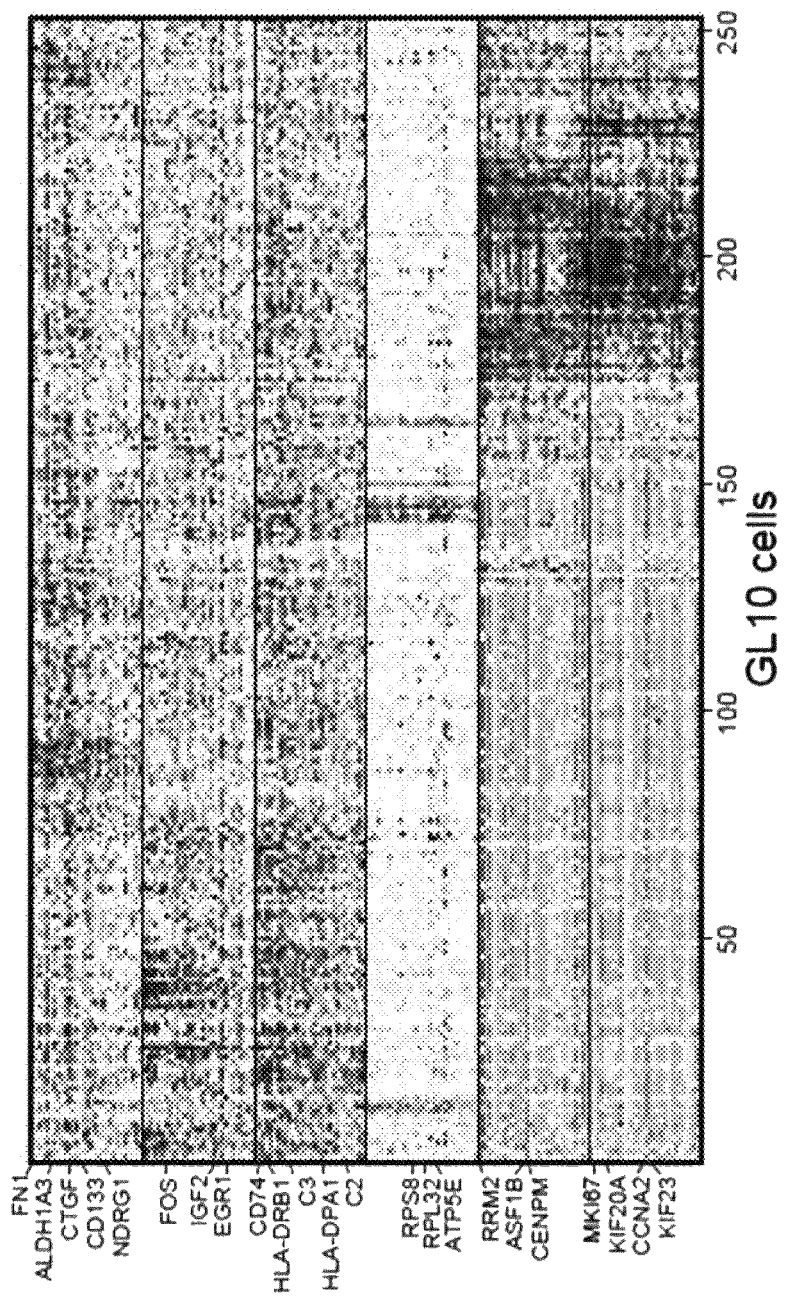
Figure 8E:
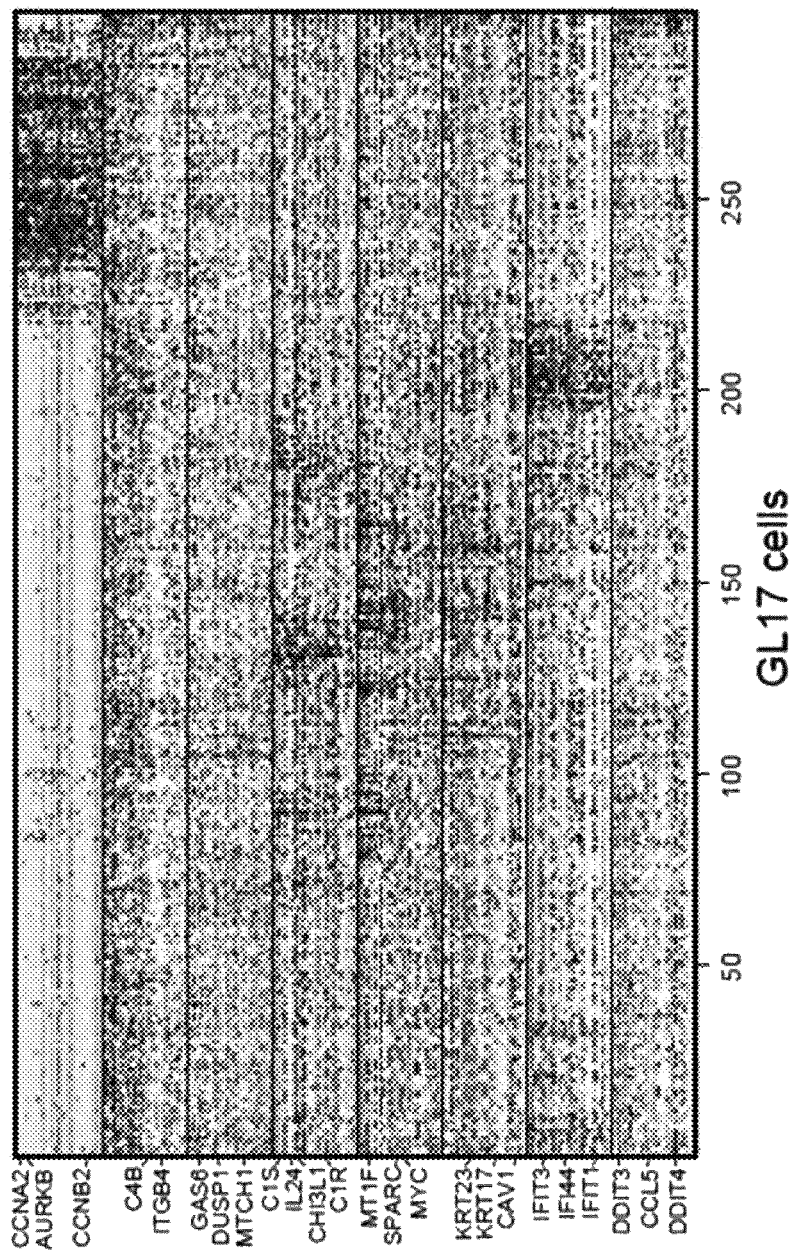

The top genes of module #1 from GL10 included ALDH1A3 and CD133 (PROM1) (FIG. 8A). The consistent expression of these prominent stem-ness markers (Silva et al., 2011 Cancer Res., 71:3991-4001) suggests that this module highlights a subset of ovarian cancer stem cells. Other top genes in this module are associated with mesenchymal phenotypes (fibronectin (FN)1, alpha-actin 2 (ACTA2) and myosin light chain gene (MYL9)) and secreted molecules, such as growth arrest specific protein 6 (GAS6), the only known ligand for the tyrosine kinase AXL, which is implicated in de-differentiation and drug resistance in several cancers (X. Wu et al., 2014 Oncotarget, 5:9546-9563). However, similar modules were not detected in any of the other four patients. As another approach to evaluate the presence of stem-ness programs, studies were performed that tested, in each tumor, the correlation among these three stem-ness markers. Consistent with the NMF analysis, the stem-ness markers were significantly ($P<0.05$) correlated only in GL10. Furthermore, the genes most correlated with these stem-ness markers in GL10 were not co-expressed in other tumors (FIG. 8D-FIG. 8E). Taken together, a putative stem-ness program in GL10 was identified, but profiling of larger patient cohorts is required to examine whether this reflects a recurrent signature in ovarian cancer.

Figure 3A:
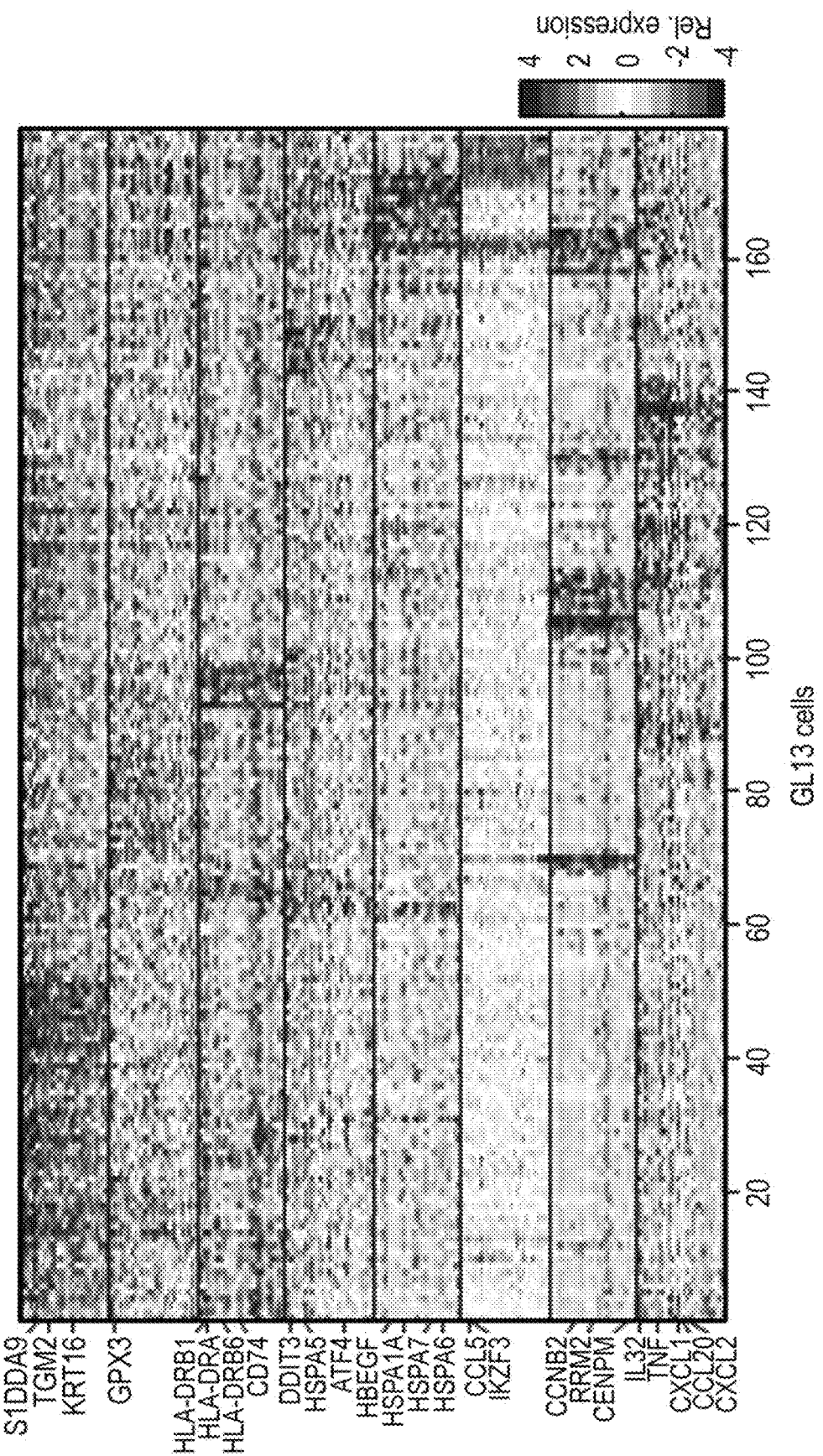
FIG. 3A-FIG. 3F are a series of graphs depicting expression modules with intra-tumoral variability among ovarian cancer cells from patient ascites samples. Distinct and shared cell state modules in platinum resistance were found. Significant heterogeneity of cell states and modules within tumors was observed. Shared programs involve cell cycle and immune related pathways (e.g. janus kinase/signal transducer and activator of transcription (JAK/STAT) signaling).
Figure 3B:
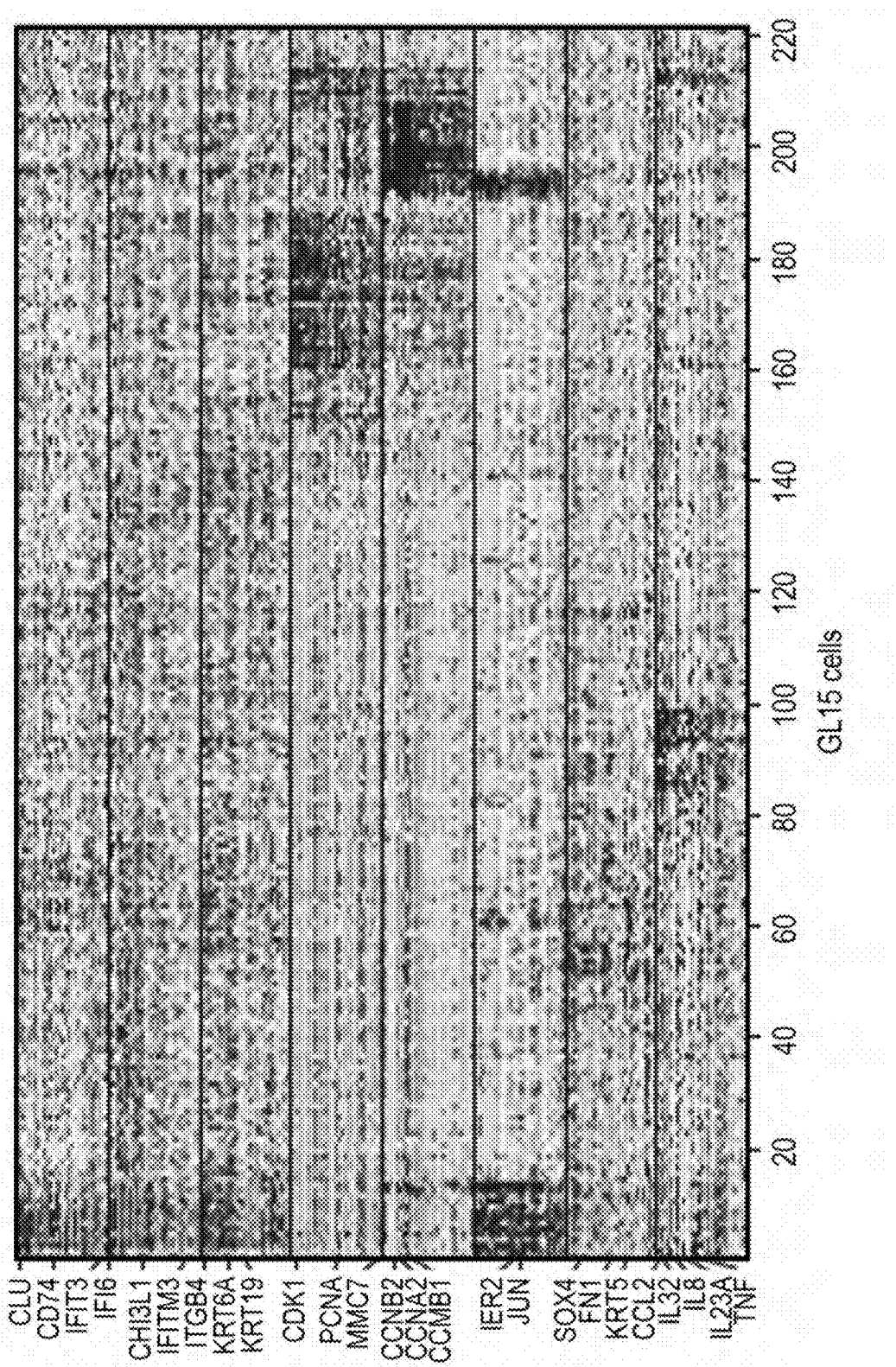
Figure 3C:
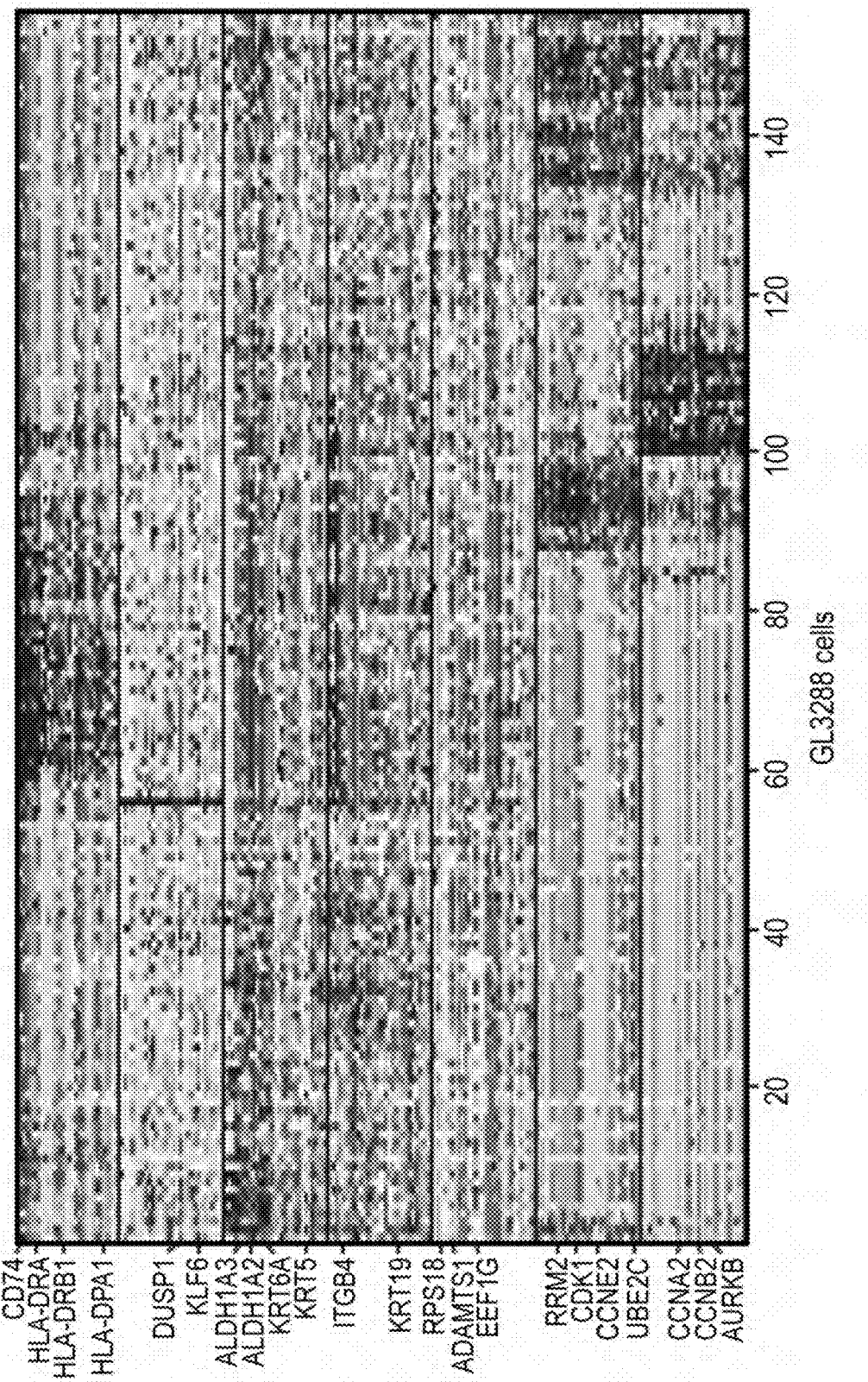
Figure 3D:
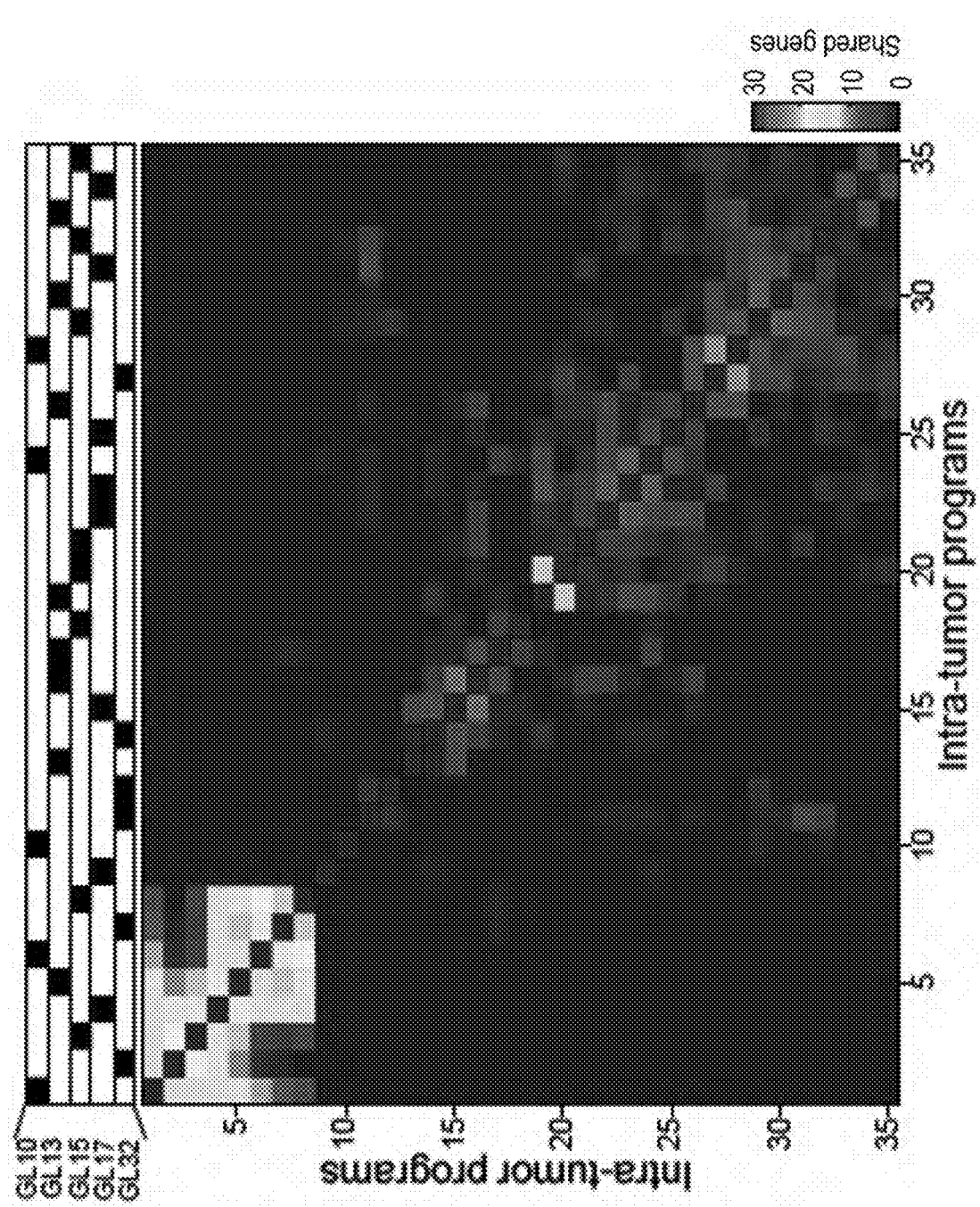
Figure 3E:
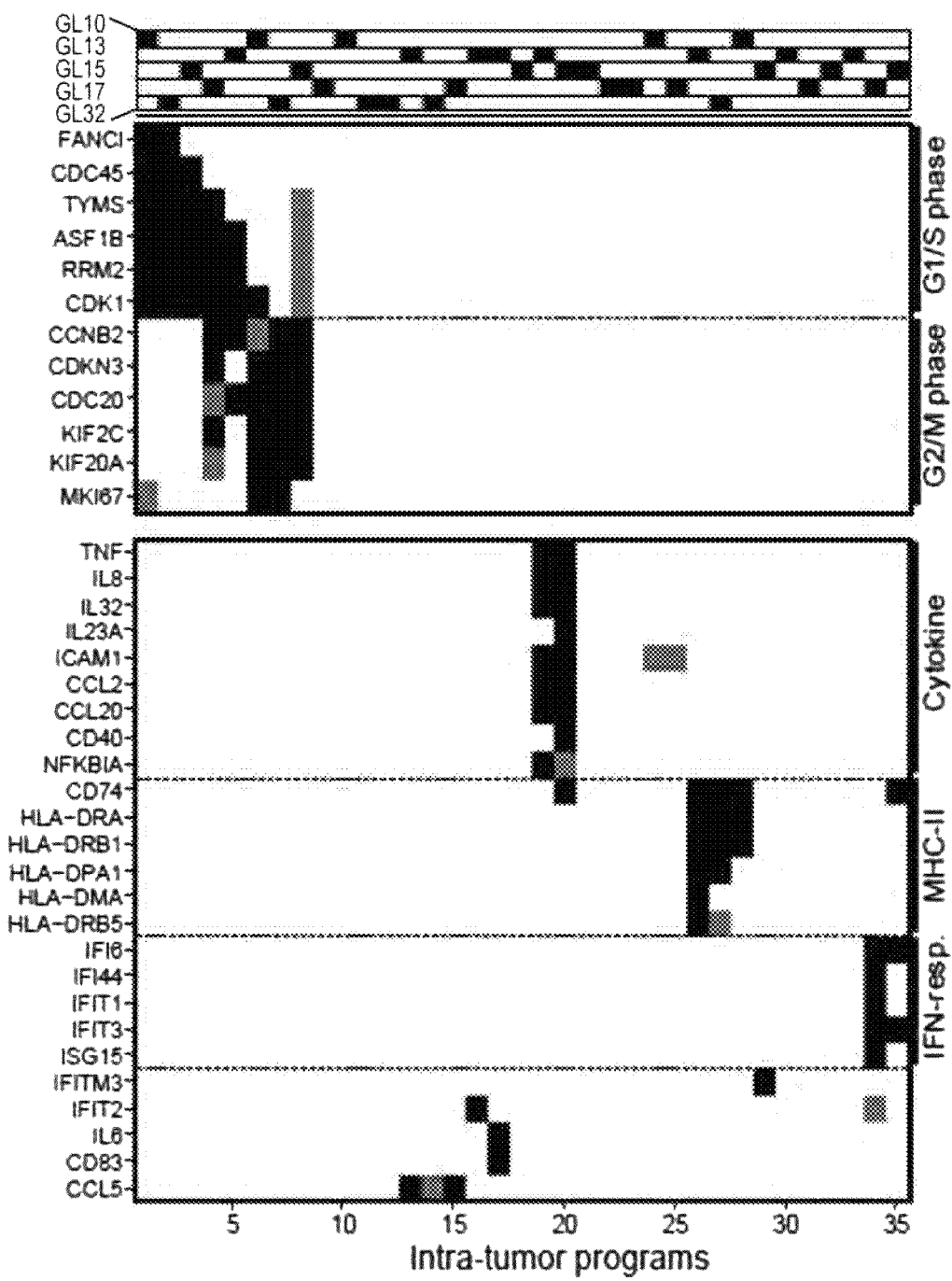
Figure 3F:
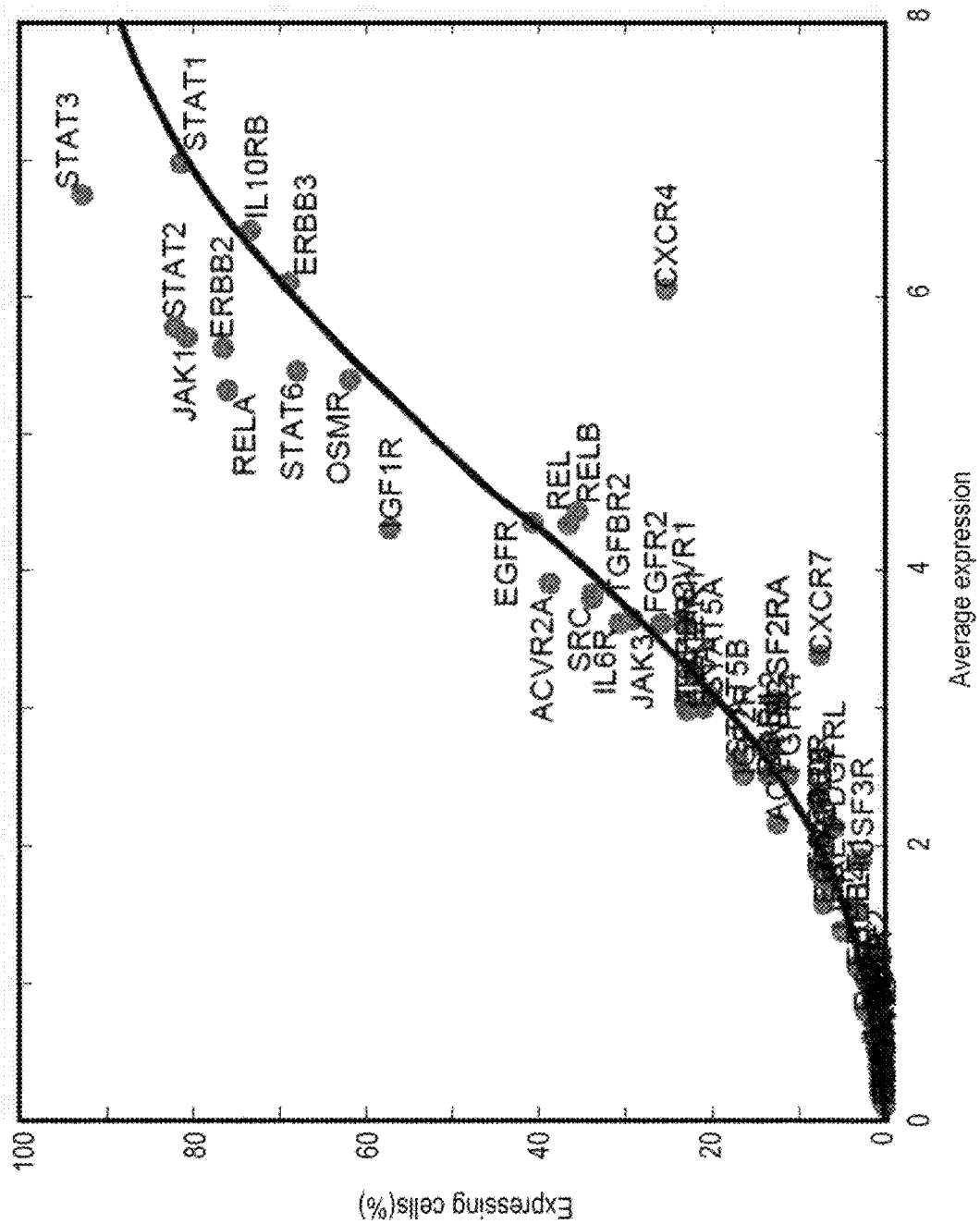

The study next examined whether there are consistent expression programs that functionally relate different tumors to each other. To this end, the overlap between the top genes for all pairs of modules defined across the five patients were examined (FIG. 3D). The most significant association among tumors was the expression of a cell cycle program (FIG. 3E), which is expected given that each tumor contains both cycling and non-cycling cells and the cell cycle programs are highly robust. Furthermore, programs dominated by immune- or inflammation-associated genes were found to be shared among two or more patients (FIG. 3E). These cancer cell expressed modules included inflammatory cytokines (e.g. IL-6, TNF, IL-8, IL-32), antigen presentation through major histocompatibility complex (MHC) class II (e.g. CD74 and HLA class II histocompatibility antigen, DR alpha chain (HLA-DRA)) and interferon response (e.g. IFI6, IFIT1, interferon-stimulated gene (ISG)15). A common feature across the vast majority of cells from platinum-resistant patients was the convergence of several of these cytokines and pathways onto the JAK/STAT pathway. Indeed, several components of the JAK/STAT pathway, including JAK1, STAT3, STAT2, STAT1, and oncostatin M receptor (OSMR) were found to be among the most highly expressed genes in platinum-resistant patients. OSMR is a recently described STAT3-regulated cytokine receptor that shares a downstream transcriptional network with STAT3 (FIG. 3F). Among these genes, JAK1 and STAT3 demonstrated strong expression above the expected within the cancer cell population, indicating that signaling occurred primarily via the JAK/STAT3 pathway, indicating the role of JAK/STAT3 pathway in platinum-resistance.

For three of the five patients described above (GL10, GL13 and GL15), samples were collected successfully with high quality single-cell transcriptomes at multiple time points. In these patients, significant differences of expression profiles between the different time points were not detected (FIG. 8A-FIG. 8E). This observation is in line with prior studies showing lack of cquired genomic aberrations in matched samples, but is likely, in part, explained by the timing of sample collection, which occurred in a relatively rapid succession (over weeks) without drastic changes in therapy. However, this experiment highlights the clinical feasibility of collecting several samples from the same patient and, when timed appropriately, provides insights into the evolution of cell heterogeneity. To gain insights into changes that occur during therapy and at the time of treatment resistance, patient-derived xenograft (PDX) models were used.

Example 4—Longitudinal Analysis of HGSC Expression Profiles in PDX Models

Figure 4A:
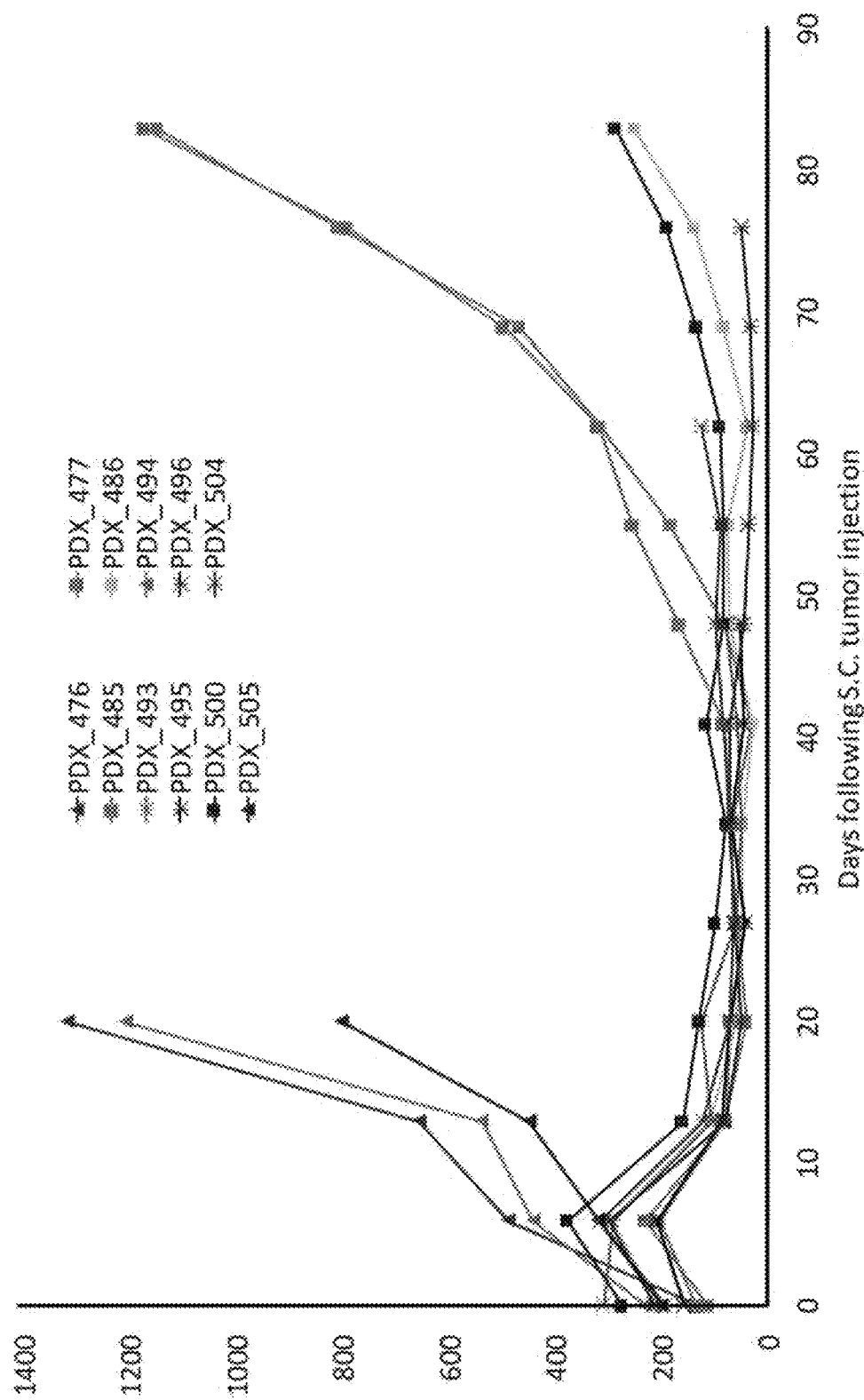
FIG. 4A-FIG. 4E are a series of graphs depicting comparisons of expression profiles across patient-derived xenograft (PDX) models before and after recurrence. Probing platinum-resistance in PDX-models reveals JAK/STAT signaling as shared resistance program.
Figure 4B:
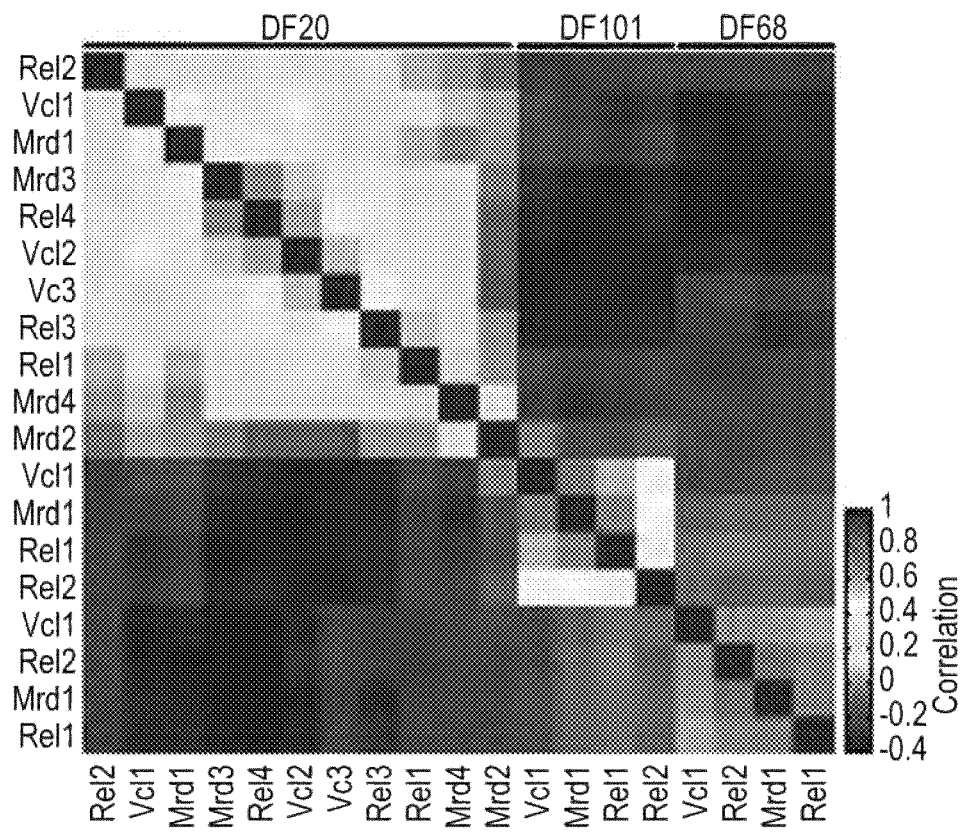
Figure 4C:
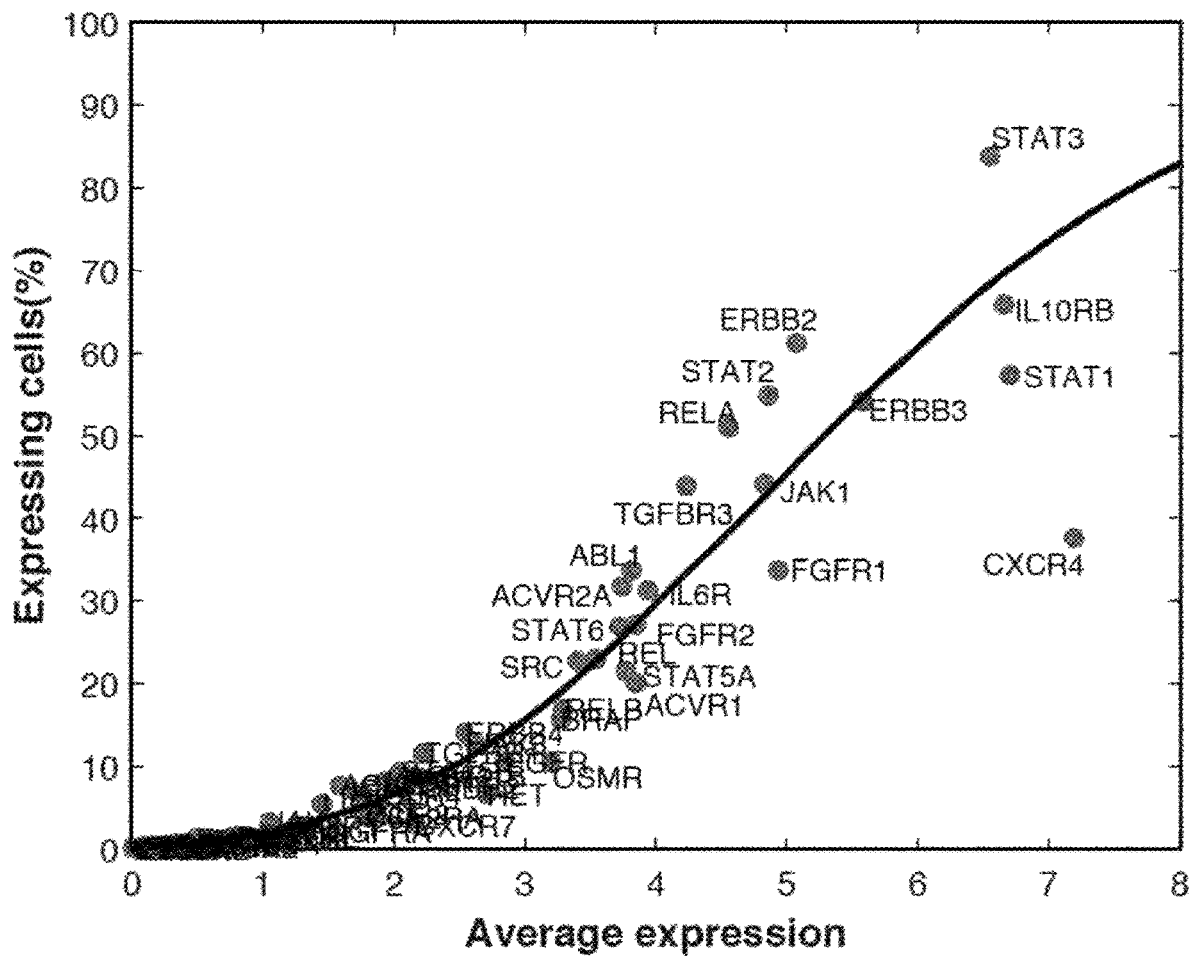
Figure 4D:
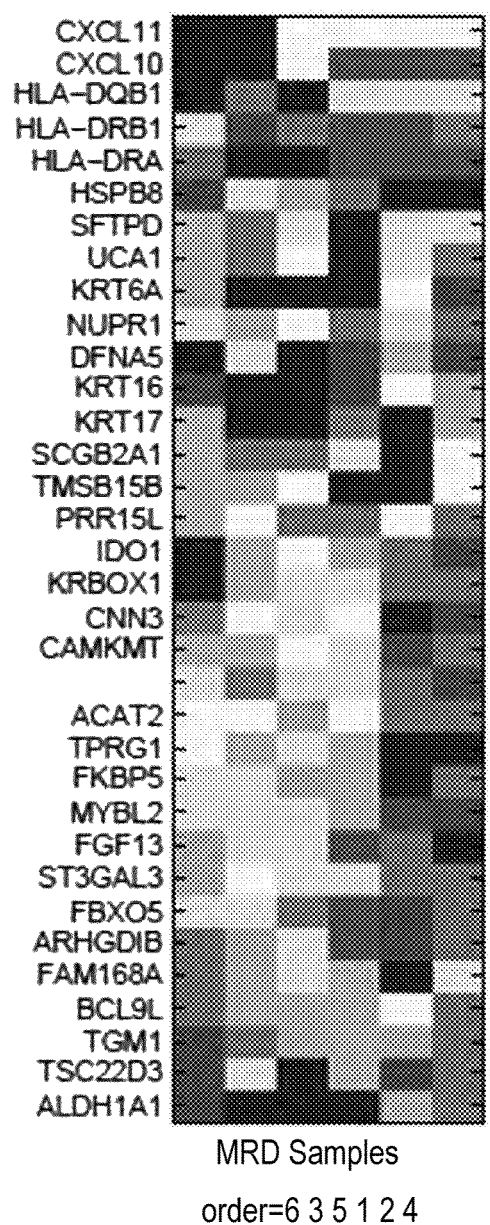
Figure 4E:
Figure 9:
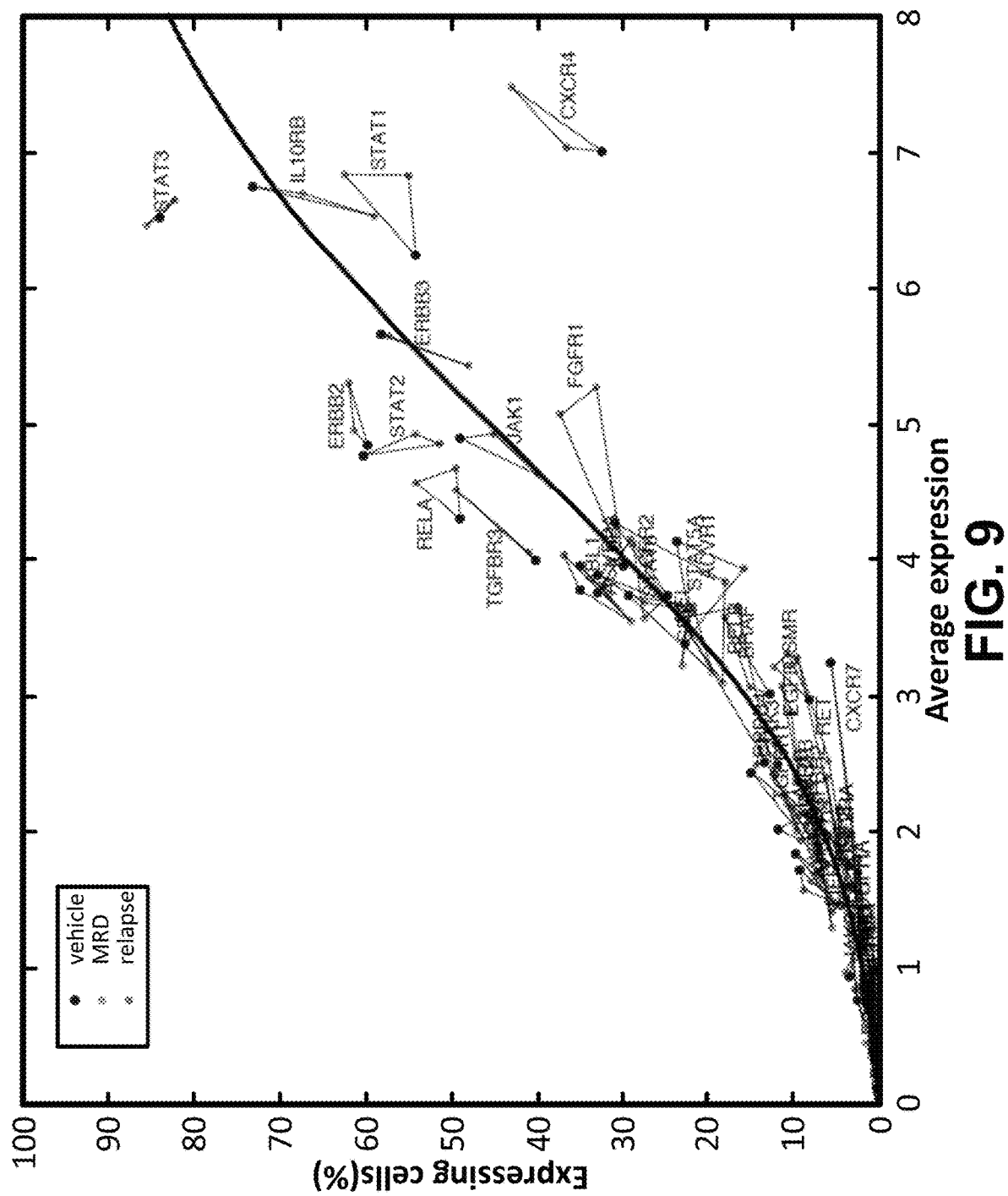
FIG. 9 is a graph of changes in highly-expressed genes in pre-treatment, MRD and relapse in PDX-models identifies high expression of JAK/STAT pathway nodes. Expression of highly-abundant transcripts in single-cells indicate high expression of key nodes of the JAK/STAT pathway, including STAT3 and others. Colored dots indicate the expression of this gene in either vehicle (blue), MRD (pink) or relapsed (red) PDX models.
Figure 10:
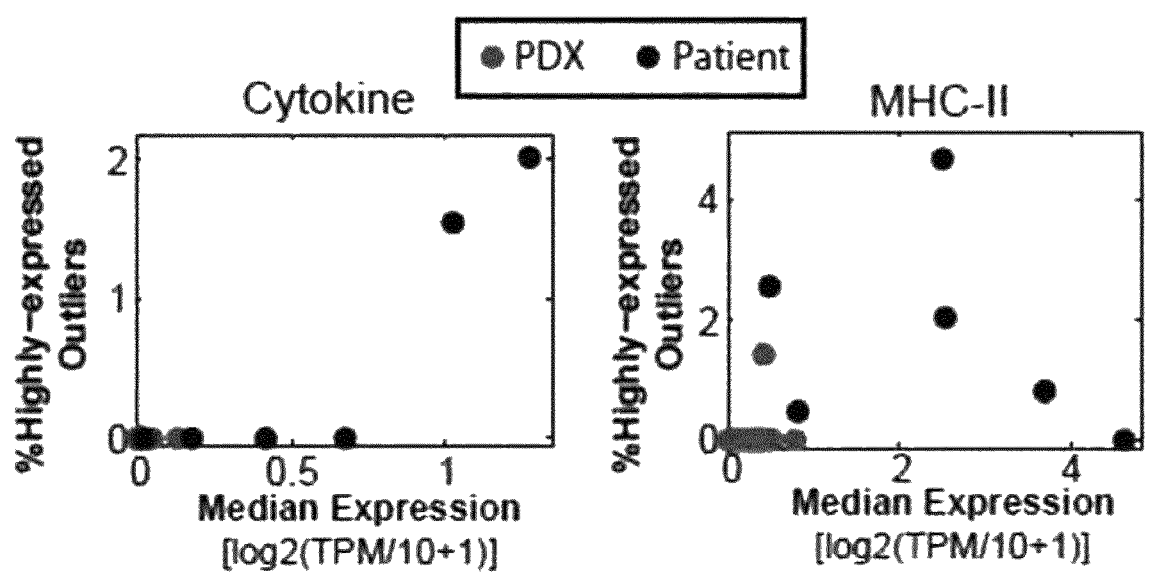
FIG. 10 is a graph of the correlation of module expression of inflammatory pathways among patients and PDX models.

Next, platinum-resistance was modeled using PDX-models. For this purpose, three previously established PDX models of ovarian cancer generated from patient-derived ovarian cancer ascites serially passaged in immunodeficient mice were used, including one BRCA-WT (DF20) and two BRCA-mutant (DF68 and DF101) models (Liu et al., 2016 Clin. Cancer Res., 23(5):1263-1273). These PDX models mimic the clinical course of patients, including initial response to platinum-based therapies and tumor regression that is followed by tumor relapse weeks to months upon completion of therapy (Liu et al., 2016 Clin. Cancer Res., 23(5):1263-1273) (FIG. 4A). As previously described (Liu et al., 2016 Clin. Cancer Res., 23(5):1263-1273), patient-derived cells were stably transfected with luciferase and mCherry, enabling non-invasive monitoring by in vivo bioluminescence imaging (BLI), and subsequent isolation of individual cells (flow-sorting for mCherry-expressing cells). PDX models developed tumors within 3 weeks following subcutaneous implantation and were treated with vehicle or carboplatin. Single-cells were harvested for sequencing from untreated animals (vehicle) and the carboplatin-treated animals were monitored for tumor regression and relapse. As expected, there was a brisk response to carboplatin (indicated by reduced tumor volume and decreased BLI signal) followed by subsequent tumor outgrowth (FIG. 4A). Single-cells were collected from one cohort of animals at the time of maximal response and minimal residual disease (MRD), and from another cohort of animals at the time they developed fully relapsed tumors (relapse). In total, scRNAseq was performed on ~800 single-cells isolated from 5 vehicle, 6 MRD and 8 relapsed animals. Global comparison of individual cells or average profiles (FIG. 4B) from these 19 mice demonstrated that they cluster based on their parental PDX-model with high similarity across experimental groups (i.e. vehicle, MRD and relapse samples). The study focused primarily on DF20 and profiled multiple mice for each experimental group (3 vehicle, 4 MRD and 4 relapse mice) and found that these 11 samples largely clustered by the model of origin and not by experimental group (FIG. 4B). To examine the possibility of more restricted changes in gene expression, profiles of MRD or relapse animals were compared to the vehicle animals of the same model and defined differentially expressed genes. The study identified upregulated genes in each model, yet their overlap across models was minimal (FIG. 4C), arguing against a consistent program of tumor relapse. Across all models, strong expression of key nodes of the JAK/STAT pathway were found, including JAK1 and STAT3 (FIG. 4D). Furthermore, the study found that STAT1, fibroblast growth factor receptor (FGFR)1 and CXCR4 (the receptor for CXCL-12-mediated JAT/STAT-activation) were more strongly expressed in the MRD/relapse samples compared to vehicle treated cells, further supporting the notion of a role of the JAK/STAT pathway in platinum-resistance (FIG. 9). Accordingly, gene sets were detected which were consistently altered across two or three samples of MRD (FIG. 4D) or relapse (FIG. 4E), and contribute to drug resistance or tumor relapse. These include several chemokines (CXCL2/10/11), MHC-II genes (HLA-DRA, and HLA class II histocompatibility antigen, DR beta chain (HLA-DRB)1, HLA class II histocompatibility antigen, DQ beta chain 1(HLA-DQB1)),the immune-suppression gene IDO1, a MYB-like transcription factor (MYBL2) which was previously associated with poor survival in breast cancer (Amatschek et al., 2004 Cancer Res., 64:844-856) and the growth factor FGF13 which was recently implicated in cancer cell survival (Bublik et al., 2017 Proc. Natl. Acad. Sci., 114:E496-E505) and in resistance to cisplatin (Okada et al., 2013 Sci. Rep., 3:2899).

Example 5—Intra-Tumor Heterogeneity in PDX Models

Figure 5A:
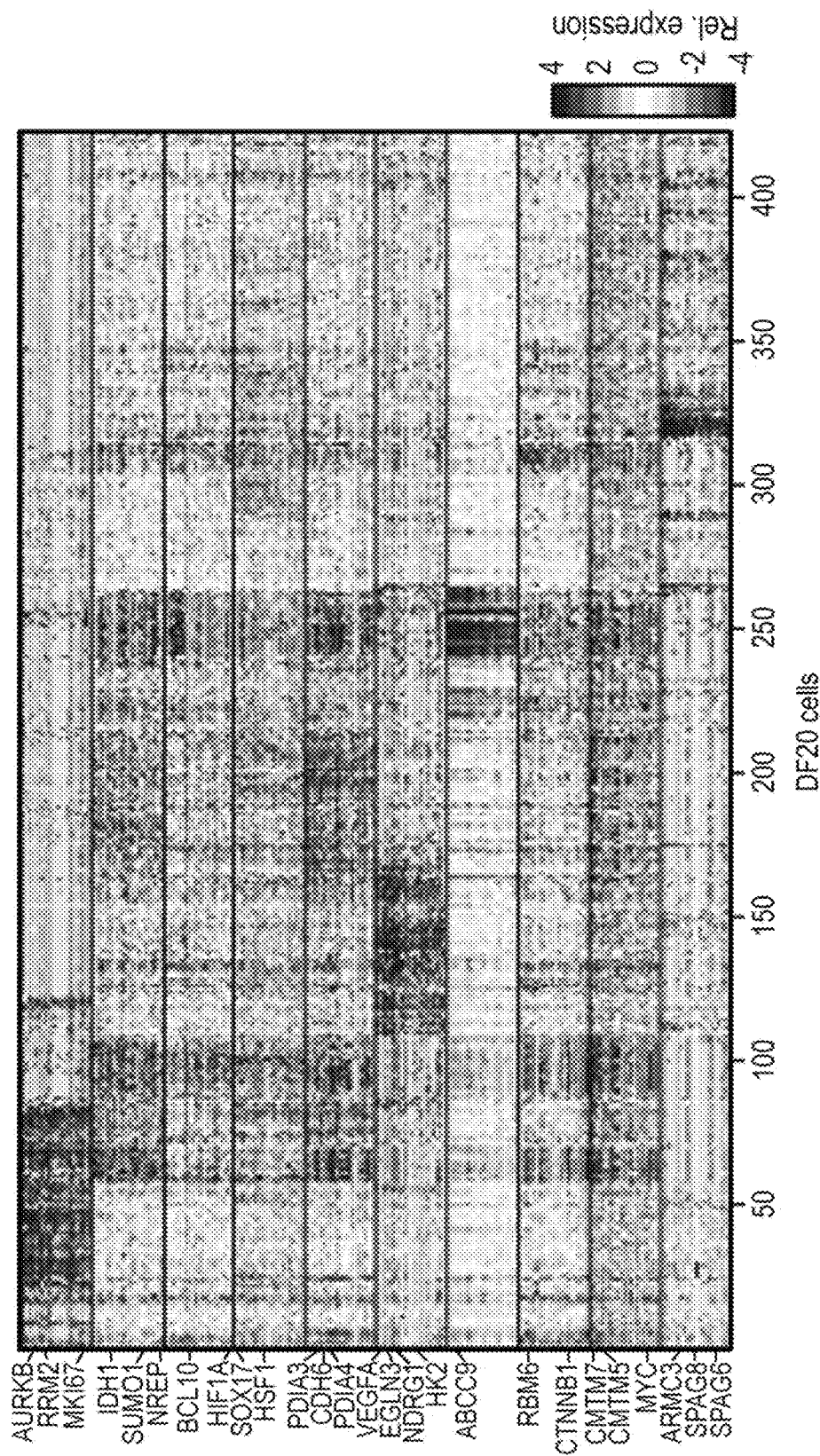
FIG. 5A-FIG. 5E are a series of graphs depicting expression modules with intra-tumoral variability among ovarian cancer cells from PDX samples.
Figure 5B:
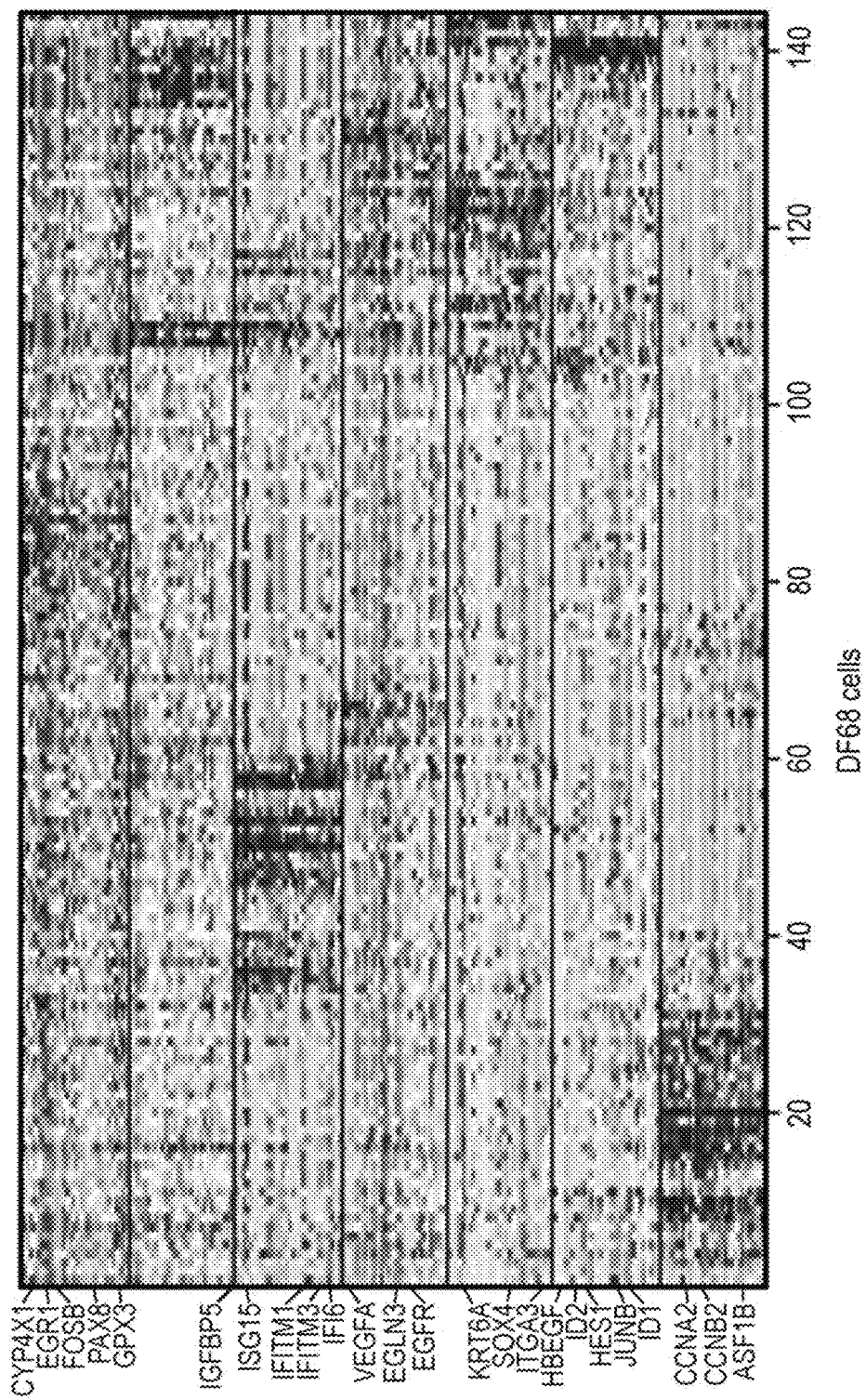
Figure 5C:
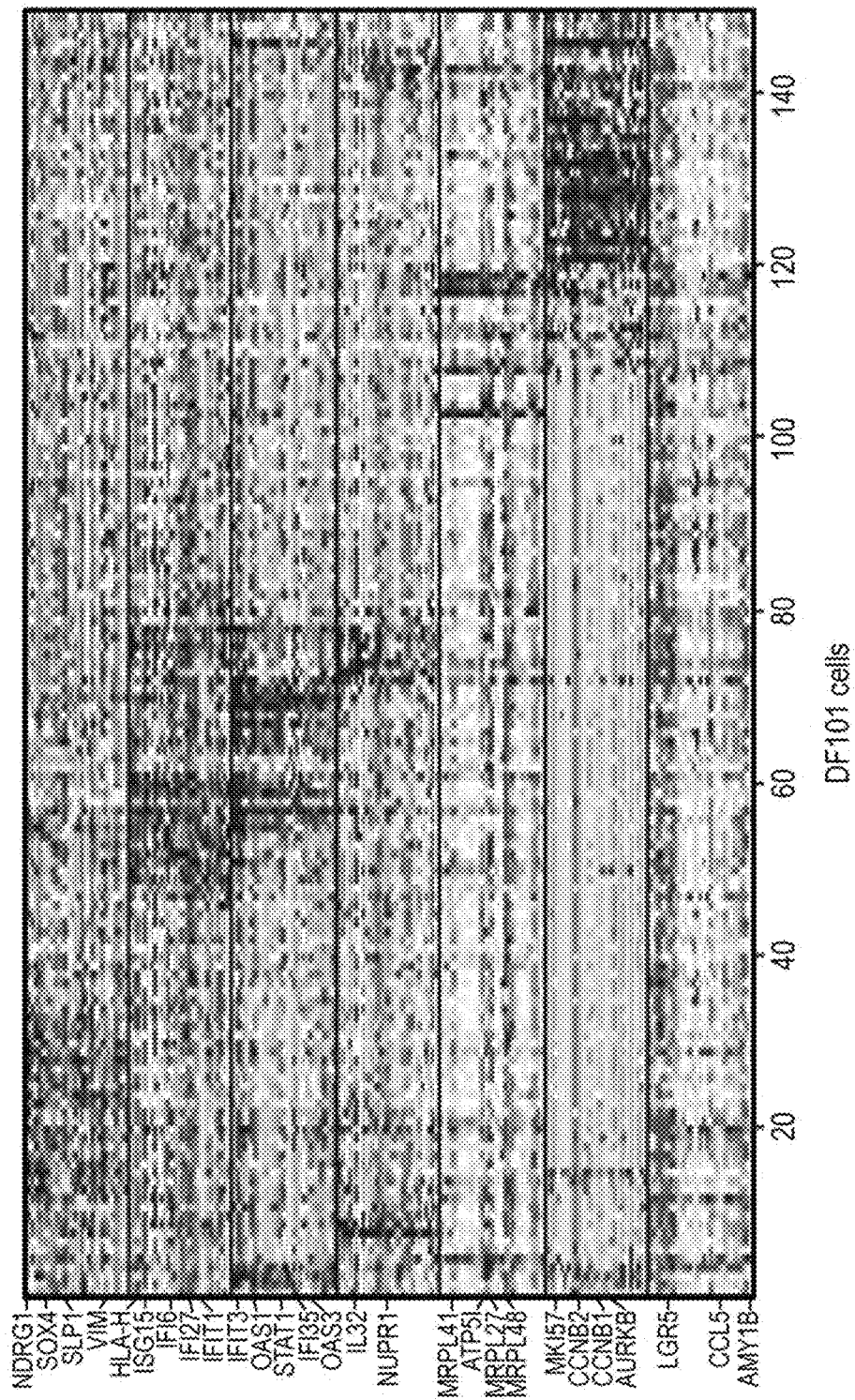
Figure 5D:
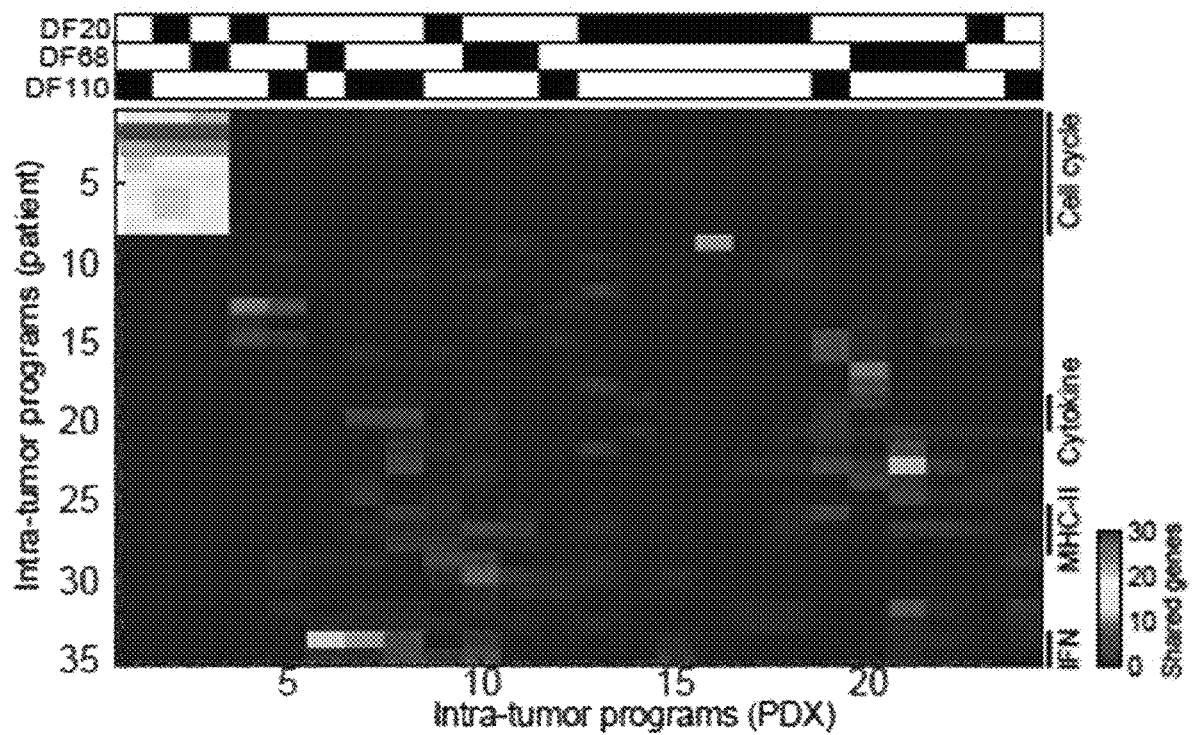
Figure 5E:
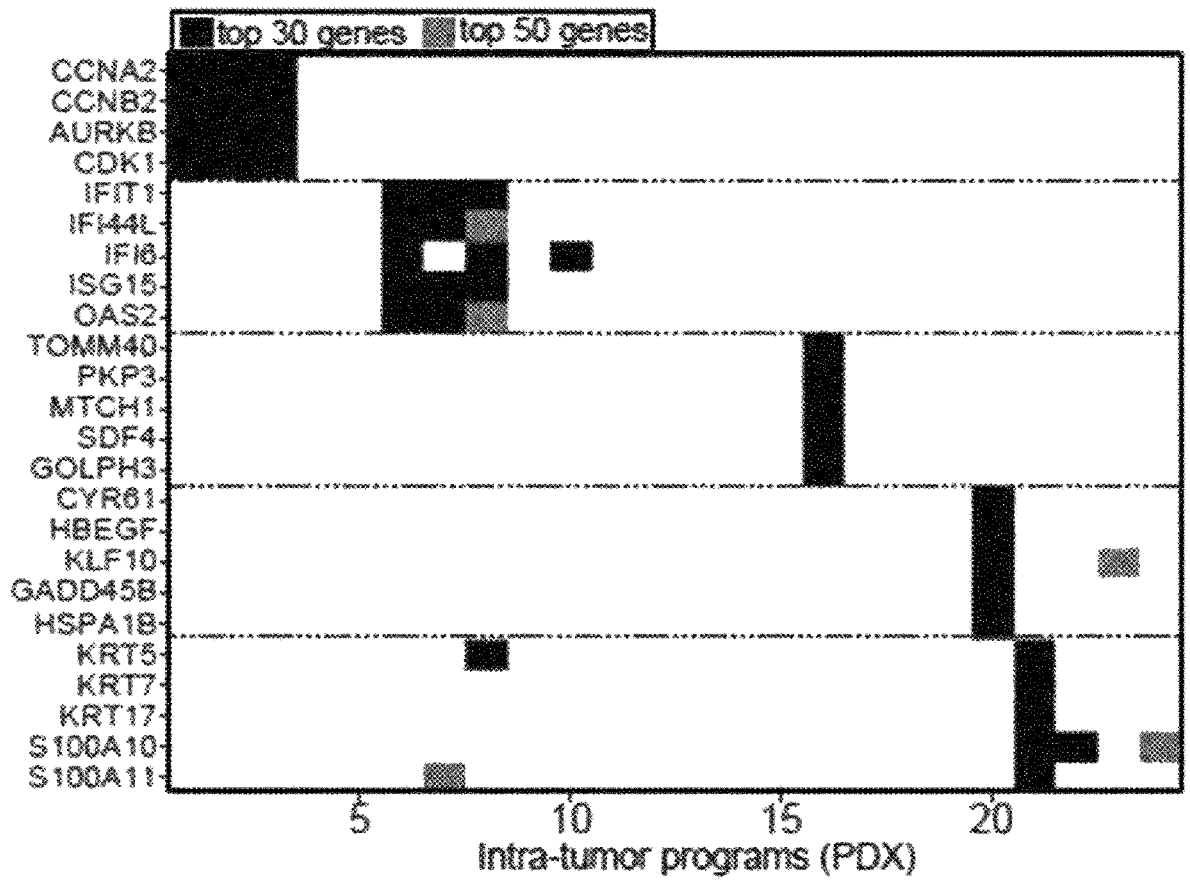

The study next examined the intra-tumor variability of cell states among individual mice and as described above for patient samples, NMF was used to identify expression modules with high variability in each of the three PDX models (FIG. 5A-FIG. 5C). PDX modules were then compared to the patient modules (FIG. 5D). As expected, the highest similarity was observed for cell cycle modules (PDX modules 1-3) (FIG. 5D and FIG. 5E). Of the three immune-related programs described in the patient analysis, the interferon program was also identified in the PDX analysis (PDX modules 6-8) (FIG. 5E). The other two immune-related programs (the cytokine and MHC-II modules) found in patients were not strongly expressed in PDX models (FIG. 10), indicating that extracellular immune cell mediated stimuli, which are mostly absent in these models, contribute to the expression of these programs.

Figure 22:
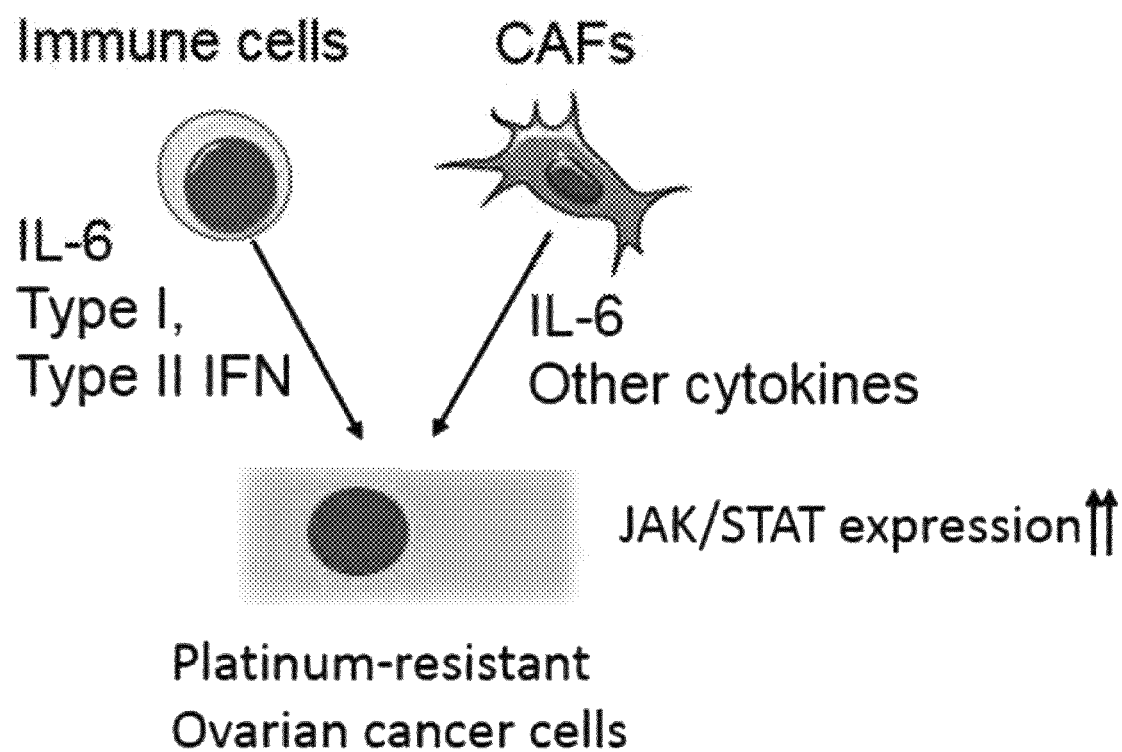
FIG. 22 is a diagram depicting immune cells and JAK/STAT expression in platinum-resistant ovarian cancer cells. A common feature of resistant cells in patient ascites and in PDX models is the cancer cell-autonomous expression on inflammatory pathways, including the JAK/STAT pathway.

While cross-comparison between platinum-resistant patients and PDX-models did not identify a single mechanism of drug resistance, a consistent observation gleaned from single-cell analyses was the significant cancer cell-autonomous expression of cell cycle modules, inflammatory and other immune related pathways, in particular expression of key JAK/STAT-pathway nodes and controlled pathways, including interferon signaling, MHC expression, interferon response elements and other cytokine markers. This notion was further supported by the expression of activators of JAK/STAT signaling by non-malignant cells, including IL6, CXCL12-CXCR4 interactions and other cytokines. Collectively, the scRNA-seq data highlighted the importance of JAK/STAT activation in ovarian cancer via both autocrine (tumor-cell intrinsic) and paracrine (tumor cell microenvironment) mechanisms. Suggesting a role for this pathway in ovarian cancer cell survival, pathophysiology in metastasis and platinum-resistance (FIG. 22 depicts immune cells and JAK/STAT expression in platinum-resistant ovarian cancer cells). The JAK/STAT pathway and its upstream activators (e.g. IL6, TNF, IFN, CXCL12) have been previously implicated in ovarian cancer cell survival, metastasis, angiogenesis, and chemo-resistance (Kulbe et al., 2012 Cancer Res., 72:66-75; Coward et al., 2011 Clin. Cancer Res. Off. J. Am. Assoc. Cancer Res., 17:6083-6096; Wen et al., 2014 Mol. Cancer Ther. 13:3037-3048; Duan et al., 2006 Clin. Cancer Res. Off. J. Am. Assoc. Cancer Res., 12:5055-5063; Saini et al., 2017 Oncogene, 36:168-181; Stone et al., 2012 N. Engl. J. Med., 366:610-618) and the study establishes the significance of this pathway in ovarian cancer at the single-cell level.

Figure 11A:
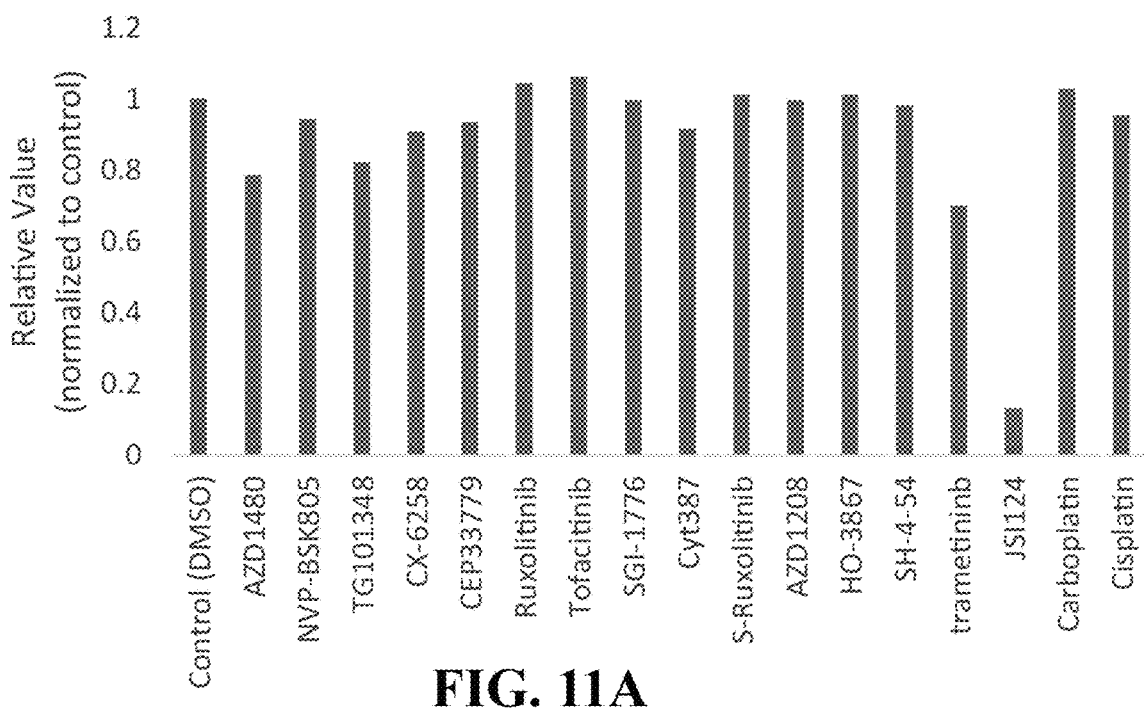
FIG. 11A-FIG. 11E are a series of histograms of OVACR4 and OVACR8 ovarian cancer cell lines grown in 2D and 3D cultures and treated with 14 JAK/STAT pathway inhibitors at 1 µM. Vability of the cells was determined using the CellTiterGlo assay. JSI-124 was identified as most effective compound leading to cell killing.
Figure 11B:
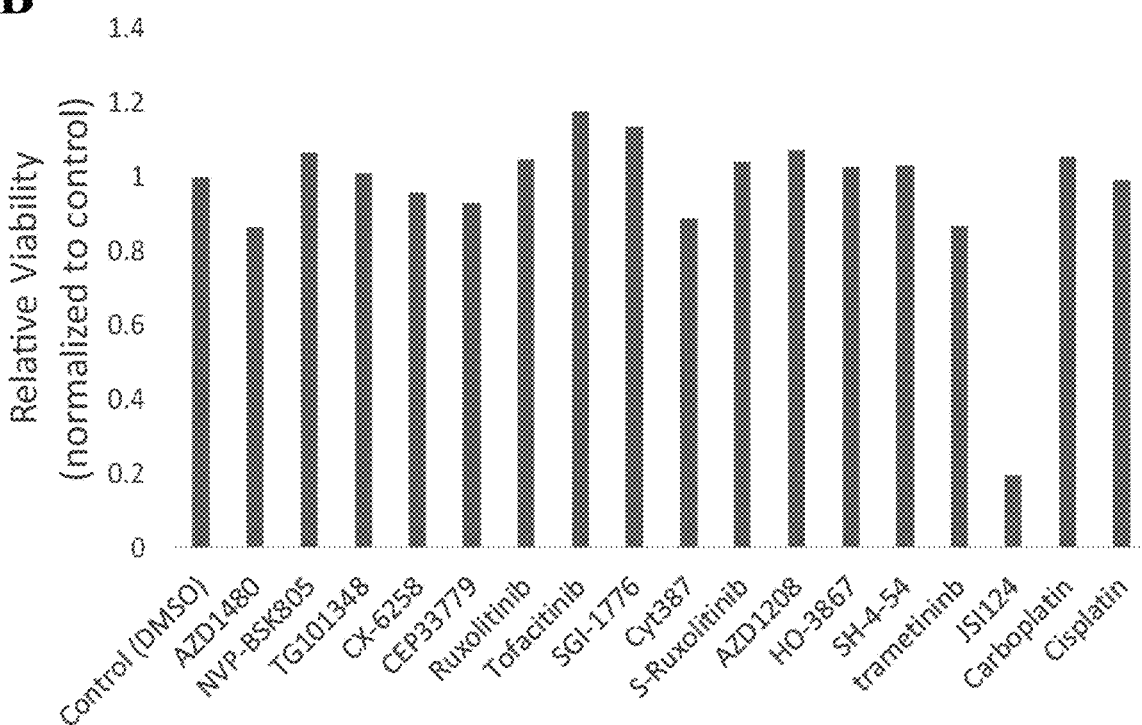
Figure 11C:
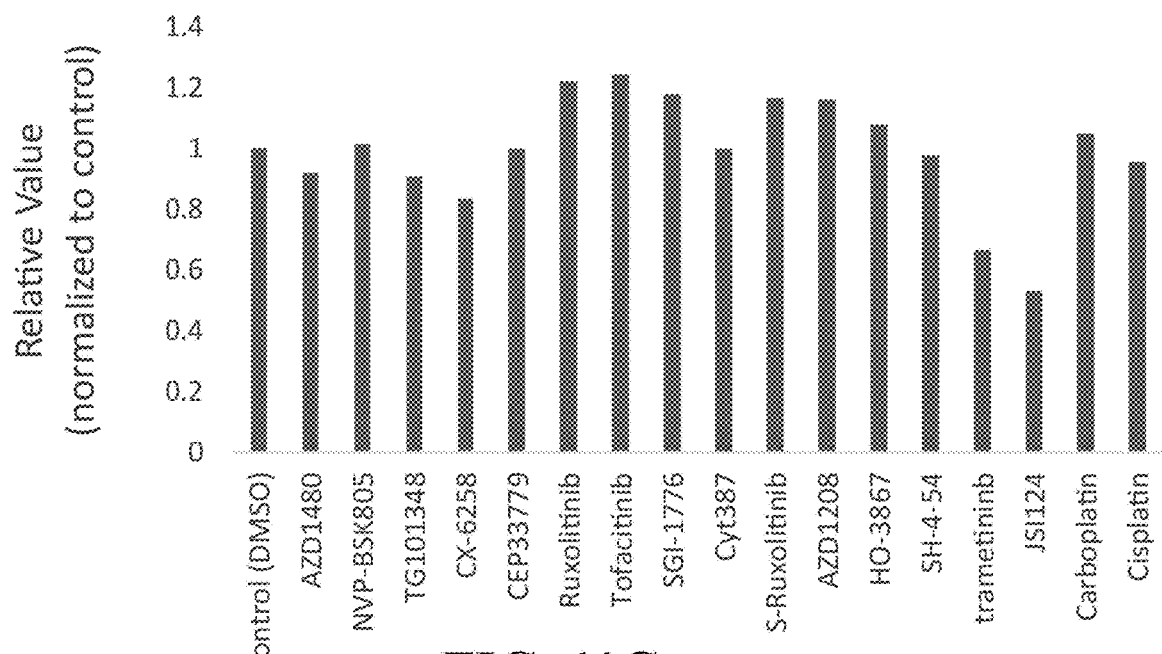
Figure 11D:
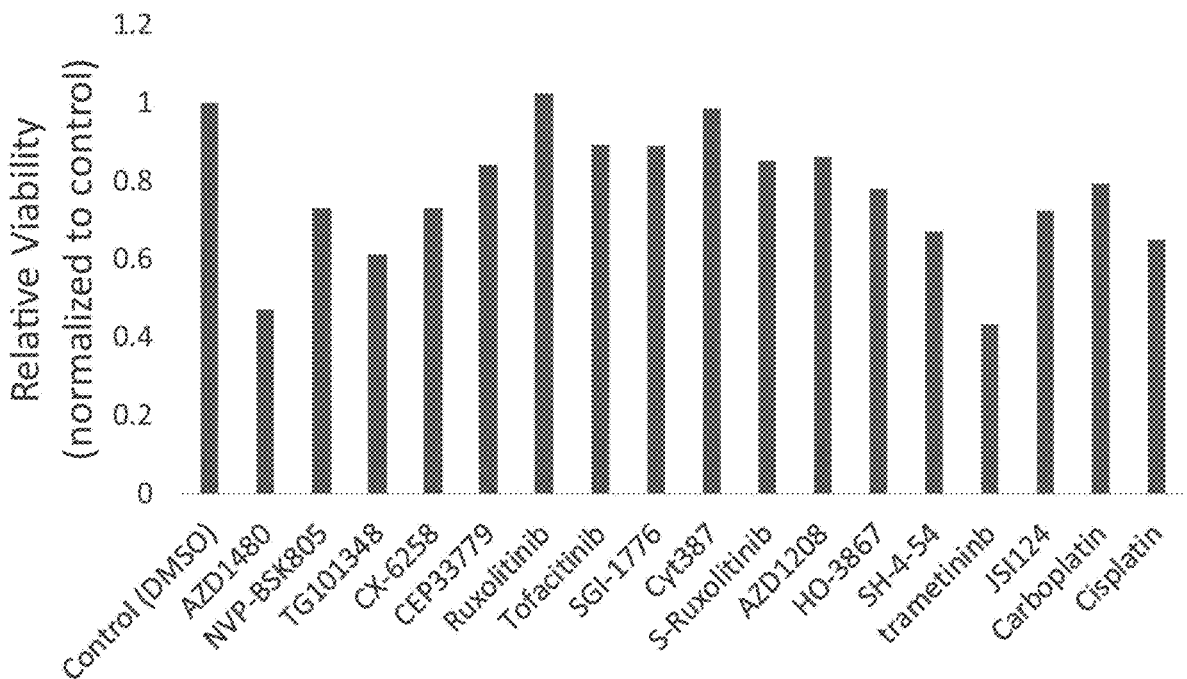
Figure 11E:
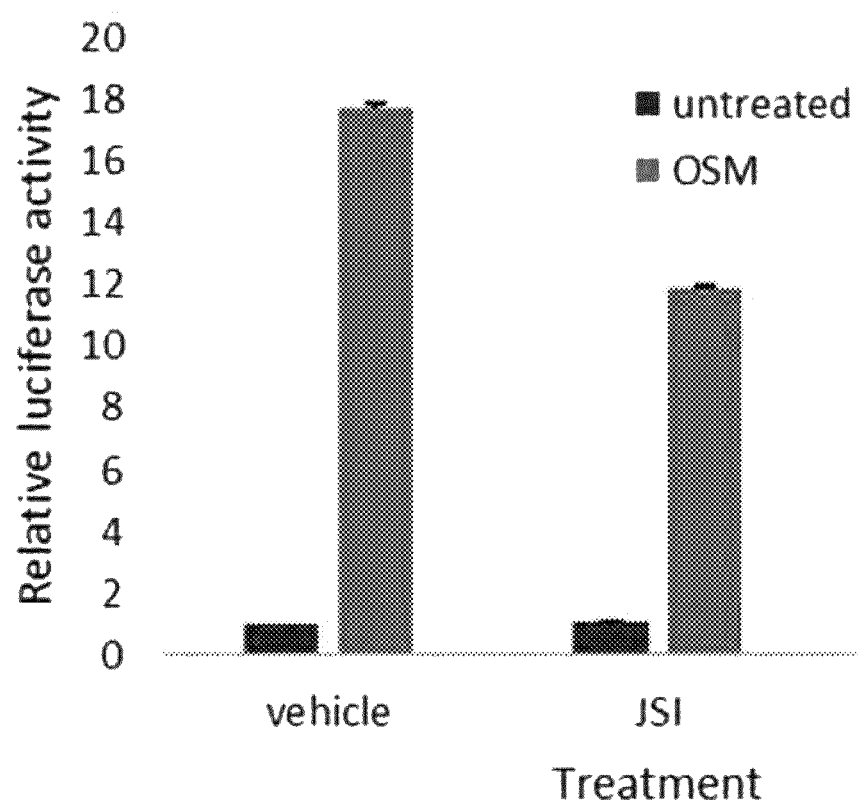

Example 6—Inhibition of JAK/STAT Signaling Inhibits Spheroid Formation, Spheroid Integrity, and Invasiveness Though a Mesothelial Monolayer and Leads to Disruption of Formed Spheroids Inhibition of the JAK/STAT pathway, represents a feasible therapeutic avenue for ovarian cancer, including chemo-resistant disease. Two-dimensional and three-dimensional cell cultures of two commonly used ovarian cancer cell lines were screened, OVACR4 and OVACR8 with a library of 14 compounds inhibiting different nodes of the JAK/STAT pathway (FIG. 6A, FIG. 11A-FIG. 11D). This initial screen identified JSI-124, a previously characterized selective JAK/STAT inhibitor (Blaskovich et al., 2003 Cancer Res., 63:1270-1279). The on-target activity of JSI-124 was confirmed using luciferase assay for STAT3 activity in oncostatin M (OSM) stimulated Heya8 cell lines (FIG. 11E).

Figure 6A:
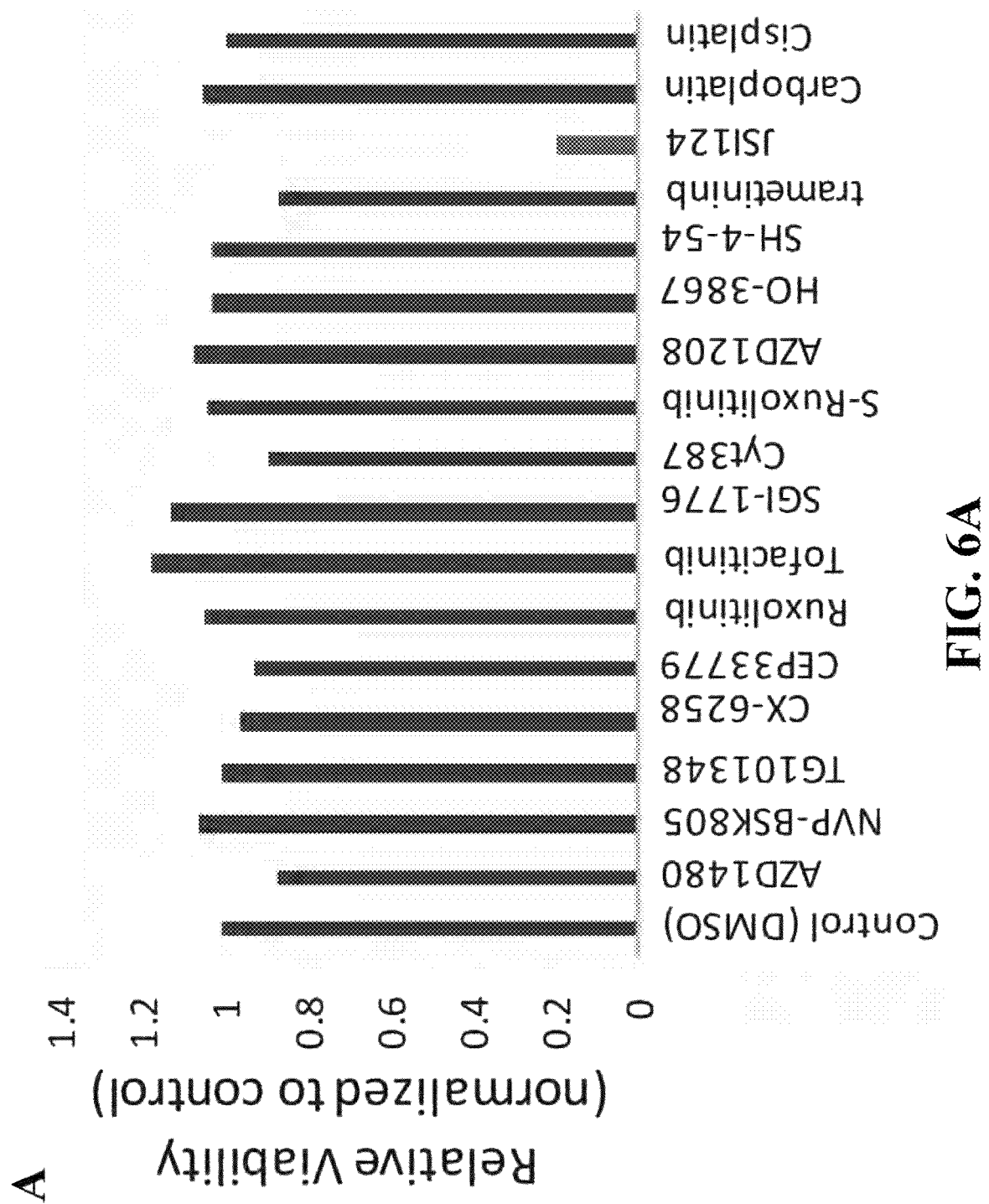
FIG. 6A-FIG. 6G are a series of graphs and images depicting the impact of JAK/STAT-inhibition on spheroid formation, invasion and killing ex vivo and in vitro.
Figure 6B:
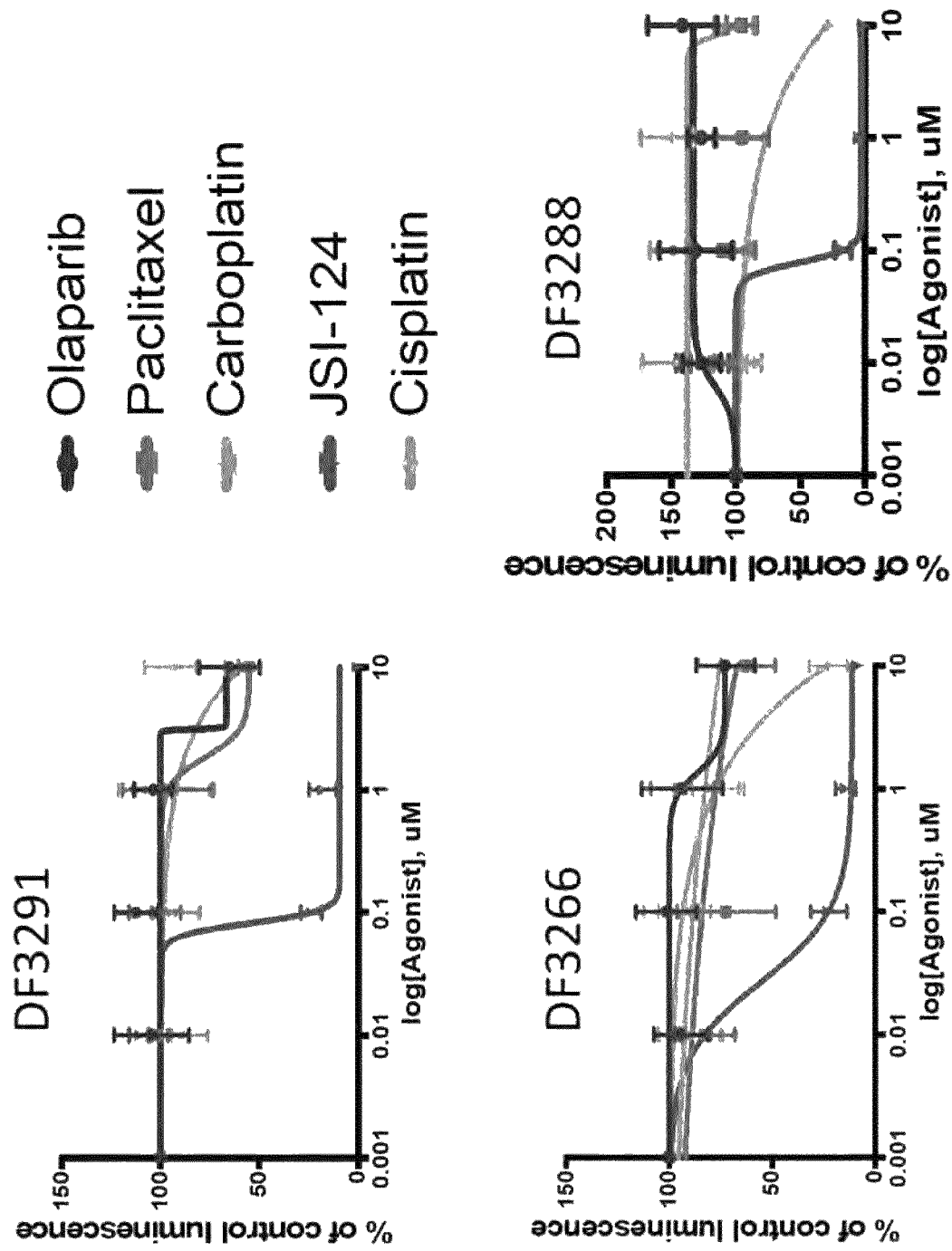
Figure 6C:
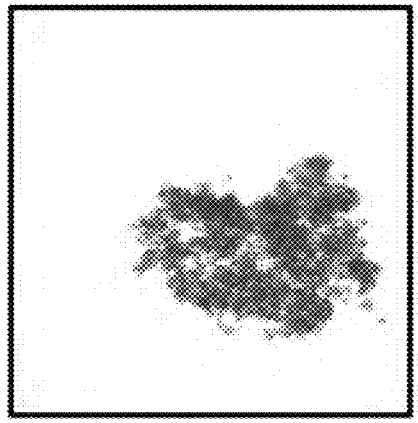
Figure 6C:
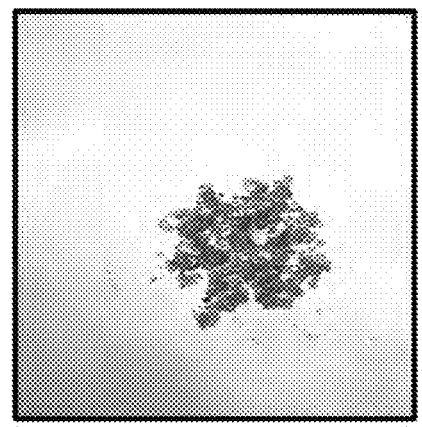
Figure 6C:
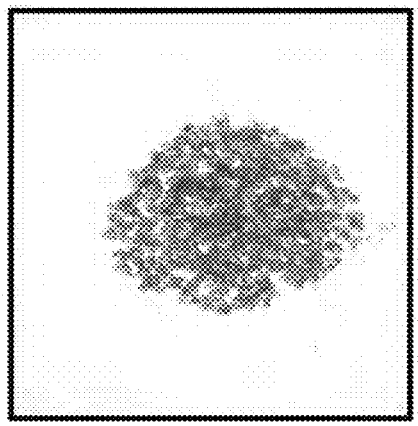
Figure 6C:
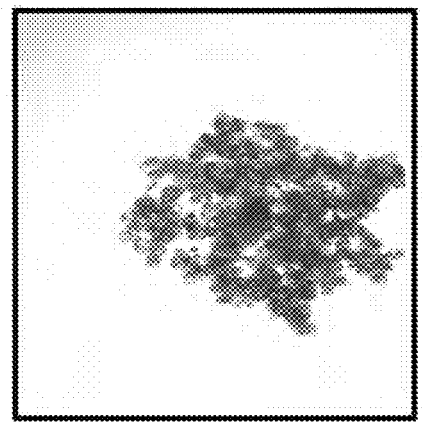
Figure 6C:
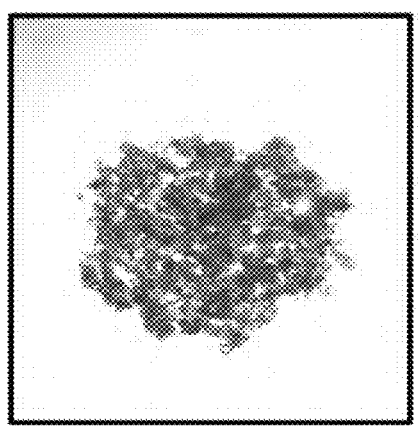
Figure 6C:
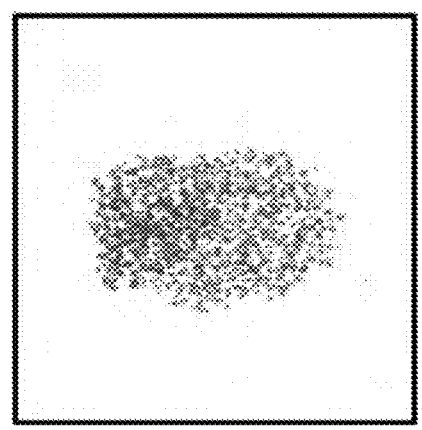
Figure 6D:
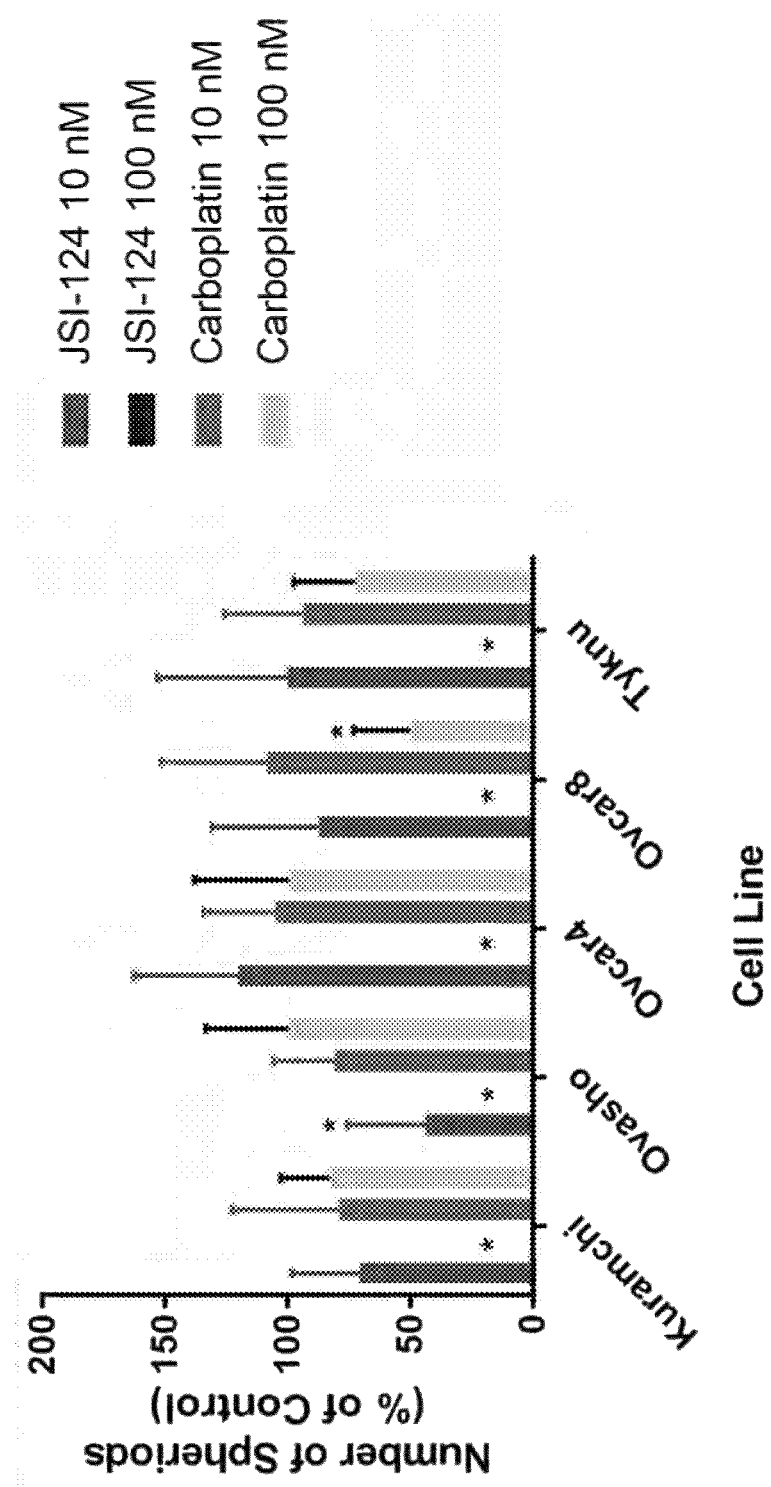
Figure 12A:
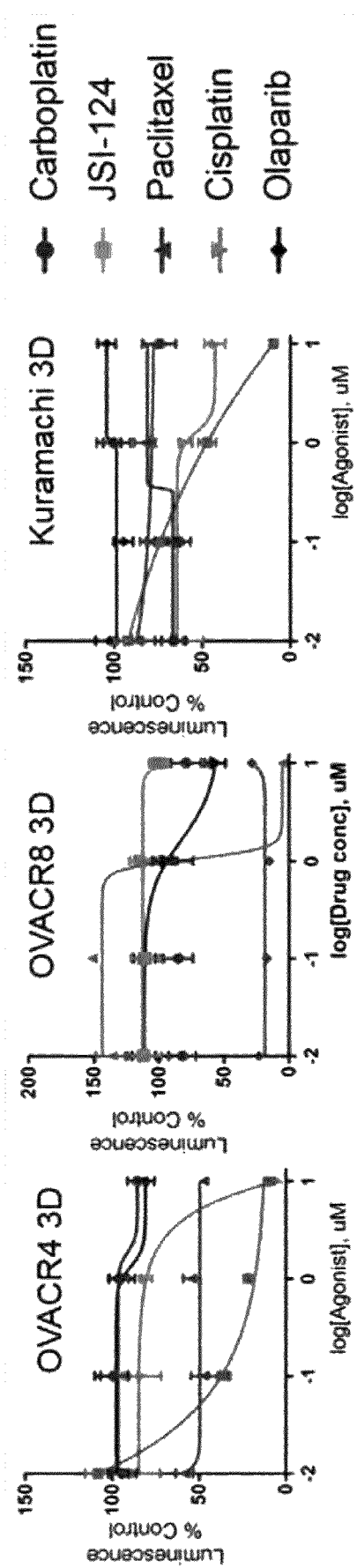
FIG. 12A-FIG. 12B are a series of graphs depicting JSI-124 effectively kills ovarian cancer cell lines grown as two-dimensional (2D) cultures or three-dimensional (3D) spheroids using ultra-low attachment growth conditions. Inhibition of JAK/STAT pathway kills 2D and 3D cultured cell lines
Figure 12B:
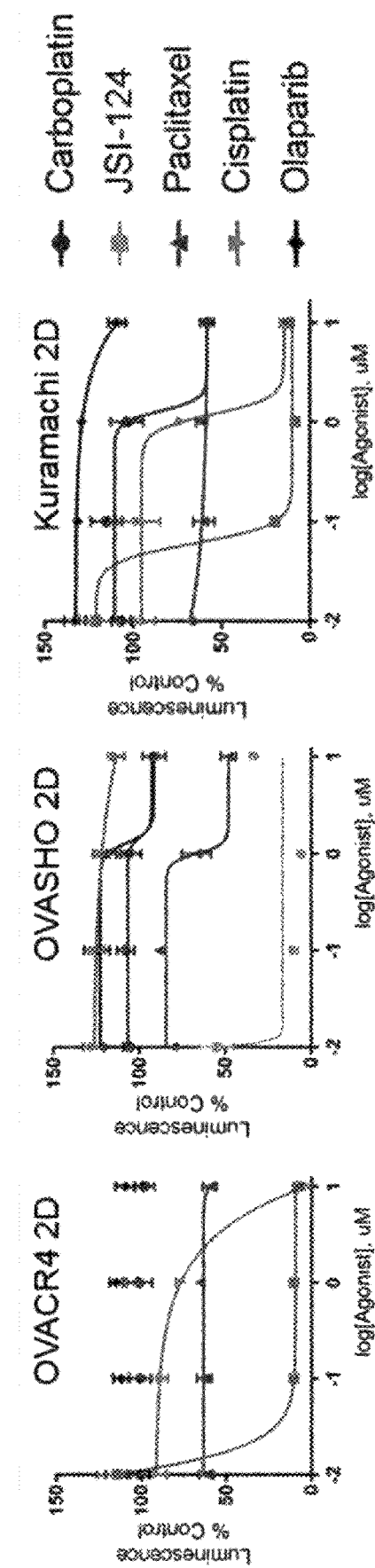
Figure 23:
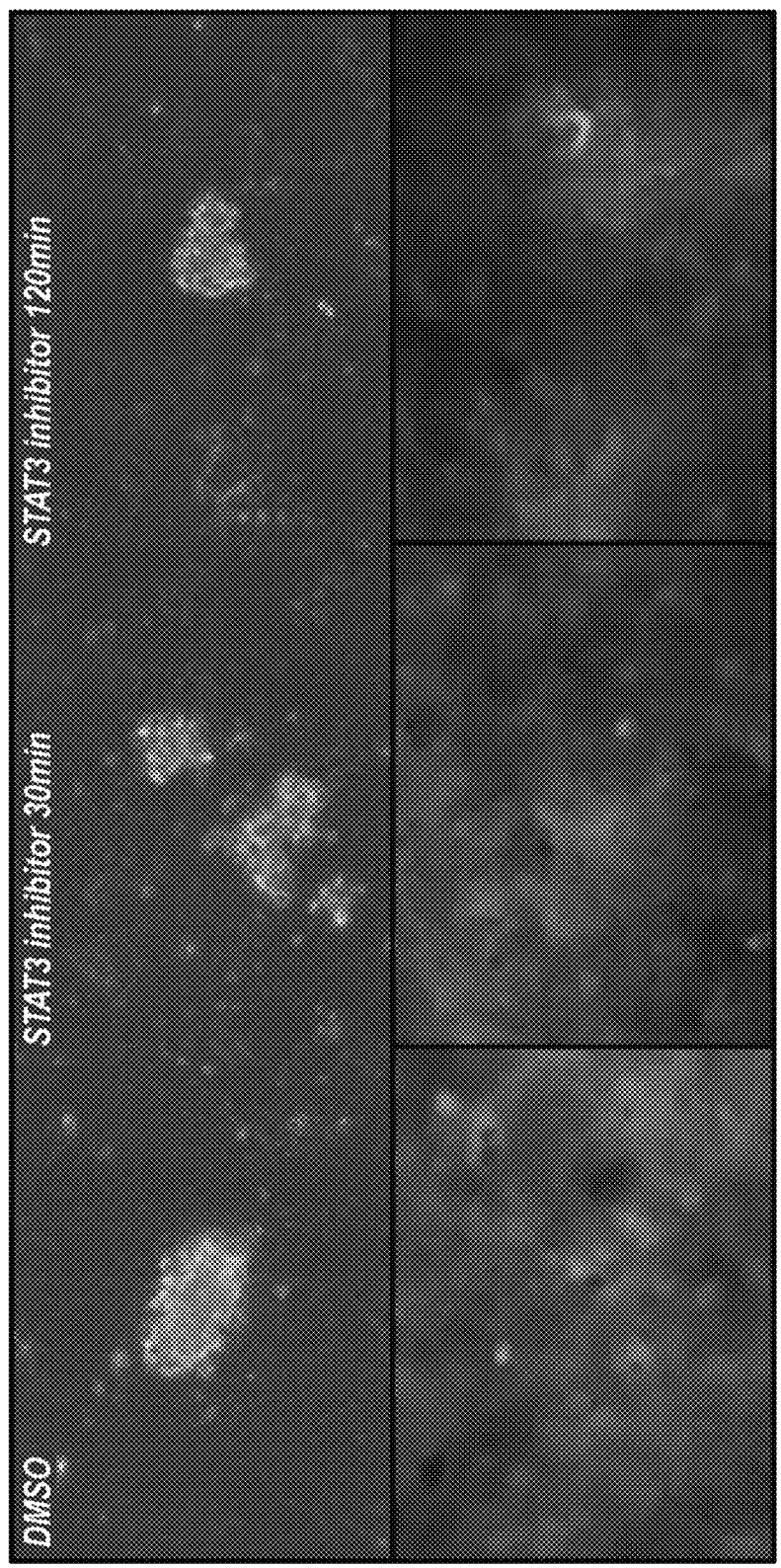
FIG. 23 is an image of cancer cells from video 1 and 2 (top row) and video 3 and 4 (bottom row) exposed to DMSO, STAT3 inhibitor for 30 min and STAT3 inhibitor for 120 min. JAK/STAT inhibition prevents spheroid formation. Further description of video 1, 2, 3, and 4 is given in the examples sections below.
Figure 36:
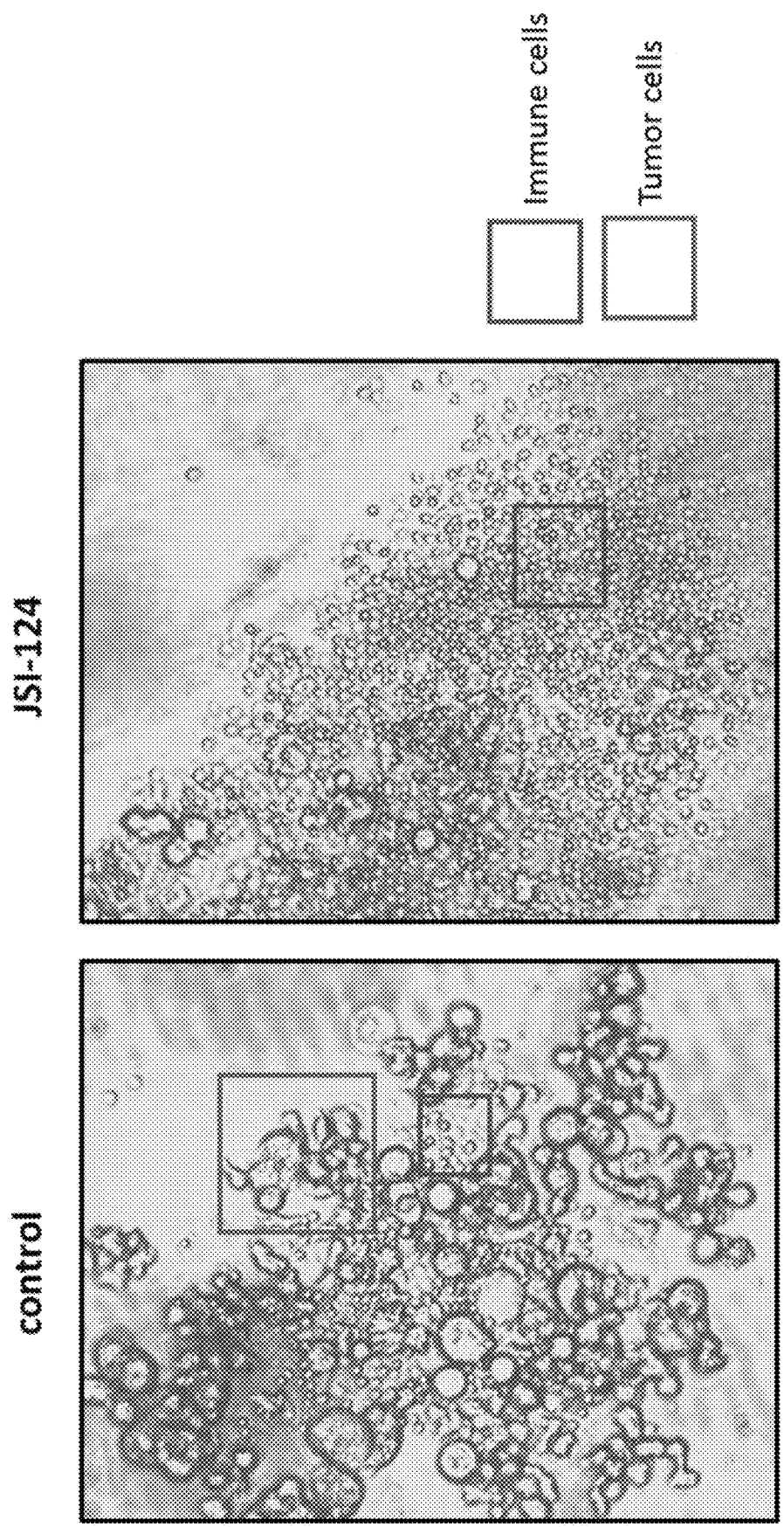
FIG. 36 is a series of photomicrographs showing morphological description of ex-vivo patient-derived ovarian cells after treatment with STAT3 inhibitor JSI124. JSI124-treated cells were observed with a majority of intact immune cells, due to massive elimination of tumor cells.

To test whether JSI-124 overcomes platinum-resistance in patient-models, ex vivo cell cultures of three platinum-resistant patients (DF3266, DF3288, DF3291) were generated. Single-cell RNA-sequencing was performed on these platinum-resistant patient samples, using the growth in low attachment (GILA) assay (Rotem et al., 2015 Proc. Natl. Acad. Sci. U.S.A, 112:5708-5713; B. Izar and A. Rotem, 2016 Curr. Protoc. Mol. Biol., 116:28.8.1-28.8.12). These ex vivo cultures were treated with JSI-124, a previously characterized highly selective JAK/STAT3 inhibitor (Blaskovich et al., 2003 Cancer Res., 63:1270-1279), and the efficacy of JSI-124 was compared to drugs that are most widely used for the treatment of ovarian cancer, including carboplatin, cisplatin, paclitaxel, and olaparib, a PARP-inhibitor. In all tested models, strong single-agent cytotoxic activity of JSI-124 with $EC_{50}$ values in nanomolar ranges, and an $E_{max}$ of up to 99% were observed (FIG. 6B). In contrast, all spheroid cultures were resistant to carboplatin, cisplatin, olaparib and paclitaxel at a similar dose range, with the exception of cisplatin with an $EC_{50}$ of ~10 μM in patients DF3266 and DF3288. Microscopic analysis of spheroids showed that while other therapies changed the morphology of spheroids, only JSI-124 led to disintegration of the solid 3D spheroid structure (FIG. 6C) that is critical for invasive potential. The activity of JSI-124 against both formed spheroids and conventional cell culture conditions were confirmed in additional established ovarian cancer cell lines from the Cancer Cell Line Encyclopedia (CCLE)(J. Barretina et al., 2012 Nature, 483:603-607, FIG. 12). FIG. 36 depicts a series of photomicrographs showing morphological description of ex-vivo patient-derived ovarian cells after treatment with STAT3 inhibitor JSI-124. FIG. 12A and FIG. 12B are a series of graphs and FIG. 23 is a series of images further supporting that JSI-124 effectively kills ovarian cancer cell lines grown as two-dimensional cultures or three-dimensional spheroids. Since the formation of spheroids is a critical step in abdominal metastasis in ovarian cancer, tests to confirm whether JSI-124 inhibited spheroid formation in vitro were completed. Compared to DMSO control, treatment with JSI-124 completely abrogated the formation of spheroids in four cell lines ovarian cancer cell lines in low adherent surface culture conditions, including OVCAR4, OVCAR8, OVASHO, and TYKNU, and significantly reduced the number of spheroids in one cell line (Kuramachi) (FIG. 6D). Importantly, this effect was not due to cell killing by JSI-124. In contrast, carboplatin modest to no effects on spheroids formation at the same treatment doses (FIG. 6C).

Figure 6E:
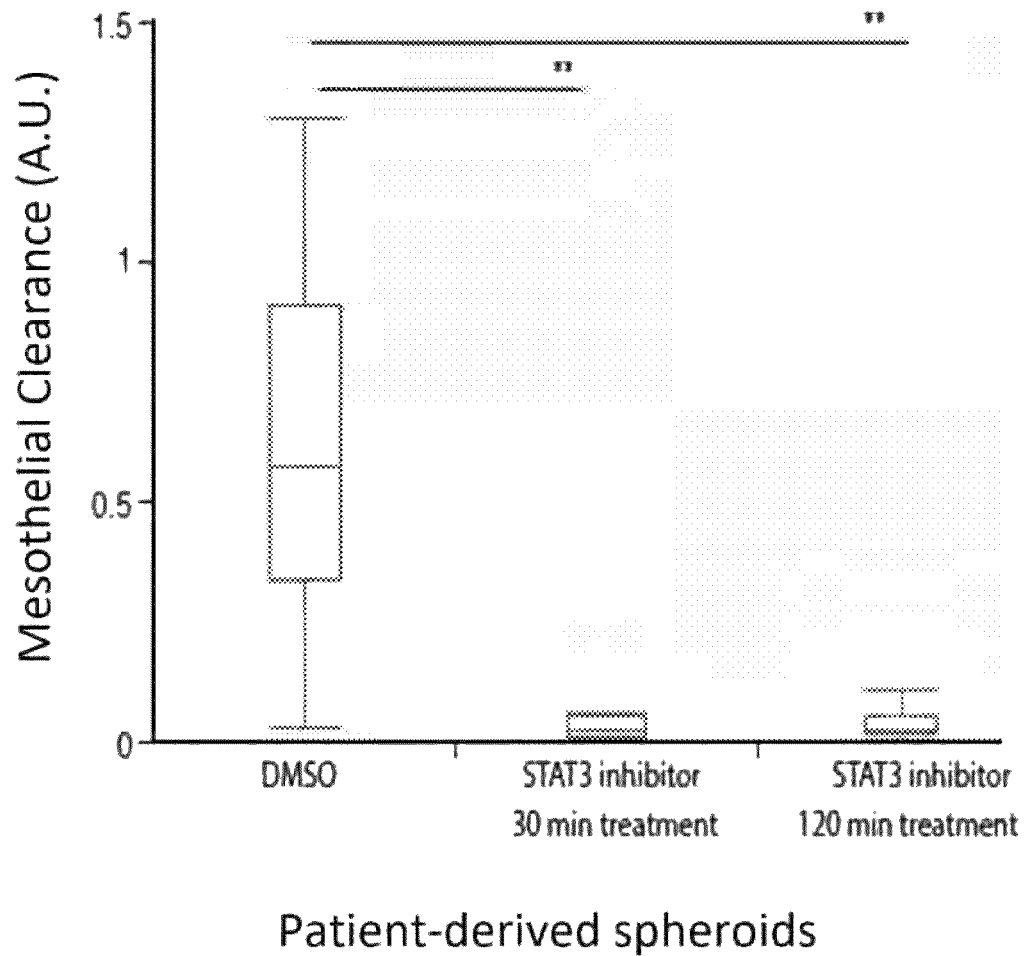
Figure 6F:
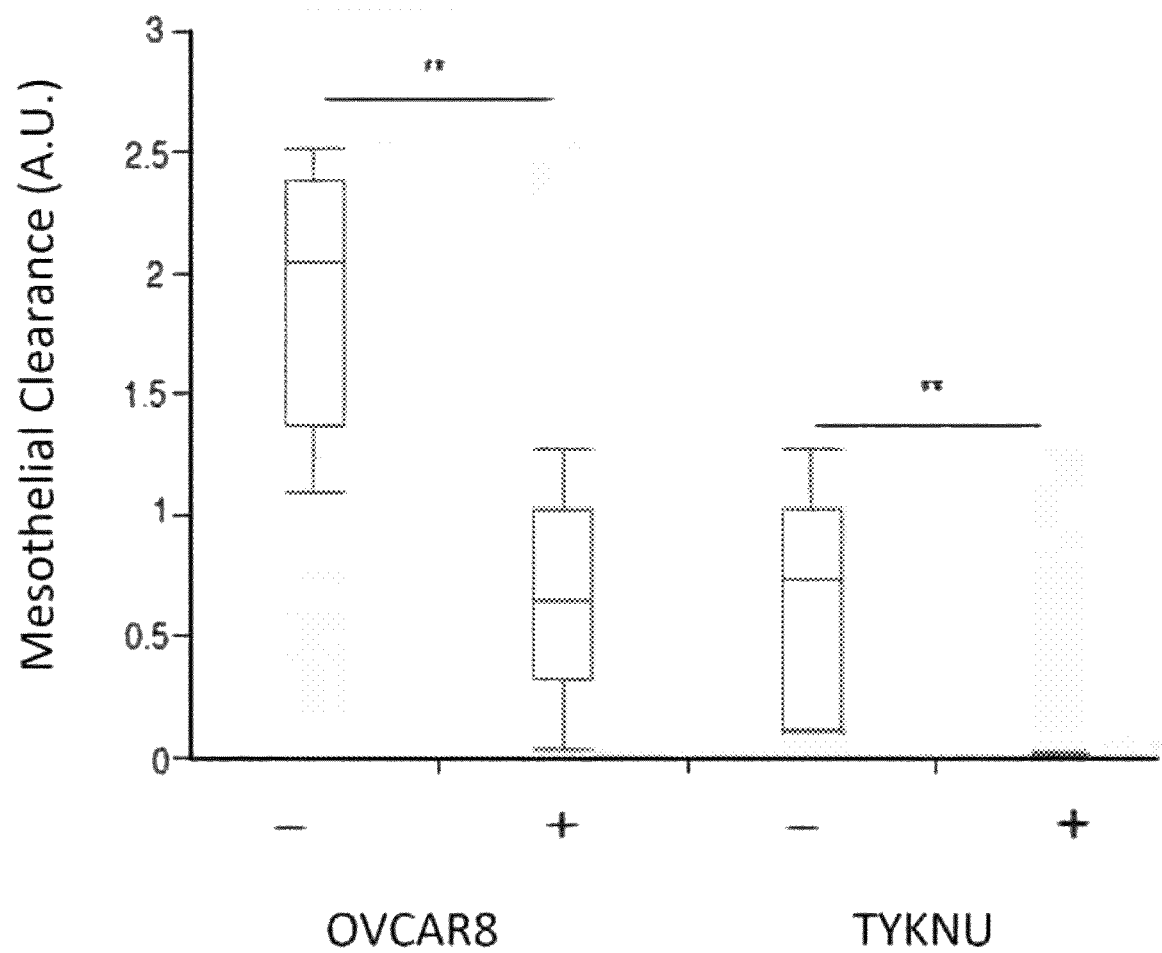
Figure 6G:
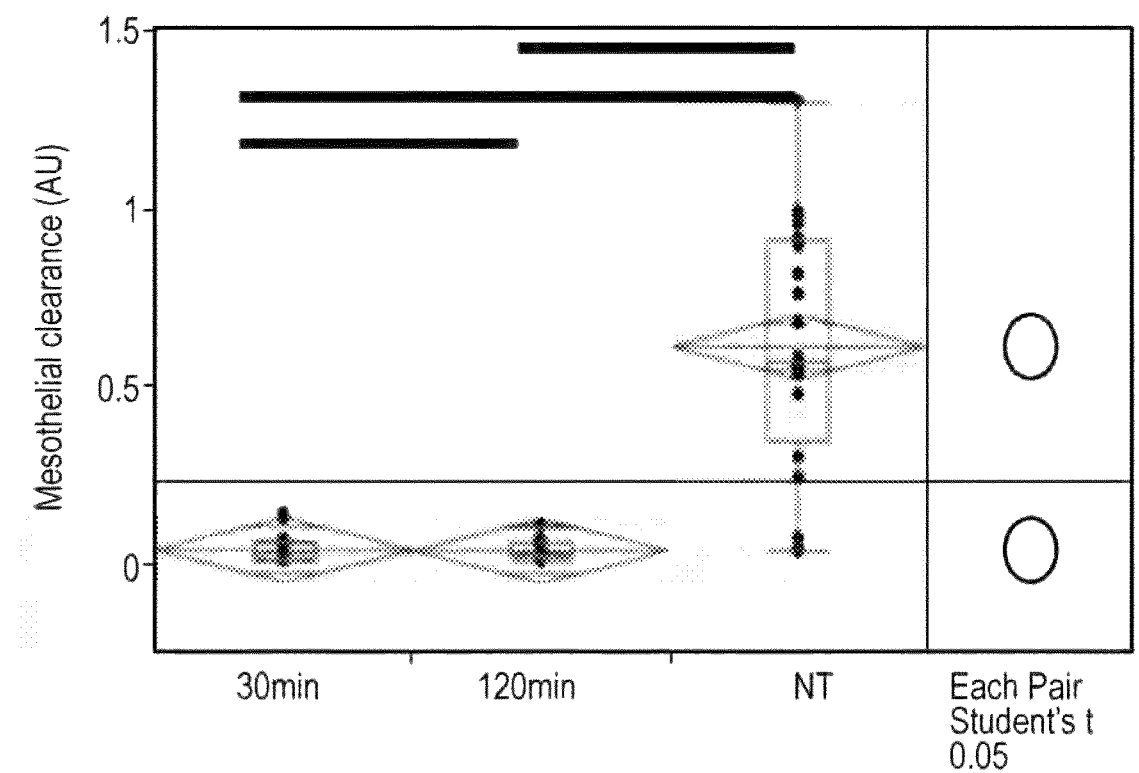
Figure 37:
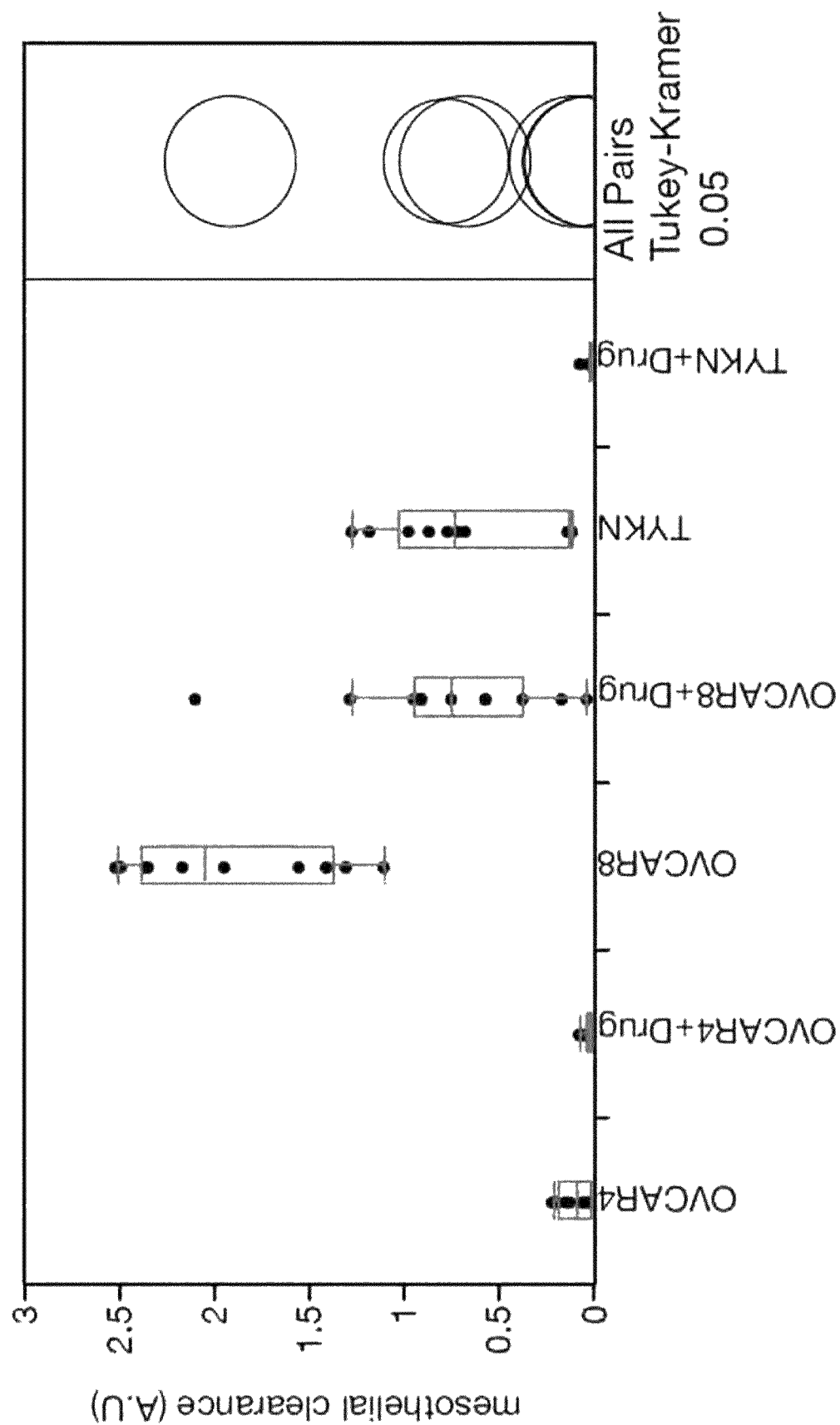
FIG. 37 is a dot plot showing mesothelial clearance.

Once spheroids are formed in the ascites ecosystem, they serve as a vehicle for malignant cells to reach intra-abdominal sites of metastases. Because abdominal organs are covered with a mesothelial cell lining, a critical step in metastasis is invasion (or clearance) through this cellular monolayer (Iwanicki et al., 2011 Cancer Discov., 1:144-157; Davidowitz et al., 2014 J. Clin. Invest., 124:2611-2625; Iwanicki et al., 20016 JCI Insight, 1). To test whether JSI-124 also inhibits invasion, a previously established system was used to determine the ability to clear a mesothelial monolayer (Iwanicki et al., 2011 Cancer Discov., 1:144-157). For this purpose, the ability of patient ascites-derived spheroids to invade mesothelium with and without pre-treatment with JSI-124 for either 30 or 120 minutes (followed by drug removal was measured. While untreated patient-derived spheroids showed a strong potential to clear the mesothelial monolayer, spheroids treated with JSI-124 for 30 minutes or 120 minutes (followed by drug removal) had a significantly reduced ability to invade the mesothelial monolayer (FIG. 6E, FIG. 37). Importantly, this effect was not explained by JSI-124 mediated disintegration of spheroids (FIG. 23 top row). This experiment was repeated with two commonly used established ovarian cancer cell lines (OVCAR8 and TKYNU) and found that inhibition with JSI-124 abolished their ability to invade the mesothelium (FIG. 6F and FIG. 6G, FIG. 23 bottom row). Together, these results indicate that JSI-124 effectively disintegrates platinum-resistant ovarian cancer spheroids, inhibits spheroids formation and invasive properties, and thereby inhibits key steps of abdominal metastasis in ovarian cancer, even in tumors resistant to standard chemotherapeutics.

Figure 7A:
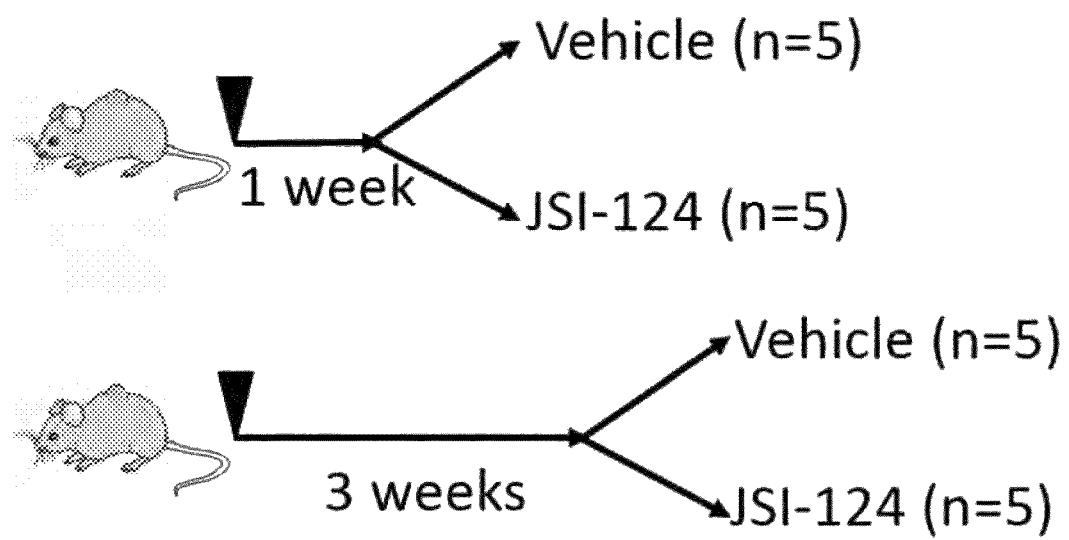
FIG. 7A-FIG. 7E are a series of graphs and images that depict the impact of JAK/STAT-inhibition on spheroid formation in vivo and anti-tumor activity.
Figure 7B:
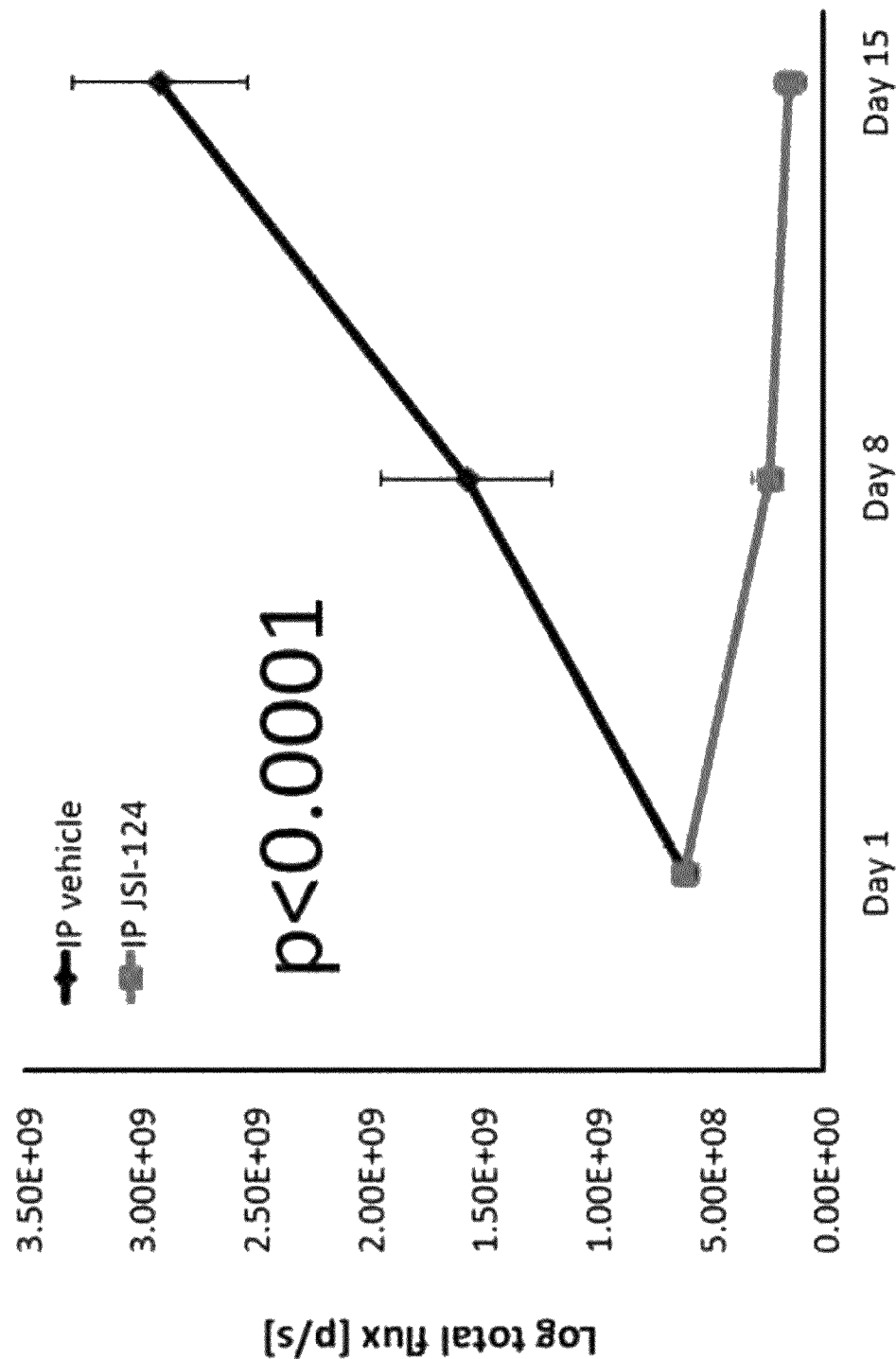
Figure 7C:
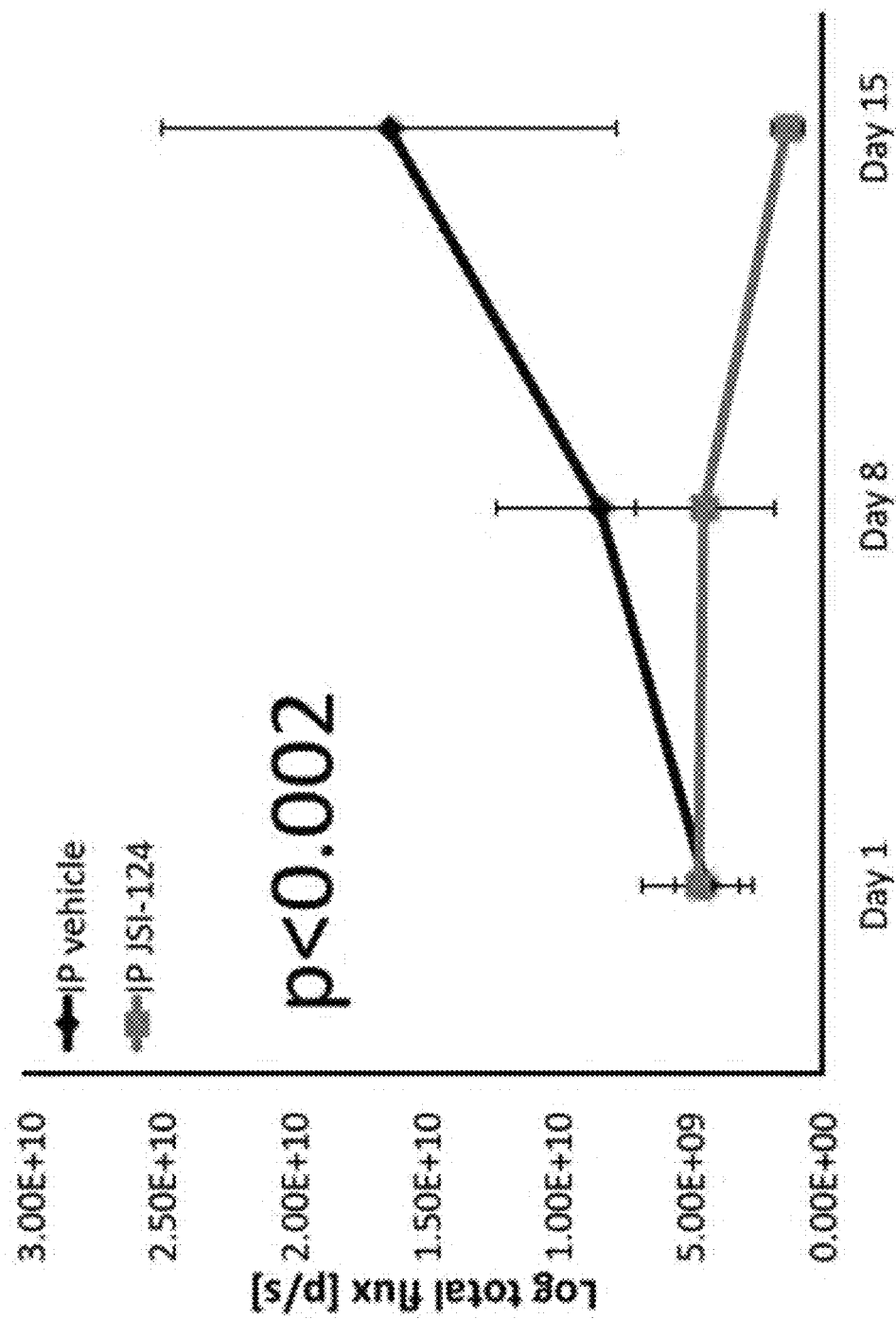
Figure 13:
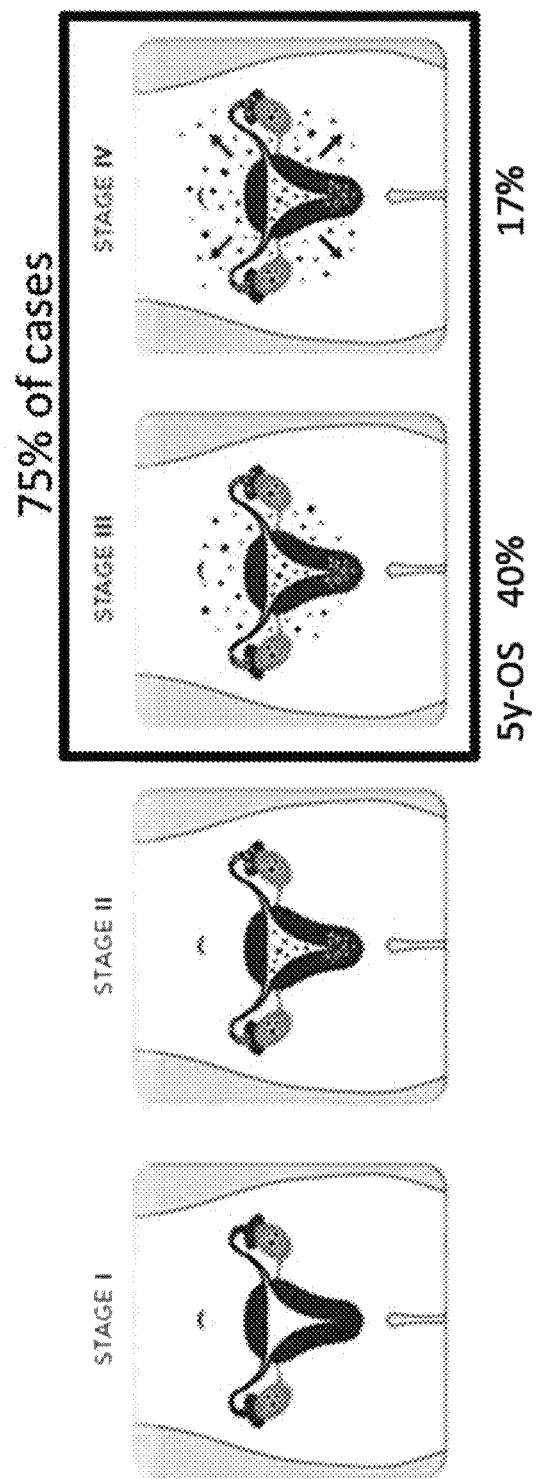
FIG. 13 is a schematic illustrating that 75% of ovarian cancer are diagnosed at stage III/IV. Stage I>90%; stage II 70%; stage III 40%; stage IV 70%.
Figure 24:
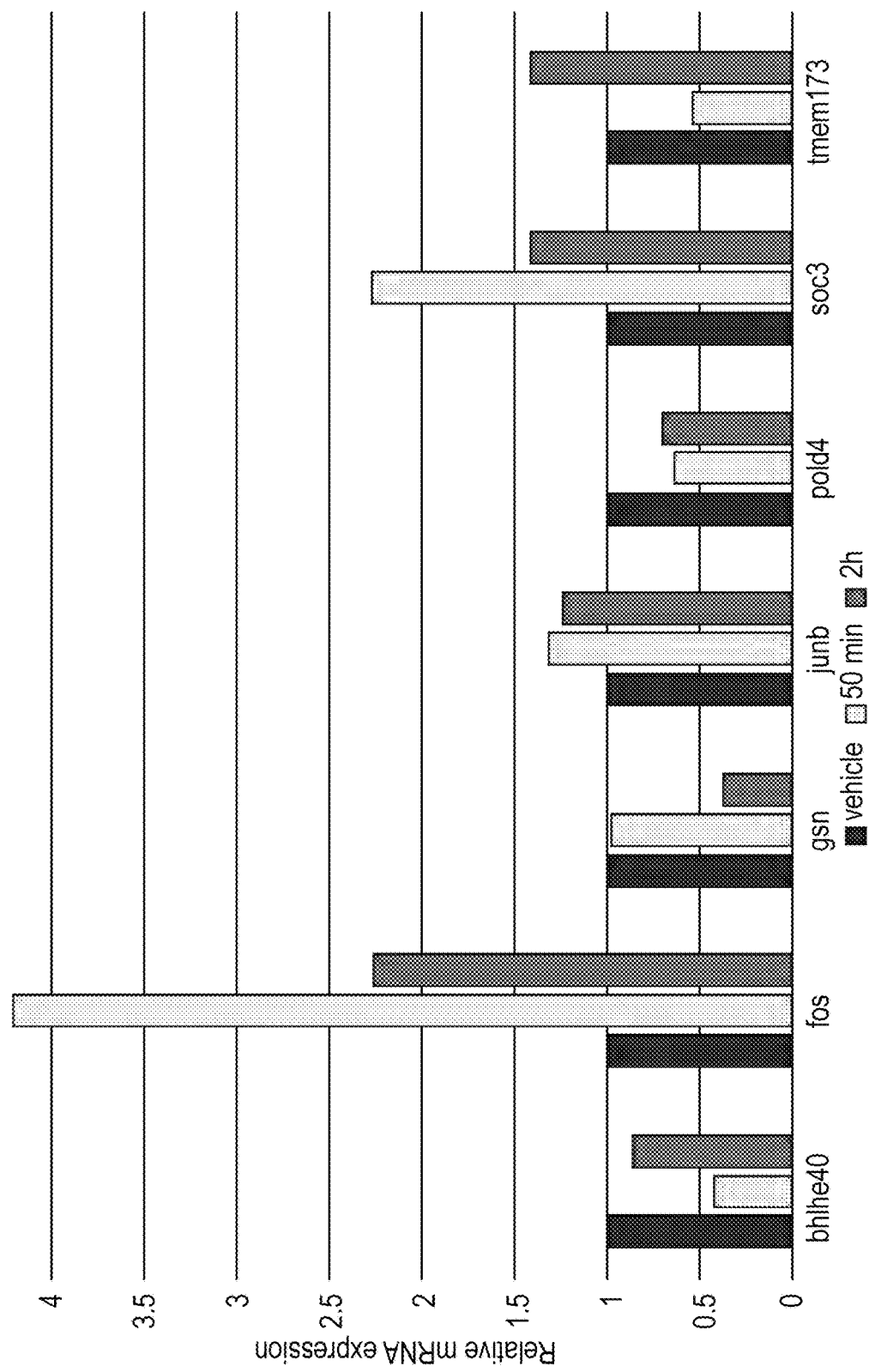
FIG. 24 is a histogram of relative mRNA expression depicting STAT target gene expression.
Figure 38:
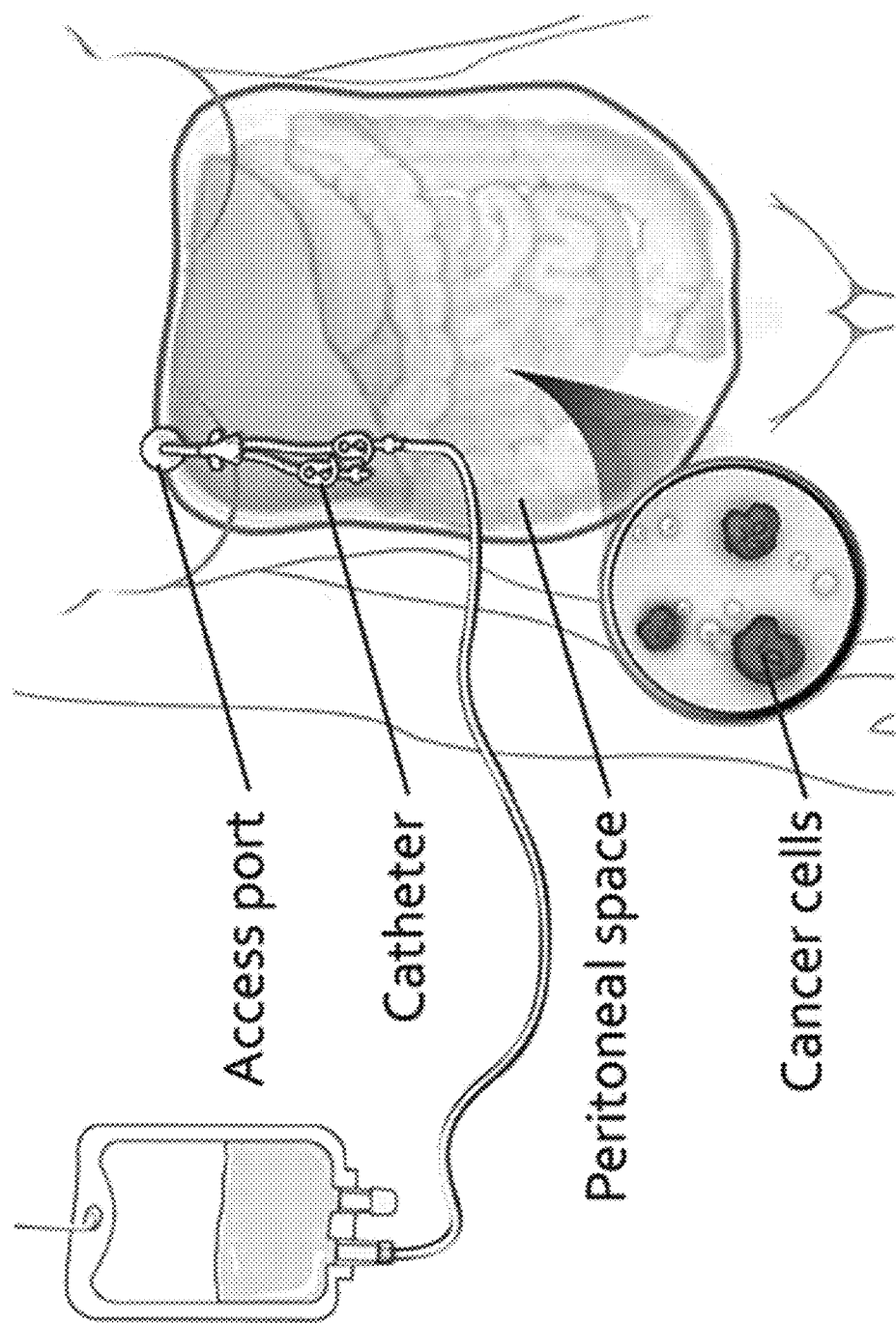
FIG. 38 is a diagram of intraperitoneal therapy for cancer.
Figure 39:
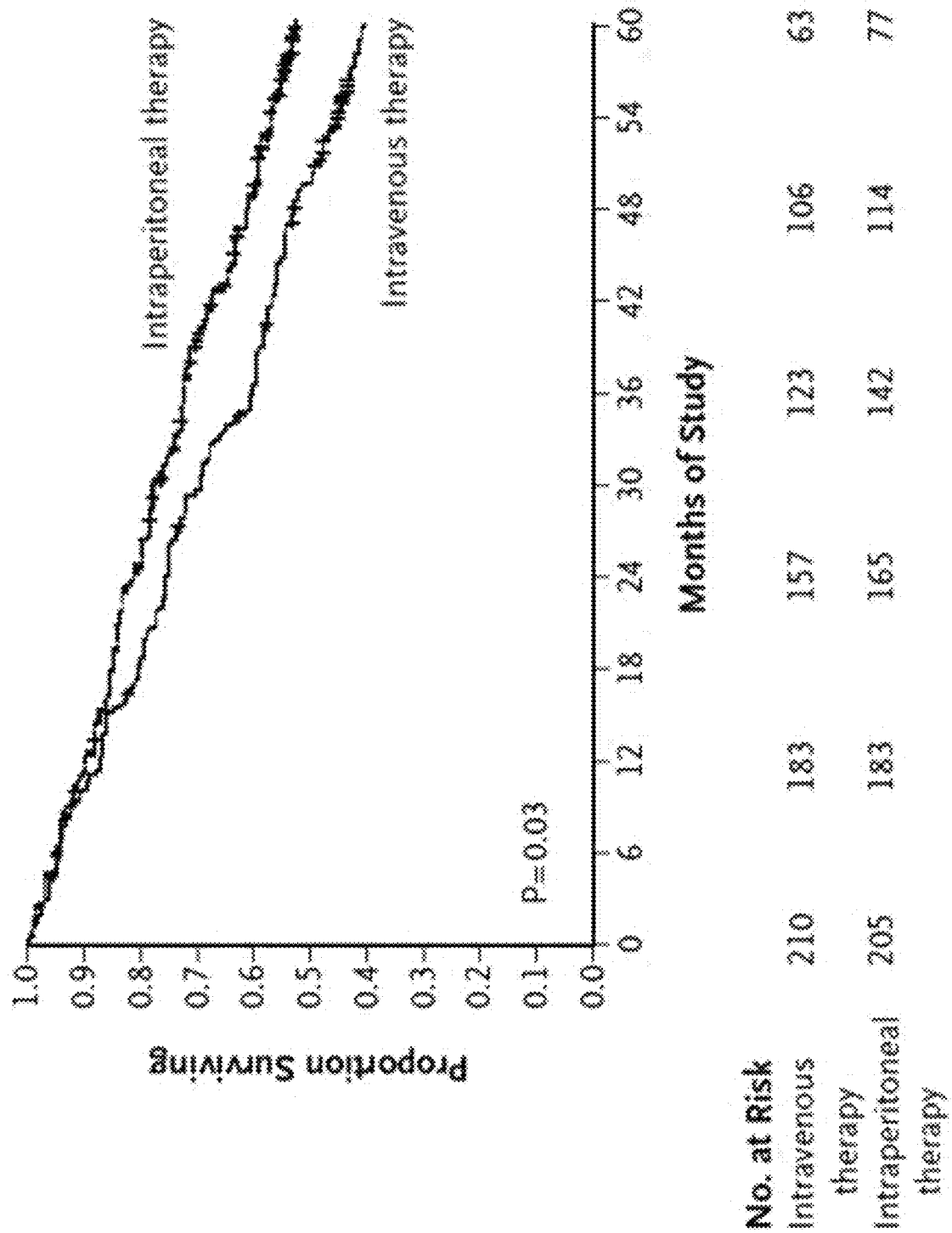
FIG. 39 is a graph comparing intraperitoneal therapy and intravenous (IV) therapy (Armstrong, NEJM, 2006).
Figure 40:
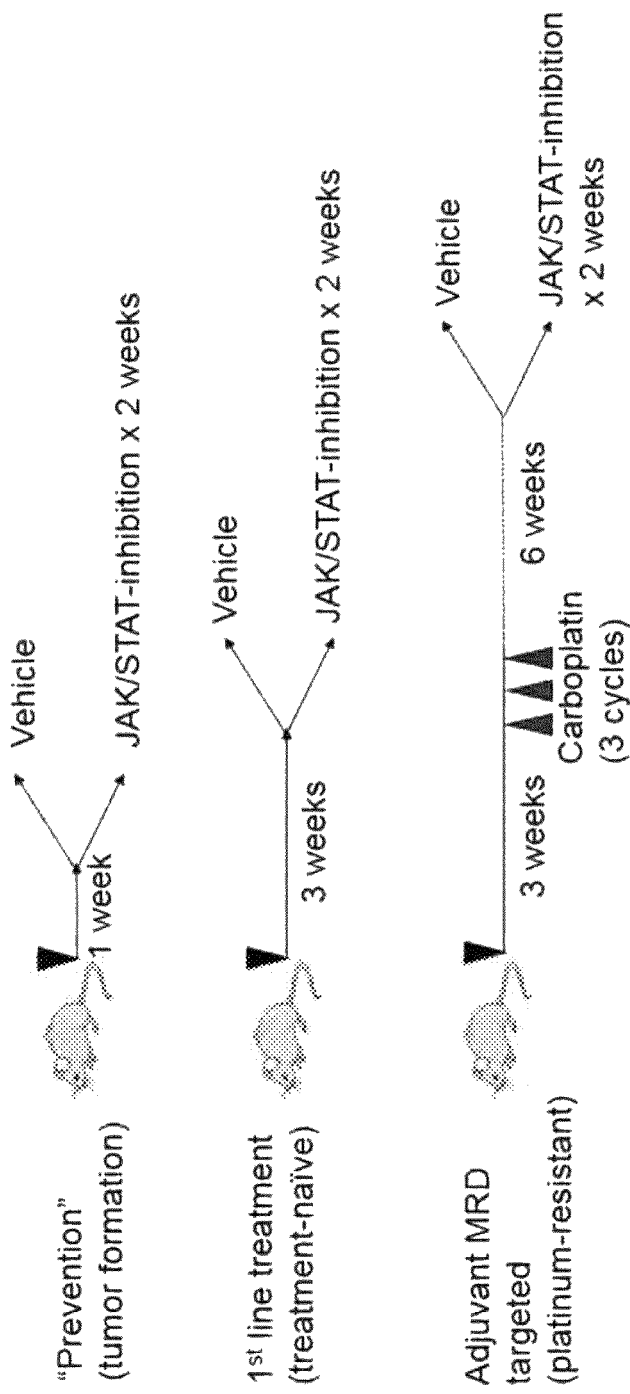
FIG. 40 is a diagram of an in-vivo study design evaluating tumor formation in mice to evaluate activity of intraperitoneal administered JAK/STAT inhibitor.

Example 7—Intraperitoneally Administered JSI-124 Prevents the Abdominal Development of Malignant Ascites Given that abdominal metastasis mediated by spheroids represents a key clinical problem in patients with ovarian cancer (FIG. 13 illustrates that 75% of ovarian cancers are diagnosed at stage III/IV), studies were completed to determine whether STAT3 inhibitor JSI-124 (FIG. 24 illustrates STAT target gene expression) abrogates the development of malignant ascites in vivo (study diagram shown in FIG. 7A and alternative study diagram shown in FIG. 40). For this purpose, the PDX-model DF20 was used to assess the BLI signal after intraperitoneal (IP) injection of cancer cells and IP treatment with JSI-124 vs. vehicle (FIG. 38 illustrates IP therapy for cancer and FIG. 39 compares IP and intravenous therapy). PDX-models were injected with tumor cells and allowed to grow for 7 days, followed by 14 days of therapy with JSI-124 delivered IP (FIG. 7A, top). Compared to controls, treatment with JSI-124 completely abrogated development of malignant ascites (FIG. 7B), mean day 15 log BLI signal±standard deviation, $2.19 \times 10^9 \pm 3.9 \times 10^8$ vs. $1.47 \times 10^8 \pm 6.5 \times 10^7$, p<0.0001, two-tailed t test). Next, it was determined whether treatment with JSI-124 eliminates established malignant ascites. For this purpose, injected cancer cells were allowed to form malignant ascites for 3 weeks prior to treatment with IP JSI-124 or vehicle (FIG. 7A, bottom). Compared to vehicle treated models, significant reduction in BLI signal of malignant ascites was found (FIG. 7C, $1.6 \times 10^{10} \pm 2.5 \times 10^9$ vs. $1.29 \times 10^9 \pm 6 \times 10^8$, p<0.0001).

Figure 7D:
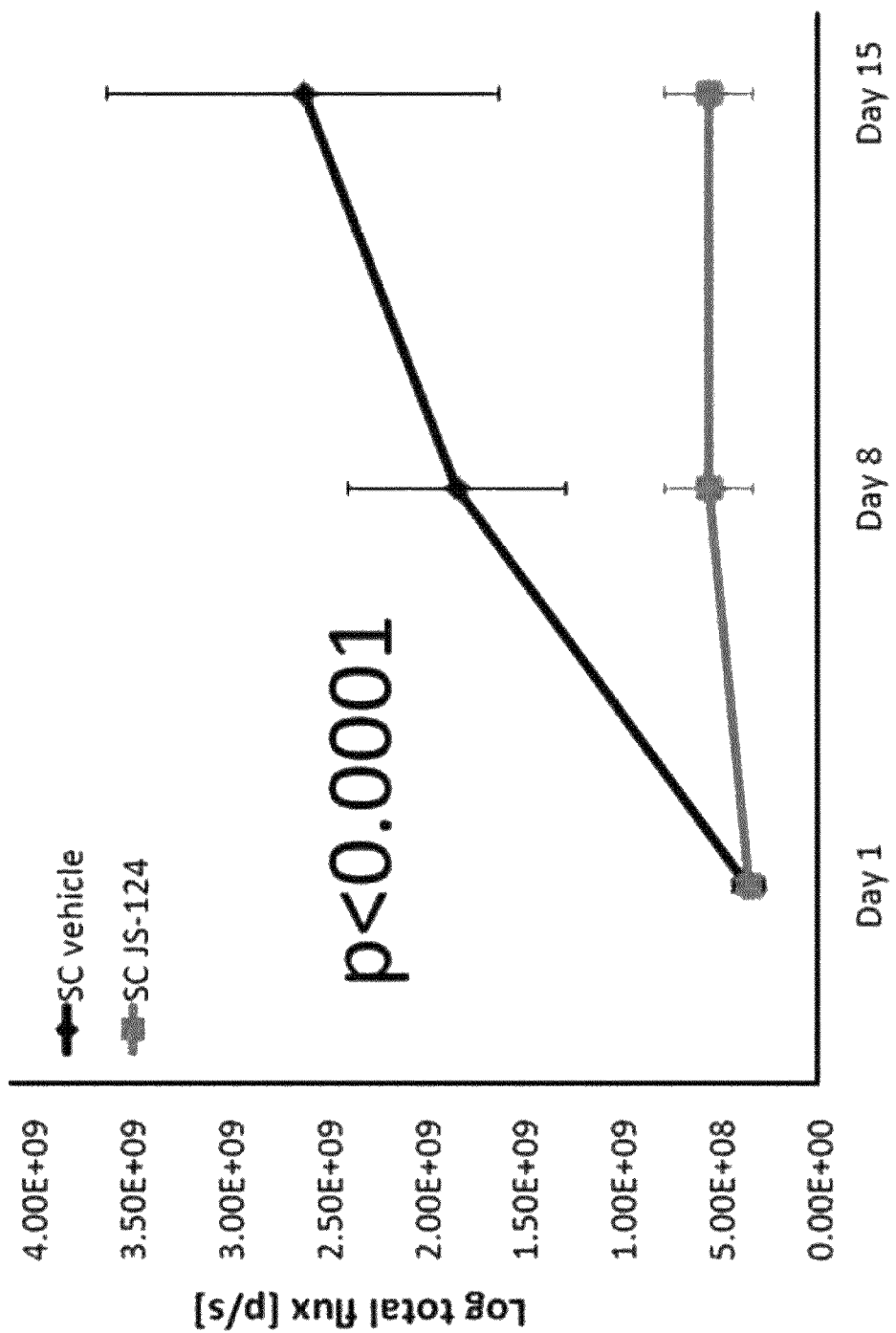
Figure 7E:
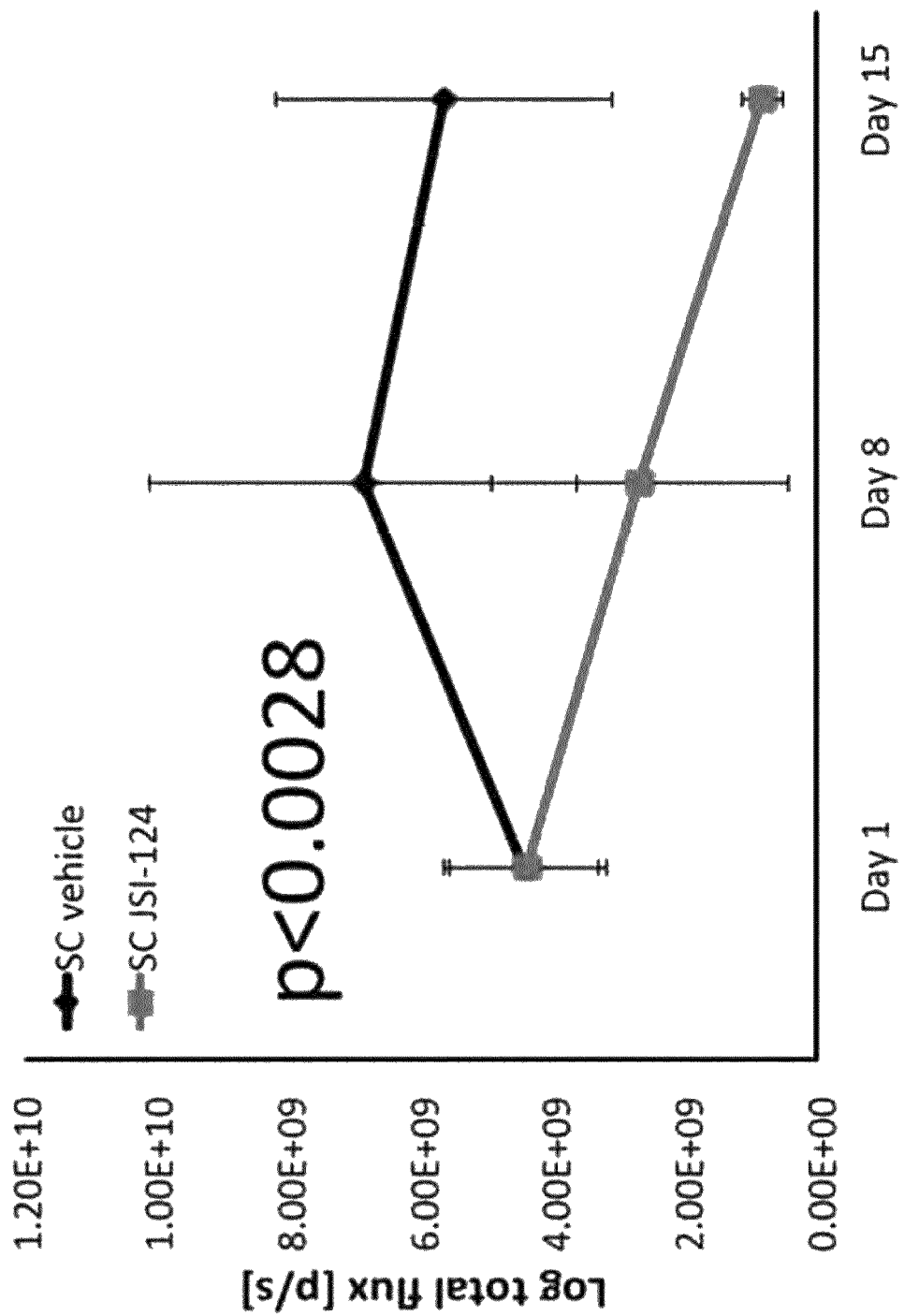

Example 8—IP Administered JSI-124 Prevents Systemic Tumor Growth and Effectively Eliminates Established Tumors A frequently used treatment modality for advanced ovarian cancer is the intraperitoneal administration of chemotherapy, such as cisplatin, which has local effects, but is also systemically reabsorbed to treat potential metastatic disease. To examine whether IP administered JSI-124 prevents systemic formation/progression of solid tumor masses, DF20 cancer cells were injected subcutaneously and tumors were allowed to establish for 7 days. Tumor growth was compared following IP JSI-124 treatment v. vehicle. JSI-124 was found to significantly inhibit development of tumors growth of SC tumors (FIG. 7D, $2.61 \times 10^9 \pm 1 \times 10^9$ vs. $5.55 \times 10^8 \pm 2.2 \times 10^8$, p=0.002) and even led to reduction of injected tumors after 14 days of therapy. To test the treatment of established tumors with IP administered JSI-124, PDX models, initiating SC tumors, were used to establish tumor for 3 weeks prior to treatment with JSI-124. Compared to vehicle, JSI-124 led to significant and near complete elimination of SC tumors (FIG. 7E, $5.65 \times 10^9 \pm 2.5 \times 10^9$ vs. $8.52 \times 10^8 \pm 3.1 \times 10^8$, p=0.0028). However, treatment with JSI-124 resulted in increased weight due to increased non-malignant ascites. The absence of malignant cells in ascites isolated from JSI-124 treated mice was confirmed, indicating that edema is an adverse effect.

Together, these results indicate that IP administration of JSI-124 has significant activity in preventing ascites formation and disrupting malignant ascites and systemic, and therefore provides a unique approach for the treatment of patients with ovarian cancer. The results presented herein suggest that small molecule JAK/STAT inhibitor JSI-124, and other JAK/STAT inhibitors, represent a feasible treatment approach for patients with ovarian cancer.

Example 9—Ovarian Cancer Heterogeneity

Figure 19A:
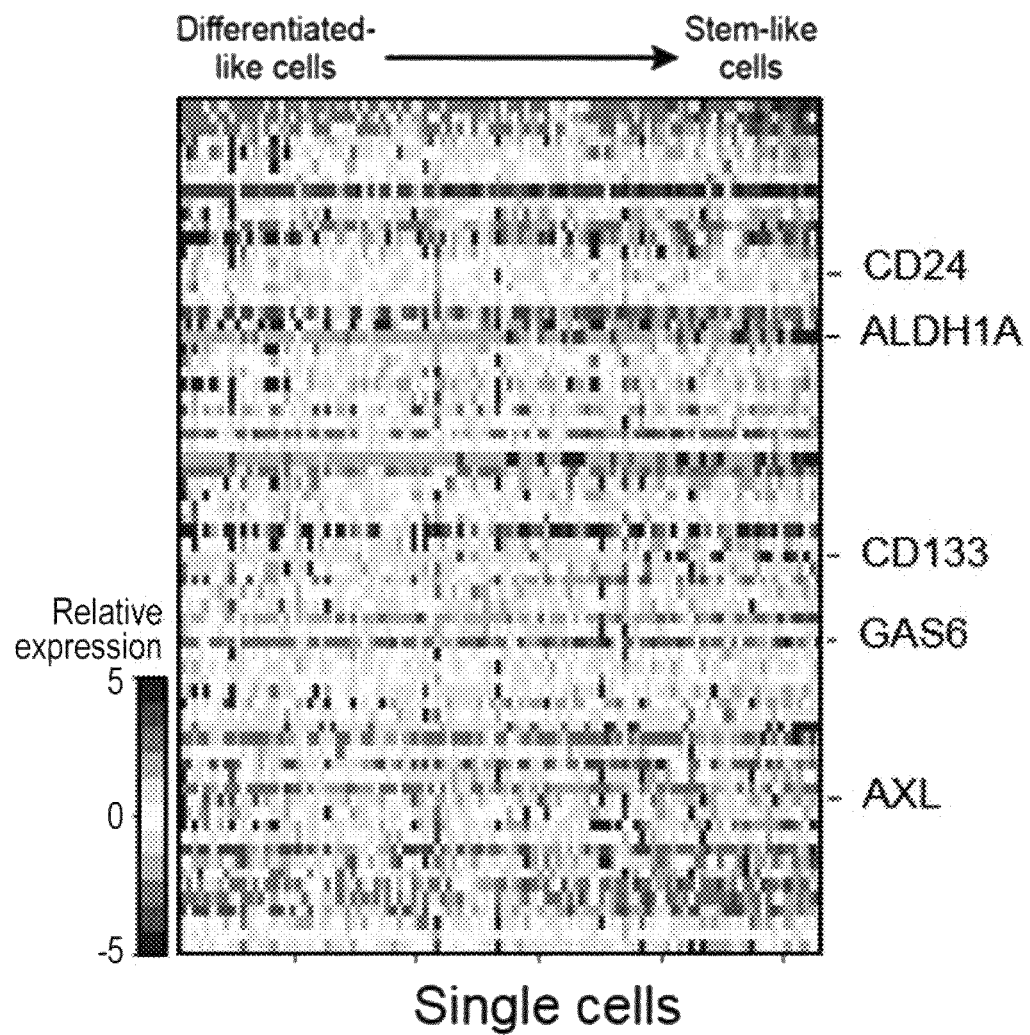
FIG. 19A-FIG. 19B are a series of heatmaps depicting ovarian cancer heterogeneity.
Figure 19B:
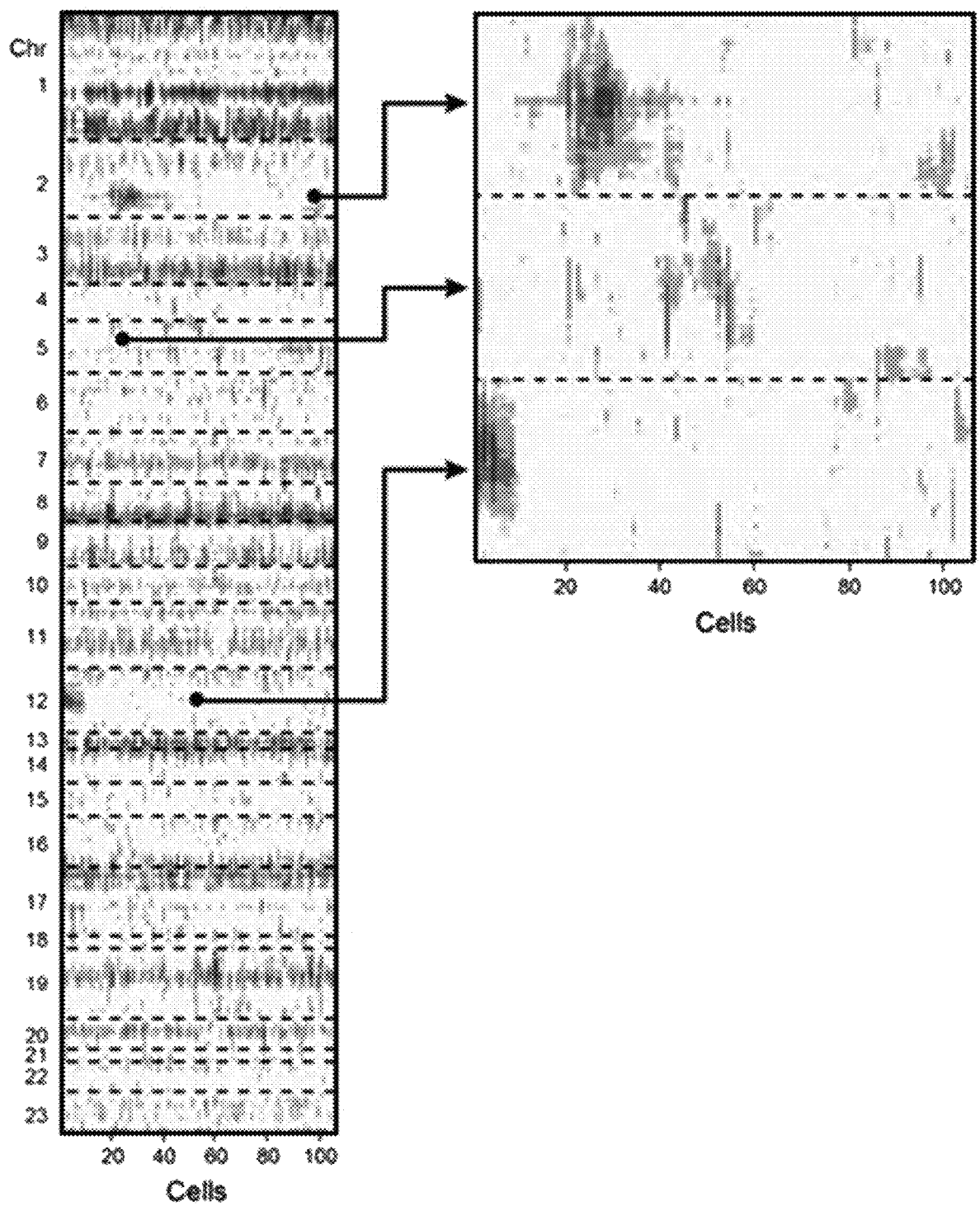

A series of graphs showing ovarian cancer heterogeneity is illustrated in FIG. 19A and FIG. 19B. This experiment utilized isolated single-cells from malignant effusions from a patient with highly resistant ovarian cancer. In this patient, 106 single-cell transcriptomes were analyzed, and the copy number variation (CNVs) were inferred as previously described. For ovarian cancer, a large burden of CNVs were identified. While most of the CNVs were shared among cells, subpopulations were identified that carried unique aberrations, such as chromosome 12 deletion.

Thus, this approach is helpful with reconstructing the clonal architecture. These patients frequently require several taps. Therefore, clonal evolution as patients undergo various treatments can be examined.

Principle component analysis (PCA) of these single-cell transcriptomes identified a gene set that was expressed variably across cells. A population of cells to the very far right expressed multiple known markers of stem-like cells, such as aldehyde dehydrogenase 1A (ALDH1A), CD133, etc., among a program that now allows further evaluation of this phenotype in other patients with ovarian cancer.

Example 10—Probing Treatment Resistance in PDX-Models

Figure 20A:
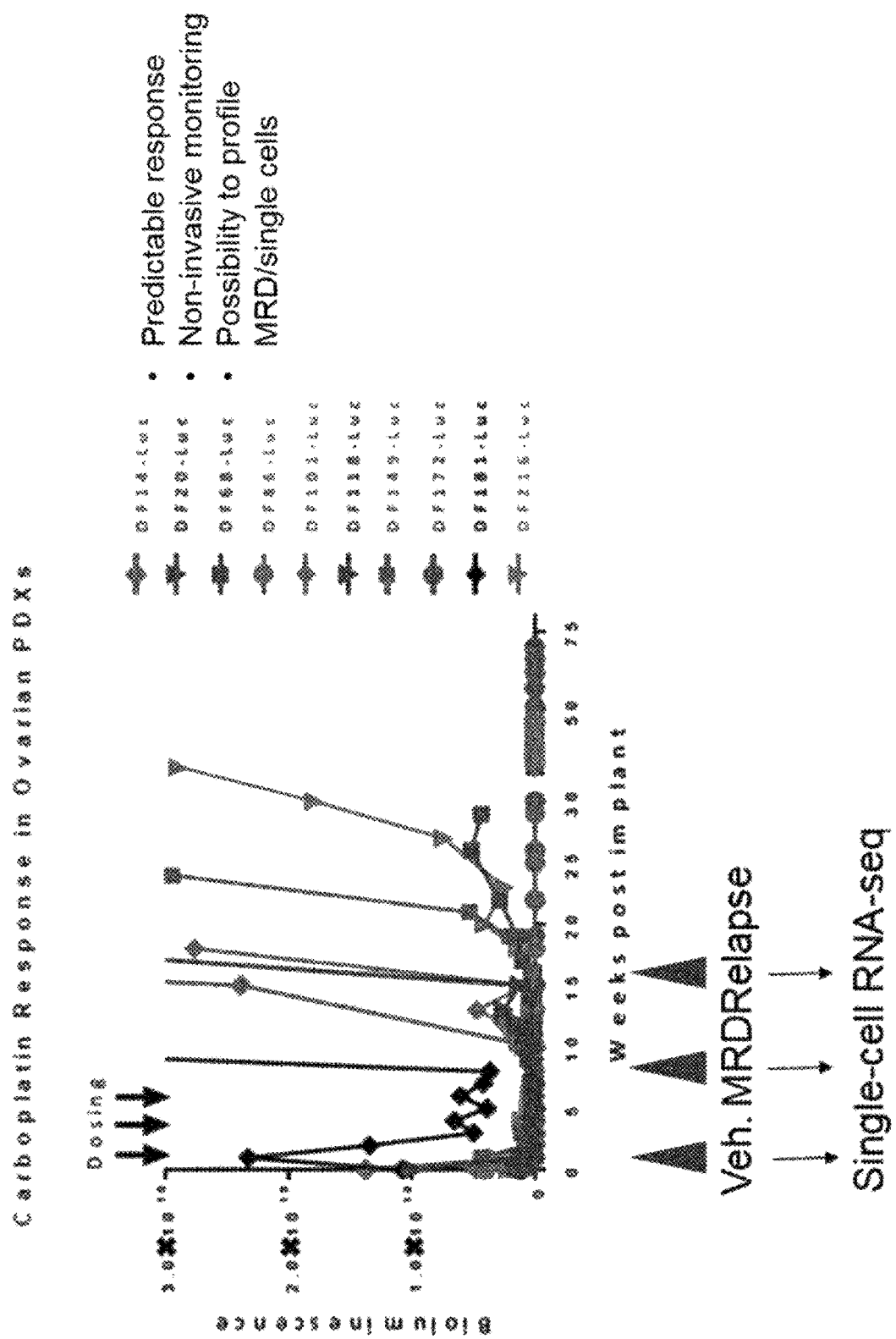
FIG. 20A-FIG. 20B are graphs of cancer treatment resistance in PDX-models.
Figure 20B:
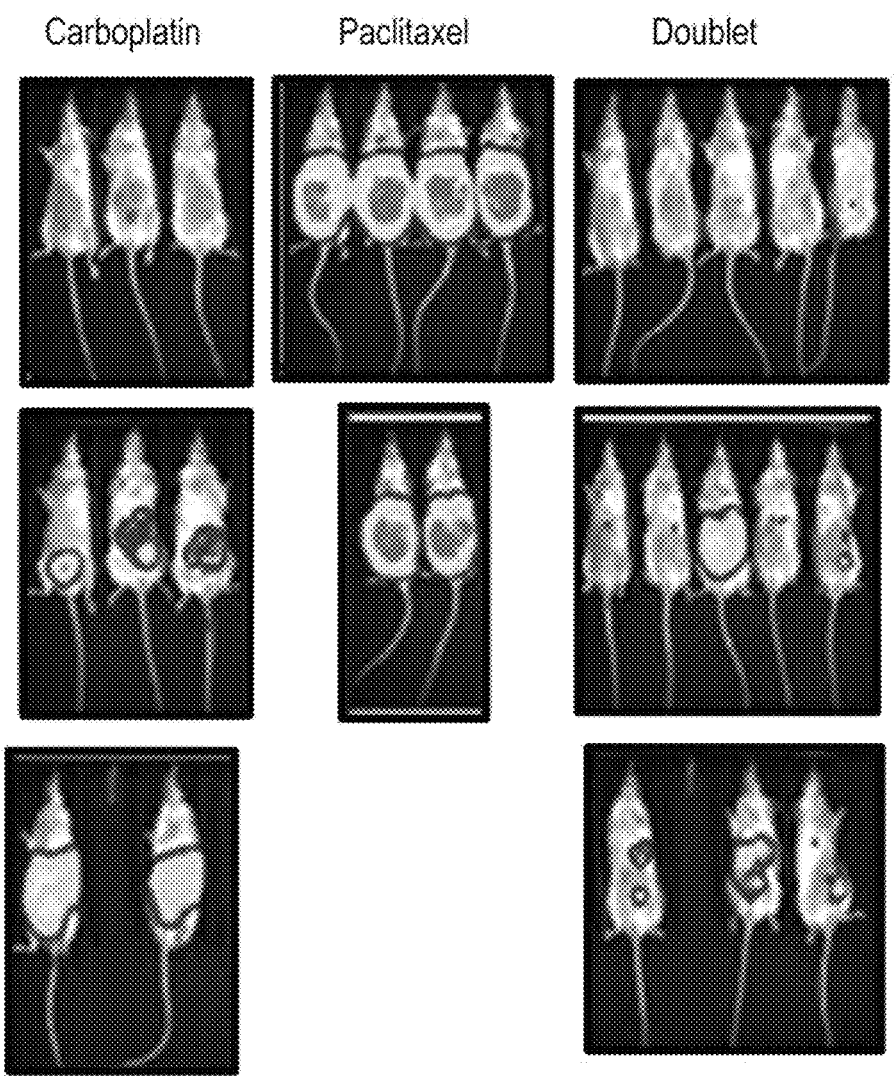

The experimental results of probing treatment resistance in patient derived xenograft (PDX)-models are shown in FIG. 20A and FIG. 20B. The results show 1) a predictable response; 2) non-invasive monitoring; and 3) the possibility to profile minimal residual disease, single cells.

Next, the method described herein was applied to PDX models generated at DFCI/Belfer Institute. Platin-based therapies elicit predictable responses and the PDX models allow non-invasive disease monitoring using BLI combined with the ability to profile individual cells. The study was a unique opportunity to probe transcriptional heterogeneity at pre-treatment, at the time of minimal residual disease, and at relapse. In the first model, DF20, mouse data nicely followed the expected dynamics, especially for time points where single-cells were collected for sequencing.

Example 11—Probing MRD and Relapse at Single-Cell Resolution

Figure 21:
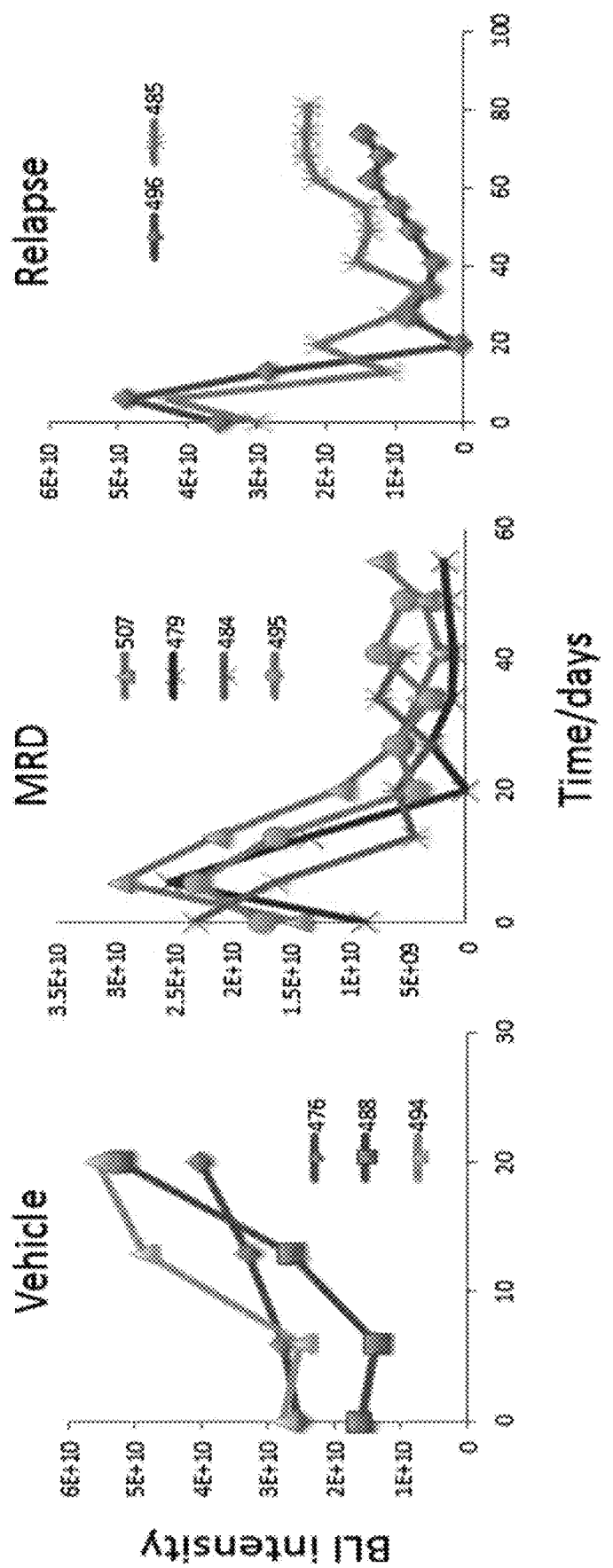
FIG. 21 is a series of line graphs showing the results of probing minimal residual disease (MRD) and relapse at single-cell resolution from DF-20 PDX model.

The results presented herein identified a unique opportunity to probe transcriptional heterogeneity pre-treatment, at the time of minimal residual disease, and relapse. In the first model of experiments, DF20, mice nicely followed the expected dynamics at which time points single-cells were collected for sequencing. The results are presented in FIG. 21.

Example 12—Ovarian Cancer JSI-124 PDX Studies

Described herein is the study design of a PDX study and a study to interrogate the role of this drug as an adjuvant therapy option in ovarian cancer.

JSI-124 Prevention Therapy Arm

Figure 25:
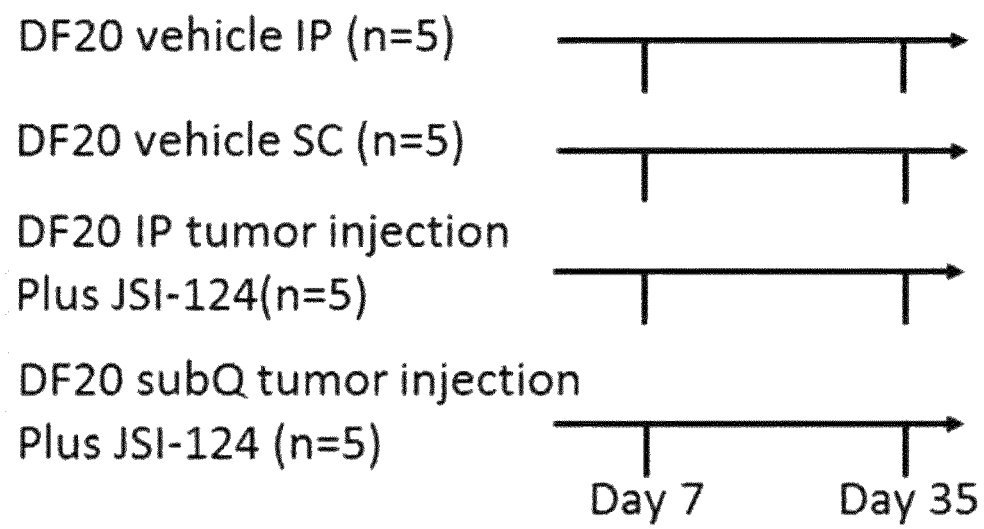
FIG. 25 is a schematic for treatment according to the JSI-124 (cucurbitacin I) prevention therapy arm.

Tumors are injected intraperitoneally (IP) or subcutaneously (subQ). After day 7, mice are treated with 1 mg/kg/daily JSI-124 daily for 4 weeks. The tumor volume/burden is measured by Calipers and BLI signal. SubQ tumors and spheroids are collected at the time of harvesting. Tumors are cryopreserved and snapfrozen for future studies (WB analysis, gene expression, clearance assay, etc.) A schematic is presented in FIG. 25.

JSI-124 Established Tumor Therapy Arm

Tumors are injected IP or subQ. Tumors are grown for 14-21 days and treated with 1 mg/kg/daily JSI-124 daily for 2 weeks. The tumor volume/burden is measured by Calipers and BLI signal. SubQ tumors and spheroids are collected at the time of harvesting.

Figure 26:
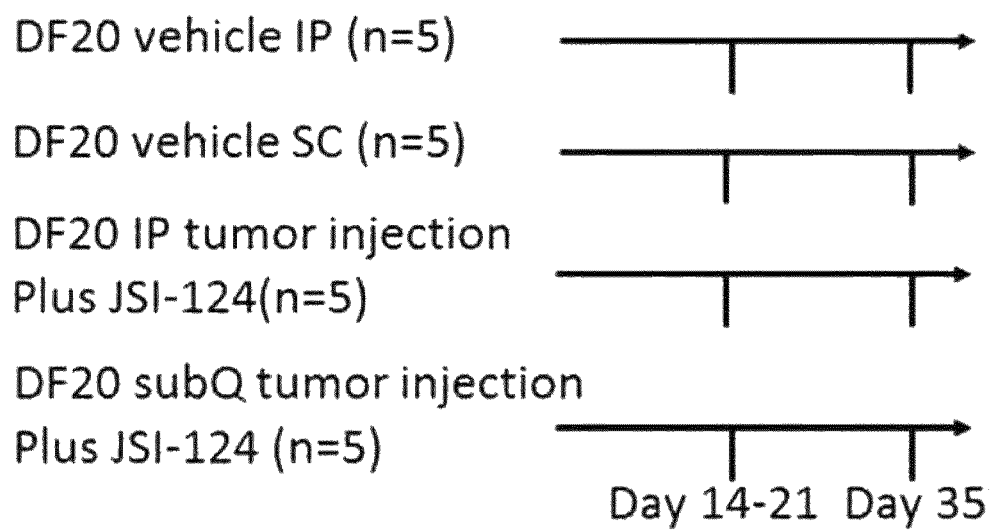
FIG. 26 is a schematic for treatment according to the JSI-124 established tumor therapy arm.

Tumors are cryopreserved and snapfrozen for future studies (WB analysis, gene expression, clearance assay, etc.). A schematic is presented in FIG. 26.

Figure 27:
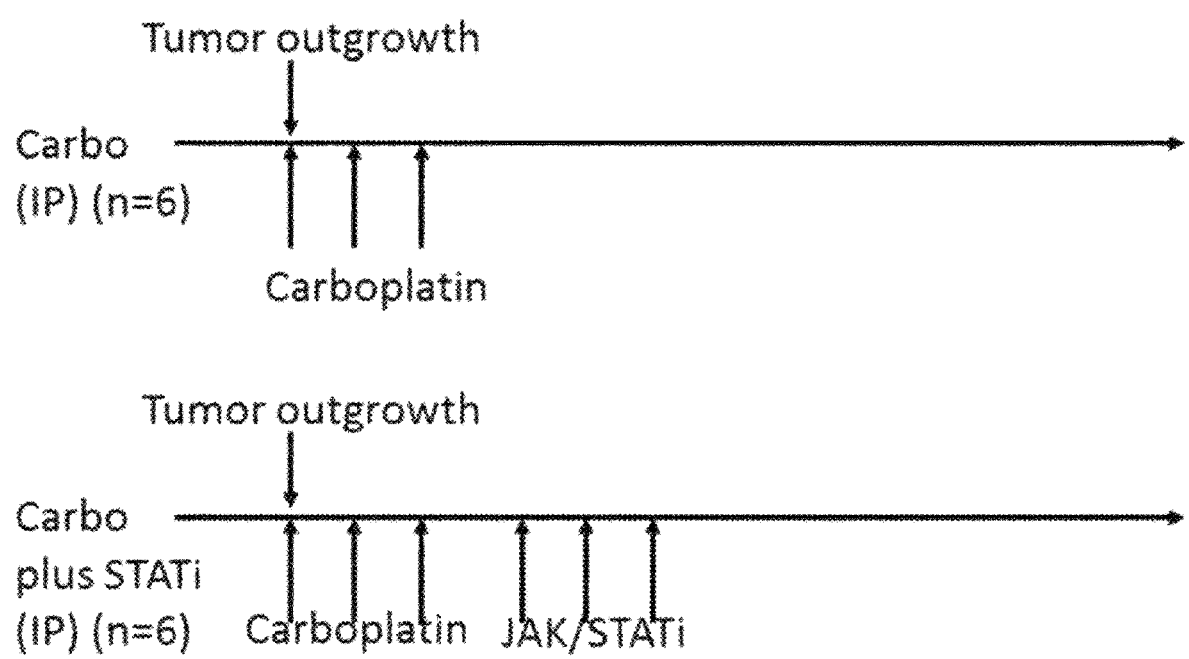
FIG. 27 is a schematic showing the effect of intraperitoneal, adjuvant JAK/STAT3 inhibition on growth of SC tumors (DF-20). Endpoint: Time to tumor recurrence.
Figure 28:
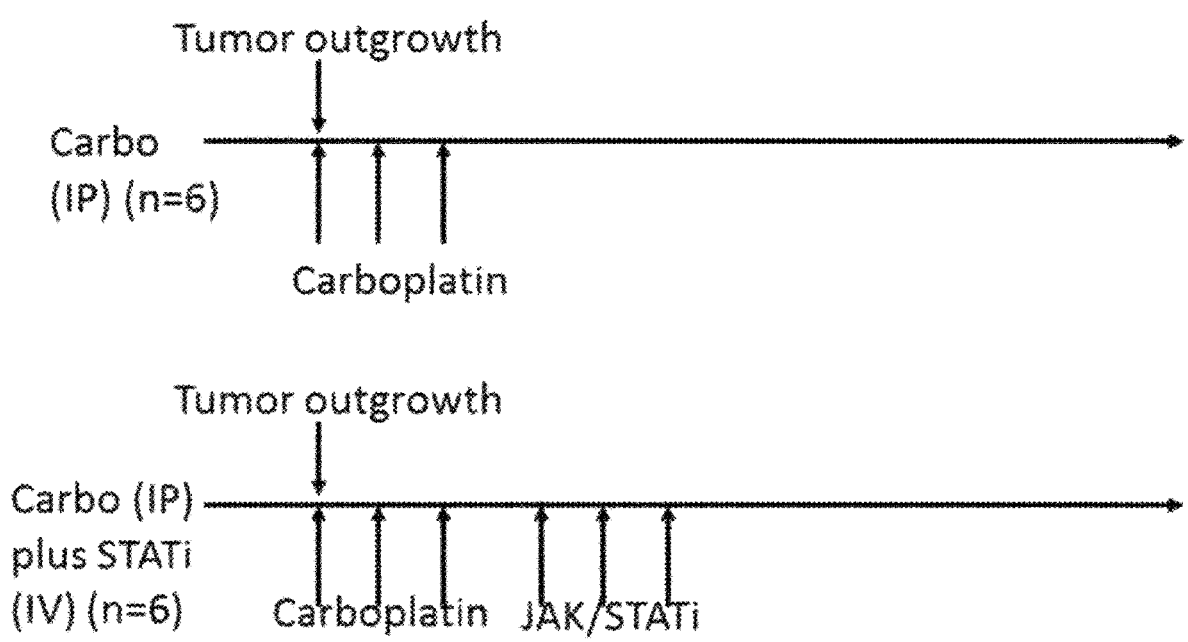
FIG. 28 is a schematic showing the effect of IV, adjuvant JAK/STAT3 inhibition on growth of SC tumors (DF-20). Endpoint: Time to tumor recurrence.

A schematic showing the effect of intraperitoneal, adjuvant JAK/STAT3 inhibition on growth of SC tumors (DF-20) is shown in FIG. 27, while a schematic showing the effect of IV, adjuvant JAK/STAT3 inhibition on growth of SC tumors (DF-20) is shown in FIG. 28.

Figure 29:
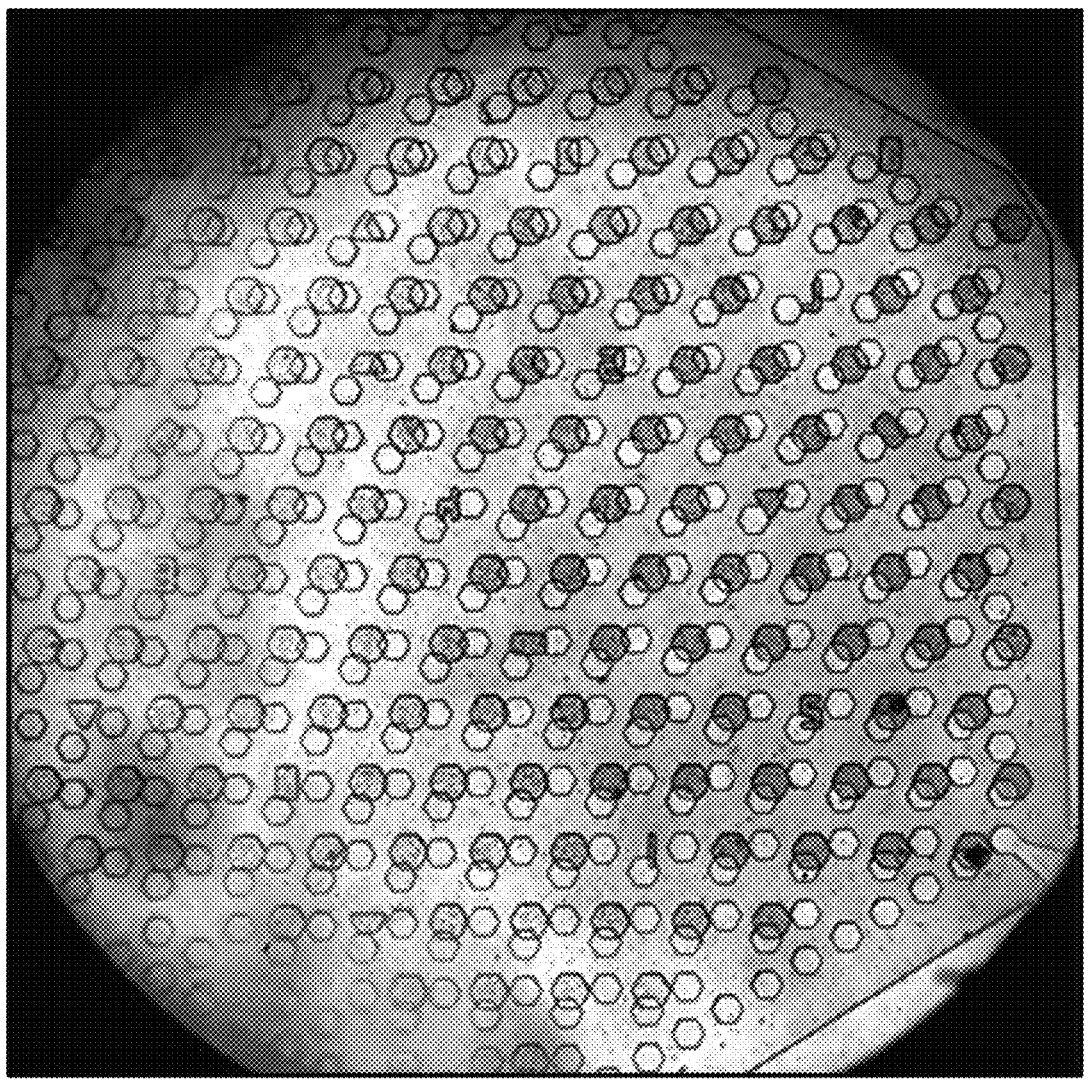
FIG. 29 is a photograph, wherein the right area contained 10 µM JS1124+blue dye, left area served as a control (patient NACT14).
Figure 30:
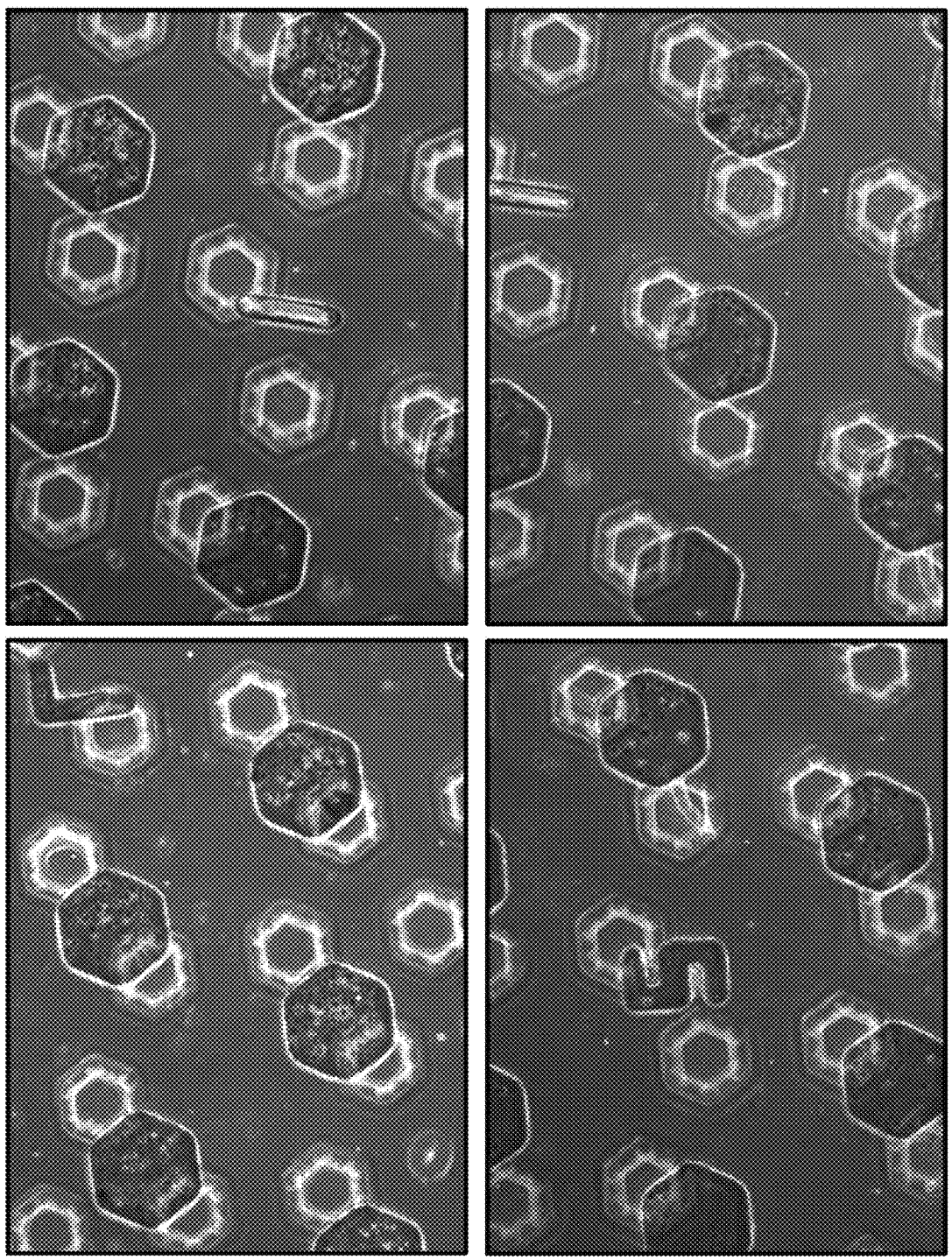
FIG. 30 is a series of photomicrographs showing the area with 10 µM JS1124 (patient NACT14 at day 1).
Figure 31:
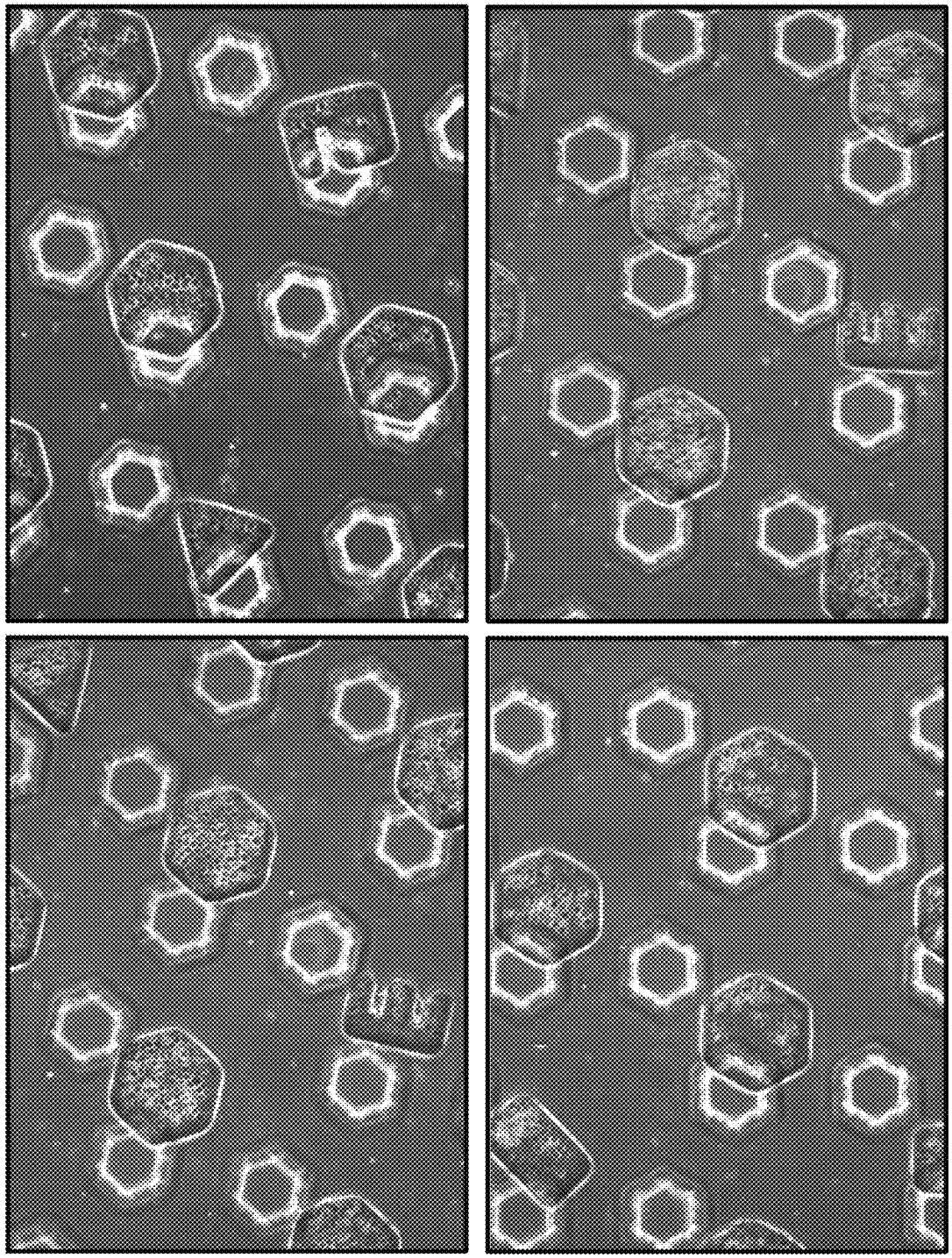
FIG. 31 is a series of photomicrographs showing the area without JSI124 (patient NACT14 at day 1).
Figure 32:
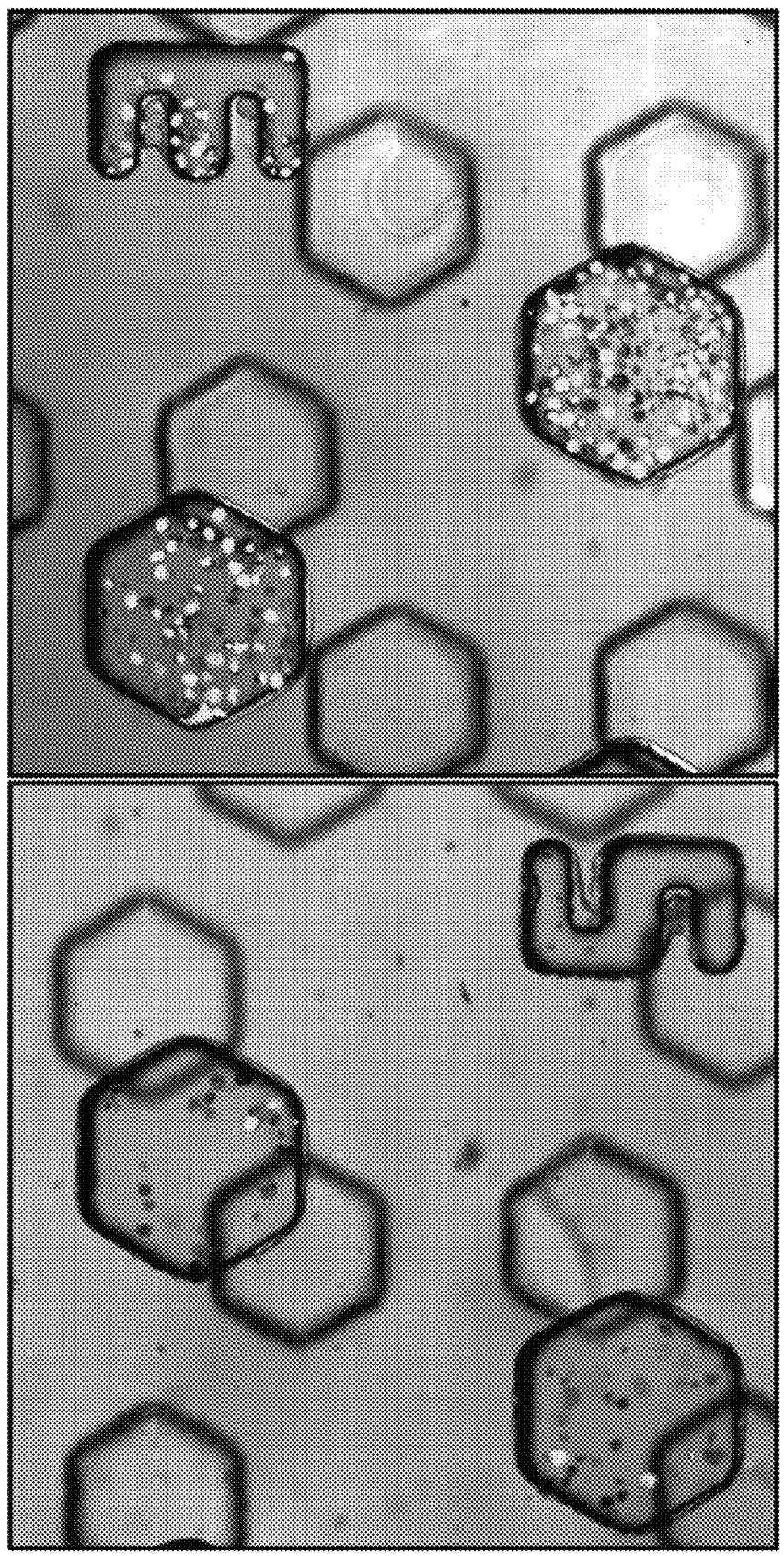
FIG. 32 is a series of photomicrographs showing 48 hours with 10 µM JSI124 (patient NACT14).
Figure 33:
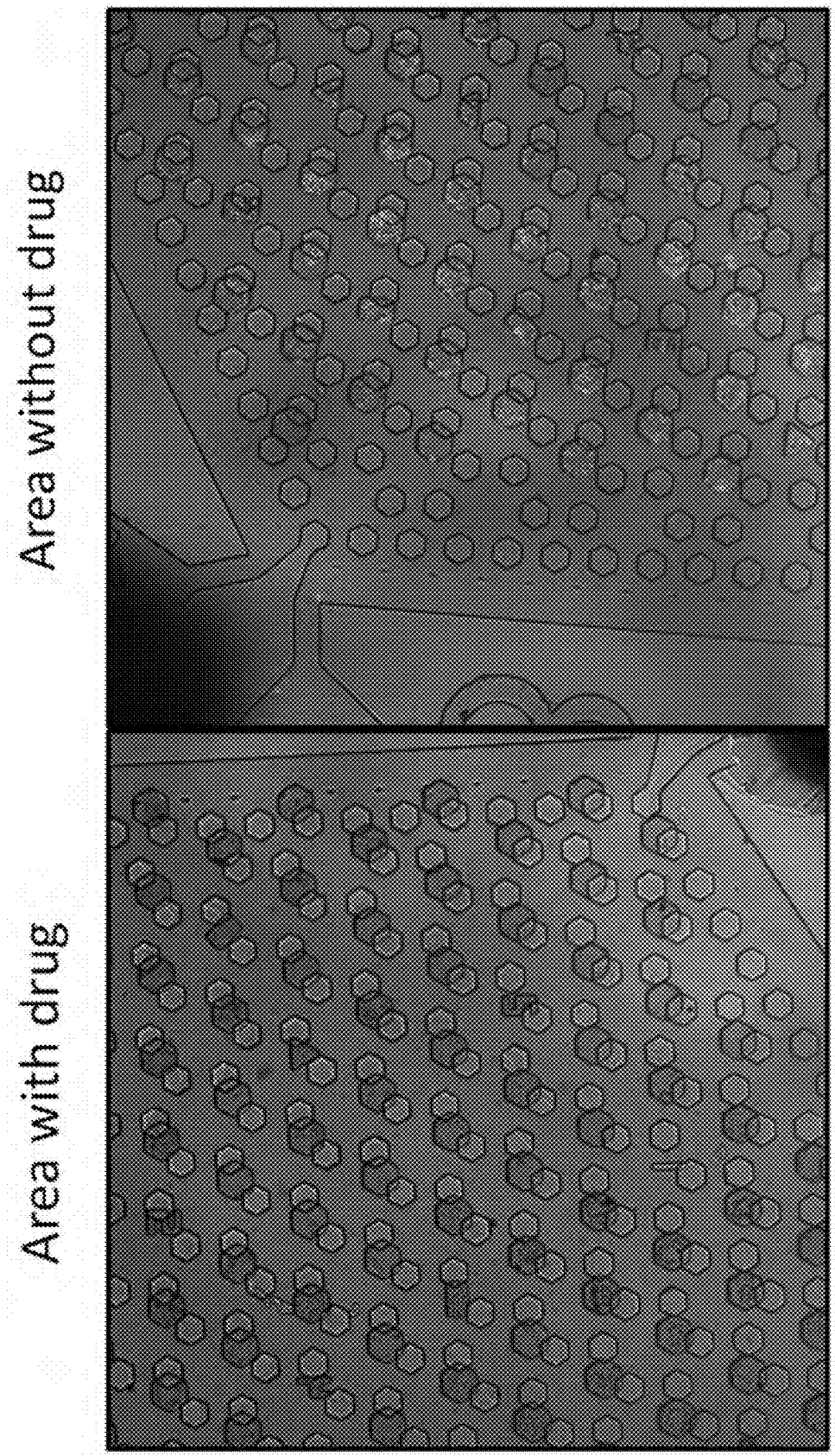
FIG. 33 is a series of photomicrographs showing 48 hours with 10 µM JSI124 (patient NACT14).
Figure 34:
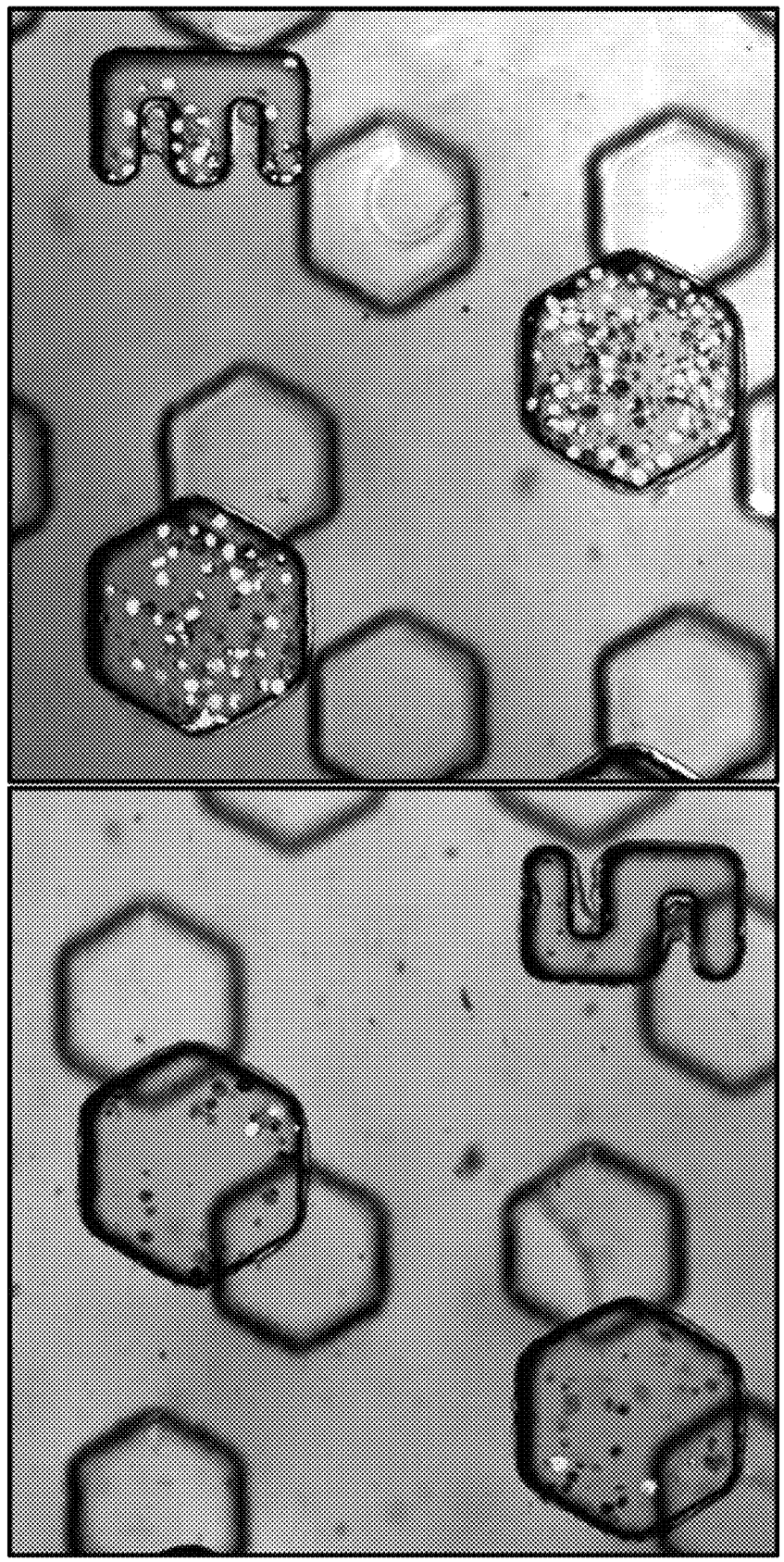
FIG. 34 is a series of photomicrographs showing 48 hours with 10 µM JSI124 (patient NACT14).
Figure 35:
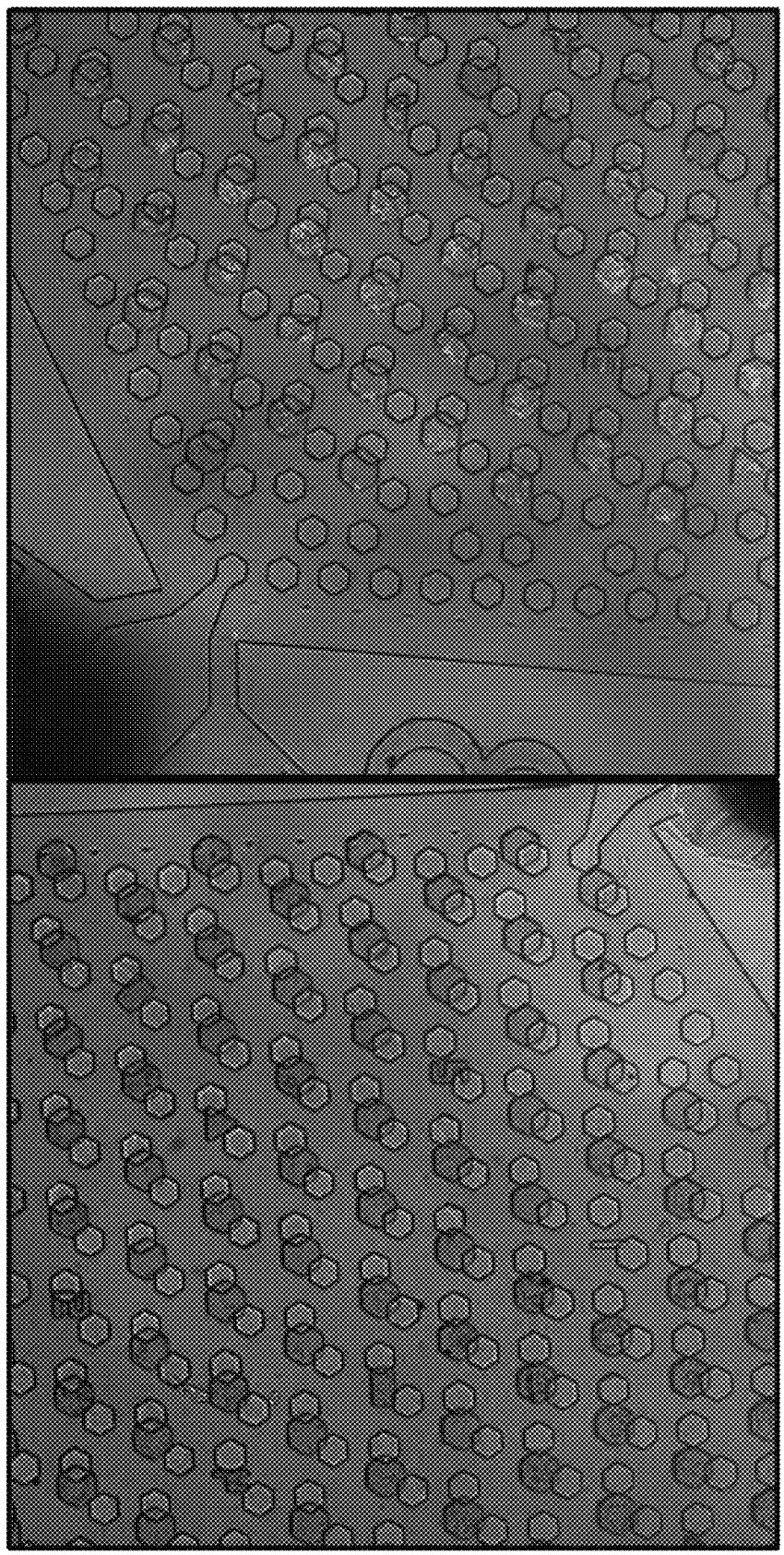
FIG. 35 is a series of photomicrographs showing 48 hours with 10 µM JSI124 (patient NACT14).

Example 13—JSI124 is Effective Against Patient-Derived Ovarian Cells in a Limited Sample Volume, Tested in a Microfluidic Device Heterogeneous cell population isolated from abdominal ascites of ovarian patient NACT14. A limited number of cells (~800 cells) in a volume of 1 microliter were tested for sensitivity of JSI124. On day 0, the cells were seeded in the microfluidic device. On day 1, drug was administered, together with a blue dye (FIG. 29-FIG. 31).

Hoechst confocal imaging (stained nuclei) was used to observe cells forty eight (48) hours after the drug was added (FIG. 32-FIG. 35).

Example 14—Online Material (Video 1-4) for Single-Cell RNA-Sequencing of Ovarian Cancer in Patients where PDX Models Reveal JAk/STAT-Inhibition as an Effective Therapeutic Strategy to Overcome Platinum-Resistance Described herein are patient derived spheroids treated with DMSO vs. JSI-124 for 30 or 120 minutes followed by drug removal. The results presented herein demonstrate invasion of DMSO-treated spheroids while JSI-124 treated spheroids are unable to invade through the mesothelial monolayer (Video 1 and 2).

Also described herein are spheroids generated from OVACR4 or TYKNU cell lines treated with DMSO vs. JSI-124 for 30 minutes followed by drug removal. The results demonstrate invasion of DMSO-treated spheroids while JSI-124 treated spheroids are unable to invade through the mesothelial monolayer (Video 3 and 4).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

---

What is claimed is:

1. A method for treating an ovarian tumor in a subject comprising:
   identifying a subject with an ovarian tumor by detecting the presence of malignant cells in ascites obtained from the subject; and
   administering to the subject a therapeutically effective amount of a signal transducer and activator of transcription 3 (STAT3) activity small molecule inhibitor to disrupt the formation, growth, and/or metastases of malignant ascites in the subject, wherein the STAT3 activity small molecule inhibitor comprises JSI-124 (cucurbitacin I),
   thereby treating the ovarian tumor in the subject.

2. The method of claim 1, wherein the subject is identified as having elevated STAT3 activity in the malignant cells in the ascites; and/or
   wherein the STAT3 activity small molecule inhibitor is administered intraperitoneally; and/or
   wherein the STAT3 activity is selected from the group consisting of STAT3 phosphorylation, STAT3 dimerization, STAT3 binding to a polynucleotide comprising a STAT3 binding site, STAT3 binding to genomic DNA, activation of a STAT3 responsive gene and STAT3 nuclear translocation.

3. The method of claim 1, wherein the JSI-124 (cucurbitacin I) is administered at a dose of about 0.1 µM.

4. The method of claim 1, further comprising administering a therapeutically effective amount of a chemotherapeutic agent.

5. The method of claim 1, wherein the subject is a human; and/or
   wherein the subject has received prior treatment for the ovarian tumor; and/or
   wherein the ovarian tumor is resistant to platinum-based chemotherapy; and/or
   wherein the subject has minimal residual disease (MRD) following platinum-based chemotherapy; and/or
   wherein the subject has minimal residue disease (MRD) or the ovarian cancer is a relapse.

6. The method of treatment according to claim 1, wherein the treatment is administered as an adjuvant or neoadjuvant therapy.

7. The method of claim 2, further comprising detecting expression or activity of one or more genes or polypeptides in single malignant cells from the ascites selected from the group consisting of JAK1, STAT3, STAT2, STAT1, IL6, TNF, and oncostatin M receptor (OSMR).

8. The method of claim 2, further comprising detecting expression or activity of one or more genes or polypeptides in single cancer-associated fibroblasts (CAFs) from the ascites selected from the group consisting of IL6, IL10, and CXCL12.

9. The method of claim 1,
   wherein tumor cell growth in the subject's abdomen is inhibited; and/or
   wherein subcutaneous tumor cell growth in the subject is inhibited; and/or
   wherein ovarian tumor cell metastases in the subject are inhibited; and/or
   wherein malignant abdominal fluid (ascites) is inhibited; and/or
   wherein tumor recurrence is prevented.

10. The method of claim 4, wherein the chemotherapeutic agent comprises a platinum-based chemotherapeutic agent or a taxane-based chemotherapeutic agent.

11. The method of claim 10, wherein the platinum-based chemotherapeutic agent comprises cisplatin or carboplatin.

12. The method of claim 4, wherein the chemotherapeutic agent is administered prior to, simultaneously with, or subsequent to administration of the STAT3 activity small molecule inhibitor.

13. The method of claim 4, wherein the STAT3 activity small molecule inhibitor is administered prior to the chemotherapeutic agent.

14. A method for treating ovarian tumor or preventing recurrence of the ovarian tumor and the development of metastases in a subject comprising:
   identifying a subject with an ovarian tumor by detecting a presence of malignant cells in ascites obtained from the subject;
   administering to the subject a therapeutically effective amount of a chemotherapeutic agent to inhibit the ovarian tumor; and
   administering to the subject a therapeutically effective amount of a STAT 3 activity small molecule inhibitor comprising JSI-124 (cucurbitacin I) to prevent the recurrence of the ovarian tumor and development of metastases.

15. The method of claim 14, wherein the JSI-124 (cucurbitacin I) is administered at a dose of about 0.1 µM.

16. The method of claim 14, wherein the chemotherapeutic agent comprises a platinum-based chemotherapeutic agent or a taxane-based chemotherapeutic agent.

17. The method of claim 16, wherein the platinum-based chemotherapeutic agent comprises cisplatin or carboplatin.

18. The method of claim 14, wherein the STAT3 activity small molecule inhibitor is administered at least one month after administration of the chemotherapeutic agent.

19. A method for treating a platinum-resistant ovarian tumor in a subject comprising:
  identifying a subject with a platinum-resistant ovarian tumor by detecting the presence of malignant cells in ascites obtained from the subject after being treated with a platinum-based chemotherapeutic agent;
  administering to the subject a therapeutically effective amount of a STAT3 activity small molecule inhibitor comprising JSI-124 (cucurbitacin I);
  administering to the subject a therapeutically effective amount of a chemotherapeutic agent.

20. The method of claim 19, wherein the JSI-124 (cucurbitacin I) is administered at a dose of about 0.1 μM.

21. The method of claim 19, wherein the platinum-based chemotherapeutic agent comprises cisplatin or carboplatin.

* * * * *